US008541363B2

(12) United States Patent
Robinson et al.

(10) Patent No.: US 8,541,363 B2
(45) Date of Patent: Sep. 24, 2013

(54) PYRUVAMIDE COMPOUNDS AS INHIBITORS OF DUST MITE GROUP 1 PEPTIDASE ALLERGEN AND THEIR USE

(75) Inventors: Clive Robinson, London (GB); Jihui Zhang, London (GB); David Ronald Garrod, Manchester (GB); Trevor Robert Perrior, Cambridge (GB); Gary Karl Newton, Cambridge (GB); Kerry Jenkins, Cambridge (GB); Rebekah Elisabeth Beevers, Cambridge (GB); Meriel Ruth Major, Cambridge (GB); Mark Richard Stewart, Cambridge (GB)

(73) Assignees: St George's Hosptial Medical School, London (GB); The University of Manchester, Manchester (GB)

( * ) Notice: Subject to any disclaimer, the term of this patent is extended or adjusted under 35 U.S.C. 154(b) by 40 days.

(21) Appl. No.: 13/521,067

(22) PCT Filed: Jan. 21, 2011

(86) PCT No.: PCT/GB2011/000079
§ 371 (c)(1),
(2), (4) Date: Jul. 9, 2012

(87) PCT Pub. No.: WO2011/089396
PCT Pub. Date: Jul. 28, 2011

(65) Prior Publication Data
US 2012/0322722 A1 Dec. 20, 2012

(30) Foreign Application Priority Data
Jan. 22, 2010 (GB) .................................. 1001070.0

(51) Int. Cl.
A61K 31/16 (2006.01)
(52) U.S. Cl.
USPC ............................................ 514/1.7; 514/4.5
(58) Field of Classification Search
None
See application file for complete search history.

(56) References Cited

U.S. PATENT DOCUMENTS

| 5,580,854 A | 12/1996 | Orlowski et al. |
| 5,633,231 A | 5/1997 | Habich et al. |
| 6,235,929 B1 | 5/2001 | Powers |
| 7,429,560 B2 * | 9/2008 | Powers et al. ........... 514/1.1 |
| 7,521,068 B2 | 4/2009 | Bosch et al. |

FOREIGN PATENT DOCUMENTS

| EP | 0100673 A2 | 2/1984 |
| EP | 0672648 A1 | 9/1995 |
| EP | 0839155 B1 | 5/1998 |
| WO | WO 90/05739 A1 | 5/1990 |
| WO | WO 96/16079 A2 | 5/1996 |
| WO | WO 96/30395 A2 | 10/1996 |
| WO | WO 97/04004 A1 | 2/1997 |
| WO | WO 97/21100 A1 | 6/1997 |
| WO | WO 97/30075 A1 | 8/1997 |
| WO | WO 99/47545 A2 | 9/1999 |
| WO | WO 01/40262 A1 | 6/2001 |
| WO | WO 02/08187 A2 | 1/2002 |
| WO | WO 2007/014946 | 2/2007 |
| WO | WO 2007/041775 A1 | 4/2007 |
| WO | WO 2011/089396 A2 | 7/2011 |
| WO | WO 2012/004554 A1 | 1/2012 |

OTHER PUBLICATIONS

Salvadori et al. (Nov. 1992) "Synthesis and pharmacological activity of N-terminal dermorphin tetrapeptide analogs with $CH_2$—NH peptide bond isosteres," *Int. J. Peptide Protein Res.* 40:437-444.
Arasappan et al., 2009, "Toward second generation hepatitis C virus NS3 serine protease inhibitors: Discovery of novel P4 modified analogues with improved potency and pharmacokinetic profile", *J. Med. Chem.*, vol. 52, pp. 2806-2817.
Arruda et al., 1991, "Exposure and sensitization to dust mite allergens among asthmatic children in Sao Paulo, Brazil", *Clin. Exp. Allergy*, vol. 21, pp. 433-439.
Asokananthan et al., 2002, "House dust mite allergens induce proinflammatory cytokines from respiratory epithelial cells: The cysteine protease allergen, Der p 1, activates protease-activated receptor (PAR)-2 and inactivates PAR-1", *J. Immunol.*, vol. 169, pp. 4572-4578.
Barrett et al., 2005, "$P^2$-$P^3$ conformationally constrained ketoamide-based inhibitors of cathepsin K", *Biorg. Med. Chem. Lett.*, vol. 15, pp. 3540-3546.
Billson et al., 1998, "The Design and Synthesis of Inhibitors of the Cysteinly Protease, *DER P* I.", *Bioorg. & Med. Chem. Lett.*, vol. 8, pp. 993-998.
Bodini et al., 2004, "Exhaled breath condensate eicosanoids and sputum eosinophils in asthmatic children: A pilot study", *Pediatr Allergy Immunol*, vol. 15, pp. 26-31.
Broide et al., 1992, "Cytokines in symptomatic asthma airways", *J. Allergy Clin. Immunol.*, vol. 89(5), pp. 958-967.
CAS Online Printout for EP 0 672 648 A1, 1995.
CAS Online Printout for WO 97/21100 A1, 1997.
Chan and White (editors), 2000, Fmoc Solid Phase Peptide Synthesis A Practical Approach (Oxford University Press), pp. 41-76.

(Continued)

*Primary Examiner* — Karlheinz R Skowronek
*Assistant Examiner* — Khalid Kader
(74) *Attorney, Agent, or Firm* — Swanson & Bratschun, L.L.C.

(57) ABSTRACT

The present invention pertains generally to the field of therapeutic compounds and more specifically to certain pyruvamide compounds of the formula (X) (for convenience, collectively referred to herein as "PVA compounds"), which, inter alia, inhibit a dust mite Group 1 peptidase allergen (e.g., Der p 1, Der f 1, Eur m 1). The present invention also pertains to pharmaceutical compositions comprising such compounds, and the use of such compounds and compositions, both in vitro and in vivo, to inhibit a dust mite Group 1 peptidase allergen, and in the treatment of diseases and disorders that are mediated by a dust mite Group 1 peptidase allergen; that are ameliorated by the inhibition of a dust mite Group 1 peptidase allergen; asthma; rhinitis; allergic conjunctivitis; atopic dermatitis; an allergic condition which is triggered by dust mites; an allergic condition which is triggered by a dust mite Group 1 peptidase allergen; and canine atopy.

66 Claims, 3 Drawing Sheets

(56) References Cited

OTHER PUBLICATIONS

Charpin et al., 1991, "Altitude and allergy to house-dust mites. A paradigm of the influence of environmental exposure on allergic sensitization", *Am. Rev. Respir. Dis.*, vol. 143, pp. 983-986.

Ciapetti et al., 1994, "$CrCl_2$ mediated allylation of N-protected α-amino aldehydes. A versatile synthesis of polypeptides containing an hydroxyethylene isostere", *Tetrahedron Lett.*, vol. 35(19), pp. 3183-3186.

Comoy et al., 1998, "The house dust mite allergen, *Dermatophagoides pteronyssinus*, promotes type 2 responses by modulating the balance between IL-4 and IFN-γ", *J Immunol*, vol. 160, pp. 2456-2462.

Deb et al., 2007, "Major house dust mite allergens *Dermatophagoides pteronyssinus* 1 and *Dermatophagoides farinae* 1 degrade and inactivate lung surfactant proteins A and D", *J. Biol. Chem.*, vol. 282(51), pp. 36808-36819.

Dowse et al., Jan. 1985, "The association between *Dermatophagoides* mites and the increasing prevalence of asthma in village communities within the Papua New Guinea highlands", *J. Allergy Clin. Immunol.*, vol. 75(1), pp. 75-83.

Eden et al., 2003, "Asthma features in severe $α_1$-antitrypsin deficiency: Experience of the National Heart, Lung, and Blood Institute Registry", *Chest*, vol. 123, pp. 765-771.

Fahy et al., 1995, "Comparison of samples collected by sputum induction and bronchoscopy from asthmatic and healthy subjects", *Am. J. Respir Crit Care Med*, vol. 152, pp. 53-58.

Fehrentz et al., 1995, "Improved solid phase synthesis of C-terminal peptide aldehydes" *Tetrahedron Lett.*, vol. 36(43), pp. 7871-7874.

Fusetani et al., 1999, "Tokaramide A, a New Cathepsin B Inhibitor from the Marine Sponge *Theonella* aff. *mirabilis*", *Bioorg. & Med. Chem.*, vol. 9, pp. 3397-3402.

Gelber et al., 1993, "Sensitization and exposure to indoor allergens as risk factors for asthma among patients presenting to hospital", *Am Rev Respir Dis*, vol. 147, pp. 573-578.

Ghaemmaghami et al., 2002, "The proteolytic activity of the major dust mite allergen Der p 1 conditions dendritic cells to produce less interleukin-12: allergen-induced Th2 bias determined at the dendritic cell level", *Clin Exp Allergy*, vol. 32, pp. 1468-1475.

Gough et al., 2001. "The proteolytic activity of the major dust mite allergen Der p 1 enhances the IgE antibody response to a bystander antigen", *Clin. Exp. Allergy*, vol. 31, pp. 1594-1598.

Gourgoulianis et al., 2001, "The influence of altitude in bronchial asthma", *Arch. Med. Res.*, vol. 32, pp. 429-431.

Grigg et al., 1985, "A simple one-step synthesis of N-substituted isoindolin-1-ones. Diastereofacially selective protonation of an intermediate isoindolinol", *J. Chem. Soc., Chem.Commun.*, No. 17, pp. 1183-1184.

Grootendorst et al., 2001, "Benefits of high altitude allergen avoidance in atopic adolescents with moderate to severe asthma, over and above treatment with high dose inhaled steroids", *Clin. Exp. Allergy*, vol. 31, pp. 400-408.

Hellings et al., 2001, "Eosinophilic rhinitis accompanies the development of lower airway inflammation and hyper-reactivity in sensitized mice exposed to aerosolized allergen", *Clin. Exp. Allergy*, vol. 31, pp. 782-790.

Holt et al., 1990, "A contiguous network of dendritic antigen-presenting cells within the respiratory epithelium", *Int. Arch. Allergy Pool. Immunol.*, vol. 91, pp. 155-159.

Holt, 2002, "The role of airway dendritic cell populations in regulation of T-cell responses to inhaled antigens: atopic asthma as a paradigm", *J.Aerosol Med.*, vol. 15(2), pp. 161-168.

Huh et al., 2003, "Bidirectional interactions between antigen-bearing respiratory tract dendritic cells (DCs) and T cells precede the late phase reaction in experimental asthma: DC activation occurs in the airway mucosa but not in the lung parenchyma", *J. Exp. Med.*, vol. 198(1), pp. 19-30.

Hyde et al., 1979, "Protease inhibitor variants in children and young adults with chronic asthma", *Ann. Allergy*, vol. 43, pp. 8-13.

IPRP for PCT/GB2011/000079 dated Jul. 24, 2012.

Jaakkola et al., 2006, "Are atopy and specific IgE to mites and molds important for adult asthma?", *J Allergy Clin Immunol*, vol. 117(3), pp. 642-648.

Kalsheker et al., 1996, "The house dust mite allergen *Der* p1 catalytically inactivates $α_1$-antitrypsin by specific reactive centre loop cleavage: A mechanism that promotes airway inflammation and asthma", *Biochem. Biophys. Res. Commun.*, vol. 221, pp. 59-61.

King et al., 1998, "Dust mite proteolytic allergens induce cytokine release from cultured airway epithelium", *J. Immunol.*, vol. 161, pp. 3645-3651.

Lambrech and Hammad, 2002, "Myeloid dendritic cells make it to the top", *Clin Exp Allergy*, vol. 32, pp. 805-810.

Lambrech and Hammad, 2003a, "Taking our breath away: dendritic cells in the pathogenesis of asthma", *Nat. Rev. Immunol.*, vol. 3, pp. 994-1003.

Lambrecht and Hammad, 2003b, "The other cells in asthma: dendritic cell and epithelial cell crosstalk", *Current Opinion in Pulmonary Medicine*, vol. 9, pp. 34-41.

Liu et al., 2004, "Hepatitis C NS3 protease inhibition by peptidyl-α-ketoamide inhibitors: kinetic mechanism and structure", *Archives of Biochem and Biophys*, vol. 421, pp. 207-216.

Loser et al., 2010, "Noncovalent Tripeptidyl Benzyl- and Cyclohexyl-amine Inhibitors of the Cysteine Protease Caspase-1", *J. Med. Chem.*, vol. 53, pp. 2651-2655.

Marcaccinin et al., 2005, "2. Post Condensation Modifications of the Passerini and Ugi Reactions", in *Multicomponent Reactions*, 1st Edition (Ed., Jieping et al., Wiley-VCH), Chapter 2, pp. 33-75, and especially pp. 41-47.

McCusker et al., 2002, "Site-specific sensitization in a murine model of allergic rhinitis: Role of the upper airway in lower airways disease", *J Allergy Clin Immunol*, vol. 110(6), pp. 891-898.

McMillan and Lloyd, 2004, "Prolonged allergen challenge in mice leads to persistent airway remodelling", *Clin Exp Allergy*, vol. 34, pp. 497-507.

Miyamoto et al., 1968, "Allergenic identity between the common floor mite (*Dermatophagoides farinae* Hughes, 1961) and house dust as a causative antigen in bronchial asthma", *J. Allergy*, vol. 42(1), pp. 14-28.

Mullersman and Preston, 1991, "Conjugation of N-acylated amino sugars to protein by reductive alkylation using sodium cyanoborohydride: application to an azo derivative of α-amanitin", *Biochem. Cell Biol.*, vol. 69, pp. 418 427.

Muraguchi et al., 1988, "The essential role of B cell stimulatory factor 2 (BSF-2/IL-6) for the terminal differentiation of B cells", *J. Exp. Med*, vol. 167, pp. 332-344.

O'Donnell et al., 2000 "UPS on Weinreb Resin: A Facile Solid-Phase Route to Aldehyde and Ketone Derivatives of "Unnatural" Amino Acids and Peptides", *J. Comb. Chem.*, vol. 2( 2), pp. 172-181.

Jenkins and Mitsunobu, "Triphenylphosphine-Diethyl Azodicarboxylate", 1995, Encyclopedia of Reagents for Organic Synthesis, Paquette (editor), (John Wiley & Sons, Ltd.,) pp. 5379-5380.

Peat and Woolcock, 1991, "Sensitivity to common allergens: relation to respiratory symptoms and bronchial hyper-responsiveness in children from three different climatic areas of Australia", *Clin. Exp. Allergy*, vol. 21, pp. 573-581.

Peat et al., 1996, "House dust mite allergens. A major risk factor for childhood asthma in Australia", *Am J Respir Crit Care Med*, vol. 153, pp. 141-146.

Peroni et al., 1994, "Effective allergen avoidance at high altitude reduces allergen-induced bronchial hyperresponsiveness", Am J Respir Cri. Care Med, vol. 149, pp. 1442-1446.

Piacentini et al., 1998, "Mite-antigen avoidance can reduce bronchial epithelial shedding in allergic asthmatic children", *Clin. Exp. Allergy*, vol. 28, pp. 561-567.

Piacentini et al., 1999, "Allergen avoidance at high altitude and urinary eosinophil protein X", *J. Allergy Clin Immunol* vol. 104(1), pp. 243-244.

Platts-Mills et al., 1987, "Seasonal variation in dust mite and grass-pollen allergens in dust from the houses of patients with asthma", *J. Allergy Clin.Immunol.*, vol. 79(5), pp. 781-791.

Platts-Mills et al., 1997, "Indoor allergens and asthma: Report of the Third International Workshop", *J Allergy Clin Immuno.*, vol. 100(6), pp. S2-24.

Platts-Mills et al., 2000, "The role of intervention in established allergy: Avoidance of indoor allergens in the treatment of chronic allergic disease", *J Allergy Clin Immunol*, vol. 106, pp. 787-804.

Pollart et al., 1989, "Epidemiology of acute asthma: IgE antibodies to common inhalant allergens as a risk factor for emergency room visits", *J. Allergy Clin. Immunol.*, vol. 83(5), pp. 875-882.

Rudolph et al., 1978, "The significance of nasal protease inhibitor concentrations in house dust allergy", *Allergy*, vol. 33, pp. 310-315.

Schultze-Werninghaus, 2006, "Should athma management include sojourns at high altitude?", *Chem. Immunol. Allergy*, vol. 91, pp. 16-29.

Seymour et al., 1998, "Aerosol-induced immunoglobulin (Ig)-E unresponsiveness to ovalbumin does not require $CD8^+$ or T cell receptor $(TCR)-\gamma/\delta^+$ T cells or interferon $(IFN)-\gamma$ in a murine model of allergen sensitization", *J. Ex. Med.*, vol. 187(5), pp. 721-731.

Siev and Semple, 2000, "Novel hydrazino-carbonyl-amino-methylated polystyrene (HCAM) resin methodology for the synthesis of $P_1$-aldehyde protease inhbitor candidates", *Org. Lett.*, vol. 2(1), pp. 19-22.

Sigsgaard et al., 2000, "S and Z $\alpha_1$-antitrypsin alleles are risk factors for bronchial hyperresponsiveness in young farmers: an example of gene/environment interaction", *Eur Respir J*, vol. 16, pp. 50-55.

Smith et al., 1969, "Clinical significance of skin reactions to mite extracts in children with asthma",*Br. Med. J*, vol. 2, pp. 723-726.

Sporik et al., 1990, "Exposure to house-dust mite allergen (*Der p* I) and the development of asthma in childhood. A prospective study", *N. Engl. J. Med.*, vol. 323(8), pp. 502-507.

Stewart and Robinson, 2003, "Allergen structure and function", in: *Middleton's Allergy. Principles and Practice*, (Eds. Adkinson et al.; Publisher: Mosby, Philadelphia), pp. 585-609.

Stick and Holt, 2003, "The airway epithelium as immune modulator: The LARC ascending", *Am. J. Respir. Cell Mol. Biol*, vol. 28, pp. 641-644.

Sture et al., 1995, "Canine atopic dermatitis: the prevalence of positive intradermal skin tests at two sites in the north and south of Great Britain", *Vet. Immunol. Immunopathol.*, vol. 44, pp. 293-308.

UK Search Report on GB1001070.0 dated Jun. 28, 2010.

UK Search Report for GB1011411.4 dated Nov. 8, 2010.

van Halteren et al., 1997, "Regulation of antigen-specific IgE, IgG1, and mast cell responses to ingested allergen by mucosal tolerance induction", *J. Immunol.*, vol. 159, pp. 3009-3015.

van Velzen et al., 1996., "Effect of allergen avoidance at high altitude on direct and indirect bronchial hyperresponsiveness and markers of inflammation in children with allergic asthma", *Thorax*, vol. 51, pp. 582-584.

Vercelli.et al., 1989, "Endogenous interleukin 6 plays an obligatory role in interleukin 4-dependent human IgE synthesis", *Eur. J. Immunol.*, vol. 19, pp. 1419-1424.

Vervloet et al., 1982, "Altitude and house dust mites", *J. Allergy Clin. Immunol.*, vol. 69(3), pp. 290-296.

Wan et al., 1999, "Der p 1 facilitates transepithelial allergen delivery by disruption of tight junctions", *J. Clin. Invest.*, vol. 104(1), pp. 123-133.

Wan et al., 2000, "Tight junction properties of the immortalized human bronchial epithelial cell lines Calu-3 and 16HBE14o-", *Eur Respir J*, vol. 15, pp. 1058-1068.

Winton et al., 1998, "Cell lines of pulmonary and non-pulmonary origin as tools to study the effects of house dust mite proteinases on the regulation of epithelial permeability", *Clin. Exp. Allergy*, vol. 28, pp. 1273-1285.

WOISA and ISR for PCT/GB2011/000079 mailed Mar. 5, 2012.

WOISA and ISR for PCT/GB2011/001011 mailed Sep. 12, 2011.

Wolfe and Buchwald, 2004, "Palladium-Catalyzed Amination of Aryl Halides and Aryl Triflates: N-Hexyl-2-Methyl-4-Methoxyaniline and N-Methyl-N-(4-Chlorophenyl)Aniline", *Org. Synth., Coll.*, vol. 10, p. 423.

Zhang et al., 2007, "Interactions between mature Der p 1 and its free prodomain indicate membership of a new family of C1 peptidases," *Allergy*, vol. 62, pp. 1302-1309.

Zhang et al., 2009, "Novel Der p 1 inhibitors attenuate House Dust Mite sensitization in mice", *Amer J Respir Crit Care Med*, vol. 179, p. A4249 (abstract).

Zhaozhao et al., 1996, "Novel peptidyl α-keto amide inhibitors of Calpains and Other Cysteine Proteases", *J. Med. Chem.*, vol. 39, pp. 4089-4098.

\* cited by examiner

PYRUVAMIDE COMPOUNDS AS INHIBITORS OF DUST MITE GROUP 1 PEPTIDASE ALLERGEN AND THEIR USE

RELATED APPLICATION

This application is a 35 U.S.C. §371 national phase application of PCT/GB2011/000079, filed Jan. 21, 2011 (WO 2011/089396), entitled "Pyruvamide Compounds as Inhibitors of Dust Mite Group 1 Peptidase Allergen and Their Use". PCT/GB2011/000079 claims priority to United Kingdom patent application number 1001070.0 filed Jan. 22, 2010, the contents of which are incorporated herein by reference in their entirety.

TECHNICAL FIELD

The present invention pertains generally to the field of therapeutic compounds, and more specifically to certain pyruvamide compounds (for convenience, collectively referred to herein as "PVA compounds"), which, inter alia, inhibit a dust mite Group 1 peptidase allergen (e.g., Der p 1, Der f 1, Eur m 1). The present invention also pertains to pharmaceutical compositions comprising such compounds, and the use of such compounds and compositions, both in vitro and in vivo, to inhibit a dust mite Group 1 peptidase allergen, and in the treatment of diseases and disorders that are mediated by a dust mite Group 1 peptidase allergen; that are ameliorated by the inhibition of a dust mite Group 1 peptidase allergen; asthma; rhinitis; allergic conjunctivitis; atopic dermatitis; an allergic condition which is triggered by dust mites; an allergic condition which is triggered by a dust mite Group 1 peptidase allergen; and canine atopy.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to about another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Allergic Diseases

Allergic diseases, such as asthma, rhinitis, conjunctivitis and eczema, are escalating global healthcare problems which have not been contained by existing medications. These clinical conditions are initiated and triggered in genetically susceptible individuals by exposure to a diverse range of substances known as allergens. Numerous sources of allergen exist, but those associated with domestic environments are especially important as disease triggers because people are exposed to them for long periods. Amongst domestic allergens, those derived from house dust mites (HDM) are globally the most significant cause of allergic disease. These mites are found abundantly in homes, in workplaces, in entertainment venues, and in public and private transport vehicles. Chronic sensitization to HDM allergens can occur at any time of life and subsequent exacerbations triggered by repeated allergen exposure increase the probability that minor conditions such as allergic rhinitis will escalate into asthma, which is more serious. In addition, house dust mites create health problems for animals that co-habit with humans. For example, the condition of canine atopy is an inherited condition that gives rise to a miscellany of allergic conditions of the skin, nose and eyes (Sture et al., 1995). Perennial symptoms are commonly associated with sensitization and subsequent re-exposure to dust mite allergens. It is well-described with house dust mites recognised as significant triggers of perennial allergic symptoms in dogs, resulting in a need for veterinary treatment to alleviate disease symptoms. The symptoms seen in dogs largely resemble those seen in human atopic dermatitis and conjunctivitis.

The pre-eminence of house dust mite allergens as triggers of allergic conditions has resulted in a need to understand why they are allergenic. Studies into the molecular basis of allergenicity have revealed that the HDM allergen of greatest clinical significance is a cysteine peptidase. Surprisingly, this peptidase activity contributes decisively to the development of allergy to HDM allergens generally and to other by-stander allergens unrelated to HDM.

Several species of dust mite are known (e.g., *Dermatophagoides pteronyssinus, Dermatophagoides farinae, Dermatophagoides siboney* and *Euroglyphus maynei*) and each of these produce numerous allergenic proteins. The allergens from the different species can be categorized into distinct groups which show immunological cross-reactivity because they are highly identical proteins with conserved amino acid sequences. In the case of HDM, the Group 1 allergens (e.g., Der p 1, Der f 1, Eur m 1) underlie >95% of HDM allergy and are a highly conserved family of cysteine peptidases. The normal function of these cysteine peptidases in mites is as digestive enzymes which have the capability of digesting the resilient structural proteins in dried flakes of exfoliated skin which form a significant component of the HDM diet. The degree of amino acid sequence conservation in HDM Group 1 cysteine peptidase allergens (>90%) is such that they may be regarded as functionally identical and, for drug discovery purposes, a single therapeutic target. It is also now known that a clinically significant allergen from another mite of more restricted geographical distribution, *Blomia tropicalis*, is a related cysteine peptidase and shows immunological reactivity with the Group 1 allergens from house dust mites. This suggests that an inhibitor of Group 1 HDM allergens may be more generally applicable as inhibitors of related molecules in all species of mite that cause allergy.

The Group 1 HDM allergens are major triggers of asthma and other allergic conditions. When inhaled, their peptidase activity cleaves proteins that (i) increases the permeability of the airway epithelium allowing access for them and other, non-peptidase allergens to dendritic antigen presenting cells, and (ii) triggers signalling events that skew immunological responses to the Th2 phenotype. Both of these events initiate allergy and must be recapitulated to maintain it. Blocking these essential, top-level steps in allergic sensitization by inhibiting the cysteine peptidase activity of the Group 1 allergens could therefore provide the basis for a unique approach to the treatment and prevention of allergy.

Group 1 HDM Allergens as a Therapeutic Target

People are exposed to house dust mite (HDM) allergens for up to 23 hours each day; consequently these allergens are of major clinical significance in a range of clinical conditions that share elevated IgE as a molecular marker of disease. Population-based cross-sectional and longitudinal studies demonstrate that a positive skin test reaction for IgE antibody to HDM allergens is associated with asthma, persistent rhinitis, allergic conjunctivitis or atopic dermatitis (Arruda et al., 1991; Gelber et al., 1993; Miyamoto et al., 1968; Peat et al., 1996; Peat et al., 1991; Pollart et al., 1989; Smith et al., 1969; Sporik et al., 1990) In genetically predisposed individuals, first encounters with these allergens can trigger the onset of disease at any time and, with repeated exposures through life, minor conditions can evolve into serious disease. Thus, the probability of developing asthma is increased 10-20 fold after rhinitis has been established. Furthermore, the largest ever study of adult-onset asthma demonstrated, contrary to previous beliefs, that HDM allergy is as important to adults as children (Jaakkola et al., 2006).

Allergy risk and severity both show dose-response relationships with allergen exposure. This increases the attraction of pharmacological intervention aimed at Group 1 HDM allergens. Clinical evidence strongly supports a threshold level of exposure above which sensitization of at-risk individuals becomes probable. Furthermore, a dose-response relationship exists between concentrations of these allergens in homes (and thus human exposure) and the importance of this sensitization to asthma (Gelber et al., 1993; Peat et al., 1991; Platts-Mills et al., 1997; Platts-Mills et al., 1987; Dowse et al., 1985; Charpin et al., 1991). These observations imply that avoidance or inactivation of these key allergens (i.e., by reducing the dose of functional allergen to which an individual is exposed) is likely to decrease sensitization, causing symptoms to wane and clinical prognosis to improve. Reducing exposure to these allergens is the basis of physical allergen avoidance strategies which have been investigated as a means of controlling allergy. The benefits of physical allergen avoidance are supported by controlled trials in which people have been moved to environments (e.g., alpine sanatoria) where allergen avoidance can be managed rigorously (Dowse et al., 1985; Platts-Mills et al., 2000; Vervloet et al., 1982; Peroni et al., 1994). The effect of a strict regime of allergen avoidance is rapid in onset, with patients showing a significant decrease in markers of inflammation or medicine usage within 2 to 4 weeks (van Velzen et al., 1996; Schultze-Werninghaus, 2006; Bodini et al., 2004; Gourgoulianis et al., 2001; Piacentini et al., 1999; Piacentini et al., 1998). However, such physical avoidance measures are generally impractical and the benefits wane upon a return to everyday life.

Given the contribution of proteolytic activity to allergic sensitization, the development of a means to inhibit the peptidase activity of Group 1 allergens would provide pharmacological allergen inactivation that would mimic the effects of physical allergen avoidance. It is envisaged that the optimum means to achieve this objective would be to treat patients with such inhibitors, either topically or systemically. One advantage of this approach is that pharmacological allergen inactivation would travel with the person being treated (i.e., it would be "portable") to achieve the benefits of continuous allergen avoidance, something which is not achievable with physical allergen avoidance measures. In addition to their use as medicines, it is likely that inhibitors of Group 1 peptidase allergens would have additional value as acaricides applied as environmental treatments. By inactivating key enzymes involved in the digestion of food by HDM, such inhibitors would deprive mites of a source of nutrition causing them to fail to thrive.

Allergens and Peptidase Activity

Two observations are relevant to an appreciation of the contribution of peptidase activity to allergic sensitization. The first is the demonstration that the proteolytic activity of a small cadre of enzymatic allergens is vital to allergic sensitization via the airways. Secondly is the ability of peptidases to drive allergic sensitization to by-stander allergens that lack proteolytic activity. When administered alone and without adjuvants, such non-enzymatic bystanders fail to evoke responses, induce tolerance or show only weak IgG-mediated reactions, even with systemic immunisation (Seymour et al., 1998; van Halteren et al., 1997; McMillan et al., 2004; McCusker et al., 2002; Hellings et al., 2001). Since the majority of allergens are non-proteolytic, the ability of individual peptidases to exert a marked influence on the development of sensitization to by-stander allergens creates an interesting therapeutic opportunity which inhibitors of Group 1 mite allergens could exploit.

Previous studies have shown that the proteolytic activity of Group 1 HDM allergens makes an essential contribution to allergy through two general mechanisms that are central to the initiation and maintenance of the allergic state. These are:

Facilitating allergen delivery across mucosal surfaces, thus gaining access to antigen presenting cells (e.g., in the lungs, dendritic cells) (Holt et al., 1990; Holt, 2002; Huh et al., 2003; Lambrecht et al., 2003a; Lambrecht et al., 2002; Lambrecht et al., 2003b; Wan et al., 2000).

Activating signal transduction pathways that favour development of allergy in the genetically predisposed (Hellings et al., 2001; Comoy et al., 1998; Stewart et al., 2003).

HDM peptidase allergens therefore exert significant effects that are independent of IgE, but which have an essential bearing on IgE sensitization and allergic responses (King et al., 1998; Asokananthan et al., 2002). These actions serve to promote sensitization to the inciting peptidase allergen but, as described above, because the effects of the general mechanisms are essentially allergen non-specific, sensitization to non-enzymatic bystander allergens also occurs (Stewart et al., 2003; Wan et al., 1999).

Allergen Delivery

Dendritic cells are the primary antigen presenting cells of the respiratory tract (Holt et al., 1990; Holt, 2002; Huh et al., 2003; Lambrecht et al., 2003a; Lambrecht et al., 2002; Lambrecht et al., 2003b). However, for effective IgE responses to develop and be maintained, the probability of contact with antigens must be increased (Lambrecht et al., 2003b). This essential step in the detection of allergen is facilitated by the cysteine peptidase activity of Group 1 mite allergens which cleaves the transmembrane adhesion proteins of epithelial tight junctions, facilitating paracellular delivery of any allergen to dendritic cells (Wan et al., 1999; Wan et al., 2000; Winton et al., 1998).

IgE-Independent Cell Activation

Peptidase allergens are thought to contribute to innate immunity and activate a variety of cells by numerous IgE-independent mechanisms. Signalling pathways activated by cleavage of tethered ligand receptors on epithelial cells is one such mechanism contributing to the chronic release of GM-CSF and IL-6. These cytokines are present in increased amounts in the airways in allergic asthma and rhinitis (Broide et al., 1992; Fahy et al., 1995; Muraguchi et al., 1988; Vercelli., 1989). They promote a Th2 allergic bias via several actions. For example, IL-6 is essential to B cell maturation and in the IL-4-dependent synthesis of IgE (Muraguchi et al., 1988; Vercelli., 1989). GM-CSF generates signals that cause dendritic cells to migrate from the airway epithelium to present captured antigens at regional lymph nodes (Stick et al., 2003). Proteolytic activity that cleaves tethered ligand receptors is thus associated with a chain of events central to both the initiation of allergic sensitization and its maintenance. Peptidase allergens activate mast cells by IgE-independent mechanisms and it follows, therefore, that a contribution to the acute bronchoconstriction resulting from allergen challenge must be due to this peptidase-dependent activation. This suggests that inhibitors of Group 1 peptidase allergens should attenuate acute allergic bronchoconstriction. Other IgE-independent mechanisms involve a cleavage of cytokine and IgE receptors that are associated with an augmentation of allergy (Ghaemmaghami et al., 2002), cleavage of antipeptidase defences (which may already be defective in allergy) and cleavage of other protective factors such as surfactant proteins (Deb et al., 2007).

Demonstrations of Proteolytic Allergen Contributions to Allergy

The potential importance of peptidase allergens as a target in allergy is demonstrated by the ease and directness with which they evoke IgE sensitization and by studies with generic inhibitors of cysteine peptidases in experimental animals.

Strong allergen-specific IgE sensitization can be achieved by non-invasive exposure of mice to Der p 1 of high specific proteolytic activity in the absence of adjuvants (Zhang et al., 2009). In Brown Norway rats, development of Der p 1-specific IgE and allergic responsiveness also occurs without the need for additional adjuvants. In contrast, the difficulties in raising high titre antibodies to recombinant Der p 1 that lacks high enzyme activity (and which therefore behaves like a by-stander allergen) are well known. The proteolytic nature of Der p 1 also augments the sensitization to non-peptidase bystander allergens from HDM and other sources (Gough et al., 2001).

The promotion of allergen delivery by peptidase allergens may be augmented by their inactivation of antipeptidase defences (Kalsheker et al., 1996). Of related significance is that the loss of functional polymorphisms in endogenous enzyme inhibitors (e.g., chromosome 5q32 LETK1, chromosome 7 PAI-I, chromosome 11 C1 esterase inhibitor, chromosome 14 serpin cluster, chromosome 18q21) predisposes the subject to allergic disease. This recent evidence supplements functional associations between allergy and protease inhibitor deficiency that have accrued over the past 25 years (Rudolph et al., 1978; Hyde et al., 1979; Eden et al., 2003; Sigsgaard et al., 2000).

SUMMARY OF THE INVENTION

Figure 1:
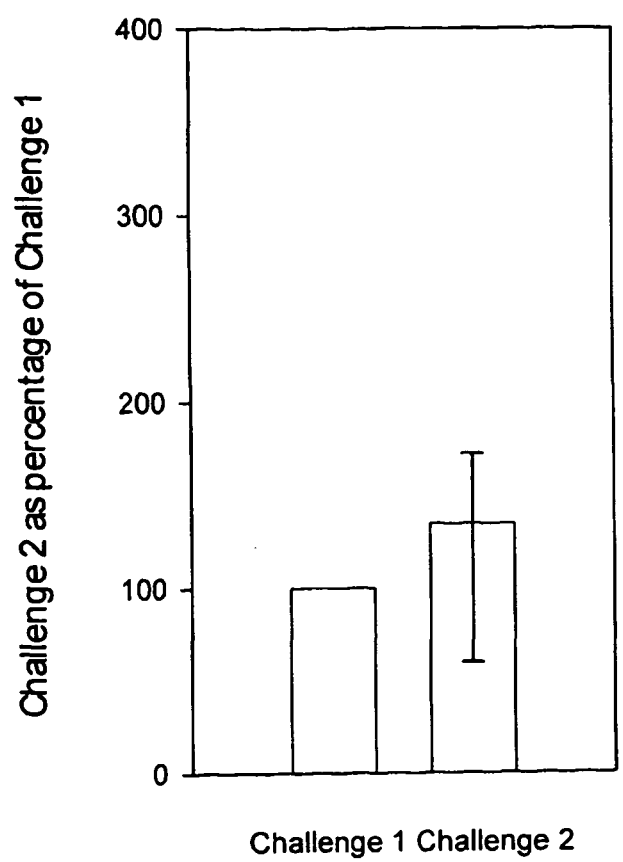
FIG. 1 is a bar graph of the magnitude of response following Challenge 1 (left) and Challenge 2 (right), expressed as a percentage of the magnitude of the response following Challenge 1. (Medians reported; error bar is for 25th/75th percentiles.)

One aspect of the invention pertains to certain pyruvamide compounds (for convenience, collectively referred to herein as "PVA compounds"), as described herein.

Another aspect of the invention pertains to a composition (e.g., a pharmaceutical composition) comprising a PVA compound, as described herein, and a pharmaceutically acceptable carrier or diluent.

Another aspect of the invention pertains to method of preparing a composition (e.g., a pharmaceutical composition) comprising the step of admixing a PVA compound, as described herein, and a pharmaceutically acceptable carrier or diluent.

Another aspect of the present invention pertains to a method of inhibiting a dust mite Group 1 peptidase allergen (e.g., Der p 1, Der f 1, Eur m 1), in vitro or in vivo, comprising contacting a dust mite Group 1 peptidase allergen with an effective amount of a PVA compound, as described herein.

Another aspect of the present invention pertains to a method of inhibiting a dust mite Group 1 peptidase allergen in a cell, in vitro or in vivo, comprising contacting the cell with an effective amount of a PVA compound, as described herein.

Another aspect of the present invention pertains to a method of treatment comprising administering to a subject in need of treatment a therapeutically-effective amount of a PVA compound, as described herein, preferably in the form of a pharmaceutical composition.

Another aspect of the present invention pertains to a PVA compound as described herein for use in a method of treatment of the human or animal body by therapy.

Another aspect of the present invention pertains to use of a PVA compound, as described herein, in the manufacture of a medicament for use in treatment.

In one embodiment, the treatment is treatment of a disease or condition that is mediated by a dust mite Group 1 peptidase allergen.

In one embodiment, the treatment is treatment of a disease or condition that is ameliorated by the inhibition of a dust mite Group 1 peptidase allergen.

In one embodiment, the treatment is treatment of: asthma, for example, atopic asthma; allergic asthma; atopic bronchial IgE-mediated asthma; bronchial asthma; extrinsic asthma; allergen-induced asthma; allergic asthma exacerbated by respiratory virus infection; infective asthma; infective asthma caused by bacterial infection; infective asthma caused by fungal infection; infective asthma caused by protozoal infection; or infective asthma caused by viral infection.

In one embodiment, the treatment is treatment of: bronchial hyperreactivity associated with asthma; or bronchial hyperresponsiveness associated with asthma.

In one embodiment, the treatment is treatment of: airway remodelling associated with an allergic lung disease, for example, airway remodelling associated with asthma.

In one embodiment, the treatment is treatment of: asthma co-presented with a chronic obstructive lung disease, for example, asthma co-presented with emphysema; or asthma co-presented with chronic bronchitis.

In one embodiment, the treatment is treatment of: rhinitis, for example, allergic rhinitis; perennial rhinitis; persistent rhinitis; or IgE-mediated rhinitis.

In one embodiment, the treatment is treatment of: allergic conjunctivitis, including, for example, IgE-mediated conjunctivitis.

In one embodiment, the treatment is treatment of: atopic dermatitis.

In one embodiment, the treatment is treatment of: an allergic condition which is triggered by dust mites.

In one embodiment, the treatment is treatment of: an allergic condition which is triggered by a dust mite Group 1 peptidase allergen (e.g., Der p 1, Der f 1, Eur m 1).

In one embodiment, the treatment is treatment of: canine atopy.

In one embodiment, the treatment further comprises treatment with one or more additional therapeutic agents, for example, one or more additional therapeutic agents selected from agents used, or likely to be used, in the treatment of a respiratory disease.

Another aspect of the present invention pertains to a PVA compound, as described herein, for use as an acaricide.

Another aspect of the present invention pertains to a composition comprising a PVA compound, as described herein, for use as an acaricide.

Another aspect of the present invention pertains to an acaricide composition comprising a PVA compound, as described herein.

Another aspect of the present invention pertains to the use of a PVA compound, as described herein, as an acaricide.

Another aspect of the present invention pertains a method of killing mites (e.g., dust mites), comprising exposing said mites to an effective amount of a PVA compound, as described herein.

Another aspect of the present invention pertains a method of controlling (e.g., limiting) a mite (e.g., dust mite) population comprising exposing mites to an effective amount of a PVA compound, as described herein.

Another aspect of the present invention pertains to a kit comprising (a) a PVA compound, as described herein, preferably provided as a pharmaceutical composition and in a suitable container and/or with suitable packaging; and (b) instructions for use, for example, written instructions on how to administer the compound.

Another aspect of the present invention pertains to a PVA compound obtainable by a method of synthesis as described herein, or a method comprising a method of synthesis as described herein.

Another aspect of the present invention pertains to a PVA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain pyruvamide compounds which are related to 3-[2-(2-acylamino-acetylamino)-acetylamino]-2-oxo-propionamide:

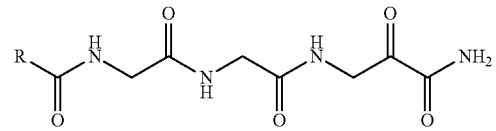

All of the compounds of the present invention have a pyruvamide linkage (i.e., —C—C(=O)—C(=O)—N<), which is related to pyruvic acid (also referred to as 2-oxo-propionic acid) and pyruvamide (also referred to as 2-oxo-propionamide).

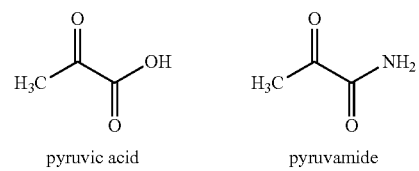

pyruvic acid      pyruvamide

Thus, one aspect of the present invention pertains to compounds selected from compounds of the following formula, and salts, hydrates, and solvates thereof (e.g., pharmaceutically acceptable salts, hydrates, and solvates thereof), wherein $R^1$, $R^2$, $R^3$, $R^4$, $R^5$, $R^6$, $R^7$, $R^8$, $R^9$, $R^{10}$, $R^{11}$, and $R^{12}$ are as defined herein (for convenience, collectively referred to herein as "PVA compounds"):

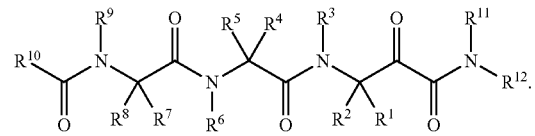

Depending upon the values of —$R^1$ and —$R^2$, the carbon atom to which they are attached may be chiral, and if so, may independently be in the (R) or (S) configuration. Unless otherwise indicated, it is intended that both configurations are encompassed. In a preferred embodiment, the configuration is (S).

Depending upon the values of —$R^4$ and —$R^5$, the carbon atom to which they are attached may be chiral, and if so, may independently be in the (R) or (S) configuration. Unless otherwise indicated, it is intended that both configurations are encompassed. In a preferred embodiment, the configuration is (S).

Depending upon the values of —$R^7$ and —$R^8$, the carbon atom to which they are attached may be chiral, and if so, may independently be in the (R) or (S) configuration. Unless otherwise indicated, it is intended that both configurations are encompassed.

Depending upon the values of —$R^1$, —$R^2$, —$R^4$, —$R^5$, —$R^7$, and —$R^8$, the compound may have one, two, or three chiral centres, giving rise to enantiomers or diastereoisomers. Unless otherwise indicated, it is intended that all such enantiomers and diastereoisomers are encompassed.

Some embodiments of the invention include the following:

(1) A compound selected from compounds of the following formulae, and pharmaceutically acceptable salts, hydrates, and solvates thereof:

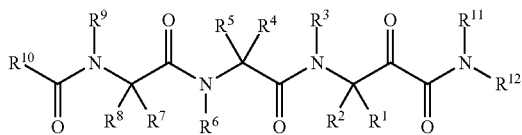

wherein:
—$R^1$ is independently —H or —$R^{1A}$;
—$R^{1A}$ is independently saturated aliphatic $C_{1-6}$alkyl, and is optionally substituted;
—$R^2$ is independently —H or —$R^{2A}$;
—$R^{2A}$ is independently saturated aliphatic $C_{1-3}$alkyl, and is optionally substituted;
or —$R^1$ and —$R^2$, taken together with the carbon atom to which they are attached, form a saturated $C_{3-7}$cycloalkyl ring or a saturated $C_{3-7}$heterocyclic ring, which is optionally substituted;
—$R^3$ is independently —H or —$R^{3A}$;
—$R^{3A}$ is independently saturated aliphatic $C_{1-3}$alkyl, and is optionally substituted;
—$R^4$ is independently —H or —$R^{4A}$;
—$R^{4A}$ is independently saturated aliphatic $C_{1-6}$alkyl, and is optionally substituted;
—$R^5$ is independently —H or —$R^{5A}$;
—$R^{5A}$ is independently saturated aliphatic $C_{1-3}$alkyl, and is optionally substituted;
—$R^6$ is independently —H or —$R^{6A}$;
—$R^{6A}$ is independently saturated aliphatic $C_{1-3}$alkyl, and is optionally substituted;
—$R^7$ is independently —H, —$R^{7A}$, or —$R^{7B}$;
—$R^{7A}$ is independently saturated aliphatic $C_{1-6}$alkyl, and is optionally substituted;
—$R^{7B}$ is independently -$L^{7B1}$-$R^{7BB}$, —$R^{7BB}$, -$L^{7B2}$-O—$R^{7BB}$, or -$L^{7B2}$-O-$L^{7B1}$-$R^{7BB}$;
-$L^{7B1}$- is independently saturated aliphatic $C_{1-3}$alkylene;
-$L^{7B2}$- is independently saturated aliphatic $C_{1-3}$alkylene;
—$R^{7BB}$ is independently —$R^{7BB1}$, —$R^{7BB2}$, —$R^{7BB3}$, or —$R^{7BB4}$;
—$R^{7BB1}$ is independently phenyl or naphthyl, and is optionally substituted;
—$R^{7BB2}$ is independently $C_{5-10}$heteroaryl, and is optionally substituted;
—$R^{7BB3}$ is independently $C_{3-7}$cycloalkyl, and is optionally substituted, or is optionally fused to a benzene ring which is optionally substituted;
—$R^{7BB4}$ is independently saturated bridged $C_{5-10}$cycloalkyl, and is optionally substituted;
—$R^8$ is independently —H or —$R^{8A}$;
—$R^{8A}$ is independently saturated aliphatic $C_{1-6}$alkyl, and is optionally substituted;
or —$R^7$ and —$R^8$, taken together with the carbon atom to which they are attached, form a saturated $C_{3-7}$cycloalkyl ring, a saturated bridged $C_{5-10}$cycloalkyl ring, or a non-aromatic $C_{3-7}$heterocyclic ring, which is optionally substituted;
—$R^9$ is independently —H or —$R^{9A}$;
—$R^{9A}$ is independently saturated aliphatic $C_{1-4}$alkyl, and is optionally substituted;

or —$R^8$ is —H, and —$R^7$ and —$R^9$, taken together with the carbon atom and nitrogen atom to which they are respectively attached, form a saturated $C_{3-7}$heterocyclic ring, which is optionally substituted, or which is optionally fused to a benzene ring which is optionally substituted;
—$R^{10}$ is independently —$R^{10A}$, —$R^{10B}$, —$R^{10C}$, or $R^{10D}$;
—$R^{10A}$ is independently phenyl or naphthyl, and is optionally substituted;
—$R^{10B}$ is independently $C_{5-10}$heteroaryl, and is optionally substituted;
—$R^{10C}$ is independently saturated $C_{3-7}$cycloalkyl, and is optionally substituted;
—$R^{10D}$ is independently non-aromatic $C_{3-10}$heterocyclyl, and is optionally substituted;
or —$R^9$ and —$R^{10}$, taken together with the nitrogen atom and carbon atom to which they are respectively attached, form a non-aromatic $C_{5-7}$heterocyclic lactam ring, which is optionally substituted, or which is optionally fused to a benzene ring which is optionally substituted;
—$R^{11}$ is independently —H, —$R^{11A}$, or —$R^{11B}$;
—$R^{11A}$ is independently —$R^{Z1}$, —$R^{Z2}$, —$R^{Z3}$, —$R^{Z4}$, —$R^{Z5}$, -$L^Z$-$R^{Z2}$, -$L^Z$-$R^{Z3}$, -$L^Z$-$R^{Z4}$, or -$L^Z$-$R^{Z5}$;
—$R^{Z1}$ is independently saturated aliphatic $C_{1-6}$alkyl, and is optionally substituted;
each —$R^{Z2}$ is independently saturated $C_{3-7}$cycloalkyl, and is optionally substituted, or is optionally fused to a benzene ring which is optionally substituted;
each —$R^{Z3}$ is independently —$R^{Z3A}$ or —$R^{Z3B}$;
each —$R^{Z3A}$ is independently non-aromatic $C_{3-7}$heterocyclyl, and is optionally substituted;
each —$R^{Z3B}$ is independently saturated bridged $C_{5-10}$heterocyclyl, and is optionally substituted;
each —$R^{Z4}$ is independently phenyl or naphthyl, and is optionally substituted;
each —$R^{Z5}$ is independently $C_{5-10}$heteroaryl, and is optionally substituted;
each -$L^Z$- is independently saturated aliphatic $C_{1-4}$alkylene;
—$R^{11B}$ is independently —$CR^{J1}R^{J2}$—$C(=O)$—$NR^{J3}R^{J4}$;
—$R^{J1}$ is independently —H or saturated aliphatic $C_{1-4}$alkyl;
—$R^{J2}$ is independently —H or saturated aliphatic $C_{1-4}$alkyl;
—$R^{J3}$ is independently —H, saturated aliphatic $C_{1-4}$alkyl, phenyl, or benzyl;
—$R^{J4}$ is independently —H, saturated aliphatic $C_{1-4}$alkyl, phenyl, or benzyl;
or —$NR^{J3}R^{J4}$ is independently a $C_{3-10}$heterocyclyl group, and is optionally substituted;
—$R^{12}$ is independently —H or —$R^{12A}$;
—$R^{12A}$ is independently saturated aliphatic $C_{1-6}$alkyl, and is optionally substituted;
or —$NR^{11}R^{12}$ is independently a $C_{3-10}$heterocyclyl group, and is optionally substituted.

For the avoidance of doubt, the index "$C_{x-y}$" in terms such as "$C_{5-10}$heteroaryl", "$C_{3-7}$heterocyclic ring", "$C_{3-7}$heterocyclyl", and the like, refers to the number of ring atoms, which may be carbon atoms or heteroatoms (e.g., N, O, S). For example, pyridyl is an example of a $C_6$heteroaryl group, and piperidino is an example of a $C_6$heterocycyl group.

For the avoidance of doubt, "heteroaryl" refers to a group that is attached to the rest of the molecule by an atom that is part of an aromatic ring, and which has one or more heteroatoms (e.g., N, O, S) forming part of the aromatic ring system. For example, pyridyl is an example of a $C_6$heteroaryl group, and quinolyl is an example of a $C_{10}$heteroaryl group. In contrast, "heterocyclyl" refers to a group that is attached to the rest of the molecule by a ring atom that is not part of an aromatic ring (i.e., the ring is fully or partially saturated), and the ring system contains one or more heteroatoms (e.g., N, O, S). For example, piperidino is an example of a $C_6$heterocycyl group.

The Groups —$R^1$ and —$R^2$ (2) A compound according to (1), wherein —$R^1$ is independently —H or —$R^{1A}$.

(3) A compound according to (1), wherein —$R^1$ is independently —$R^{1A}$.

(4) A compound according to (1), wherein —$R^1$ is independently —H.

(5) A compound according to any one of (1) to (4), wherein —$R^2$ is independently —H or —$R^{2A}$.

(6) A compound according to any one of (1) to (4), wherein —$R^2$ is independently —$R^{2A}$.

(7) A compound according to any one of (1) to (4), wherein —$R^2$ is independently —H.

(8) A compound according to (1), wherein:
—$R^1$ is independently —H or —$R^{1A}$; and
—$R^2$ is independently —H or —$R^{2A}$.

(9) A compound according to (1), wherein:
—$R^1$ is independently —H or —$R^{1A}$; and
—$R^2$ is independently —H.

(10) A compound according to (1), wherein:
—$R^1$ is independently —$R^{1A}$; and
—$R^2$ is independently —H.

(11) A compound according to (1), wherein:
—$R^1$ is independently —H; and
—$R^2$ is independently —H.

The Group —$R^{1A}$

(12) A compound according to any one of (1) to (11), wherein —$R^{1A}$, if present, is independently saturated aliphatic $C_{1-6}$alkyl, and is optionally substituted, for example, with one or more substituents —$R^{X1}$.

(13) A compound according to any one of (1) to (11), wherein —$R^{1A}$, if present, is independently saturated aliphatic $C_{1-6}$alkyl.

(14) A compound according to any one of (1) to (11), wherein —$R^{1A}$, if present, is independently saturated aliphatic $C_{1-4}$alkyl, and is optionally substituted, for example, with one or more substituents —$R^{X1}$.

(15) A compound according to any one of (1) to (11), wherein —$R^{1A}$, if present, is independently saturated aliphatic $C_{1-4}$alkyl.

(16) A compound according to any one of (1) to (11), wherein —$R^{1A}$, if present, is independently -Me, -Et, -nPr, -iPr, -nBu, -iBu, -sBu, or -tBu.

(17) A compound according to any one of (1) to (11), wherein —$R^{1A}$, if present, is independently saturated aliphatic $C_{3-4}$alkyl.

(18) A compound according to any one of (1) to (11), wherein —$R^{1A}$, if present, is independently -nPr, -iPr, -nBu, -iBu, -sBu, or -tBu.

(19) A compound according to any one of (1) to (11), wherein —$R^{1A}$, if present, is independently -iPr, -nBu, -iBu, or -sBu.

(20) A compound according to any one of (1) to (11), wherein —$R^{1A}$, if present, is independently -iPr, -nBu, -iBu, or -tBu.

(21) A compound according to any one of (1) to (11), wherein —$R^{1A}$, if present, is independently -iPr or -nBu.

(22) A compound according to any one of (1) to (11), wherein —$R^{1A}$, if present, is independently -iPr.

(23) A compound according to any one of (1) to (11), wherein —$R^{1A}$, if present, is independently -nBu.

The Group —$R^{2A}$

(24) A compound according to any one of (1) to (23), wherein —$R^{2A}$, if present, is independently saturated aliphatic $C_{1-3}$alkyl, and is optionally substituted, for example, with one or more substituents —$R^{X1}$.

(25) A compound according to any one of (1) to (23), wherein —$R^{2A}$, if present, is independently saturated aliphatic $C_{1-3}$alkyl.

(26) A compound according to any one of (1) to (23), wherein —$R^{2A}$, if present, is independently -Me, -Et, -nPr, or -iPr.

(27) A compound according to any one of (1) to (23), wherein —$R^{2A}$, if present, is independently -Me or -Et.

(28) A compound according to any one of (1) to (23), wherein —$R^{2A}$, if present, is independently -Me.

The Group —$C(R^1)(R^2)$—

(29) A compound according to (1), wherein —$R^1$ and —$R^2$, taken together with the carbon atom to which they are attached, form a saturated $C_{3-7}$cycloalkyl ring or a non-aromatic $C_{3-7}$heterocyclic ring, which is optionally substituted, for example, with one or more substituents —$R^{X2}$.

(30) A compound according to (1), wherein —$R^1$ and —$R^2$, taken together with the carbon atom to which they are attached, form a saturated $C_{3-7}$cycloalkyl ring or a non-aromatic $C_{3-7}$heterocyclic ring.

(31) A compound according to (1), wherein —$R^1$ and —$R^2$, taken together with the carbon atom to which they are attached, form a saturated $C_{3-7}$cycloalkyl ring, which is optionally substituted, for example, with one or more substituents —$R^{X2}$.

(32) A compound according to (1), wherein —$R^1$ and —$R^2$, taken together with the carbon atom to which they are attached, form a saturated $C_{3-7}$cycloalkyl ring.

(33) A compound according to (1), wherein —$R^1$ and —$R^2$, taken together with the carbon atom to which they are attached, form cyclopropyl, cyclobutyl, cyclopentyl, or cyclohexyl, and is optionally substituted, for example, with one or more substituents —$R^{X2}$.

(34) A compound according to (1), wherein —$R^1$ and —$R^2$, taken together with the carbon atom to which they are attached, form cyclopropyl, cyclobutyl, cyclopentyl, or cyclohexyl.

(35) A compound according to (1), wherein —$R^1$ and —$R^2$, taken together with the carbon atom to which they are attached, form a non-aromatic $C_{3-7}$heterocyclic ring, which is optionally substituted, for example, with one or more substituents —$R^{X2}$.

(36) A compound according to (1), wherein —$R^1$ and —$R^2$, taken together with the carbon atom to which they are attached, form a non-aromatic $C_{3-7}$heterocyclic ring.

The Group —$R^3$

(37) A compound according to any one of (1) to (36), wherein —$R^3$ is independently —H.

(38) A compound according to any one of (1) to (36), wherein —$R^3$ is independently —$R^{3A}$.

The Group —$R^{3A}$

(39) A compound according to any one of (1) to (38), wherein —$R^{3A}$, if present, is independently saturated aliphatic $C_{1-3}$alkyl, and is optionally substituted, for example, with one or more substituents —$R^{X1}$.

(40) A compound according to any one of (1) to (38), wherein —$R^{3A}$, if present, is independently saturated aliphatic $C_{1-3}$alkyl.

(41) A compound according to any one of (1) to (38), wherein —$R^{3A}$, if present, is independently -Me, -Et, -nPr, or -iPr.

(42) A compound according to any one of (1) to (38), wherein —$R^{3A}$, if present, is independently -Me or -Et.

(43) A compound according to any one of (1) to (38), wherein —$R^{3A}$, if present, is independently -Me.

The Groups —R⁴ and —R⁵

(44) A compound according to any one of (1) to (43), wherein —R⁴ is independently —H or —R⁴ᴬ.

(45) A compound according to any one of (1) to (43), wherein —R⁴ is independently —R⁴ᴬ.

(46) A compound according to any one of (1) to (43), wherein —R⁴ is independently —H.

(47) A compound according to any one of (1) to (46), wherein —R⁵ is independently —H or —R⁵ᴬ.

(48) A compound according to any one of (1) to (46), wherein —R⁵ is independently —R⁵ᴬ.

(49) A compound according to any one of (1) to (46), wherein —R⁵ is independently —H.

(50) A compound according to any one of (1) to (43), wherein:
—R⁴ is independently —H or —R⁴ᴬ; and
—R⁵ is independently —H or —R⁵ᴬ.

(51) A compound according to any one of (1) to (43), wherein:
—R⁴ is independently —H or —R⁴ᴬ; and
—R⁵ is independently —H.

(52) A compound according to any one of (1) to (43), wherein:
—R⁴ is independently —R⁴ᴬ; and
—R⁵ is independently —H.

(53) A compound according to any one of (1) to (43), wherein:
—R⁴ is independently —H; and
—R⁵ is independently —H.

The Group —R⁴ᴬ

(54) A compound according to any one of (1) to (53), wherein —R⁴ᴬ, if present, is independently saturated aliphatic $C_{1-6}$alkyl, and is optionally substituted, for example, with one or more substituents —R^{X1}.

(55) A compound according to any one of (1) to (53), wherein —R⁴ᴬ, if present, is independently saturated aliphatic $C_{1-6}$alkyl.

(56) A compound according to any one of (1) to (53), wherein —R⁴ᴬ, if present, is independently saturated aliphatic $C_{1-4}$alkyl, and is optionally substituted, for example, with one or more substituents —R^{X1}.

(57) A compound according to any one of (1) to (53), wherein —R⁴ᴬ, if present, is independently saturated aliphatic $C_{1-4}$alkyl.

(58) A compound according to any one of (1) to (53), wherein —R⁴ᴬ, if present, is independently -Me, -Et, -nPr, -iPr, -nBu, -iBu, -sBu, or -tBu.

(59) A compound according to any one of (1) to (53), wherein —R⁴ᴬ, if present, is independently saturated aliphatic $C_{1-3}$alkyl, and is optionally substituted, for example, with one or more substituents —R^{X1}.

(60) A compound according to any one of (1) to (53), wherein —R⁴ᴬ, if present, is independently saturated aliphatic $C_{1-3}$alkyl.

(61) A compound according to any one of (1) to (53), wherein —R⁴ᴬ, if present, is independently -Me, -Et, -nPr, or -iPr.

(62) A compound according to any one of (1) to (53), wherein —R⁴ᴬ, if present, is independently -Me, -nPr, or —CH₂C(=O)NH₂.

(63) A compound according to any one of (1) to (53), wherein —R⁴ᴬ, if present, is independently -Me or -nPr.

(64) A compound according to any one of (1) to (53), wherein —R⁴ᴬ, if present, is independently -Me.

The Group —R⁵ᴬ

(65) A compound according to any one of (1) to (64), wherein —R⁵ᴬ, if present, is independently saturated aliphatic $C_{1-3}$alkyl, and is optionally substituted, for example, with one or more substituents —R^{X1}.

(66) A compound according to any one of (1) to (64), wherein —R⁵ᴬ, if present, is independently saturated aliphatic $C_{1-3}$alkyl.

(67) A compound according to any one of (1) to (64), wherein —R⁵ᴬ, if present, is independently -Me, -Et, -nPr, or -iPr.

(68) A compound according to any one of (1) to (64), wherein —R⁵ᴬ, if present, is independently -Me or -Et.

(69) A compound according to any one of (1) to (64), wherein —R⁵ᴬ, if present, is independently -Me.

The Group —R⁶

(70) A compound according to any one of (1) to (69), wherein —R⁶ is independently —H.

(71) A compound according to any one of (1) to (69), wherein —R⁶ is independently —R⁶ᴬ.

The Group —R⁶ᴬ

(72) A compound according to any one of (1) to (71), wherein —R⁶ᴬ, if present, is independently saturated aliphatic $C_{1-3}$alkyl, and is optionally substituted, for example, with one or more substituents —R^{X1}.

(73) A compound according to any one of (1) to (71), wherein —R⁶ᴬ, if present, is independently saturated aliphatic $C_{1-3}$alkyl.

(74) A compound according to any one of (1) to (71), wherein —R⁶ᴬ, if present, is independently -Me, -Et, -nPr, or -iPr.

(75) A compound according to any one of (1) to (71), wherein —R⁶ᴬ, if present, is independently -Me or -Et.

(76) A compound according to any one of (1) to (71), wherein —R⁶ᴬ, if present, is independently -Me.

The Group —R⁷

(77) A compound according to any one of (1) to (76), wherein —R⁷ is independently —R⁷ᴬ or —R⁷ᴮ.

(78) A compound according to any one of (1) to (76), wherein —R⁷ is independently —R⁷ᴬ.

(79) A compound according to any one of (1) to (76), wherein —R⁷ is independently —R⁷ᴮ.

(80) A compound according to any one of (1) to (76), wherein —R⁷ is independently —H.

The Group —R⁷ᴬ

(81) A compound according to any one of (1) to (80), wherein —R⁷ᴬ, if present, is independently saturated aliphatic $C_{1-6}$alkyl, and is optionally substituted, for example, with one or more substituents —R^{X1}.

(82) A compound according to any one of (1) to (80), wherein —R⁷ᴬ, if present, is independently saturated aliphatic $C_{1-6}$alkyl.

(83) A compound according to any one of (1) to (80), wherein —R⁷ᴬ, if present, is independently saturated aliphatic $C_{1-4}$alkyl, and is optionally substituted, for example, with one or more substituents —R^{X1}.

(84) A compound according to any one of (1) to (80), wherein —R⁷ᴬ, if present, is independently saturated aliphatic $C_{1-4}$alkyl.

(85) A compound according to any one of (1) to (80), wherein —R⁷ᴬ, if present, is independently -Me, -Et, -nPr, -iPr, -nBu, -sBu, -iBu, or -tBu.

(86) A compound according to any one of (1) to (80), wherein —R⁷ᴬ, if present, is independently saturated aliphatic $C_{3-4}$alkyl.

(87) A compound according to any one of (1) to (80), wherein —R⁷ᴬ, if present, is independently -nPr, -iPr, -nBu, -sBu, -iBu, or -tBu.

(88) A compound according to any one of (1) to (80), wherein —R⁷ᴬ, if present, is independently -tBu.

The Group —$R^{7B}$

(89) A compound according to any one of (1) to (88), wherein —$R^{7B}$, if present, is independently -$L^{7B1}$-$R^{7BB}$, -$L^{7B2}$-O—$R^{7BB}$, or -$L^{7B2}$-O-$L^{7B1}$-$R^{7BB}$.

(90) A compound according to any one of (1) to (88), wherein —$R^{7B}$, if present, is independently -$L^{7B1}$-$R^{7BB}$ or -$L^{7B2}$-O-$L^{7B1}$-$R^{7BB}$.

(91) A compound according to any one of (1) to (88), wherein —$R^{7B}$, if present, is independently -$L^{7B1}$-$R^{7BB}$ or —$R^{7BB}$.

(92) A compound according to any one of (1) to (88), wherein —$R^{7B}$, if present, is independently -$L^{7B1}$-$R^{7BB}$.

(93) A compound according to any one of (1) to (88), wherein —$R^{7B}$, if present, is independently -$L^{7B2}$-O-$L^{7B1}$-$R^{7BB}$.

(94) A compound according to any one of (1) to (88), wherein —$R^{7B}$, if present, is independently -$L^{7B2}$-O—$R^{7BB}$.

(95) A compound according to any one of (1) to (88), wherein —$R^{7B}$, if present, is independently —$R^{7BB}$.

The Group -$L^{7B1}$-

(96) A compound according to any one of (1) to (95), wherein -$L^{7B1}$-, if present, is independently —$CH_2$—, —CH(Me)-, —$C(Me)_2$-, —$CH_2CH_2$—, or —$CH_2CH_2CH_2$—.

(97) A compound according to any one of (1) to (95), wherein -$L^{7B1}$-, if present, is independently —$CH_2$— or —$CH_2CH_2$—.

(98) A compound according to any one of (1) to (95), wherein -$L^{7B1}$-, if present, is independently —$CH_2$—.

(99) A compound according to any one of (1) to (95), wherein -$L^{7B1}$-, if present, is independently —$C(Me)_2$-.

The Group -$L^{7B2}$-

(100) A compound according to any one of (1) to (99), wherein -$L^{7B2}$-, if present, is independently —$CH_2$—, —CH(Me)-, —$C(Me)_2$-, —$CH_2CH_2$—, or —$CH_2CH_2CH_2$—.

(101) A compound according to any one of (1) to (99), wherein -$L^{7B2}$-, if present, is independently —$CH_2$— or —$CH_2CH_2$—.

(102) A compound according to any one of (1) to (99), wherein -$L^{7B2}$-, if present, is independently —$CH_2$—.

The Group —$R^{7BB}$ (103) A compound according to any one of (1) to (102), wherein —$R^{7BB}$, if present, is independently —$R^{7BB1}$, —$R^{7BB2}$, or —$R^{7BB3}$.

(104) A compound according to any one of (1) to (102), wherein —$R^{7BB}$, if present, is independently —$R^{7BB1}$.

(105) A compound according to any one of (1) to (102), wherein —$R^{7BB}$, if present, is independently —$R^{7BB2}$.

(106) A compound according to any one of (1) to (102), wherein —$R^{7BB}$, if present, is independently —$R^{7BB3}$.

(107) A compound according to any one of (1) to (102), wherein —$R^{7BB}$, if present, is independently —$R^{7BB4}$.

The Group —$R^{7BB1}$ (108) A compound according to any one of (1) to (107), wherein —$R^{7BB1}$, if present, is independently phenyl or naphthyl, and is optionally substituted, for example, with one or more substituents —$R^{X3}$.

(109) A compound according to any one of (1) to (107), wherein —$R^{7BB1}$, if present, is independently phenyl or naphthyl, and is optionally substituted, for example, with one or more substituents independently selected from —F, —Cl, —Br, —I, -Me, —$CF_3$, -Ph, —$NH_2$, —NHMe, —$NMe_2$, pyrrolidino, piperidino, morpholino, piperizino, and N-(methyl)piperizino.

(110) A compound according to any one of (1) to (107), wherein —$R^{7BB1}$, if present, is independently phenyl or naphthyl, and is optionally substituted, for example, with one or more substituents independently selected from —F, —Cl, —Br, —I, -Me, and -Ph.

(111) A compound according to any one of (1) to (107), wherein —$R^{7BB1}$, if present, is independently phenyl or naphthyl.

(112) A compound according to any one of (1) to (107), wherein —$R^{7BB1}$, if present, is independently phenyl, and is optionally substituted, for example, with one or more substituents —$R^{X3}$.

(113) A compound according to any one of (1) to (107), wherein —$R^{7BB1}$, if present, is independently phenyl, and is optionally substituted, for example, with one or more substituents independently selected from —F, —Cl, —Br, —I, -Me, —$CF_3$, -Ph, —$NH_2$, —NHMe, —$NMe_2$, pyrrolidino, piperidino, morpholino, piperizino, and N-(methyl)-piperizino.

(114) A compound according to any one of (1) to (107), wherein —$R^{7BB1}$, if present, is independently phenyl, and is optionally substituted, for example, with one or more substituents independently selected from —F, —Cl, —Br, —I, -Me, and -Ph.

(115) A compound according to any one of (1) to (107), wherein —$R^{7BB1}$, if present, is independently phenyl.

(116) A compound according to any one of (1) to (107), wherein —$R^{7BB1}$, if present, is independently naphthyl, and is optionally substituted, for example, with one or more substituents —$R^{X3}$.

(117) A compound according to any one of (1) to (107), wherein —$R^{7BB1}$, if present, is independently naphthyl, and is optionally substituted, for example, with one or more substituents independently selected from —F, —Cl, —Br, —I, -Me, —$CF_3$, -Ph, —$NH_2$, —NHMe, —$NMe_2$, pyrrolidino, piperidino, morpholino, piperizino, and N-(methyl)-piperizino.

(118) A compound according to any one of (1) to (107), wherein —$R^{7BB1}$, if present, is independently naphthyl, and is optionally substituted, for example, with one or more substituents independently selected from —F, —Cl, —Br, —I, -Me, and -Ph.

(119) A compound according to any one of (1) to (107), wherein —$R^{7BB1}$, if present, is independently naphthyl.

The Group —$R^{7BB2}$ (120) A compound according to any one of (1) to (119), wherein —$R^{7BB2}$, if present, is independently $C_{5-10}$heteroaryl, and is optionally substituted, for example, with one or more substituents —$R^{X3}$.

(121) A compound according to any one of (1) to (119), wherein —$R^{7BB2}$, if present, is independently $C_{5-10}$heteroaryl.

(122) A compound according to any one of (1) to (119), wherein —$R^{7BB2}$, if present, is independently $C_{5-8}$heteroaryl, and is optionally substituted, for example, with one or more substituents —$R^{X3}$.

(123) A compound according to any one of (1) to (119), wherein —$R^{7BB2}$, if present, is independently $C_{5-6}$heteroaryl.

(124) A compound according to any one of (1) to (119), wherein —$R^{7BB2}$, if present, is independently furanyl, thienyl, pyrrolyl, imidazolyl, pyrazolyl, oxazolyl, isoxazolyl, thiazolyl, isothiazolyl, triazolyl (e.g., 1H-[1,2,3]triazolyl, 2H-[1,2,3]triazolyl, 4H-[1,2,4]triazolyl, 1H-[1,2,4]triazolyl), oxadiazolyl (e.g., [1,2,3]oxadiazolyl, furazanyl, [1,3,4]oxadiazolyl, [1,2,4]oxadiazolyl), thiadiazolyl (e.g., [1,2,3]thiadiazolyl, [1,2,5]thiadiazolyl, [1,3,4]thiadiazolyl, [1,2,4]thiadiazolyl), pyridyl, pyrimidinyl, pyrazinyl, pyridazinyl, or triazinyl (e.g., [1,3,5]-triazinyl), and is optionally substituted, for example, with one or more substituents —$R^{X3}$.

(125) A compound according to any one of (1) to (119), wherein —$R^{7BB2}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl, and is optionally substituted, for example, with one or more substituents —$R^{X3}$.

(126) A compound according to any one of (1) to (119), wherein —$R^{7BB2}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl.

(127) A compound according to any one of (1) to (119), wherein —$R^{7BB2}$, if present, is independently pyridyl, and is optionally substituted, for example, with one or more substituents —$R^{X3}$.

(128) A compound according to any one of (1) to (119), wherein —$R^{7BB2}$, if present, is independently pyridyl.

(129) A compound according to any one of (1) to (119), wherein —$R^{7BB2}$, if present, is independently $C_{9-10}$heteroaryl, and is optionally substituted, for example, with one or more substituents —$R^{X3}$.

(130) A compound according to any one of (1) to (119), wherein —$R^{7BB2}$, if present, is independently $C_{9-10}$heteroaryl.

(131) A compound according to any one of (1) to (119), wherein —$R^{7BB2}$, if present, is independently quinolinyl, isoquinolinyl, or indolyl, and is optionally substituted, for example, with one or more substituents —$R^{X3}$.

(132) A compound according to any one of (1) to (119), wherein —$R^{7BB2}$, if present, is independently quinolinyl, isoquinolinyl, or indolyl.

The Group —$R^{7BB3}$ (133) A compound according to any one of (1) to (132), wherein —$R^{7BB3}$, if present, is independently $C_{3-7}$cycloalkyl, and is optionally substituted, for example, with one or more substituents —$R^{X2}$, or is optionally fused to a benzene ring which is optionally substituted with one or more substituents —$R^{X3}$.

(134) A compound according to any one of (1) to (132), wherein —$R^{7BB3}$, if present, is independently $C_{3-7}$cycloalkyl, and is optionally substituted, for example, with one or more substituents —$R^{X2}$, or is optionally fused to a benzene ring.

(135) A compound according to any one of (1) to (132), wherein —$R^{7BB3}$, if present, is independently $C_{3-7}$cycloalkyl, and is optionally substituted, for example, with one or more substituents —$R^{X2}$.

(136) A compound according to any one of (1) to (132), wherein —$R^{7BB3}$, if present, is independently cyclopropyl, cyclobutyl, cyclopentyl, cyclohexyl, or cycloheptyl, and is optionally substituted, for example, with one or more substituents —$R^{X2}$.

(137) A compound according to any one of (1) to (132), wherein —$R^{7BB2}$, if present, is independently cyclopropyl, cyclobutyl, cyclopentyl, cyclohexyl, or cycloheptyl.

(138) A compound according to any one of (1) to (132), wherein —$R^{7BB3}$, if present, is independently $C_{3-6}$cycloalkyl, and is optionally fused to a benzene ring.

(139) A compound according to any one of (1) to (132), wherein —$R^{7BB3}$, if present, is independently cyclopropyl, cyclobutyl, cyclopentyl, cyclohexyl, or cycloheptyl, and is optionally fused to a benzene ring.

(140) A compound according to any one of (1) to (132), wherein —$R^{7BB3}$, if present, is independently cyclopentyl fused to a benzene ring; as in, for example, indan-2-yl.

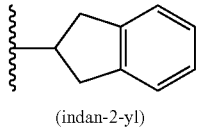 [SMILES: *C1Cc2ccccc2C1]

(indan-2-yl)

The Group —$R^{7BB4}$ (141) A compound according to any one of (1) to (140), wherein —$R^{7BB4}$, if present, is independently saturated bridged $C_{5-10}$cycloalkyl, and is optionally substituted, for example, with one or more substituents —$R^{X2}$.

(142) A compound according to any one of (1) to (140), wherein —$R^{7BB4}$, if present, is independently saturated bridged $C_{5-10}$cycloalkyl.

(143) A compound according to any one of (1) to (140), wherein —$R^{7BB4}$, if present, is independently bicyclo[1.1.1]pentyl or adamantyl, and is optionally substituted, for example, with one or more substituents —$R^{X2}$.

(144) A compound according to any one of (1) to (140), wherein —$R^{7BB4}$, if present, is independently bicyclo[1.1.1]pentyl (an example of a saturated bridged $C_5$cycloalkyl group) or adamantyl (an example of a saturated bridged $C_{10}$cycloalkyl group).

(145) A compound according to any one of (1) to (140), wherein —$R^{7BB4}$, if present, is independently adamantyl.

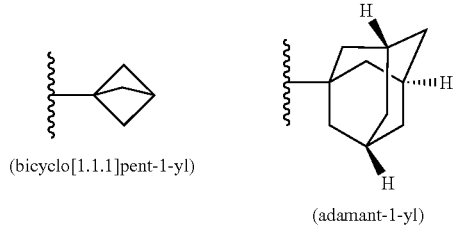 [SMILES: *C12CC(C1)C2 ; *C12C[C@H]3C[C@@H](C1)C[C@@H](C2)C3]

(bicyclo[1.1.1]pent-1-yl)    (adamant-1-yl)

The Group —$R^8$ (146) A compound according to any one of (1) to (145), wherein —$R^8$ is independently —H.

(147) A compound according to any one of (1) to (145), wherein —$R^8$ is independently —$R^{8A}$.

The Group —$R^{8A}$ (148) A compound according to any one of (1) to (147), wherein —$R^{8A}$, if present, is independently saturated aliphatic $C_{1-6}$alkyl, and is optionally substituted, for example, with one or more substituents —$R^{X1}$.

(149) A compound according to any one of (1) to (147), wherein —$R^{8A}$, if present, is independently saturated aliphatic $C_{1-6}$alkyl.

(150) A compound according to any one of (1) to (147), wherein —$R^{8A}$, if present, is independently saturated aliphatic $C_{1-4}$alkyl, and is optionally substituted, for example, with one or more substituents —$R^{X1}$.

(151) A compound according to any one of (1) to (147), wherein —$R^{8A}$, if present, is independently saturated aliphatic $C_{1-4}$alkyl.

(152) A compound according to any one of (1) to (147), wherein —$R^{8A}$, if present, is independently -Me, -Et, -nPr, -iPr, -nBu, -sBu, -iBu, or -tBu.

(153) A compound according to any one of (1) to (147), wherein —$R^{8A}$, if present, is independently -Me, -Et, -nPr, or -iPr.

(154) A compound according to any one of (1) to (147), wherein —$R^{8A}$, if present, is independently -Me.

The Group —C(R⁷)(R⁸)—

(155) A compound according to any one of (1) to (76), wherein —R⁷ and —R⁸, taken together with the carbon atom to which they are attached, form a saturated $C_{3-7}$cycloalkyl ring, a saturated bridged $C_{5-10}$cycloalkyl ring, or a non-aromatic $C_{3-7}$heterocyclic ring, which is optionally substituted, for example, with one or more substituents —$R^{X2}$.

(156) A compound according to any one of (1) to (76), wherein —R⁷ and —R⁸, taken together with the carbon atom to which they are attached, form a saturated $C_{3-7}$cycloalkyl ring, which is optionally substituted, for example, with one or more substituents —$R^{X2}$.

(157) A compound according to any one of (1) to (76), wherein —R⁷ and —R⁸, taken together with the carbon atom to which they are attached, form a saturated $C_{3-7}$cycloalkyl ring.

(158) A compound according to any one of (1) to (76), wherein —R⁷ and —R⁸, taken together with the carbon atom to which they are attached, form cyclopropyl, cyclobutyl, cyclopentyl, or cyclohexyl, and is optionally substituted, for example, with one or more substituents —$R^{X2}$.

(159) A compound according to any one of (1) to (76), wherein —R⁷ and —R⁸, taken together with the carbon atom to which they are attached, form cyclopropyl, cyclobutyl, cyclopentyl, or cyclohexyl.

(160) A compound according to any one of (1) to (76), wherein —R⁷ and —R⁸, taken together with the carbon atom to which they are attached, form cyclohexyl.

(161) A compound according to any one of (1) to (76), wherein —R⁷ and —R⁸, taken together with the carbon atom to which they are attached, form a saturated bridged $C_{5-10}$cycloalkyl ring, which is optionally substituted, for example, with one or more substituents —$R^{X2}$.

(162) A compound according to any one of (1) to (76), wherein —R⁷ and —R⁸, taken together with the carbon atom to which they are attached, form a saturated bridged $C_{5-10}$cycloalkyl ring.

(163) A compound according to any one of (1) to (76), wherein —R⁷ and —R⁸, taken together with the carbon atom to which they are attached, form a non-aromatic $C_{3-7}$heterocyclic ring, which is optionally substituted, for example, with one or more substituents —$R^{X2}$.

(164) A compound according to any one of (1) to (76), wherein —R⁷ and —R⁸, taken together with the carbon atom to which they are attached, form a non-aromatic $C_{3-7}$heterocyclic ring.

(165) A compound according to any one of (1) to (76), wherein —R⁷ and —R⁸, taken together with the carbon atom to which they are attached, form a non-aromatic $C_{5-7}$heterocyclic ring, which is optionally substituted, for example, with one or more substituents —$R^{X2}$.

(166) A compound according to any one of (1) to (76), wherein —R⁷ and —R⁸, taken together with the carbon atom to which they are attached, form a non-aromatic $C_{5-7}$heterocyclic ring.

(167) A compound according to any one of (1) to (76), wherein —R⁷ and —R⁸, taken together with the carbon atom to which they are attached, form a non-aromatic $C_6$heterocyclic ring, which is optionally substituted, for example, with one or more substituents —$R^{X2}$.

(168) A compound according to any one of (1) to (76), wherein —R⁷ and —R⁸, taken together with the carbon atom to which they are attached, form a non-aromatic $C_6$heterocyclic ring.

The Group —R⁹

(169) A compound according to any one of (1) to (168), wherein —R⁹ is independently —H.

(170) A compound according to any one of (1) to (168), wherein —R⁹ is independently —$R^{9A}$.

The Group —$R^{9A}$ (171) A compound according to any one of (1) to (170), wherein —$R^{9A}$, if present, is independently saturated aliphatic $C_{1-4}$alkyl, and is optionally substituted, for example, with one or more substituents —$R^{X1}$.

(172) A compound according to any one of (1) to (170), wherein —$R^{9A}$, if present, is independently saturated aliphatic $C_{1-4}$alkyl.

(173) A compound according to any one of (1) to (170), wherein —$R^{9A}$, if present, is independently -Me, -Et, -nPr, -iPr, -nBu, -sBu, -iBu, or -tBu.

(174) A compound according to any one of (1) to (170), wherein —$R^{9A}$, if present, is independently -Me, -Et, -nPr, or -iPr.

(175) A compound according to any one of (1) to (170), wherein —$R^{9A}$, if present, is independently -Me.

The Group —NR⁹—C(R⁷)(R⁸)—

(176) A compound according to any one of (1) to (76), wherein —R⁸ is —H; and —R⁷ and —R⁹, taken together with the carbon atom and nitrogen atom to which they are respectively attached, form a non-aromatic $C_{3-7}$heterocyclic ring, which is optionally substituted, for example, with one or more substituents —$R^{X2}$, or which is optionally fused to a benzene ring which is optionally substituted with one or more substituents —$R^{X3}$.

(177) A compound according to any one of (1) to (76), wherein —R⁸ is —H; and —R⁷ and —R⁹, taken together with the carbon atom and nitrogen atom to which they are respectively attached, form a non-aromatic $C_{3-7}$heterocyclic ring, which is optionally substituted, for example, with one or more substituents —$R^{X2}$, or which is optionally fused to a benzene ring.

(178) A compound according to any one of (1) to (76), wherein —R⁸ is —H; and —R⁷ and —R⁹, taken together with the carbon atom and nitrogen atom to which they are respectively attached, form a pyrrolidine ring or a piperidine ring, which is optionally substituted, for example, with one or more substituents —$R^{X2}$, or which is optionally fused to a benzene ring.

(179) A compound according to any one of (1) to (76), wherein —R⁸ is —H; and —R⁷ and —R⁹, taken together with the carbon atom and nitrogen atom to which they are respectively attached, form a pyrrolidine ring or a piperidine ring, which is optionally fused to a benzene ring.

(180) A compound according to any one of (1) to (76), wherein —R⁸ is —H; and —R⁷ and —R⁹, taken together with the carbon atom and nitrogen atom to which they are respectively attached, form a pyrrolidine ring; as in, for example:

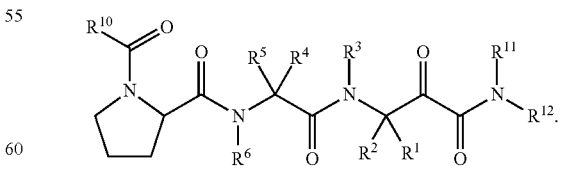

(181) A compound according to any one of (1) to (76), wherein —R⁸ is —H; and —R⁷ and —R⁹, taken together with the carbon atom and nitrogen atom to which they are respectively attached, form a piperidine ring, which is fused to a benzene ring; as in, for example:

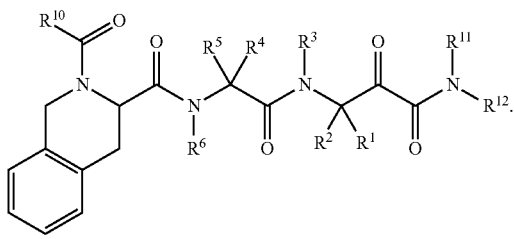

The Group $R^{10}$—C(=O)—N($R^9$)—

(182) A compound according to any one of (1) to (168), wherein —$R^9$ and —$R^{10}$, taken together with the nitrogen atom and carbon atom to which they are respectively attached, form a non-aromatic $C_{5-7}$ heterocyclic lactam ring, which is optionally substituted, for example, with one or more substituents —$R^{X2}$, or which is optionally fused to a benzene ring which is optionally substituted, for example, with one or more substituents —$R^{X3}$.

(183) A compound according to any one of (1) to (168), wherein —$R^9$ and —$R^{10}$, taken together with the nitrogen atom and carbon atom to which they are respectively attached, form a pyrrolidin-2-one ring or a piperidin-2-one ring, which is optionally substituted, for example, with one or more substituents —$R^{X2}$, or which is optionally fused to a benzene ring which is optionally substituted, for example, with one or more substituents —$R^{X3}$.

(184) A compound according to any one of (1) to (168), wherein —$R^9$ and —$R^{10}$, taken together with the nitrogen atom and carbon atom to which they are respectively attached, form a pyrrolidin-2-one ring or a piperidin-2-one ring, which is fused to a benzene ring.

(185) A compound according to any one of (1) to (168), wherein —$R^9$ and —$R^{10}$, taken together with the nitrogen atom and carbon atom to which they are respectively attached, form a pyrrolidin-2-one ring, which is fused to a benzene ring; for example, where the group —N($R^9$)—C(=O)—$R^{10}$ is the following group:

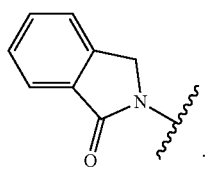 [SMILES: *N1Cc2ccccc2C1=O]

as in, for example:

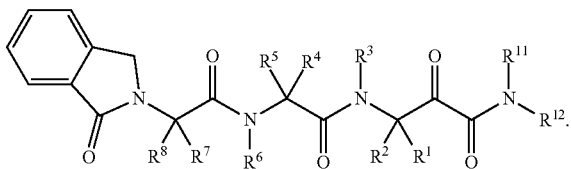

(186) A compound according to any one of (1) to (168), wherein —$R^9$ and —$R^{10}$, taken together with the carbon atom and nitrogen atom to which they are respectively attached, form a pyrrolidin-2-one ring; for example, where the group —N($R^9$)—C(=O)—$R^{10}$ is the following group:

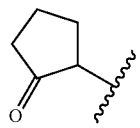 [SMILES: *C1CCCC1=O]

as in, for example:

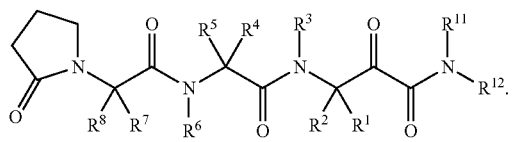

Some Preferred Combinations (187) A compound according to (1), wherein: —$R^2$ is —H; —$R^3$ is —H; —$R^5$ is —H; —$R^6$ is —H; for example, as shown below:

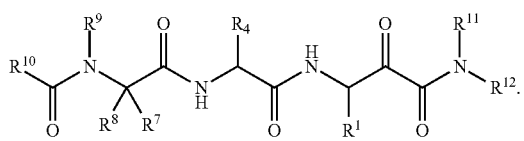

(188) A compound according to (187), wherein the carbon atom to which —$R^4$ and —$R^5$ is attached has the configuration shown in the following formula:

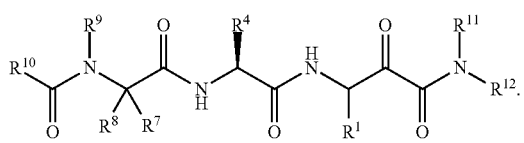

(189) A compound according to (187), wherein the carbon atom to which —$R^4$ and —$R^5$ is attached, and the carbon atom to which —$R^1$ and —$R^2$ is attached, have the configurations shown in the following formula:

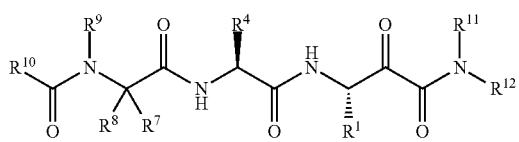

(190) A compound according to any one of (187) to (189), wherein: —$R^1$ is -iPr and —$R^4$ is -Me; for example, as shown below:

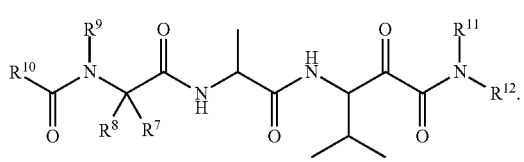

(191) A compound according to (1), wherein: —$R^2$ is —H; —$R^3$ is —H; —$R^5$ is —H; —$R^6$ is —H; —$R^8$ is —H; and —$R^9$ is —H; for example, as shown below:

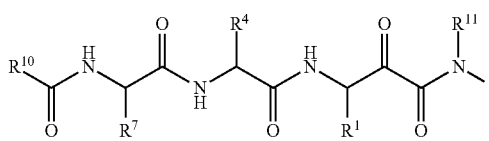

(192) A compound according to (191), wherein the carbon atom to which —R⁴ and —R⁵ is attached has the configuration shown in the following formula:

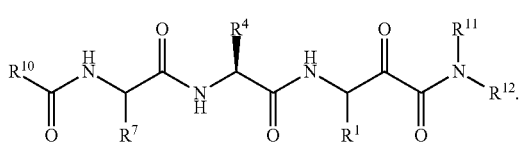

(193) A compound according to (191), wherein the carbon atom to which —R⁴ and —R⁵ is attached, and the carbon atom to which —R¹ and —R² is attached, have the configurations shown in the following formula:

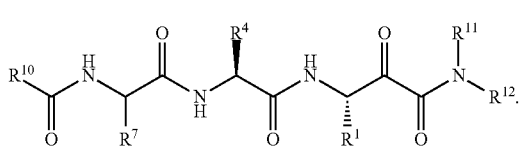

(194) A compound according to (191), wherein the carbon atom to which —R⁴ and —R⁵ is attached, the carbon atom to which —R¹ and —R² is attached, and the carbon atom to which —R⁷ and —R⁸ are attached, have the configurations shown in the following formula:

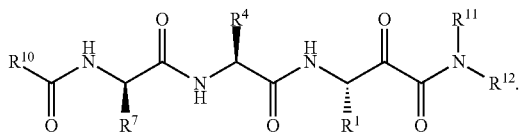

(195) A compound according to (191), wherein the carbon atom to which —R⁴ and —R⁵ is attached, the carbon atom to which —R¹ and —R² is attached, and the carbon atom to which —R⁷ and —R⁸ are attached, have the configurations shown in the following formula:

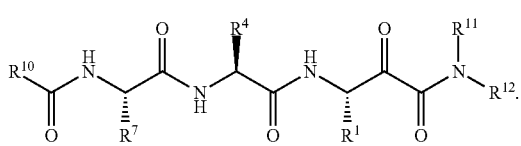

(196) A compound according to any one of (191) to (195), wherein: —R¹ is -iPr and —R⁴ is -Me; for example, as shown below:

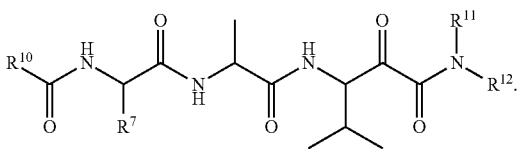

(197) A compound according to any one of (191) to (195), wherein —R⁷ is —CH₂—R⁷ᴮᴮ; for example, as shown below:

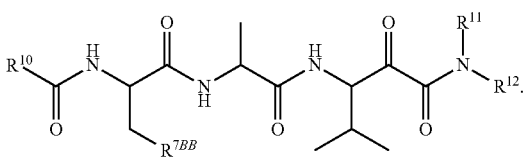

(198) A compound according to any one of (191) to (195), wherein —R⁷ is —CH₂-Ph; for example, as shown below:

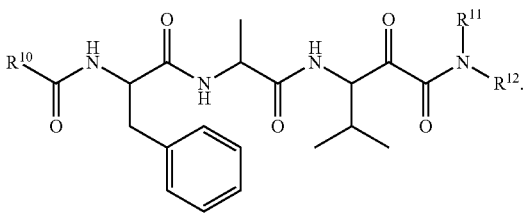

(199) A compound according to any one of (191) to (195), wherein —R⁷ is —R⁷ᴬ; for example, as shown below:

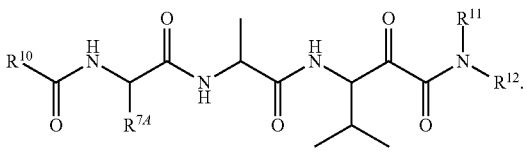

(200) A compound according to any one of (191) to (195), wherein —R⁷ is -tBu; for example, as shown below:

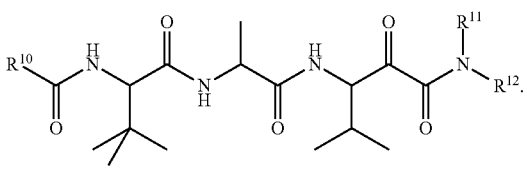

(201) A compound according to any one of (191) to (195), wherein —R⁷ is —R⁷ᴮᴮ; for example, as shown below:

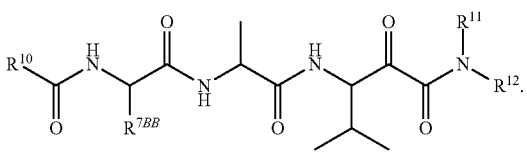

(202) A compound according to any one of (191) to (195), wherein —R$^7$ is -tBu; for example, as shown below:

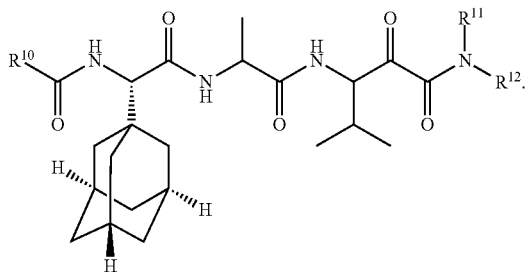

The Group —R$^{10}$ (203) A compound according to any one of (1) to (181) and (187) to (202), wherein —R$^{10}$ is independently —R$^{10A}$, —R$^{10B}$, or —R$^{10C}$.

(204) A compound according to any one of (1) to (181) and (187) to (202), wherein —R$^{10}$ is independently —R$^{10A}$, —R$^{10B}$, or —R$^{10D}$.

(205) A compound according to any one of (1) to (181) and (187) to (202), wherein —R$^{10}$ is independently —R$^{10A}$ or —R$^{10B}$.

(206) A compound according to any one of (1) to (181) and (187) to (202), wherein —R$^{10}$ is independently —R$^{10A}$.

(207) A compound according to any one of (1) to (181) and (187) to (202), wherein —R$^{10}$ is independently —R$^{10B}$.

(208) A compound according to any one of (1) to (181) and (187) to (202), wherein —R$^{10}$ is independently —R$^{10C}$.

(209) A compound according to any one of (1) to (181) and (187) to (202), wherein —R$^{10}$ is independently —R$^{10D}$.

The Group —R$^{10A}$ (210) A compound according to any one of (1) to (181) and (187) to (209), wherein —R$^{10A}$, if present, is independently phenyl or naphthyl, and is optionally substituted, for example, with one or more substituents —R$^{X3}$.

(211) A compound according to any one of (1) to (181) and (187) to (209), wherein —R$^{10A}$, if present, is independently phenyl or naphthyl, and is optionally substituted, for example, with one or more substituents independently selected from:
—F, —Cl, —Br, —I, —CF$_3$,
—C(=O)OH, —C(=O)O(C$_{1-4}$alkyl),
—S(=O)$_2$(C$_{1-4}$alkyl),
phenyl, —O-phenyl,
—NH$_2$, —NH(C$_{1-4}$alkyl), —N(C$_{1-4}$alkyl)$_2$,
pyrrolidino, piperidino, morpholino, piperizino, N—(C$_{1-4}$alkyl)-piperizino, —O—CH$_2$CH$_2$—NH$_2$, —O—CH$_2$CH$_2$—NH(C$_{1-4}$alkyl), —O—CH$_2$CH$_2$—N(C$_{1-4}$alkyl)$_2$, —O—CH$_2$CH$_2$-pyrrolidino, —O—CH$_2$CH$_2$-piperidino, —O—CH$_2$CH$_2$-morpholino, —O—CH$_2$CH$_2$-piperizino, —O—CH$_2$CH$_2$—{N—(C$_{1-4}$alkyl)-piperizino}, —O—CH$_2$-imidazol-2-yl, and —O—CH$_2$-{N—(C$_{1-4}$alkyl)-imidazol-2-yl}.

(212) A compound according to any one of (1) to (181) and (187) to (209), wherein —R$^{10A}$, if present, is independently phenyl or naphthyl, and is optionally substituted, for example, with one or more substituents independently selected from:
phenyl, —O-phenyl,
—NH$_2$, —NH(C$_{1-4}$alkyl), —N(C$_{1-4}$alkyl)$_2$,
pyrrolidino, piperidino, morpholino, piperizino, N—(C$_{1-4}$alkyl)-piperizino, —O—CH$_2$CH$_2$—NH$_2$, —O—CH$_2$CH$_2$—NH(C$_{1-4}$alkyl), —O—CH$_2$CH$_2$—N(C$_{1-4}$alkyl)$_2$, —O—CH$_2$CH$_2$-pyrrolidino, —O—CH$_2$CH$_2$-piperidino, —O—CH$_2$CH$_2$-morpholino, —O—CH$_2$CH$_2$-piperizino, —O—CH$_2$CH$_2$—{N—(C$_{1-4}$alkyl)-piperizino}, —O—CH$_2$-imidazol-2-yl, and —O—CH$_2$-{N—(C$_{1-4}$alkyl)-imidazol-2-yl}.

(213) A compound according to any one of (1) to (181) and (187) to (209), wherein —R$^{10A}$, if present, is independently phenyl or naphthyl, and is optionally substituted, for example, with one or more substituents independently selected from:
—F, —Cl, —Br, —I, —CF$_3$,
—C(=O)OH, —C(=O)O(C$_{1-4}$alkyl),
—S(=O)$_2$(C$_{1-4}$alkyl),
pyrrolidino, piperidino, morpholino, piperizino, N—(C$_{1-4}$alkyl)-piperizino, —O—CH$_2$-imidazol-2-yl, and —O—CH$_2$-{N—(C$_{1-4}$alkyl)-imidazol-2-yl}.

(214) A compound according to any one of (1) to (181) and (187) to (209), wherein —R$^{10A}$, if present, is independently phenyl, and is optionally substituted, for example, with one or more substituents —R$^{X3}$.

(215) A compound according to any one of (1) to (181) and (187) to (209), wherein —R$^{10A}$, if present, is independently phenyl, and is optionally substituted, for example, with one or more substituents independently selected from:
—F, —Cl, —Br, —I, —CF$_3$,
—C(=O)OH, —C(=O)O(C$_{1-4}$alkyl),
—S(=O)$_2$(C$_{1-4}$alkyl),
phenyl, —O-phenyl,
—NH$_2$, —NH(C$_{1-4}$alkyl), —N(C$_{1-4}$alkyl)$_2$,
pyrrolidino, piperidino, morpholino, piperizino, N—(C$_{1-4}$alkyl)-piperizino, —O—CH$_2$CH$_2$—NH$_2$, —O—CH$_2$CH$_2$—NH(C$_{1-4}$alkyl), —O—CH$_2$CH$_2$—N(C$_{1-4}$alkyl)$_2$, —O—CH$_2$CH$_2$-pyrrolidino, —O—CH$_2$CH$_2$-piperidino, —O—CH$_2$CH$_2$-morpholino, —O—CH$_2$CH$_2$-piperizino, —O—CH$_2$CH$_2$—{N—(C$_{1-4}$alkyl)-piperizino}, —O—CH$_2$-imidazol-2-yl, and —O—CH$_2$-{N—(C$_{1-4}$alkyl)-imidazol-2-yl}.

(216) A compound according to any one of (1) to (181) and (187) to (209), wherein —R$^{10A}$, if present, is independently phenyl, and is optionally substituted, for example, with one or more substituents independently selected from:
phenyl, —O-phenyl,
—NH$_2$, —NH(C$_{1-4}$alkyl), —N(C$_{1-4}$alkyl)$_2$,
pyrrolidino, piperidino, morpholino, piperizino, N—(C$_{1-4}$alkyl)-piperizino, —O—CH$_2$CH$_2$—NH$_2$, —O—CH$_2$CH$_2$—NH(C$_{1-4}$alkyl), —O—CH$_2$CH$_2$—N(C$_{1-4}$alkyl)$_2$, —O—CH$_2$CH$_2$-pyrrolidino, —O—CH$_2$CH$_2$-piperidino, —O—CH$_2$CH$_2$-morpholino, —O—CH$_2$CH$_2$-piperizino, —O—CH$_2$CH$_2$—{N—(C$_{1-4}$alkyl)-piperizino}, —O—CH$_2$-imidazol-2-yl, and —O—CH$_2$-{N—(C$_{1-4}$alkyl)-imidazol-2-yl}.

(217) A compound according to any one of (1) to (181) and (187) to (209), wherein —R$^{10A}$, if present, is independently phenyl, and is optionally substituted, for example, with one or more substituents independently selected from:
—F, —Cl, —Br, —I, —CF$_3$,
—C(=O)OH, —C(=O)O(C$_{1-4}$alkyl),
—S(=O)$_2$(C$_{1-4}$alkyl),
pyrrolidino, piperidino, morpholino, piperizino, N—(C$_{1-4}$alkyl)-piperizino, —O—CH$_2$-imidazol-2-yl, and —O—CH$_2$-{N—(C$_{1-4}$alkyl)-imidazol-2-yl}.

(218) A compound according to any one of (1) to (181) and (187) to (209), wherein —R$^{10A}$, if present, is independently phenyl.

(219) A compound according to any one of (1) to (181) and (187) to (209), wherein —$R^{10A}$, if present, is independently naphthyl, and is optionally substituted, for example, with one or more substituents —$R^{X3}$.

(220) A compound according to any one of (1) to (181) and (187) to (209), wherein —$R^{10A}$, if present, is independently naphthyl.

The Group —$R^{10B}$ (221) A compound according to any one of (1) to (181) and (187) to (220), wherein —$R^{10B}$, if present, is independently $C_{5-10}$heteroaryl, and is optionally substituted, for example, with one or more substituents —$R^{X3}$.

(222) A compound according to any one of (1) to (181) and (187) to (220), wherein —$R^{10B}$, if present, is independently furanyl, thienyl, pyrrolyl, imidazolyl, pyrazolyl, oxazolyl, isoxazolyl, thiazolyl, isothiazolyl, triazolyl (e.g., 1H-[1,2,3]triazolyl, 2H-[1,2,3]triazolyl, 4H-[1,2,4]triazolyl, 1H-[1,2,4]triazolyl), oxadiazolyl (e.g., [1,2,3]oxadiazolyl, furazanyl, [1,3,4]oxadiazolyl, [1,2,4]oxadiazolyl), thiadiazolyl (e.g., [1,2,3]thiadiazolyl, [1,2,5]thiadiazolyl, [1,3,4]thiadiazolyl, [1,2,4]thiadiazolyl), pyridyl, pyrimidinyl, pyrazinyl, pyridazinyl, triazinyl (e.g., [1,3,5]-triazinyl), indolyl, isoindolyl, indazolyl, benzofuranyl, isobenzofuranyl, benzothienyl, isobenzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl, and is optionally substituted, for example, with one or more substituents —$R^{X3}$.

(223) A compound according to any one of (1) to (181) and (187) to (220), wherein —$R^{10B}$, if present, is independently $C_{5-6}$heteroaryl, and is optionally substituted, for example, with one or more substituents —$R^{X3}$.

(224) A compound according to any one of (1) to (181) and (187) to (220), wherein —$R^{10B}$, if present, is independently $C_{5-6}$heteroaryl, and is optionally substituted, for example, with one or more substituents independently selected from:
saturated aliphatic $C_{1-4}$alkyl,
—$NH_2$, —$NH(C_{1-4}alkyl)$, —$N(C_{1-4}alkyl)_2$,
pyrrolidino, piperidino, morpholino, piperizino, N—($C_{1-4}$alkyl)-piperizino,
—$NHC(=O)(C_{1-4}alkyl)$, and
—OH.

(225) A compound according to any one of (1) to (181) and (187) to (220), wherein —$R^{10B}$, if present, is independently $C_{5-6}$heteroaryl, and is optionally substituted, for example, with one or more substituents independently selected from:
—$NH_2$, —$NH(C_{1-4}alkyl)$, —$N(C_{1-4}alkyl)_2$,
pyrrolidino, piperidino, morpholino, piperizino, N—($C_{1-4}$alkyl)-piperizino,
—$NHC(=O)(C_{1-4}alkyl)$, and
—OH.

(226) A compound according to any one of (1) to (181) and (187) to (220), wherein —$R^{10B}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl, and is optionally substituted, for example, with one or more substituents —$R^{X3}$.

(227) A compound according to any one of (1) to (181) and (187) to (220), wherein —$R^{10B}$, if present, is independently pyrazolyl, pyridyl, pyrimidinyl, pyrazinyl, or pyridazinyl, and is optionally substituted, for example, with one or more substituents —$R^{X3}$.

(228) A compound according to any one of (1) to (181) and (187) to (220), wherein —$R^{10B}$, if present, is independently pyridyl, pyrimidinyl, pyrazinyl, or pyridazinyl, and is optionally substituted, for example, with one or more substituents —$R^{X3}$.

(229) A compound according to any one of (1) to (181) and (187) to (220), wherein —$R^{10B}$, if present, is independently pyridyl, pyrimidinyl, or pyrazinyl, and is optionally substituted, for example, with one or more substituents —$R^{X3}$.

(230) A compound according to any one of (1) to (181) and (187) to (220), wherein —$R^{10B}$, if present, is independently pyridyl, pyrimidinyl, or pyrazinyl, and is optionally substituted, for example, with one or more substituents independently selected from:
—$NH_2$, —$NH(C_{1-4}alkyl)$, —$N(C_{1-4}alkyl)_2$,
pyrrolidino, piperidino, morpholino, piperizino, N—($C_{1-4}$alkyl)-piperizino,
—$NHC(=O)(C_{1-4}alkyl)$, and
—OH.

(231) A compound according to any one of (1) to (181) and (187) to (220), wherein —$R^{10B}$, if present, is independently pyridyl, and is optionally substituted, for example, with one or more substituents —$R^{X3}$.

(232) A compound according to any one of (1) to (181) and (187) to (220), wherein —$R^{10B}$, if present, is independently pyridyl, and is optionally substituted, for example, with one or more substituents independently selected from:
—$NH_2$, —$NH(C_{1-4}alkyl)$, —$N(C_{1-4}alkyl)_2$,
pyrrolidino, piperidino, morpholino, piperizino, N—($C_{1-4}$alkyl)-piperizino,
—$NHC(=O)(C_{1-4}alkyl)$, and
—OH.

(233) A compound according to any one of (1) to (181) and (187) to (220), wherein —$R^{10B}$, if present, is independently pyrazolyl, and is optionally substituted, for example, with one or more substituents —$R^{X3}$.

(234) A compound according to any one of (1) to (181) and (187) to (220), wherein —$R^{10B}$, if present, is independently pyrazolyl, and is optionally substituted, for example, with one or more substituents independently selected from: saturated aliphatic $C_{1-4}$alkyl.

(235) A compound according to any one of (1) to (181) and (187) to (220), wherein —$R^{10B}$, if present, is independently $C_{9-10}$heteroaryl, and is optionally substituted, for example, with one or more substituents —$R^{X3}$.

(236) A compound according to any one of (1) to (181) and (187) to (220), wherein —$R^{10B}$, if present, is independently indolyl, isoindolyl, indazolyl, benzofuranyl, isobenzofuranyl, benzothienyl, isobenzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl, and is optionally substituted, for example, with one or more substituents —$R^{X3}$.

(237) A compound according to any one of (1) to (181) and (187) to (220), wherein —$R^{10B}$, if present, is independently indazolyl, benzimidazolyl, benzothiazolyl, quinolinyl, or isoquinolinyl, and is optionally substituted, for example, with one or more substituents —$R^{X3}$.

(238) A compound according to any one of (1) to (181) and (187) to (220), wherein —$R^{10B}$, if present, is independently indazolyl, and is optionally substituted, for example, with one or more substituents —$R^{X3}$.

(239) A compound according to any one of (1) to (181) and (187) to (220), wherein —$R^{10B}$, if present, is independently benzimidazolyl, and is optionally substituted, for example, with one or more substituents —$R^{X3}$.

(240) A compound according to any one of (1) to (181) and (187) to (220), wherein —$R^{10B}$, if present, is independently benzothiazolyl, quinolinyl, or isoquinolinyl, and is optionally substituted, for example, with one or more substituents —$R^{X3}$.

(241) A compound according to any one of (1) to (181) and (187) to (220), wherein —$R^{10B}$, if present, is independently benzothiazolyl, and is optionally substituted, for example, with one or more substituents —$R^{X3}$.

(242) A compound according to any one of (1) to (181) and (187) to (220), wherein —$R^{10B}$, if present, is independently quinolinyl or isoquinolinyl, and is optionally substituted, for example, with one or more substituents —$R^{X3}$.

The Group —$R^{10C}$ (243) A compound according to any one of (1) to (181) and (187) to (242), wherein —$R^{10C}$, if present, is independently saturated $C_{3-7}$cycloalkyl, and is optionally substituted, for example, with one or more substituents —$R^{X2}$.

(244) A compound according to any one of (1) to (181) and (187) to (242), wherein —$R^{10C}$, if present, is independently cyclopropyl, cyclobutyl, cyclopentyl, or cyclohexyl, and is optionally substituted, for example, with one or more substituents —$R^{X2}$.

(245) A compound according to any one of (1) to (181) and (187) to (242), wherein —$R^{10C}$, if present, is independently cyclopropyl, cyclobutyl, cyclopentyl, or cyclohexyl.

(246) A compound according to any one of (1) to (181) and (187) to (242), wherein —$R^{10C}$, if present, is independently cyclopentyl or cyclohexyl, and is optionally substituted, for example, with one or more substituents —$R^{X2}$.

(247) A compound according to any one of (1) to (181) and (187) to (242), wherein —$R^{10C}$, if present, is independently cyclopentyl or cyclohexyl.

The Group-$R^{10D}$ (248) A compound according to any one of (1) to (181) and (187) to (247), wherein —$R^{10D}$, if present, is independently non-aromatic $C_{3-10}$heterocyclyl, and is optionally substituted, for example, with one or more substituents —$R^{X2}$.

(249) A compound according to any one of (1) to (181) and (187) to (247), wherein —$R^{10D}$, if present, is independently non-aromatic $C_{3-10}$heterocyclyl, and is optionally substituted, for example, with one or more substituents independently selected from $C_{1-4}$alkyl.

(250) A compound according to any one of (1) to (181) and (187) to (247), wherein —$R^{10D}$, if present, is independently non-aromatic $C_{3-10}$heterocyclyl.

(251) A compound according to any one of (1) to (181) and (187) to (247), wherein —$R^{10D}$, if present, is independently non-aromatic $C_{5-7}$heterocyclyl, and is optionally substituted, for example, with one or more substituents —$R^{X2}$.

(252) A compound according to any one of (1) to (181) and (187) to (247), wherein —$R^{10D}$, if present, is independently non-aromatic $C_{5-7}$heterocyclyl, and is optionally substituted, for example, with one or more substituents independently selected from $C_{1-4}$alkyl.

(253) A compound according to any one of (1) to (181) and (187) to (247), wherein —$R^{10D}$, if present, is independently non-aromatic $C_{5-7}$heterocyclyl.

(254) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, dioxanyl, azepanyl, or diazepanyl, and is optionally substituted, for example, with one or more substituents —$R^{X2}$.

(255) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, dioxanyl, azepanyl, or diazepanyl, and is optionally substituted, for example, with one or more substituents independently selected from $C_{1-4}$alkyl.

(256) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, dioxanyl, azepanyl, or diazepanyl.

(257) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, or dioxanyl, and is optionally substituted, for example, with one or more substituents —$R^{X2}$.

(258) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, or dioxanyl, and is optionally substituted, for example, with one or more substituents independently selected from $C_{1-4}$alkyl.

(259) A compound according to any one of (1) to (181) and (187) to (247), wherein —$R^{10D}$ is independently pyrrolidinyl, piperidinyl, morpholinyl, piperizinyl, tetrahydrofuranyl, tetrahydropyranyl, or dioxanyl.

(260) A compound according to any one of (1) to (181) and (187) to (247), wherein —$R^{10D}$ is independently piperidinyl, morpholinyl, or piperizinyl, and is optionally substituted, for example, with one or more substituents —$R^{X2}$.

(261) A compound according to any one of (1) to (181) and (187) to (247), wherein —$R^{10D}$ is independently piperidinyl, morpholinyl, or piperizinyl, and is optionally substituted, for example, with one or more substituents independently selected from $C_{1-4}$alkyl.

(262) A compound according to any one of (1) to (181) and (187) to (247), wherein —$R^{10D}$ is independently piperidinyl, morpholinyl, or piperizinyl.

(263) A compound according to any one of (1) to (181) and (187) to (247), wherein —$R^{10D}$ is independently piperidinyl, and is optionally substituted, for example, with one or more substituents —$R^{X2}$.

(264) A compound according to any one of (1) to (181) and (187) to (247), wherein —$R^{10D}$ is independently piperidinyl, and is optionally substituted, for example, with one or more substituents independently selected from $C_{1-4}$alkyl.

(265) A compound according to any one of (1) to (181) and (187) to (247), wherein —$R^{10D}$ is independently piperidin-4-yl, and is optionally substituted, for example, with one or more substituents —$R^{X2}$.

(266) A compound according to any one of (1) to (181) and (187) to (247), wherein —$R^{10D}$ is independently piperidin-4-yl, and is optionally substituted, for example, with one or more substituents independently selected from $C_{1-4}$alkyl.

(267) A compound according to any one of (1) to (181) and (187) to (247), wherein —$R^{10D}$ is independently N—($C_{1-4}$alkyl)-piperidin-4-yl, for example, N-(methyl)-piperidin-4-yl or N-(isopropyl)-piperidin-4-yl, as shown below:

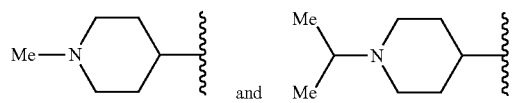

and (268) A compound according to any one of (1) to (181) and (187) to (247), wherein —$R^{10D}$ is independently N,N-(di-$C_{1-4}$alkyl)-piperidin-4-yl, for example, N,N-(di-methyl)-piperidin-4-yl, as shown below:

(269) A compound according to any one of (1) to (181) and (187) to (247), wherein —$R^{10D}$ is independently piperizinyl, and is optionally substituted, for example, with one or more substituents —$R^{X2}$.

(270) A compound according to any one of (1) to (181) and (187) to (247), wherein —$R^{10D}$ is independently piperizinyl, and is optionally substituted, for example, with one or more substituents independently selected from $C_{1-4}$alkyl.

(271) A compound according to any one of (1) to (181) and (187) to (247), wherein —$R^{10D}$ is independently piperizino, and is optionally substituted, for example, with one or more substituents —$R^{X2}$.

(272) A compound according to any one of (1) to (181) and (187) to (247), wherein —$R^{10D}$ is independently piperizino, and is optionally substituted, for example, with one or more substituents independently selected from $C_{1-4}$alkyl.

(273) A compound according to any one of (1) to (181) and (187) to (247), wherein —$R^{10D}$ is independently N—($C_{1-4}$alkyl)-piperizino, for example, N-(methyl)-piperizino, as shown below:

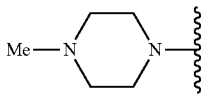

(274) A compound according to any one of (1) to (181) and (187) to (247), wherein —$R^{10D}$ is independently N,N-(di-$C_{1-4}$alkyl)-piperizino, for example, N,N-(di-methyl)-piperizino, as shown below:

For the avoidance of doubt, it is intended that a cationic group, for example, a group containing a quaternary nitrogen, for example, N,N-(di-methyl)-piperidin-4-yl and N,N-(di-methyl)-piperizino illustrated above, is accompanied by an appropriate counter anion, for example, halide anion, for example, $Cl^-$.

The Group —$R^{11}$ (275) A compound according to any one of (1) to (274), wherein —$R^{11}$ is independently —H or —$R^{11A}$.

(276) A compound according to any one of (1) to (274), wherein —$R^{11}$ is independently —$R^{11A}$.

(277) A compound according to any one of (1) to (274), wherein —$R^{11}$ is independently —$R^{11B}$.

(278) A compound according to any one of (1) to (274), wherein —$R^{11}$ is independently —H.

The Group —$R^{11A}$ (279) A compound according to any one of (1) to (278), wherein —$R^{11A}$, if present, is independently —$R^{Z1}$, —$R^{Z2}$, —$R^{Z3}$, —$R^{Z4}$, —$R^{Z5}$, -$L^Z$-$R^{Z2}$, -$L^Z$-$R^{Z3}$, -$L^Z$-$R^{Z4}$, or -$L^Z$-$R^{Z5}$.

(280) A compound according to any one of (1) to (278), wherein —$R^{11A}$, if present, is independently —$R^{Z1}$, —$R^{Z2}$, —$R^{Z3}$, —$R^{Z4}$, —$R^{Z5}$, -$L^Z$-$R^{Z4}$, or -$L^Z$-$R^{Z5}$.

(281) A compound according to any one of (1) to (278), wherein —$R^{11A}$, if present, is independently —$R^{Z1}$, —$R^{Z2}$, —$R^{Z3}$, —$R^{Z4}$, -$L^Z$-$R^{Z4}$, or -$L^Z$-$R^{Z5}$.

(282) A compound according to any one of (1) to (278), wherein —$R^{11A}$, if present, is independently —$R^{Z1}$, —$R^{Z2}$, -$L^Z$-$R^{Z4}$, or -$L^Z$-$R^{Z5}$.

(283) A compound according to any one of (1) to (278), wherein —$R^{11A}$, if present, is independently —$R^{Z2}$ or -$L^Z$-$R^{Z4}$.

(284) A compound according to any one of (1) to (278), wherein —$R^{11A}$, if present, is independently —$R^{Z1}$.

(285) A compound according to any one of (1) to (278), wherein —$R^{11A}$, if present, is independently —$R^{Z2}$.

(286) A compound according to any one of (1) to (278), wherein —$R^{11A}$, if present, is independently —$R^{Z3}$.

(287) A compound according to any one of (1) to (278), wherein —$R^{11A}$, if present, is independently —$R^{Z4}$.

(288) A compound according to any one of (1) to (278), wherein —$R^{11A}$, if present, is independently -$L^Z$-$R^{Z2}$.

(289) A compound according to any one of (1) to (278), wherein —$R^{11A}$, if present, is independently -$L^Z$-$R^{Z3}$.

(290) A compound according to any one of (1) to (278), wherein —$R^{11A}$, if present, is independently -$L^Z$-$R^{Z4}$.

(291) A compound according to any one of (1) to (278), wherein —$R^{11A}$, if present, is independently -$L^Z$-$R^{Z5}$.

The Group —$R^{Z1}$ (292) A compound according to any one of (1) to (291), wherein —$R^{Z1}$, if present, is independently saturated aliphatic $C_{1-6}$alkyl, and is optionally substituted, for example, with one or more substituents —$R^{X1}$.

(293) A compound according to any one of (1) to (291), wherein —$R^{Z1}$, if present, is independently saturated aliphatic $C_{1-6}$alkyl.

(294) A compound according to any one of (1) to (291), wherein —$R^{Z1}$, if present, is independently saturated aliphatic $C_{1-4}$alkyl, and is optionally substituted, for example, with one or more substituents —$R^{X1}$.

(295) A compound according to any one of (1) to (291), wherein —$R^{Z1}$, if present, is independently saturated aliphatic $C_{1-4}$alkyl, —$CH_2CH_2$—OMe, —$CH_2CH_2$-pyrrolidino, —$CH_2CH_2$-piperizino, or —$CH_2CH_2$—(N-methyl)piperizino.

(296) A compound according to any one of (1) to (291), wherein —$R^{Z1}$, if present, is independently saturated aliphatic $C_{1-4}$alkyl, —$CH_2CH_2$—OMe, or —$CH_2CH_2$-pyrrolidino.

(297) A compound according to any one of (1) to (291), wherein —$R^{Z1}$, if present, is independently -Me, -iPr, —$CH_2CH_2$—OMe, —$CH_2CH_2$-pyrrolidino, —$CH_2CH_2$-piperizino, or —$CH_2CH_2$—(N-methyl)piperizino.

(298) A compound according to any one of (1) to (291), wherein —$R^{Z1}$, if present, is independently -iPr, —$CH_2CH_2$—OMe, or —$CH_2CH_2$-pyrrolidino.

(299) A compound according to any one of (1) to (291), wherein —$R^{Z1}$, if present, is independently saturated aliphatic $C_{1-4}$alkyl.

(300) A compound according to any one of (1) to (291), wherein —$R^{Z1}$, if present, is independently -Me, -Et, -nPr, -iPr, -nBu, -iBu, -sBu, or -tBu.

(301) A compound according to any one of (1) to (291), wherein —$R^{Z1}$, if present, is independently -Me.

(302) A compound according to any one of (1) to (291), wherein —$R^{Z1}$, if present, is independently saturated aliphatic $C_{3-4}$alkyl, and is optionally substituted, for example, with one or more substituents —$R^{X1}$.

(303) A compound according to any one of (1) to (291), wherein —$R^{Z1}$, if present, is independently saturated aliphatic $C_{3-4}$alkyl.

(304) A compound according to any one of (1) to (291), wherein —$R^{Z1}$, if present, is independently -nPr, -iPr, -nBu, -iBu, -sBu, or -tBu.

(305) A compound according to any one of (1) to (291), wherein —$R^{Z1}$, if present, is independently -iPr, -nBu, -sBu, or -tBu.

(306) A compound according to any one of (1) to (291), wherein —$R^{Z1}$, if present, is independently -iPr.

The Group —$R^{Z2}$ (307) A compound according to any one of (1) to (306), wherein each —$R^{Z2}$, if present, is independently saturated $C_{3-7}$cycloalkyl, and is optionally substituted, for example, with one or more substituents —$R^{X2}$, or is optionally fused to a benzene ring which is optionally substituted with one or more substituents —$R^{X3}$.

(308) A compound according to any one of (1) to (306), wherein each —$R^{Z2}$, if present, is independently saturated $C_{3-7}$cycloalkyl, and is optionally substituted, for example, with one or more substituents —$R^{X2}$.

(309) A compound according to any one of (1) to (306), wherein each —$R^{Z2}$, if present, is independently saturated $C_{3-7}$cycloalkyl.

(310) A compound according to any one of (1) to (306), wherein each —$R^{Z2}$, if present, is independently saturated $C_{3-7}$cycloalkyl, and is fused to a benzene ring.

(311) A compound according to any one of (1) to (306), wherein each —$R^{Z2}$, if present, is independently cyclopropyl, cyclobutyl, cyclopentyl, or cyclohexyl, and is optionally substituted, for example, with one or more substituents —$R^{X2}$.

(312) A compound according to any one of (1) to (306), wherein each —$R^{Z2}$, if present, is independently cyclopropyl, cyclobutyl, cyclopentyl, or cyclohexyl.

(313) A compound according to any one of (1) to (306), wherein each —$R^{Z2}$, if present, is independently cyclopentyl or cyclohexyl, and is optionally substituted, for example, with one or more substituents —$R^{X2}$.

(314) A compound according to any one of (1) to (306), wherein each —$R^{Z2}$, if present, is independently cyclopentyl or cyclohexyl.

(315) A compound according to any one of (1) to (306), wherein each —$R^{Z2}$, if present, is independently cyclopentyl or cyclohexyl, and is fused to a benzene ring.

(316) A compound according to any one of (1) to (306), wherein each —$R^{Z2}$, if present, is independently cyclopentyl, and is fused to a benzene ring, for example, the following group:

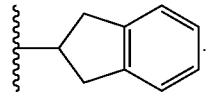 [SMILES: *C1Cc2ccccc2C1]

(317) A compound according to any one of (1) to (306), wherein each —$R^{Z2}$, if present, is independently cyclohexyl, and is optionally substituted, for example, with one or more substituents —$R^{X2}$.

(318) A compound according to any one of (1) to (306), wherein each —$R^{Z2}$, if present, is independently cyclohexyl.

(319) A compound according to any one of (1) to (306), wherein each —$R^{Z2}$, if present, is independently cyclopropyl, and is optionally substituted, for example, with one or more substituents —$R^{X2}$.

(320) A compound according to any one of (1) to (306), wherein each —$R^{Z2}$, if present, is independently cyclopropyl.

The Group —$R^{Z3}$ (321) A compound according to any one of (1) to (320), wherein each —$R^{Z3}$, if present, is independently —$R^{Z3A}$.

(322) A compound according to any one of (1) to (320), wherein each —$R^{Z3}$, if present, is independently —$R^{Z3B}$.

The Group —$R^{Z3A}$ (323) A compound according to any one of (1) to (322), wherein each —$R^{Z3A}$, if present, is independently non-aromatic $C_{3-7}$heterocyclyl, and is optionally substituted, for example, with one or more substituents —$R^{X2}$.

(324) A compound according to any one of (1) to (322), wherein each —$R^{Z3A}$, if present, is independently non-aromatic $C_{3-4}$heterocyclyl, and is optionally substituted, for example, with one or more substituents independently selected from $C_{1-4}$alkyl.

(325) A compound according to any one of (1) to (322), wherein each —$R^{Z3A}$, if present, is independently pyrrolidinyl, piperidinyl, piperizinyl, morpholinyl, tetrahydrofuranyl, tetrahydropyranyl, dioxanyl, azepanyl, or diazepanyl, and is optionally substituted, for example, with one or more substituents —$R^{X2}$.

(326) A compound according to any one of (1) to (322), wherein each —$R^{Z3A}$, if present, is independently pyrrolidinyl, piperidinyl, piperizinyl, morpholinyl, tetrahydrofuranyl, tetrahydropyranyl, dioxanyl, azepanyl, or diazepanyl, and is optionally substituted, for example, with one or more substituents independently selected from $C_{1-4}$alkyl.

(327) A compound according to any one of (1) to (322), wherein each —$R^{Z3A}$, if present, is independently pyrrolidinyl, piperidinyl, piperizinyl, or tetrahydropyranyl, and is optionally substituted, for example, with one or more substituents —$R^{X2}$.

(328) A compound according to any one of (1) to (322), wherein each —$R^{Z3A}$, if present, is independently pyrrolidinyl, piperidinyl, piperizinyl, or tetrahydropyranyl, and is optionally substituted, for example, with one or more substituents independently selected from $C_{1-4}$alkyl.

(329) A compound according to any one of (1) to (322), wherein each —$R^{Z3A}$, if present, is independently selected from:

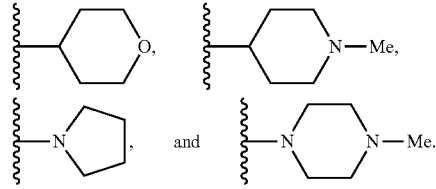

(330) A compound according to any one of (1) to (322), wherein each —$R^{Z3A}$, if present, is independently piperidinyl or tetrahydropyranyl, and is optionally substituted, for example, with one or more substituents —$R^{X2}$.

(331) A compound according to any one of (1) to (322), wherein each —$R^{Z3A}$, if present, is independently piperidinyl or tetrahydropyranyl, and is optionally substituted, for example, with one or more substituents independently selected from $C_{1-4}$alkyl.

(332) A compound according to any one of (1) to (322), wherein each —$R^{Z3A}$, if present, is independently selected from:

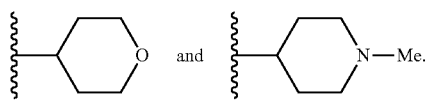 and 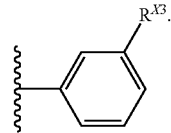

The Group —R$^{Z3B}$ (333) A compound according to any one of (1) to (332), wherein each —R$^{Z3B}$, if present, is independently saturated bridged C$_{5-10}$heterocyclyl, and is optionally substituted, for example, with one or more substituents —R$^{X2}$.

(334) A compound according to any one of (1) to (332), wherein each —R$^{Z3B}$, if present, is independently saturated bridged C$_{5-10}$heterocyclyl, and is optionally substituted, for example, with one or more substituents independently selected from C$_{1-4}$alkyl.

(335) A compound according to any one of (1) to (332), wherein each —R$^{Z3B}$, if present, is independently:

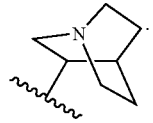 [SMILES: *C1CN2CCC1CC2]

The Group —R$^{Z4}$ (336) A compound according to any one of (1) to (335), wherein each —R$^{Z4}$, if present, is independently phenyl or naphthyl, and is optionally substituted, for example, with one or more substituents —R$^{X3}$.

(337) A compound according to any one of (1) to (335), wherein each —R$^{Z4}$, if present, is independently phenyl or naphthyl, and is optionally substituted, for example, with one or more substituents independently selected from —F, —Cl, —Br, —I, -Me, -Et, -nPr, -iPr, -tBu, —C(=O)OH, —C(=O)OMe, —C(=O)OEt, —C(=O)O(nPr), —C(=O)O(iPr), —C(=O)O(tBu), —OH, —OMe, —OEt, —CF$_3$, —OCF$_3$, —CN, —S(=O)$_2$NH$_2$, —S(=O)$_2$NHMe, —C(=O)NH$_2$, —C(=O)NHMe, piperizino, N-(methyl)-piperizino, —CH$_2$—NMe$_2$, —CH$_2$-piperidino, —NHC(=O)NH$_2$, and —OCH$_2$O—.

(338) A compound according to any one of (1) to (335), wherein each —R$^{Z4}$, if present, is independently phenyl or naphthyl, and is optionally substituted, for example, with one or more substituents independently selected from —F, —Cl, —Br, —I, -Me, -Et, —C(=O)OH, —C(=O)OMe, —C(=O)OEt, —OH, —OMe, —OEt, and —OCH$_2$O—.

(339) A compound according to any one of (1) to (335), wherein each —R$^{Z4}$, if present, is independently phenyl, and is optionally substituted, for example, with one or more substituents —R$^{X3}$.

(340) A compound according to any one of (1) to (335), wherein each —R$^{Z4}$, if present, is independently selected from:

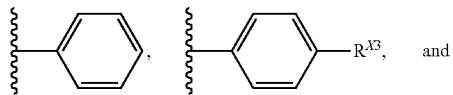

(341) A compound according to any one of (1) to (335), wherein each —R$^{Z4}$, if present, is independently phenyl, and is optionally substituted, for example, with one or more substituents independently selected from —F, —Cl, —Br, —I, -Me, -Et, -nPr, -iPr, -tBu, —C(=O)OH, —C(=O)OMe, —C(=O)OEt, —C(=O)O(nPr), —C(=O)O(iPr), —C(=O)O(tBu), —OH, —OMe, —OEt, —CF$_3$, —OCF$_3$, —CN, —S(=O)$_2$NH$_2$, —S(=O)$_2$NHMe, —C(=O)NH$_2$, —C(=O)NHMe, piperizino, N-(methyl)-piperizino, —CH$_2$—NMe$_2$, —CH$_2$-piperidino, —NHC(=O)NH$_2$, and —OCH$_2$O—.

(342) A compound according to any one of (1) to (335), wherein each —R$^{Z4}$, if present, is independently phenyl, and is optionally substituted at the meta- or para-position with a substituent independently selected from —C(=O)OH, —C(=O)OMe, —C(=O)OEt, —C(=O)O(nPr), —C(=O)O(iPr), —C(=O)O(tBu), —S(=O)$_2$NH$_2$, —S(=O)$_2$NHMe, —C(=O)NH$_2$, —C(=O)NHMe, piperizino, N-(methyl)-piperizino, —CH$_2$—NMe$_2$, —CH$_2$-piperidino, or —NHC(=O)NH$_2$.

(343) A compound according to any one of (1) to (335), wherein each —R$^{Z4}$, if present, is independently phenyl, and is optionally substituted, for example, with one or more substituents independently selected from —F, —Cl, —Br, —I, -Me, -Et, —C(=O)OH, —C(=O)OMe, —C(=O)OEt, —OH, —OMe, —OEt, and —OCH$_2$O—.

(344) A compound according to any one of (1) to (335), wherein each —R$^{Z4}$, if present, is independently phenyl.

(345) A compound according to any one of (1) to (335), wherein each —R$^{Z4}$, if present, is independently naphthyl, and is optionally substituted, for example, with one or more substituents —R$^{X3}$.

(346) A compound according to any one of (1) to (335), wherein each —R$^{Z4}$, if present, is independently naphthyl.

The Group —R$^{Z5}$ (347) A compound according to any one of (1) to (346), wherein each —R$^{Z5}$, if present, is independently C$_{5-10}$heteroaryl, and is optionally substituted, for example, with one or more substituents —R$^{X3}$.

(348) A compound according to any one of (1) to (346), wherein each —R$^{Z5}$, if present, is independently C$_{5-10}$heteroaryl.

(349) A compound according to any one of (1) to (346), wherein each —R$^{Z5}$, if present, is independently furanyl, thienyl, pyrrolyl, imidazolyl, pyrazolyl, oxazolyl, isoxazolyl, thiazolyl, isothiazolyl, triazolyl (e.g., 1H-[1,2,3]triazolyl, 2H-[1,2,3]triazolyl, 4H-[1,2,4]triazolyl, 1H-[1,2,4]triazolyl), oxadiazolyl (e.g., [1,2,3]oxadiazolyl, furazanyl, [1,3,4]oxadiazolyl, [1,2,4]oxadiazolyl), thiadiazolyl (e.g., [1,2,3]thiadiazolyl, [1,2,5]thiadiazolyl, [1,3,4]thiadiazolyl, [1,2,4]thiadiazolyl), pyridyl, pyrimidinyl, pyrazinyl, pyridazinyl, triazinyl (e.g., (1,3,5)-triazinyl), indolyl, isoindolyl, indazolyl, benzofuranyl, isobenzofuranyl, benzothienyl, isobenzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl, and is optionally substituted, for example, with one or more substituents —R$^{X3}$.

(350) A compound according to any one of (1) to (346), wherein each —$R^{Z5}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, pyridazinyl, indolyl, isoindolyl, indazolyl, benzofuranyl, isobenzofuranyl, benzothienyl, isobenzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl, and is optionally substituted, for example, with one or more substituents —$R^{X3}$.

(351) A compound according to any one of (1) to (346), wherein each —$R^{Z5}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, pyridazinyl, indolyl, isoindolyl, indazolyl, benzofuranyl, isobenzofuranyl, benzothienyl, isobenzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl.

(352) A compound according to any one of (1) to (346), wherein each —$R^{Z5}$, if present, is independently $C_{5-6}$heteroaryl, and is optionally substituted, for example, with one or more substituents —$R^{X3}$.

(353) A compound according to any one of (1) to (346), wherein each —$R^{Z5}$, if present, is independently $C_{5-6}$heteroaryl.

(354) A compound according to any one of (1) to (346), wherein each —$R^{Z5}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl, and is optionally substituted, for example, with one or more substituents —$R^{X3}$.

(355) A compound according to any one of (1) to (346), wherein each —$R^{Z5}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl.

(356) A compound according to any one of (1) to (346), wherein each —$R^{Z5}$, if present, is independently pyridyl, pyrimidinyl, pyrazinyl, or pyridazinyl, and is optionally substituted, for example, with one or more substituents —$R^{X3}$.

(357) A compound according to any one of (1) to (346), wherein each —$R^{Z5}$, if present, is independently pyridyl, pyrimidinyl, pyrazinyl, or pyridazinyl.

(358) A compound according to any one of (1) to (346), wherein each —$R^{Z5}$, if present, is independently pyridyl, and is optionally substituted, for example, with one or more substituents —$R^{X3}$.

(359) A compound according to any one of (1) to (346), wherein each —$R^{Z5}$, if present, is independently pyridyl, and is optionally substituted, for example, with one or more substituents independently selected from:
—$NH_2$, —$NH(C_{1-4}alkyl)$, —$N(C_{1-4}alkyl)_2$,
pyrrolidino, piperidino, morpholino, piperizino, N—($C_{1-4}alkyl$)-piperizino,
—$NHC(=O)(C_{1-4}alkyl)$, and
—OH.

(360) A compound according to any one of (1) to (346), wherein each —$R^{Z5}$, if present, is independently pyridyl or pyridonyl.

(361) A compound according to any one of (1) to (346), wherein each —$R^{Z5}$, if present, is independently pyridyl.

(362) A compound according to any one of (1) to (346), wherein each —$R^{Z5}$, if present, is independently imidazolyl, pyrazolyl, oxazolyl, isoxazolyl, and is optionally substituted, for example, with one or more substituents —$R^{X3}$.

(363) A compound according to any one of (1) to (346), wherein each —$R^{Z5}$, if present, is independently imidazolyl, pyrazolyl, oxazolyl, isoxazolyl, and is optionally substituted, for example, with one or more substituents selected from $C_{1-4}$alkyl.

(364) A compound according to any one of (1) to (346), wherein each —$R^{Z5}$, if present, is independently pyrazolyl, and is optionally substituted, for example, with one or more substituents —$R^{X3}$.

(365) A compound according to any one of (1) to (346), wherein each —$R^{Z5}$, if present, is independently pyrazolyl, and is optionally substituted, for example, with one or more substituents selected from $C_{1-4}$alkyl.

The Group -$L^Z$-

(366) A compound according to any one of (1) to (365), wherein each -$L^Z$-, if present, is independently —$CH_2$—, —$CH(Me)$-, —$C(Me)_2$, —$CH_2CH_2$— or —$CH_2CH_2CH_2$—

(367) A compound according to any one of (1) to (365), wherein each -$L^Z$-, if present, is independently —$CH_2$—, —$CH(Me)$-, or —$CH_2CH_2$—.

(368) A compound according to any one of (1) to (365), wherein each -$L^Z$-, if present, is independently —$CH_2$— or —$CH(Me)$-.

(369) A compound according to any one of (1) to (365), wherein each -$L^Z$-, if present, is independently —$CH_2$—.

The Group —$R^{11B}$ (370) A compound according to any one of (1) to (369), wherein —$R^{J1}$, if present, is independently —H, -Me, -Et, -nPr, or -iPr.

(371) A compound according to any one of (1) to (369), wherein —$R^{J1}$, if present, is independently —H, -Me, or -Et.

(372) A compound according to any one of (1) to (369), wherein —$R^{J1}$, if present, is independently —H.

(373) A compound according to any one of (1) to (372), wherein —$R^{J2}$, if present, is independently —H, -Me, -Et, -nPr, or -iPr.

(374) A compound according to any one of (1) to (372), wherein —$R^{J2}$, if present, is independently —H, -Me, or -Et.

(375) A compound according to any one of (1) to (372), wherein —$R^{J2}$, if present, is independently —H.

(376) A compound according to any one of (1) to (375), wherein —$R^{J3}$, if present, is independently saturated aliphatic $C_{1-4}$alkyl, phenyl, or benzyl.

(377) A compound according to any one of (1) to (375), wherein —$R^{J3}$, if present, is independently saturated aliphatic $C_{1-4}$alkyl.

(378) A compound according to any one of (1) to (377), wherein —$R^{J4}$, if present, is independently —H, saturated aliphatic $C_{1-4}$alkyl, phenyl, or benzyl.

(379) A compound according to any one of (1) to (377), wherein —$R^{J4}$, if present, is independently saturated aliphatic $C_{1-4}$alkyl, phenyl, or benzyl.

(380) A compound according to any one of (1) to (377), wherein —$R^{J4}$, if present, is independently —H or saturated aliphatic $C_{1-4}$alkyl.

(381) A compound according to any one of (1) to (377), wherein —$R^{J4}$, if present, is independently saturated aliphatic $C_{1-4}$alkyl.

(382) A compound according to any one of (1) to (375), wherein —$NR^{J3}R^{J4}$, if present, is independently a $C_{3-10}$heterocyclyl group, and is optionally substituted, for example, with one or more substituents —$R^{X2}$.

(383) A compound according to any one of (1) to (375), wherein —$NR^{J3}R^{J4}$, if present, is independently a $C_{3-10}$heterocyclyl group, and is optionally substituted, for example, with one or more substituents independently selected from $C_{1-4}$alkyl.

(384) A compound according to any one of (1) to (375), wherein —NR$^{J3}$R$^{J4}$, if present, is independently pyrrolidino, piperidino, morpholino, piperizino, azepino, diazepino, [1,4]-oxazepan-4-yl, 1,2,3,4-tetrahydro-quinolin-1-yl, 1,2,3,4-tetrahydro-isoquinolin-2-yl, 1,2,3,4-tetrahydro-quinoxalin-1-yl, 3,4-dihydro-2H-benzo[1,4]oxazin-4-yl, 2,3-dihydro-1H-indol-1-yl, or 2,3-dihydro-1H-isoindol-2-yl, and is optionally substituted, for example, with one or more substituents —R$^{X2}$.

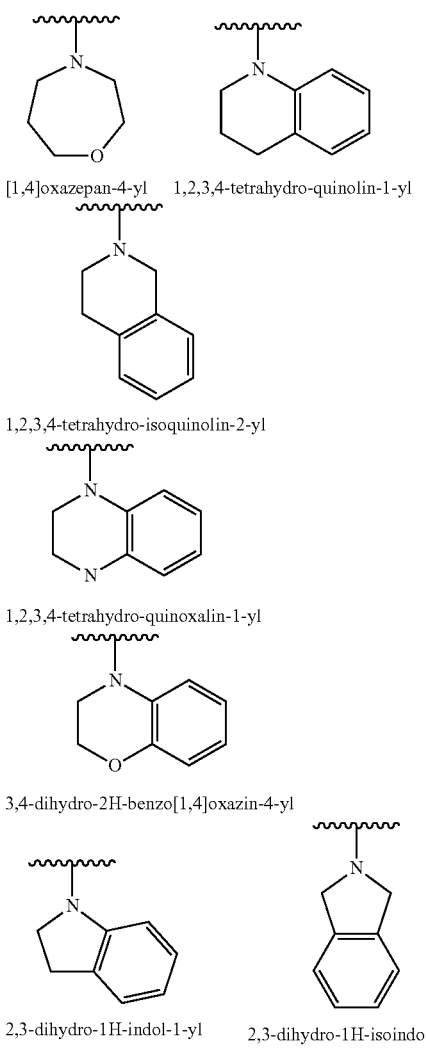

(385) A compound according to any one of (1) to (375), wherein —NR$^{J3}$R$^{J4}$, if present, is independently 1,2,3,4-tetrahydro-isoquinolin-2-yl or 2,3-dihydro-1H-indol-1-yl, and is optionally substituted, for example, with one or more substituents —R$^{X2}$.

(386) A compound according to any one of (1) to (375), wherein —NR$^{J3}$R$^{J4}$, if present, is independently 1,2,3,4-tetrahydro-isoquinolin-2-yl and is optionally substituted, for example, with one or more substituents —R$^{X2}$.

(387) A compound according to any one of (1) to (306), wherein —NR$^{J3}$R$^{J4}$, if present, is independently pyrrolidino, piperidino, morpholino, piperizino, azepino, diazepino, [1,4]-oxazepan-4-yl, 1,2,3,4-tetrahydro-quinolin-1-yl, 1,2,3,4-tetrahydro-isoquinolin-2-yl, 1,2,3,4-tetrahydro-quinoxalin-1-yl, 3,4-dihydro-2H-benzo[1,4]oxazin-4-yl, 2,3-dihydro-1H-indol-1-yl, or 2,3-dihydro-1H-isoindol-2-yl, and is optionally substituted, for example, with one or more substituents independently selected from C$_{1-4}$alkyl.

(388) A compound according to any one of (1) to (375), wherein —NR$^{J3}$R$^{J4}$, if present, is independently 1,2,3,4-tetrahydro-isoquinolin-2-yl or 2,3-dihydro-1H-indol-1-yl, and is optionally substituted, with one or more substituents independently selected from C$_{1-4}$alkyl.

(389) A compound according to any one of (1) to (375), wherein —NR$^{J3}$R$^{J4}$, if present, is independently 1,2,3,4-tetrahydro-isoquinolin-2-yl and is optionally substituted, with one or more substituents independently selected from C$_{1-4}$alkyl.

(390) A compound according to any one of (1) to (375), wherein —NR$^{J3}$R$^{J4}$, if present, is independently 1,2,3,4-tetrahydro-isoquinolin-2-yl or 2,3-dihydro-1H-indol-1-yl.

(391) A compound according to any one of (1) to (375), wherein —NR$^{J3}$R$^{J4}$, if present, is independently 1,2,3,4-tetrahydro-isoquinolin-2-yl.

(392) A compound according to any one of (1) to (375), wherein —NR$^{J3}$R$^{J4}$, if present, is independently a non-aromatic C$_{3-7}$heterocyclyl group, and is optionally substituted, for example, with one or more substituents —R$^{X2}$.

(393) A compound according to any one of (1) to (375), wherein —NR$^{J3}$R$^{J4}$, if present, is independently a non-aromatic C$_{3-7}$heterocyclyl group, and is optionally substituted, for example, with one or more substituents independently selected from C$_{1-4}$alkyl.

(394) A compound according to any one of (1) to (375), wherein —NR$^{J3}$R$^{J4}$, if present, is independently pyrrolidino, piperidino, morpholino, or piperizino, and is optionally substituted, for example, with one or more substituents —R$^{X2}$.

(395) A compound according to any one of (1) to (375), wherein —NR$^{J3}$R$^{34}$, if present, is independently pyrrolidino, piperidino, morpholino, or piperizino, and is optionally substituted, for example, with one or more substituents independently selected from C$_{1-4}$alkyl.

(396) A compound according to any one of (1) to (375), wherein —NR$^{J3}$R$^{J4}$, if present, is independently selected from:

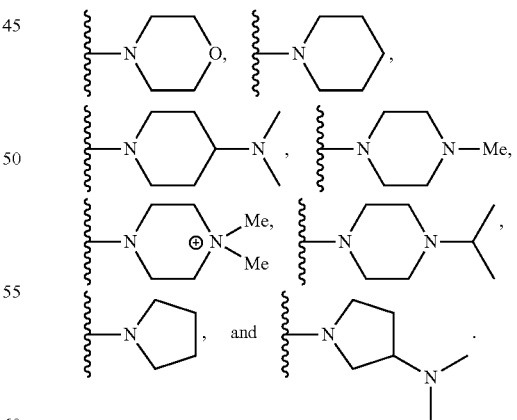

(397) A compound according to any one of (1) to (375), wherein —NR$^{J3}$R$^{J4}$, if present, is independently piperidino, morpholino, or piperizino, and is optionally substituted, for example, with one or more substituents —R$^{X2}$.

(398) A compound according to any one of (1) to (375), wherein —NR$^{J3}$R$^{J4}$, if present, is independently piperidino, morpholino, or piperizino, and is optionally substituted, for example, with one or more substituents independently selected from $C_{1-4}$alkyl.

(399) A compound according to any one of (1) to (375), wherein —$NR^{J3}R^{J4}$, if present, is independently selected from:

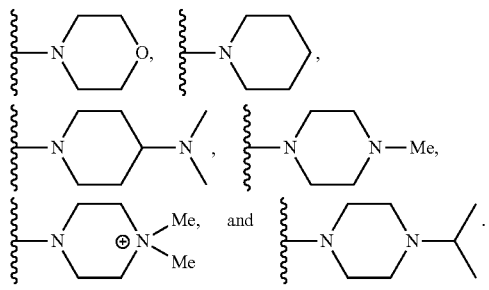

(400) A compound according to any one of (1) to (375), wherein —$NR^{J3}R^{J4}$, if present, is independently selected from:

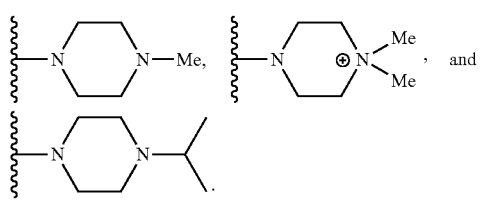

(401) A compound according to any one of (1) to (375), wherein —$NR^{J3}R^{J4}$, if present, is independently:

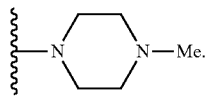

(402) A compound according to any one of (1) to (375), wherein —$NR^{J3}R^{J4}$, if present, is independently:

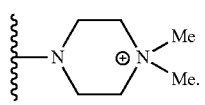

Again, for the avoidance of doubt, it is intended that a cationic group, for example, a group containing a quaternary nitrogen, for example, N,N-(di-methyl)-piperizino illustrated above, is accompanied by an appropriate counter anion, for example, halide anion, for example, Cl⁻.

(403) A compound according to any one of (1) to (375), wherein —$NR^{J3}R^{J4}$, if present, is independently:

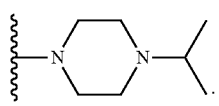

(404) A compound according to any one of (1) to (375), wherein —$NR^{J3}R^{J4}$, if present, is independently piperidino, morpholino, piperizino, or N—($C_{1-4}$alkyl)-piperizino.

(405) A compound according to any one of (1) to (369), wherein —$R^{11B}$, if present, is independently selected from:

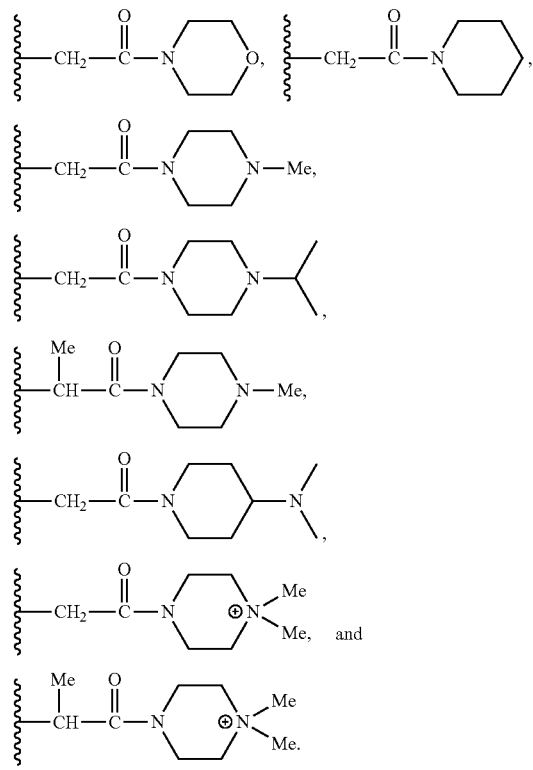

(406) A compound according to any one of (1) to (369), wherein —$R^{11B}$, if present, is independently selected from:

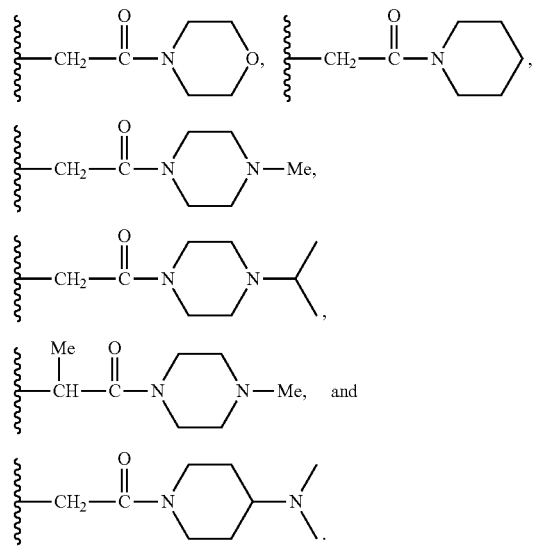

43

(407) A compound according to any one of (1) to (369), wherein —$R^{11B}$, if present, is independently:

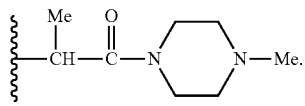

(408) A compound according to any one of (1) to (369), wherein —$R^{11B}$, if present, is independently selected from:

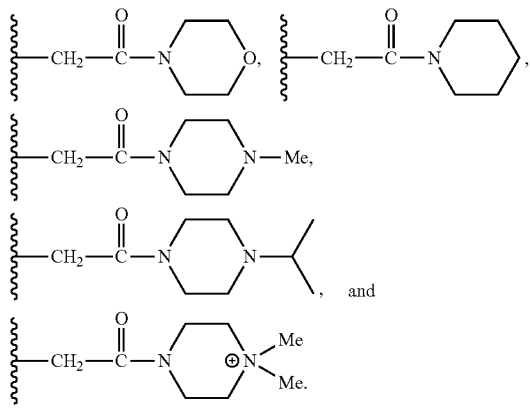

(409) A compound according to any one of (1) to (369), wherein —$R^{11B}$, if present, is independently selected from:

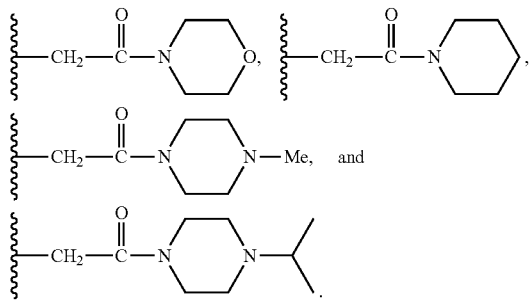

The Group —$R^{12}$ (410) A compound according to any one of (1) to (409), wherein —$R^{12}$ is independently —H or —$R^{12A}$.

(411) A compound according to any one of (1) to (409), wherein —$R^{12}$ is independently —H.

(412) A compound according to any one of (1) to (409), wherein —$R^{12}$ is independently —$R^{12A}$.

The Group —$R^{12A}$ (413) A compound according to any one of (1) to (412), wherein —$R^{12A}$, if present, is independently saturated aliphatic $C_{1-6}$alkyl, and is optionally substituted, for example, with one or more substituents —$R^{X1}$.

(414) A compound according to any one of (1) to (412), wherein —$R^{12A}$, if present, is independently saturated aliphatic $C_{1-6}$alkyl.

(415) A compound according to any one of (1) to (412), wherein —$R^{12A}$, if present, is independently saturated aliphatic $C_{1-4}$alkyl, and is optionally substituted, for example, with one or more substituents —$R^{X1}$.

44

(416) A compound according to any one of (1) to (412), wherein —$R^{12A}$, if present, is independently saturated aliphatic $C_{1-4}$alkyl.

(417) A compound according to any one of (1) to (412), wherein —$R^{12A}$, if present, is independently -Me, -Et, -nPr, -iPr, -nBu, -sBu, -iBu, or -tBu.

(418) A compound according to any one of (1) to (412), wherein —$R^{12A}$, if present, is independently -Me, -Et, -nPr, or -iPr.

(419) A compound according to any one of (1) to (412), wherein —$R^{12A}$, if present, is independently -Me.

The Group —$NR^{11}R^{12}$ (420) A compound according to any one of (1) to (274), wherein —$NR^{11}R^{12}$ is independently a $C_{3-10}$heterocyclyl group, and is optionally substituted, for example, with one or more substituents —$R^{X2}$.

(421) A compound according to any one of (1) to (274), wherein —$NR^{11}R^{12}$ is independently pyrrolidino, piperidino, morpholino, piperizino, azepino, tetrahydroquinolino, or tetrahydroisoquinolinyl and is optionally substituted, for example, with one or more substituents —$R^{X2}$.

(422) A compound according to any one of (1) to (274), wherein —$NR^{11}R^{12}$ is independently a non-aromatic $C_{3-7}$heterocyclyl group, and is optionally substituted, for example, with one or more substituents —$R^{X2}$.

(423) A compound according to any one of (1) to (274), wherein —$NR^{11}R^{12}$ is independently pyrrolidino, piperidino, morpholino, piperizino, or azepino, and is optionally substituted, for example, with one or more substituents —$R^{X2}$.

(424) A compound according to any one of (1) to (274), wherein —$NR^{11}R^{12}$ is independently pyrrolidino, piperidino, morpholino, or piperizino, and is optionally substituted, for example, with one or more substituents —$R^{X2}$.

(425) A compound according to any one of (1) to (274), wherein —$NR^{11}R^{12}$ is independently selected from:

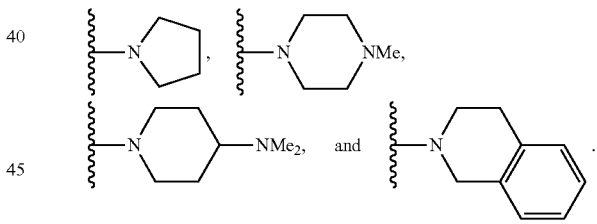

The Optional Substituents —$R^{X1}$ (426) A compound according to any one of (1) to (425), wherein each —$R^{X1}$, if present, is independently selected from:
—F, —Cl, —Br, —I, phenyl, —$CF_3$, —OH, —$OR^S$, —$OCF_3$, —$NH_2$, —$NHR^S$, —$NR^S_2$, pyrrolidino, piperidino, morpholino, piperizino, N—($C_{1-4}$alkyl)-piperizino, —$NHC(=O)R^S$, —$NR^SC(=O)R^S$, —$C(=O)R^S$, —$C(=O)OH$, —$C(=O)OR^S$, —$C(=O)NH_2$, —$C(=O)NHR^S$, —$C(=O)NR^S_2$, —$C(=O)$-pyrrolidino, —$C(=O)$-piperidino, —$C(=O)$-morpholino, —$C(=O)$-piperizino, —$C(=O)$—{N—($C_{1-4}$alkyl)-piperizino}-, —$SR^S$, —$S(=O)R^S$, and —$S(=O)_2R^S$;
wherein each —$R^S$ is independently saturated aliphatic $C_{1-6}$alkyl, phenyl, or —$CH_2$-phenyl;
wherein each phenyl is optionally substituted with one or more groups selected from: —F, —Cl, —Br, —I, —$R^{SS}$, —$CF_3$, —OH, —$OR^{SS}$, or —$OCF_3$, wherein each —$R^{SS}$ is independently saturated aliphatic $C_{1-4}$alkyl.

(427) A compound according to (426), wherein each —$R^{X1}$, if present, is independently selected from:
- —F, —Cl, —Br, —I, —OH, —$OR^S$, —$NH_2$, —$NHR^S$, —$NR^S{}_2$, pyrrolidino, piperidino, morpholino, piperizino, N—($C_{1-4}$alkyl)-piperizino, —NHC(=O)$R^S$, —$NR^SC(=O)R^S$, —C(=O)$NH_2$, —C(=O)$NHR^S$, —C(=O)$NR^S{}_2$, —C(=O)-pyrrolidino, —C(=O)-piperidino, —C(=O)-morpholino, —C(=O)-piperizino, and —C(=O)—{N—($C_{1-4}$alkyl)-piperizino}-.

(428) A compound according to (426), wherein each —$R^{X1}$, if present, is independently selected from:
- —OH, —$OR^S$, —$NH_2$, —$NHR^S$, —$NR^S{}_2$, pyrrolidino, piperidino, morpholino, piperizino, N—($C_{1-4}$alkyl)-piperizino, —NHC(=O)$R^S$, —$NR^SC(=O)R^S$, —C(=O)$NH_2$, —C(=O)$NHR^S$, —C(=O)$NR^S{}_2$, —C(=O)-pyrrolidino, —C(=O)-piperidino, —C(=O)-morpholino, —C(=O)-piperizino, and —C(=O)—{N—($C_{1-4}$alkyl)-piperizino}-.

(429) A compound according to any one of (426) to (428), wherein each —$R^S$, if present, is independently saturated aliphatic $C_{1-6}$alkyl.

(430) A compound according to any one of (426) to (428), wherein each —$R^S$, if present, is independently saturated aliphatic $C_{1-4}$alkyl.

The Optional Substituents —$R^{X2}$ (431) A compound according to any one of (1) to (430), wherein each —$R^{X2}$, if present, is independently selected from:
- —F, —Cl, —Br, —I, —$R^T$, phenyl, —OH, —$OR^T$, —C(=O)$R^T$, —$NH_2$, —$NHR^T$, —$NR^T{}_2$, pyrrolidino, piperidino, morpholino, piperizino, N—($C_{1-4}$alkyl)-piperizino, —NHC(=O)$R^T$, and —$NR^TC(=O)R^T$;
- wherein each —$R^T$ is independently saturated aliphatic $C_{1-6}$alkyl, phenyl, or —$CH_2$-phenyl;
- wherein each phenyl is optionally substituted with one or more groups selected from: —F, —Cl, —Br, —I, —$R^{TT}$, —$CF_3$, —OH, —$OR^{TT}$, or —$OCF_3$, wherein each —$R^{TT}$ is independently saturated aliphatic $C_{1-4}$alkyl.

(432) A compound according to (431), wherein each —$R^{X2}$, if present, is independently selected from:
- —$R^T$, —OH, —$OR^T$, —C(=O)$R^T$, —$NH_2$, —$NHR^T$, —$NR^T{}_2$, pyrrolidino, piperidino, morpholino, piperizino, N—($C_{1-4}$alkyl)-piperizino, —NHC(=O)$R^T$, and —$NR^TC(=O)R^T$.

(433) A compound according to (431), wherein each —$R^{X2}$, if present, is independently selected from:
- —$R^T$, —C(=O)$R^T$, —$NH_2$, —$NHR^T$, —$NR^T{}_2$, pyrrolidino, piperidino, morpholino, piperizino, N—($C_{1-4}$alkyl)-piperizino, —NHC(=O)$R^T$, and —$NR^TC(=O)R^T$.

(434) A compound according to (431), wherein each —$R^{X2}$, if present, is independently selected from:
- —$R^T$, —$NH_2$, —$NHR^T$, —$NR^T{}_2$, pyrrolidino, piperidino, morpholino, piperizino, N—($C_{1-4}$alkyl)-piperizino, —NHC(=O)$R^T$, and —$NR^TC(=O)R^T$.

(435) A compound according to (431), wherein each —$R^{X2}$, if present, is independently selected from:
- —$R^T$, —$NH_2$, —$NHR^T$, —$NR^T{}_2$, pyrrolidino, piperidino, morpholino, piperizino, and N—($C_{1-4}$alkyl)-piperizino.

(436) A compound according to any one of (431) to (435), wherein each —$R^T$, if present, is independently saturated aliphatic $C_{1-6}$alkyl.

(437) A compound according to any one of (431) to (435), wherein each —$R^T$, if present, is independently saturated aliphatic $C_{1-4}$alkyl.

The Optional Substituents —$R^{X3}$ (438) A compound according to any one of (1) to (437), wherein each —$R^{X3}$, if present, is independently selected from:
- —F, —Cl, —Br, —I,
- —$R^V$,
- —CH=$CH_2$, —C≡CH, cyclopropyl,
- —$CF_3$, —$CHF_2$, —$OCF_3$, —$OCHF_2$,
- —CN,
- —$NO_2$,
- —OH, —$OR^V$,
- -$L^V$-OH, -$L^V$-$OR^V$,
- —O-$L^V$-OH, —O-$L^V$-$OR^V$,
- —$NH_2$, —$NHR^V$, —$NR^V{}_2$,
- pyrrolidino, piperidino, morpholino,
- piperizino, N—($C_{1-4}$alkyl)-piperizino,
- -$L^V$-$NH_2$, -$L^V$-$NHR^V$, -$L^V$-$NR^V{}_2$,
- -$L^V$-pyrrolidino, -$L^V$-piperidino, -$L^V$-morpholino,
- -$L^V$-piperizino, -$L^V$-{N—($C_{1-4}$alkyl)-piperizino},
- -$L^V$-imidazol-2-yl, -$L^V$-{N—($C_{1-4}$alkyl)-imidazol-2-yl},
- —O-$L^V$-$NH_2$, —O-$L^V$-$NHR^V$, —O-$L^V$-$NR^V{}_2$,
- —O-$L^V$-pyrrolidino, —O-$L^V$-piperidino, —O-$L^V$-morpholino,
- —O-$L^V$-piperizino, —O-$L^V$-{N—($C_{1-4}$alkyl)-piperizino},
- —O-$L^V$-imidazol-2-yl, —O-$L^V$-{N—($C_{1-4}$alkyl)-imidazol-2-yl},
- —NHC(=O)$R^V$, —$NR^VC(=O)R^V$,
- —C(=O)$R^V$,
- —C(=O)OH, —C(=O)$OR^V$,
- —C(=O)$NH_2$, —C(=O)$NHR^V$, —C(=O)$NR^V{}_2$.
- —C(=O)-pyrrolidino, —C(=O)-piperidino, —C(=O)-morpholino,
- —C(=O)-piperizino, —C(=O)—{N—($C_{1-4}$alkyl)-piperizino}-,
- —NHC(=O)$NH_2$, —NHC(=O)$NHR^V$, —NHC(=O)$NR^V{}_2$,
- —NHC(=O)-pyrrolidino, —NHC(=O)-piperidino, —NHC(=O)-morpholino,
- —NHC(=O)-piperizino, —NHC(=O)—{N—($C_{1-4}$alkyl)-piperizino}-,
- —S(=O)$_2R^V$,
- —S(=O)$_2NH_2$, —S(=O)$_2NHR^V$, —S(=O)$_2NR^2$, and =O;
- wherein each -$L^V$- is independently saturated aliphatic $C_{1-4}$alkylene;
- wherein each —$R^V$ is independently saturated aliphatic $C_{1-6}$alkyl, phenyl, —$CH_2$-phenyl, $C_{5-6}$heteroaryl, or —$CH_2$-$C_{5-6}$heteroaryl;
- wherein each phenyl is optionally substituted with one or more groups selected from: —F, —Cl, —Br, —I, —$R^{VV}$, —$CF_3$, —OH, —$OR^{VV}$, or —$OCF_3$;
- wherein each $C_{5-6}$heteroaryl is optionally substituted with one or more groups selected from: —F, —Cl, —Br, —I, —$R^{VV}$, —$CF_3$, —OH, —$OR^{VV}$, or —$OCF_3$;
- wherein each —$R^{VV}$ is independently saturated aliphatic $C_{1-4}$alkyl;
- and additionally, two adjacent groups —$R^{X3}$ may together form —$OCH_2O$—, —$OCH_2CH_2O$—, —$CH_2OCH_2$— or —$OCH_2CH_2$—;
- and additionally, two adjacent groups —$R^{X3}$ may, together with the ring atoms to which they are attached, form a $C_{5-7}$-carbocyclic ring or a $C_{5-7}$heterocyclic ring.

(439) A compound according to (438), wherein each —$R^{X3}$, if present, is independently selected from:
- —F, —Cl, —Br, —I,
- —$R^V$,
- —CH=$CH_2$, —C≡CH, cyclopropyl, —CF$_3$, —CHF$_2$, —OCF$_3$, —OCHF$_2$,
—CN,
—NO$_2$,
—OH, —OR$^V$,
-L$^V$-OH, -L$^V$-OR$^V$,
—O-L$^V$-OH, —O-L$^V$-OR$^V$,
—NH$_2$, —NHR$^V$, —NR$^V_2$,
pyrrolidino, piperidino, morpholino,
piperizino, N—(C$_{1-4}$alkyl)-piperizino,
-L$^V$-NH$_2$, -L$^V$-NHR$^V$, -L$^V$-NR$^V_2$,
-L$^V$-pyrrolidino, -L$^V$-piperidino, -L$^V$-morpholino,
-L$^V$-piperizino, -L$^V$-{N—(C$_{1-4}$alkyl)-piperizino},
-L$^V$-imidazol-2-yl, -L$^V$-{N—(C$_{1-4}$alkyl)-piperizino},
—O-L$^V$-NH$_2$, —O-L$^V$-NHR$^V$, —O-L$^V$-NR$^V_2$,
—O-L$^V$-pyrrolidino, —O-L$^V$-piperidino, —O-L$^V$-morpholino,
—O-L$^V$-piperizino, —O-L$^V$-{N—(C$_{1-4}$alkyl)-piperizino},
—O-L$^V$-imidazol-2-yl, —O-L$^V$-{N—(C$_{1-4}$alkyl)-imidazol-2-yl},
—NHC(=O)R$^V$, —NR$^V$C(=O)R$^V$,
—C(=O)R$^V$,
—C(=O)OH, —C(=O)OR$^V$,
—C(=O)NH$_2$, —C(=O)NHR$^V$, —C(=O)NR$^V_2$,
—C(=O)-pyrrolidino, —C(=O)-piperidino, —C(=O)-morpholino,
—C(=O)-piperizino, —C(=O)—{N—(C$_{1-4}$alkyl)-piperizino}-,
—NHC(=O)NH$_2$, —NHC(=O)NHR$^V$, —NHC(=O)NR$^V_2$,
—NHC(=O)-pyrrolidino, —NHC(=O)-piperidino, —NHC(=O)-morpholino,
—NHC(=O)-piperizino, —NHC(=O)—{N—(C$_{1-4}$alkyl)-piperizino}-,
—S(=O)$_2$R$^V$,
—S(=O)$_2$NH$_2$, —S(=O)$_2$NHR$^V$, —S(=O)$_2$NR$^V_2$, and
=O;
and additionally, two adjacent groups —R$^{X3}$ may together form —OCH$_2$O—, —OCH$_2$CH$_2$O—, —CH$_2$OCH$_2$— or —OCH$_2$CH$_2$—.

(440) A compound according to (438), wherein each —R$^{X3}$, if present, is independently selected from:
—F, —Cl, —Br, —I,
—R$^V$,
—OH, —OR$^V$,
—NH$_2$, —NHR$^V$, —NR$^V_2$,
pyrrolidino, piperidino, morpholino,
piperizino, and N—(C$_{1-4}$alkyl)-piperizino.

(441) A compound according to (438), wherein each —R$^{X3}$, if present, is independently selected from:
—F, —Cl, —Br, —I,
—R$^V$,
—OH, —OR$^V$,
—NH$_2$, —NHR$^V$, and —NR$^V_2$.

(442) A compound according to any one of (438) to (441), wherein each -L$^V$-, if present, is independently —CH$_2$—, —CH$_2$CH$_2$—, —CH$_2$CH$_2$CH$_2$—, or —CH$_2$CH$_2$CH$_2$CH$_2$—.

(443) A compound according to any one of (438) to (441), wherein each -L$^V$-, if present, is independently saturated aliphatic C$_{2-4}$alkylene.

(444) A compound according to any one of (438) to (441), wherein each -L$^V$-, if present, is independently —CH$_2$CH$_2$—, —CH$_2$CH$_2$CH$_2$—, or —CH$_2$CH$_2$CH$_2$CH$_2$—.

(445) A compound according to any one of (438) to (444), wherein each —R$^V$, if present, is independently saturated aliphatic C$_{1-6}$alkyl.

(446) A compound according to any one of (438) to (444), wherein each —R$^V$, if present, is independently saturated aliphatic C$_{1-4}$alkyl.

Molecular Weight (447) A compound according to any one of (1) to (446), wherein the compound has a molecular weight of from 258 to 1200.

(448) A compound according to (447), wherein the bottom of range is 275, 300, 325, 350, 375, 400, or 500.

(449) A compound according to (447) or (448), wherein the top of range is 1100, 1000, 900, 800, 700, or 600.

(450) A compound according to any one of (1) to (446), wherein the compound has a molecular weight of range from 500 to 800.

Specific Compounds (451) A compound according to (1), selected from compounds of the following formulae and pharmaceutically acceptable salts, hydrates, and solvates thereof:

| Code | Structure |
|---|---|
| PVA-001 | 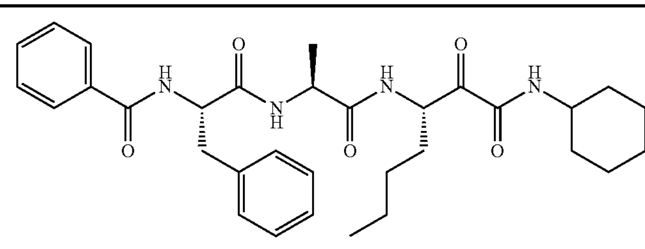 |
| PVA-002 | 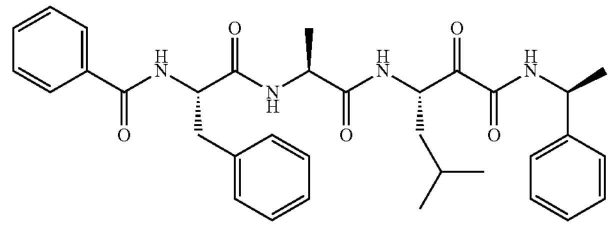 [SMILES: CC(C)C[C@H](NC(=O)[C@H](C)NC(=O)[C@H](Cc1ccccc1)NC(=O)c1ccccc1)C(=O)C(=O)N[C@@H](C)c1ccccc1] |

-continued

| Code | Structure |
|---|---|
| PVA-003 | 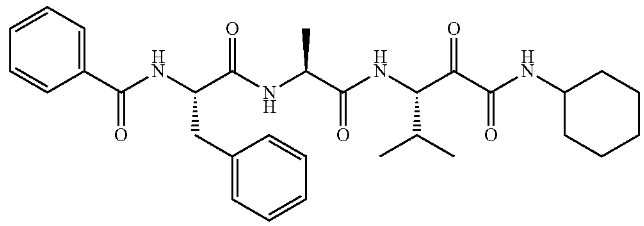 [SMILES: CC(C)[C@H](NC(=O)[C@H](C)NC(=O)[C@H](Cc1ccccc1)NC(=O)c1ccccc1)C(=O)C(=O)NC1CCCCC1] |
| PVA-004 | 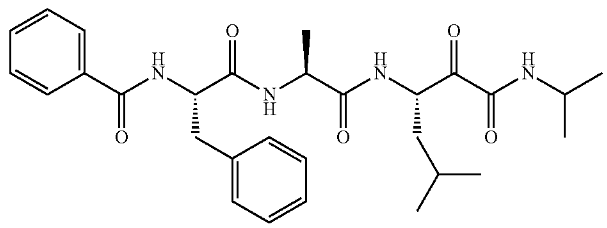 [SMILES: CC(C)C[C@H](NC(=O)[C@H](C)NC(=O)[C@H](Cc1ccccc1)NC(=O)c1ccccc1)C(=O)C(=O)NC(C)C] |
| PVA-005 | 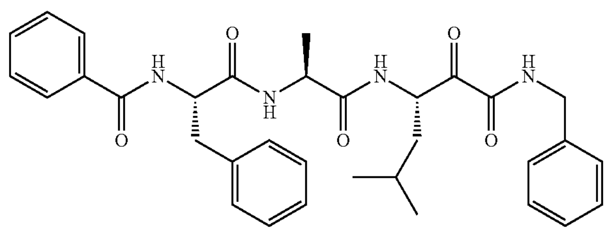 [SMILES: CC(C)C[C@H](NC(=O)[C@H](C)NC(=O)[C@H](Cc1ccccc1)NC(=O)c1ccccc1)C(=O)C(=O)NCc1ccccc1] |
| PVA-006 | 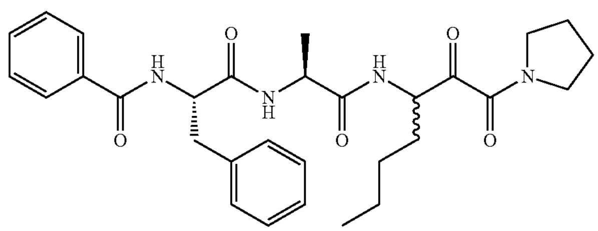 [SMILES: CCCCC(NC(=O)[C@H](C)NC(=O)[C@H](Cc1ccccc1)NC(=O)c1ccccc1)C(=O)C(=O)N1CCCC1] |
| PVA-007 | 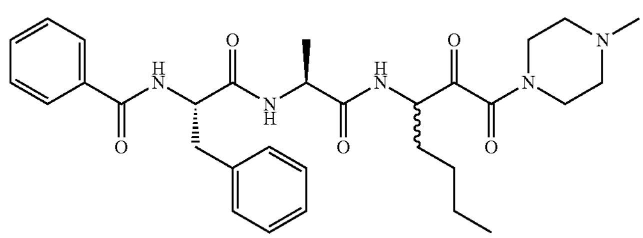 [SMILES: CCCCC(NC(=O)[C@H](C)NC(=O)[C@H](Cc1ccccc1)NC(=O)c1ccccc1)C(=O)C(=O)N1CCN(C)CC1] |
| PVA-008 | 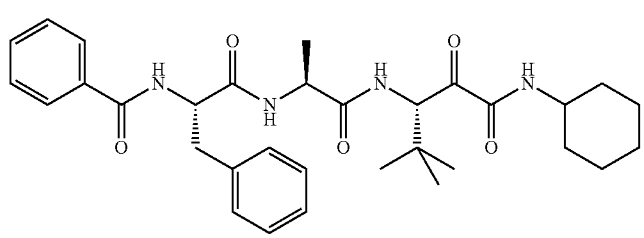 [SMILES: C[C@H](NC(=O)[C@H](Cc1ccccc1)NC(=O)c1ccccc1)C(=O)N[C@H](C(=O)C(=O)NC1CCCCC1)C(C)(C)C] |

| Code | Structure |
|---|---|
| PVA-009 | 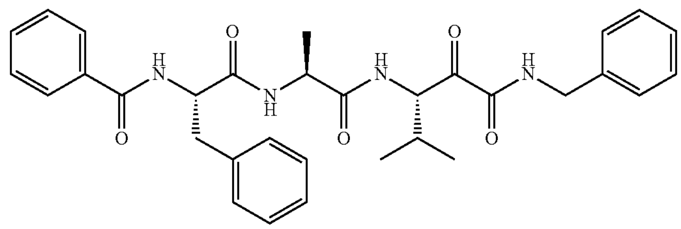 [SMILES: CC(C)[C@H](NC(=O)[C@H](C)NC(=O)[C@H](Cc1ccccc1)NC(=O)c1ccccc1)C(=O)C(=O)NCc1ccccc1] |
| PVA-010 | 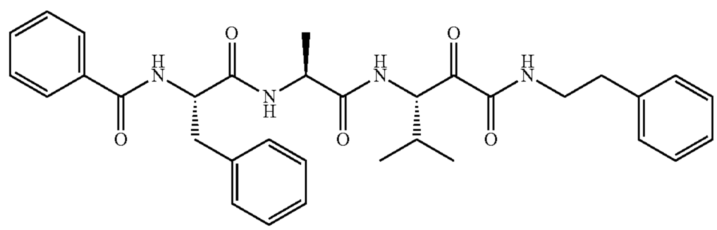 [SMILES: CC(C)[C@H](NC(=O)[C@H](C)NC(=O)[C@H](Cc1ccccc1)NC(=O)c1ccccc1)C(=O)C(=O)NCCc1ccccc1] |
| PVA-011 | 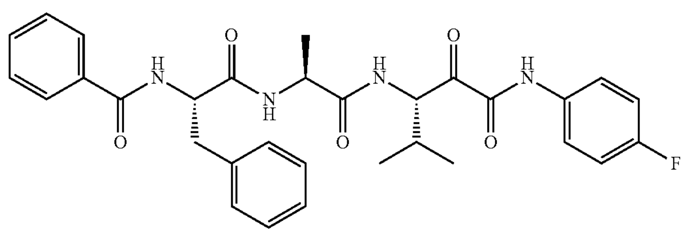 [SMILES: CC(C)[C@H](NC(=O)[C@H](C)NC(=O)[C@H](Cc1ccccc1)NC(=O)c1ccccc1)C(=O)C(=O)Nc1ccc(F)cc1] |
| PVA-012 | 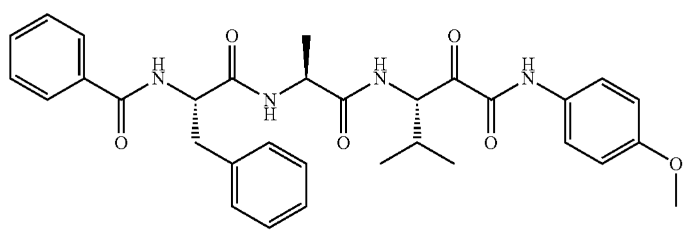 [SMILES: COc1ccc(NC(=O)C(=O)[C@@H](NC(=O)[C@H](C)NC(=O)[C@H](Cc2ccccc2)NC(=O)c2ccccc2)C(C)C)cc1] |
| PVA-013 | 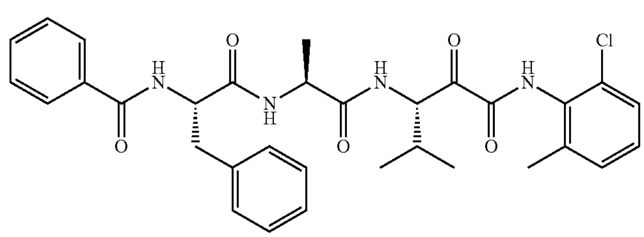 [SMILES: Cc1cccc(Cl)c1NC(=O)C(=O)[C@@H](NC(=O)[C@H](C)NC(=O)[C@H](Cc1ccccc1)NC(=O)c1ccccc1)C(C)C] |
| PVA-014 | 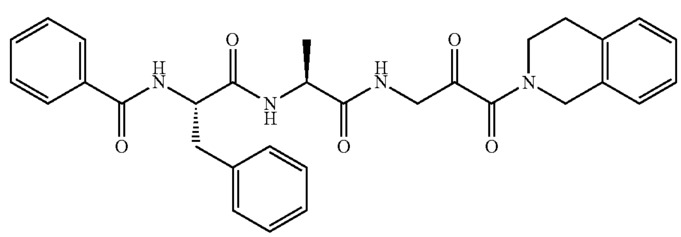 [SMILES: C[C@H](NC(=O)[C@H](Cc1ccccc1)NC(=O)c1ccccc1)C(=O)NCC(=O)C(=O)N1CCc2ccccc2C1] |

| Code | Structure |
|---|---|
| PVA-015 | 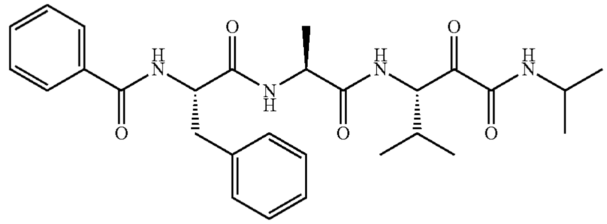 [SMILES: CC(C)NC(=O)C(=O)[C@@H](NC(=O)[C@H](C)NC(=O)[C@H](Cc1ccccc1)NC(=O)c1ccccc1)C(C)C] |
| PVA-016 | 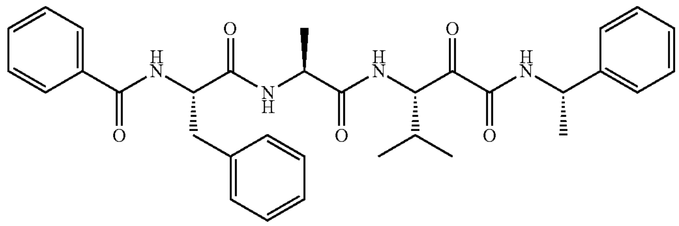 [SMILES: CC(C)[C@H](NC(=O)[C@H](C)NC(=O)[C@H](Cc1ccccc1)NC(=O)c1ccccc1)C(=O)C(=O)N[C@@H](C)c1ccccc1] |
| PVA-017 | 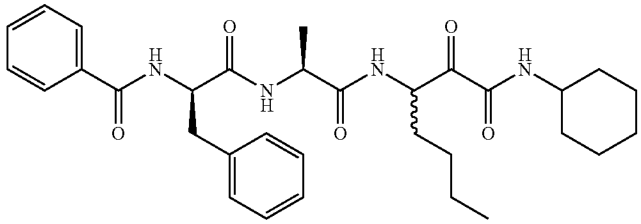 [SMILES: CCCCC(NC(=O)[C@H](C)NC(=O)[C@@H](Cc1ccccc1)NC(=O)c1ccccc1)C(=O)C(=O)NC1CCCCC1] |
| PVA-018 | 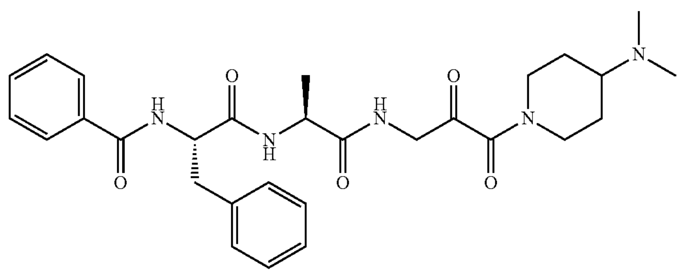 [SMILES: C[C@H](NC(=O)[C@H](Cc1ccccc1)NC(=O)c1ccccc1)C(=O)NCC(=O)C(=O)N1CCC(N(C)C)CC1] |
| PVA-019 | 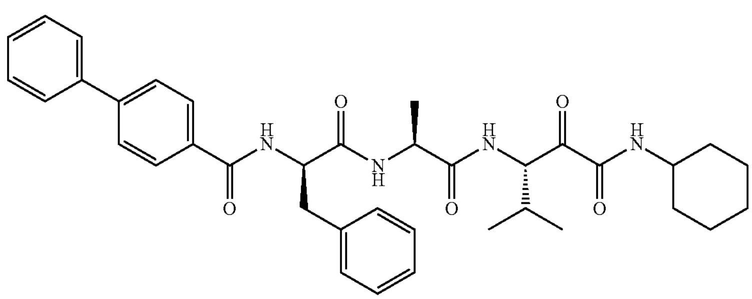 [SMILES: CC(C)[C@H](NC(=O)[C@H](C)NC(=O)[C@@H](Cc1ccccc1)NC(=O)c1ccc(-c2ccccc2)cc1)C(=O)C(=O)NC1CCCCC1] |
| PVA-020 | 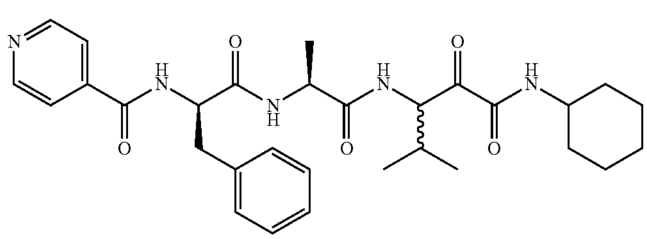 [SMILES: CC(C)C(NC(=O)[C@H](C)NC(=O)[C@@H](Cc1ccccc1)NC(=O)c1ccncc1)C(=O)C(=O)NC1CCCCC1] |

-continued

| Code | Structure |
|---|---|
| PVA-021 | 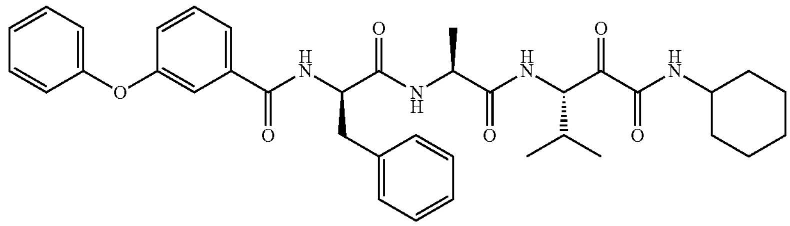 [SMILES: CC(C)[C@H](NC(=O)[C@H](C)NC(=O)[C@@H](Cc1ccccc1)NC(=O)c1cccc(Oc2ccccc2)c1)C(=O)C(=O)NC1CCCCC1] |
| PVA-022 | 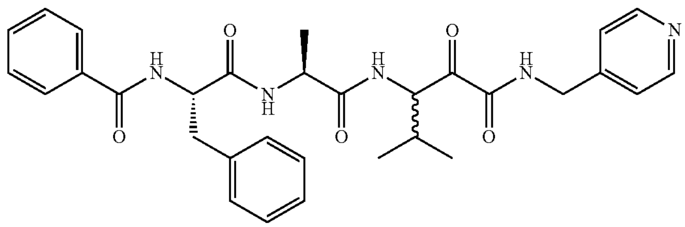 [SMILES: CC(C)C(NC(=O)[C@H](C)NC(=O)[C@H](Cc1ccccc1)NC(=O)c1ccccc1)C(=O)C(=O)NCc1ccncc1] |
| PVA-023 | 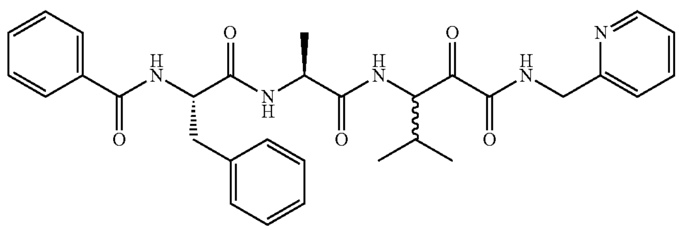 [SMILES: CC(C)C(NC(=O)[C@H](C)NC(=O)[C@H](Cc1ccccc1)NC(=O)c1ccccc1)C(=O)C(=O)NCc1ccccn1] |
| PVA-024 | 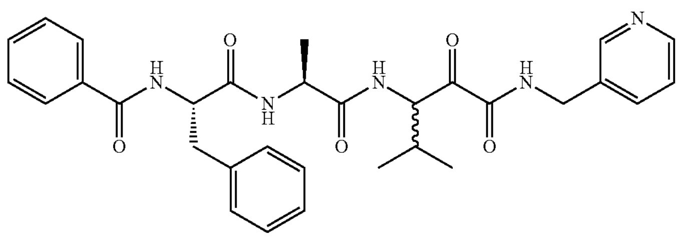 [SMILES: CC(C)C(NC(=O)[C@H](C)NC(=O)[C@H](Cc1ccccc1)NC(=O)c1ccccc1)C(=O)C(=O)NCc1cccnc1] |
| PVA-025 | 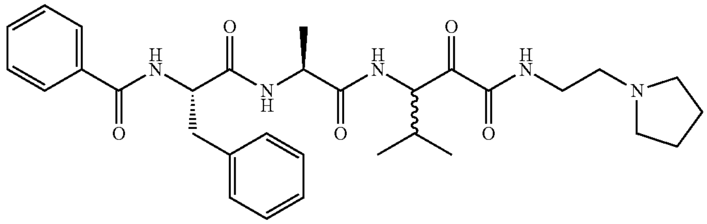 [SMILES: CC(C)C(NC(=O)[C@H](C)NC(=O)[C@H](Cc1ccccc1)NC(=O)c1ccccc1)C(=O)C(=O)NCCN1CCCC1] |
| PVA-026 | 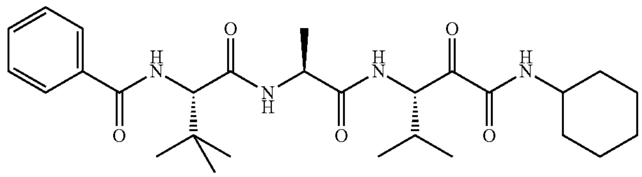 [SMILES: CC(C)[C@H](NC(=O)[C@H](C)NC(=O)[C@@H](NC(=O)c1ccccc1)C(C)(C)C)C(=O)C(=O)NC1CCCCC1] |

-continued
| Code | Structure |
|---|---|
| PVA-027 | 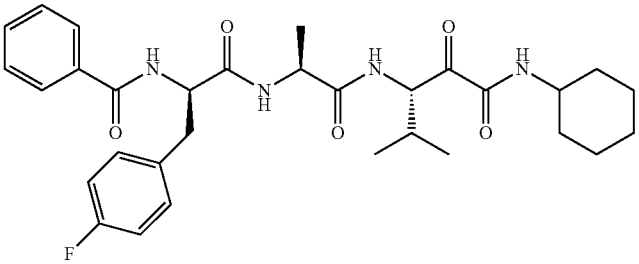 [SMILES: CC(C)[C@H](NC(=O)[C@H](C)NC(=O)[C@@H](Cc1ccc(F)cc1)NC(=O)c1ccccc1)C(=O)C(=O)NC1CCCCC1] |
| PVA-028 | 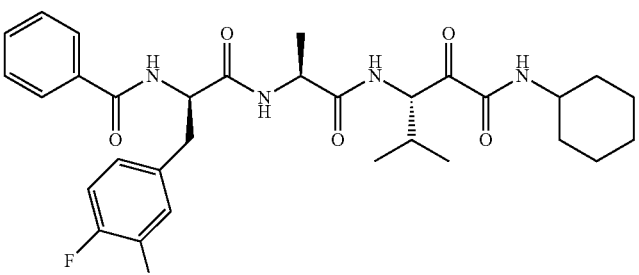 |
| PVA-029 | 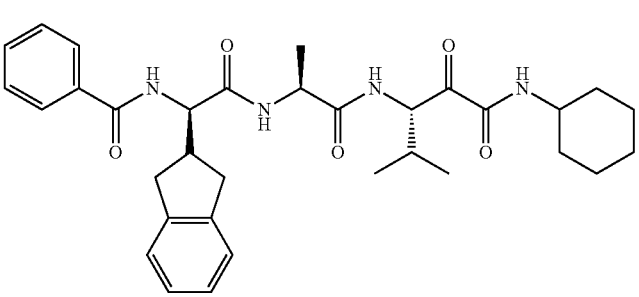 [SMILES: CC(C)[C@H](NC(=O)[C@H](C)NC(=O)[C@H](NC(=O)c1ccccc1)C1Cc2ccccc2C1)C(=O)C(=O)NC1CCCCC1] |
| PVA-030 | 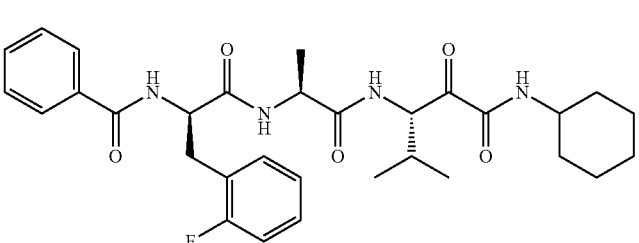 |
| PVA-031 | 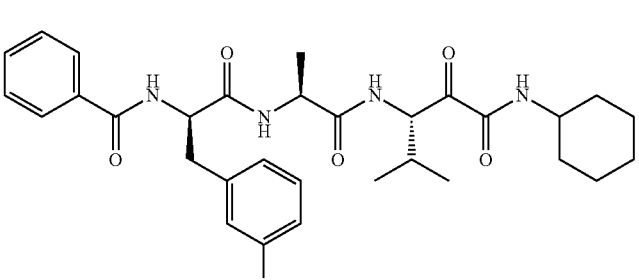 |

-continued

| Code | Structure |
|---|---|
| PVA-032 | 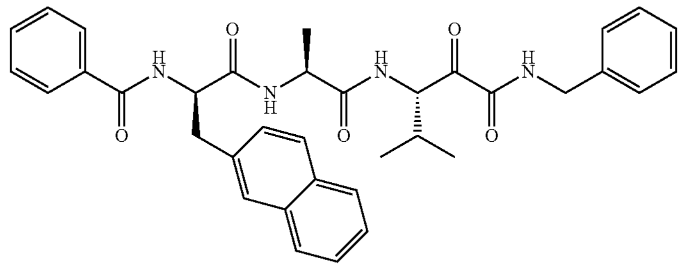 [SMILES: CC(C)[C@H](NC(=O)[C@H](C)NC(=O)[C@@H](Cc1ccc2ccccc2c1)NC(=O)c1ccccc1)C(=O)C(=O)NCc1ccccc1] |
| PVA-033 | 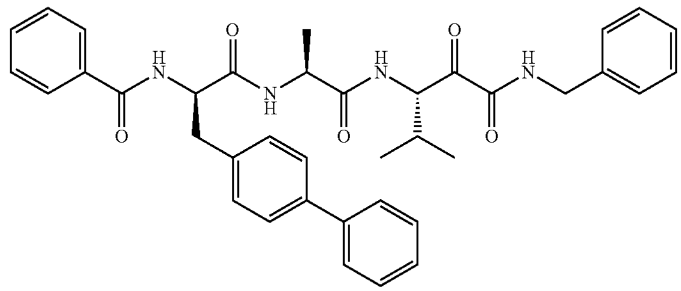 [SMILES: CC(C)[C@H](NC(=O)[C@H](C)NC(=O)[C@@H](Cc1ccc(-c2ccccc2)cc1)NC(=O)c1ccccc1)C(=O)C(=O)NCc1ccccc1] |
| PVA-034 | 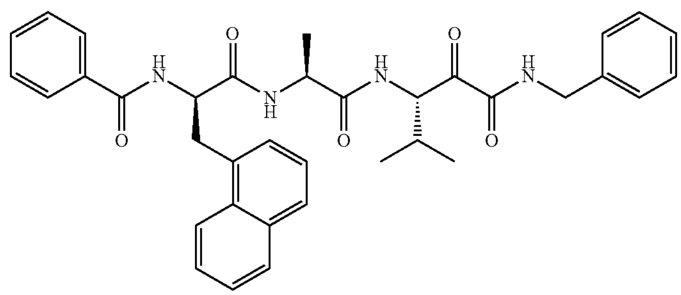 [SMILES: CC(C)[C@H](NC(=O)[C@H](C)NC(=O)[C@@H](Cc1cccc2ccccc12)NC(=O)c1ccccc1)C(=O)C(=O)NCc1ccccc1] |
| PVA-035 | 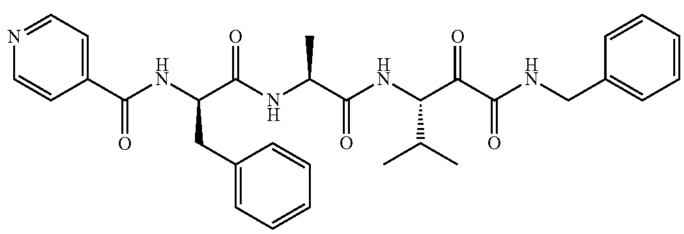 [SMILES: CC(C)[C@H](NC(=O)[C@H](C)NC(=O)[C@@H](Cc1ccccc1)NC(=O)c1ccncc1)C(=O)C(=O)NCc1ccccc1] |
| PVA-036 | 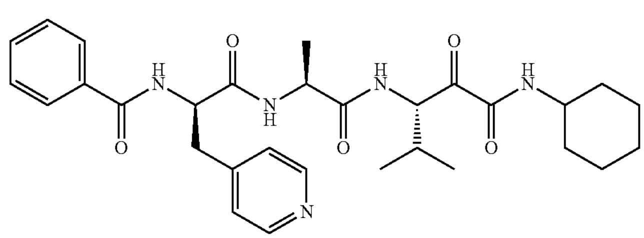 [SMILES: CC(C)[C@H](NC(=O)[C@H](C)NC(=O)[C@@H](Cc1ccncc1)NC(=O)c1ccccc1)C(=O)C(=O)NC1CCCCC1] |
| PVA-037 | 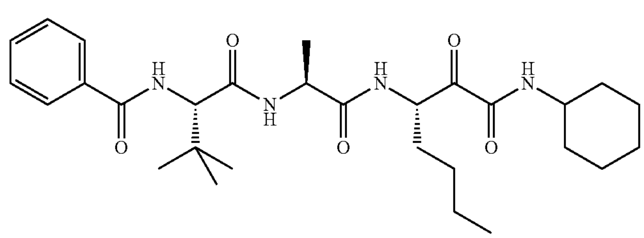 [SMILES: CCCC[C@H](NC(=O)[C@H](C)NC(=O)[C@@H](NC(=O)c1ccccc1)C(C)(C)C)C(=O)C(=O)NC1CCCCC1] |

-continued

| Code | Structure |
|---|---|
| PVA-038 | 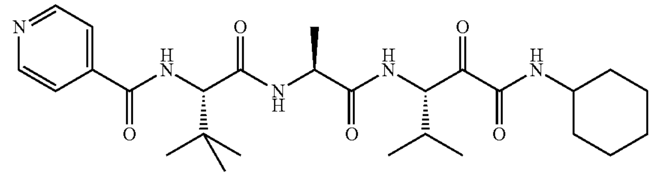 [SMILES: CC(C)[C@H](NC(=O)[C@H](C)NC(=O)[C@@H](NC(=O)c1ccncc1)C(C)(C)C)C(=O)C(=O)NC1CCCCC1] |
| PVA-039 | 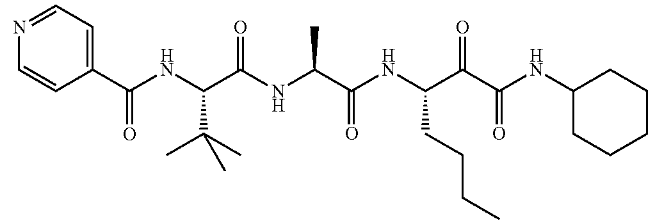 [SMILES: CCCC[C@H](NC(=O)[C@H](C)NC(=O)[C@@H](NC(=O)c1ccncc1)C(C)(C)C)C(=O)C(=O)NC1CCCCC1] |
| PVA-040 | 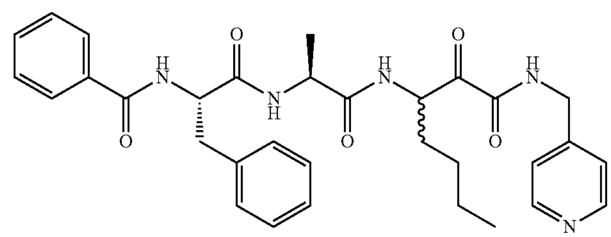 [SMILES: CCCCC(NC(=O)[C@H](C)NC(=O)[C@H](Cc1ccccc1)NC(=O)c1ccccc1)C(=O)C(=O)NCc1ccncc1] |
| PVA-041 | 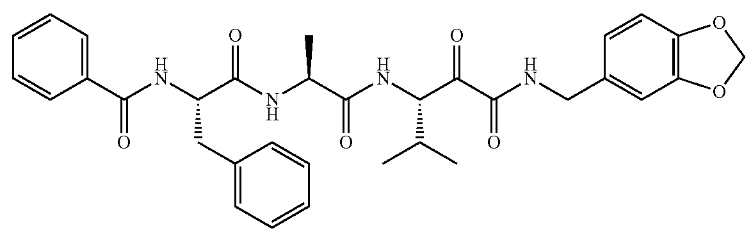 [SMILES: CC(C)[C@H](NC(=O)[C@H](C)NC(=O)[C@H](Cc1ccccc1)NC(=O)c1ccccc1)C(=O)C(=O)NCc1ccc2c(c1)OCO2] |
| PVA-042 | 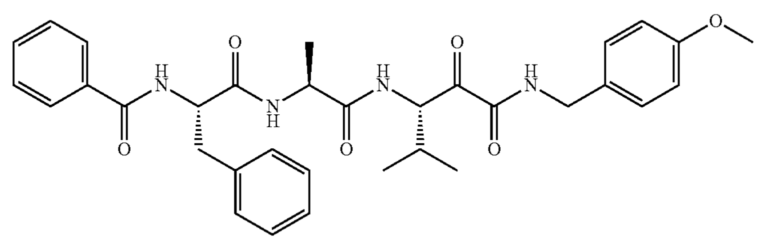 [SMILES: COc1ccc(CNC(=O)C(=O)[C@@H](NC(=O)[C@H](C)NC(=O)[C@H](Cc2ccccc2)NC(=O)c2ccccc2)C(C)C)cc1] |
| PVA-043 | 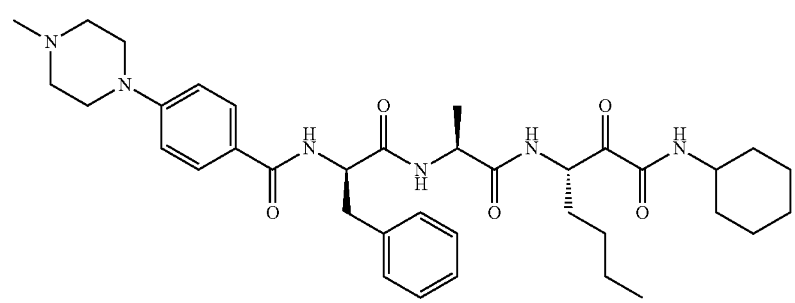 [SMILES: CCCC[C@H](NC(=O)[C@H](C)NC(=O)[C@@H](Cc1ccccc1)NC(=O)c1ccc(N2CCN(C)CC2)cc1)C(=O)C(=O)NC1CCCCC1] |

-continued

| Code | Structure |
|---|---|
| PVA-044 | 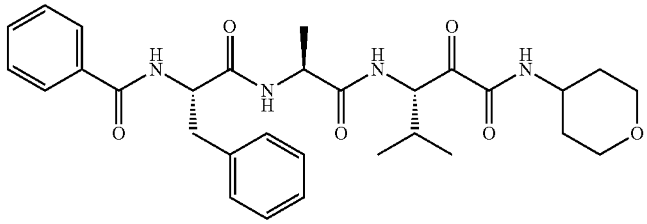 [SMILES: CC(C)[C@H](NC(=O)[C@H](C)NC(=O)[C@H](Cc1ccccc1)NC(=O)c1ccccc1)C(=O)C(=O)NC1CCOCC1] |
| PVA-045 | 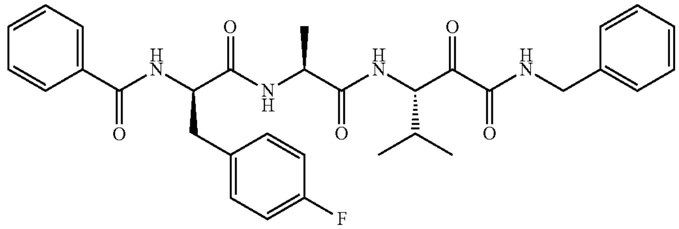 [SMILES: CC(C)[C@H](NC(=O)[C@H](C)NC(=O)[C@@H](Cc1ccc(F)cc1)NC(=O)c1ccccc1)C(=O)C(=O)NCc1ccccc1] |
| PVA-046 | 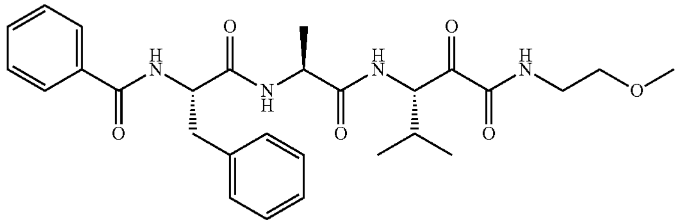 [SMILES: COCCNC(=O)C(=O)[C@@H](NC(=O)[C@H](C)NC(=O)[C@H](Cc1ccccc1)NC(=O)c1ccccc1)C(C)C] |
| PVA-047 | 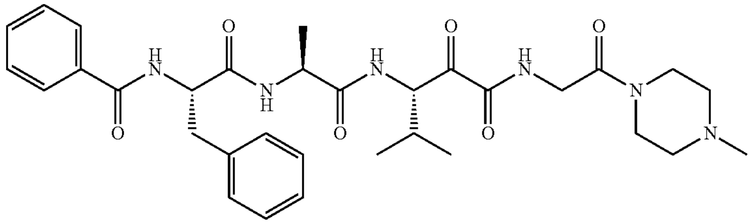 [SMILES: CC(C)[C@H](NC(=O)[C@H](C)NC(=O)[C@H](Cc1ccccc1)NC(=O)c1ccccc1)C(=O)C(=O)NCC(=O)N1CCN(C)CC1] |
| PVA-048 | 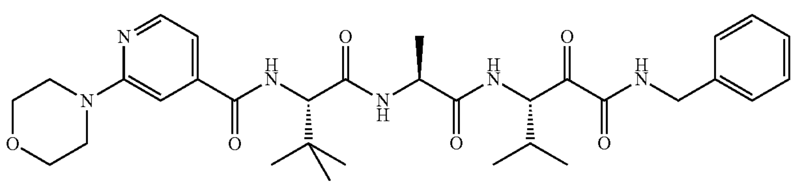 [SMILES: CC(C)[C@H](NC(=O)[C@H](C)NC(=O)[C@@H](NC(=O)c1ccnc(N2CCOCC2)c1)C(C)(C)C)C(=O)C(=O)NCc1ccccc1] |
| PVA-049 | 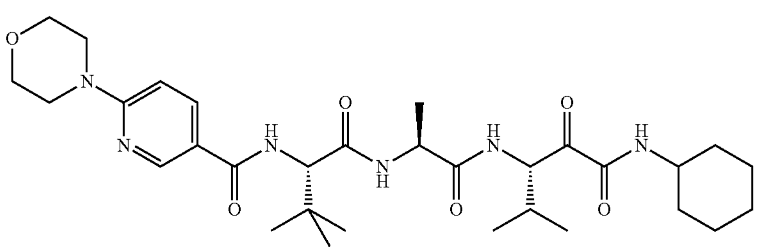 [SMILES: CC(C)[C@H](NC(=O)[C@H](C)NC(=O)[C@@H](NC(=O)c1ccc(N2CCOCC2)nc1)C(C)(C)C)C(=O)C(=O)NC1CCCCC1] |
| PVA-050 | 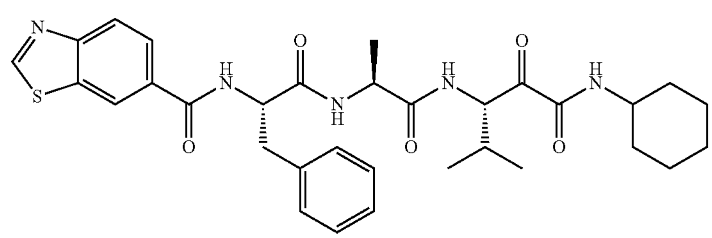 [SMILES: CC(C)[C@H](NC(=O)[C@H](C)NC(=O)[C@H](Cc1ccccc1)NC(=O)c1ccc2ncsc2c1)C(=O)C(=O)NC1CCCCC1] |

-continued
| Code | Structure |
|---|---|
| PVA-051 | 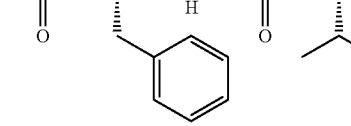 |
| PVA-052 | 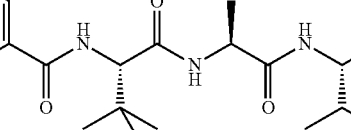 |
| PVA-053 | 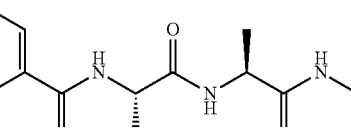 |
| PVA-054 | 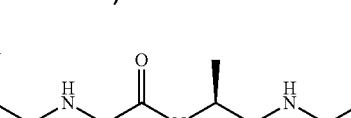 |
| PVA-055 | 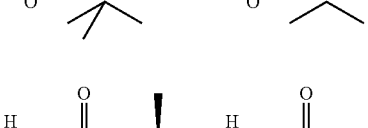 |
| PVA-056 | 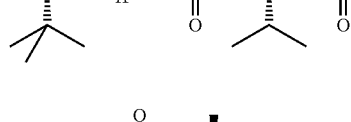 |
| PVA-057 | 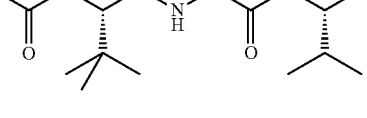 |
| PVA-058 | 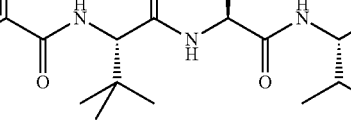 |

| Code | Structure |
|---|---|
| PVA-059 | 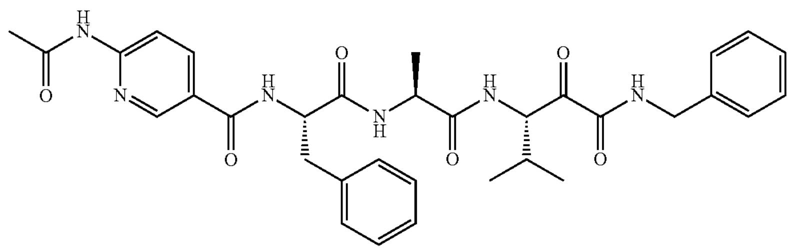 [SMILES: CC(=O)Nc1ccc(C(=O)N[C@@H](Cc2ccccc2)C(=O)N[C@@H](C)C(=O)N[C@H](C(=O)C(=O)NCc2ccccc2)C(C)C)cn1] |
| PVA-060 | 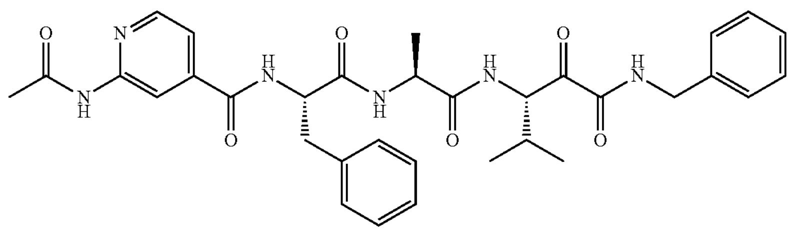 [SMILES: CC(=O)Nc1cc(C(=O)N[C@@H](Cc2ccccc2)C(=O)N[C@@H](C)C(=O)N[C@H](C(=O)C(=O)NCc2ccccc2)C(C)C)ccn1] |
| PVA-061 | 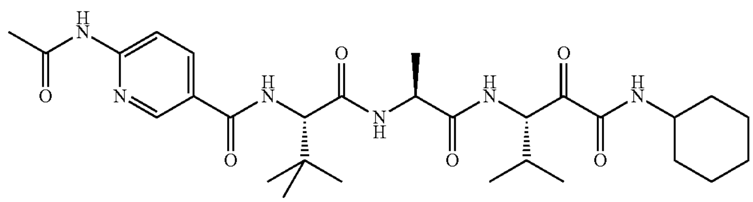 [SMILES: CC(=O)Nc1ccc(C(=O)N[C@H](C(=O)N[C@@H](C)C(=O)N[C@H](C(=O)C(=O)NC2CCCCC2)C(C)C)C(C)(C)C)cn1] |
| PVA-062 | 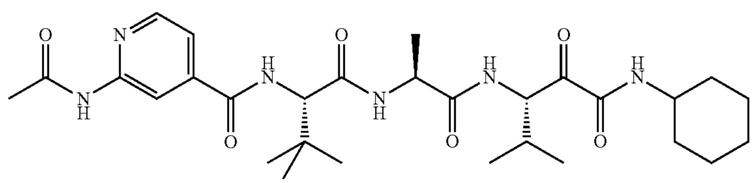 [SMILES: CC(=O)Nc1cc(C(=O)N[C@H](C(=O)N[C@@H](C)C(=O)N[C@H](C(=O)C(=O)NC2CCCCC2)C(C)C)C(C)(C)C)ccn1] |
| PVA-063 | 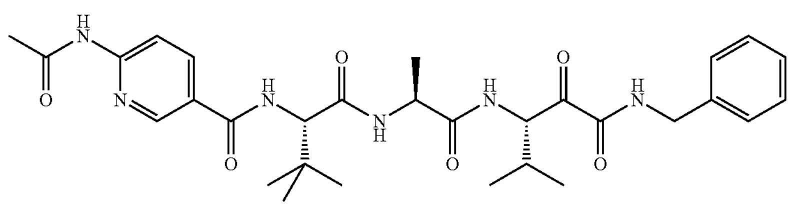 [SMILES: CC(=O)Nc1ccc(C(=O)N[C@H](C(=O)N[C@@H](C)C(=O)N[C@H](C(=O)C(=O)NCc2ccccc2)C(C)C)C(C)(C)C)cn1] |
| PVA-064 | 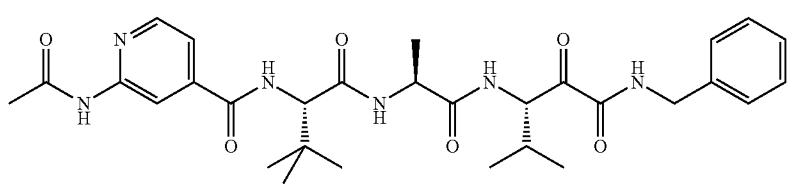 [SMILES: CC(=O)Nc1cc(C(=O)N[C@H](C(=O)N[C@@H](C)C(=O)N[C@H](C(=O)C(=O)NCc2ccccc2)C(C)C)C(C)(C)C)ccn1] |
| PVA-065 | 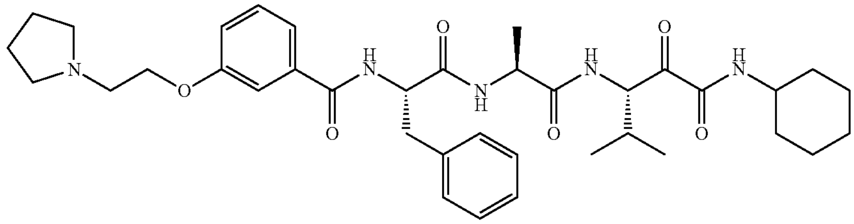 [SMILES: CC(C)[C@H](NC(=O)[C@H](C)NC(=O)[C@H](Cc1ccccc1)NC(=O)c1cccc(OCCN2CCCC2)c1)C(=O)C(=O)NC1CCCCC1] |

-continued

| Code | Structure |
|---|---|
| PVA-066 | 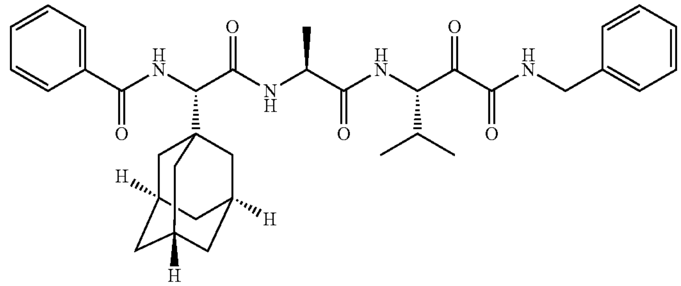 [SMILES: CC(C)[C@H](NC(=O)[C@H](C)NC(=O)[C@@H](NC(=O)c1ccccc1)C12C[C@H]3C[C@@H](C1)C[C@@H](C2)C3)C(=O)C(=O)NCc1ccccc1] |
| PVA-067 | 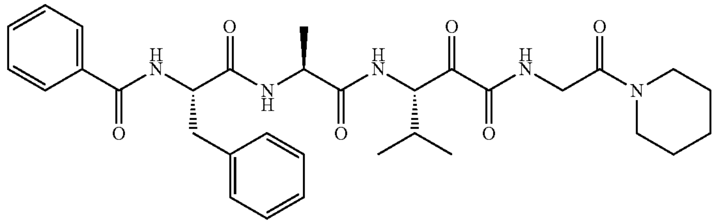 [SMILES: CC(C)[C@H](NC(=O)[C@H](C)NC(=O)[C@H](Cc1ccccc1)NC(=O)c1ccccc1)C(=O)C(=O)NCC(=O)N1CCCCC1] |
| PVA-068 | 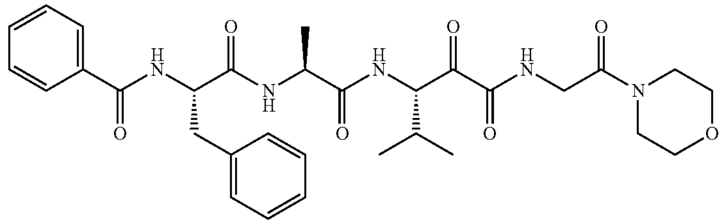 [SMILES: CC(C)[C@H](NC(=O)[C@H](C)NC(=O)[C@H](Cc1ccccc1)NC(=O)c1ccccc1)C(=O)C(=O)NCC(=O)N1CCOCC1] |
| PVA-069 | 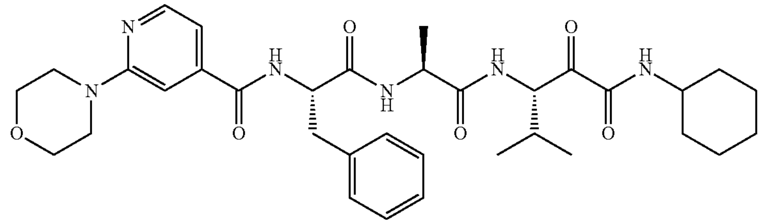 [SMILES: CC(C)[C@H](NC(=O)[C@H](C)NC(=O)[C@H](Cc1ccccc1)NC(=O)c1ccnc(N2CCOCC2)c1)C(=O)C(=O)NC1CCCCC1] |
| PVA-070 | 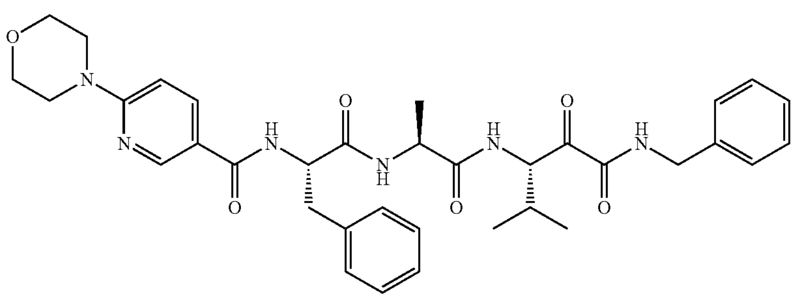 [SMILES: CC(C)[C@H](NC(=O)[C@H](C)NC(=O)[C@H](Cc1ccccc1)NC(=O)c1ccc(N2CCOCC2)nc1)C(=O)C(=O)NCc1ccccc1] |
| PVA-071 | 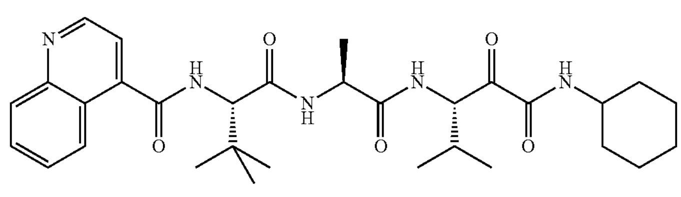 [SMILES: CC(C)[C@H](NC(=O)[C@H](C)NC(=O)[C@@H](NC(=O)c1ccnc2ccccc12)C(C)(C)C)C(=O)C(=O)NC1CCCCC1] |

| Code | Structure |
|---|---|
| PVA-072 | 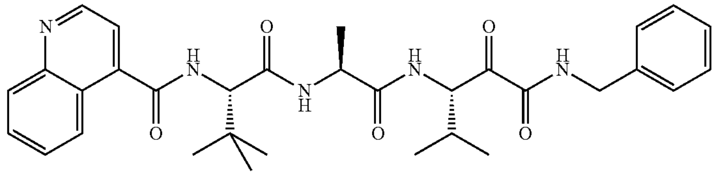 [SMILES: CC(C)[C@H](NC(=O)[C@H](C)NC(=O)[C@@H](NC(=O)c1ccnc2ccccc12)C(C)(C)C)C(=O)C(=O)NCc1ccccc1] |
| PVA-073 | 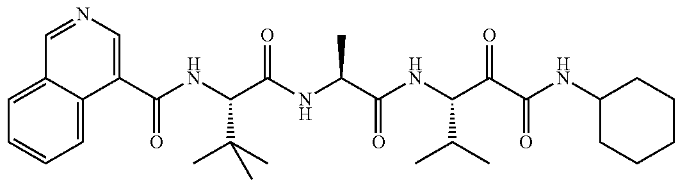 [SMILES: CC(C)[C@H](NC(=O)[C@H](C)NC(=O)[C@@H](NC(=O)c1cncc2ccccc12)C(C)(C)C)C(=O)C(=O)NC1CCCCC1] |
| PVA-074 | 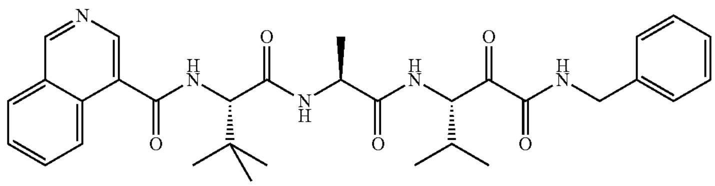 [SMILES: CC(C)[C@H](NC(=O)[C@H](C)NC(=O)[C@@H](NC(=O)c1cncc2ccccc12)C(C)(C)C)C(=O)C(=O)NCc1ccccc1] |
| PVA-075 | 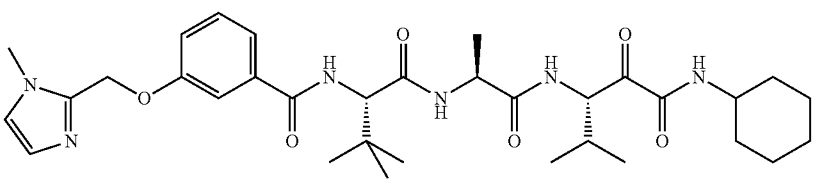 [SMILES: CC(C)[C@H](NC(=O)[C@H](C)NC(=O)[C@@H](NC(=O)c1cccc(OCc2nccn2C)c1)C(C)(C)C)C(=O)C(=O)NC1CCCCC1] |
| PVA-076 | 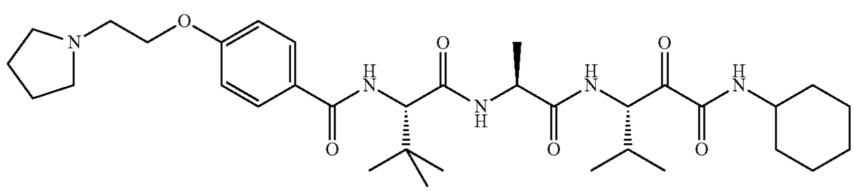 [SMILES: CC(C)[C@H](NC(=O)[C@H](C)NC(=O)[C@@H](NC(=O)c1ccc(OCCN2CCCC2)cc1)C(C)(C)C)C(=O)C(=O)NC1CCCCC1] |
| PVA-077 | 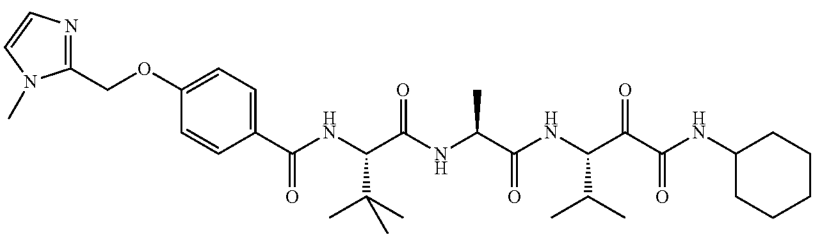 [SMILES: CC(C)[C@H](NC(=O)[C@H](C)NC(=O)[C@@H](NC(=O)c1ccc(OCc2nccn2C)cc1)C(C)(C)C)C(=O)C(=O)NC1CCCCC1] |
| PVA-078 | 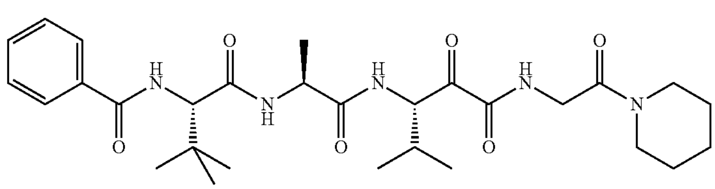 [SMILES: CC(C)[C@H](NC(=O)[C@H](C)NC(=O)[C@@H](NC(=O)c1ccccc1)C(C)(C)C)C(=O)C(=O)NCC(=O)N1CCCCC1] |
| PVA-079 | 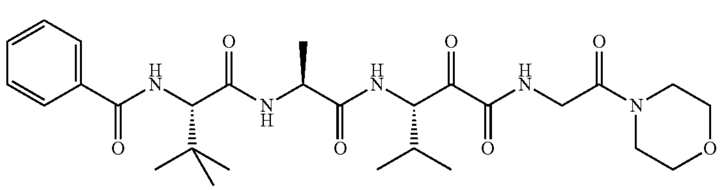 [SMILES: CC(C)[C@H](NC(=O)[C@H](C)NC(=O)[C@@H](NC(=O)c1ccccc1)C(C)(C)C)C(=O)C(=O)NCC(=O)N1CCOCC1] |

-continued

| Code | Structure |
|---|---|
| PVA-080 | 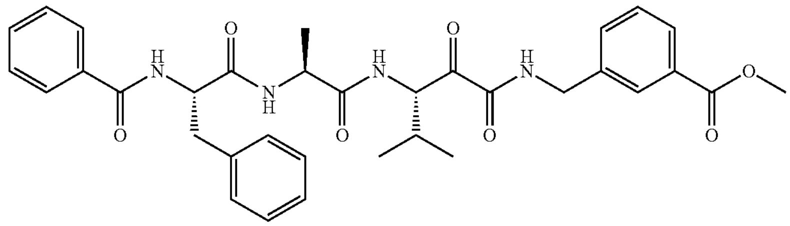 [SMILES: COC(=O)c1cccc(CNC(=O)C(=O)[C@@H](NC(=O)[C@H](C)NC(=O)[C@H](Cc2ccccc2)NC(=O)c2ccccc2)C(C)C)c1] |
| PVA-081 | 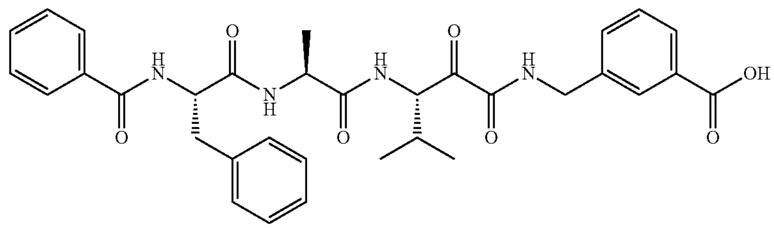 [SMILES: CC(C)[C@H](NC(=O)[C@H](C)NC(=O)[C@H](Cc1ccccc1)NC(=O)c1ccccc1)C(=O)C(=O)NCc1cccc(C(=O)O)c1] |
| PVA-082 | 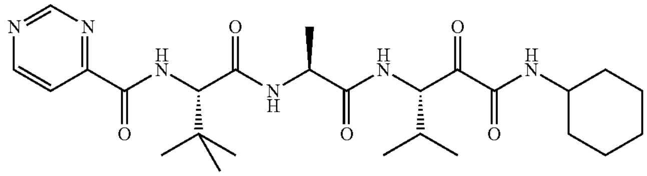 [SMILES: CC(C)[C@H](NC(=O)[C@H](C)NC(=O)[C@@H](NC(=O)c1ccncn1)C(C)(C)C)C(=O)C(=O)NC1CCCCC1] |
| PVA-083 | 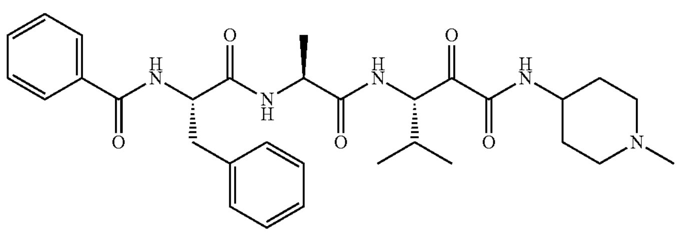 [SMILES: CC(C)[C@H](NC(=O)[C@H](C)NC(=O)[C@H](Cc1ccccc1)NC(=O)c1ccccc1)C(=O)C(=O)NC1CCN(C)CC1] |
| PVA-084 | 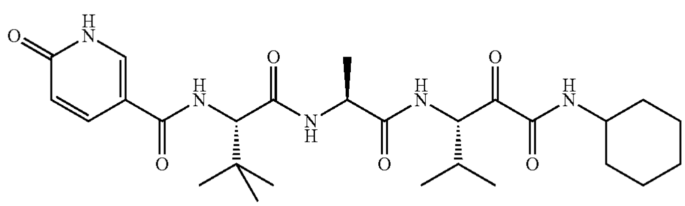 [SMILES: CC(C)[C@H](NC(=O)[C@H](C)NC(=O)[C@@H](NC(=O)c1ccc(=O)[nH]c1)C(C)(C)C)C(=O)C(=O)NC1CCCCC1] |
| PVA-085 | 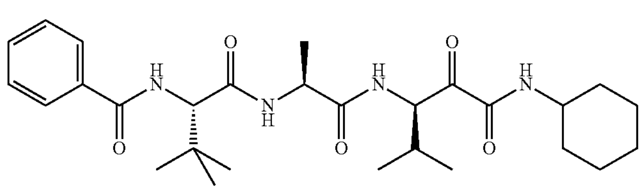 [SMILES: CC(C)[C@@H](NC(=O)[C@H](C)NC(=O)[C@@H](NC(=O)c1ccccc1)C(C)(C)C)C(=O)C(=O)NC1CCCCC1] |
| PVA-086 | 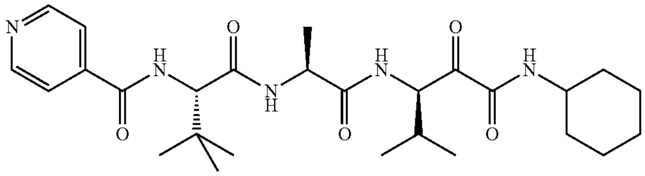 [SMILES: CC(C)[C@@H](NC(=O)[C@H](C)NC(=O)[C@@H](NC(=O)c1ccncc1)C(C)(C)C)C(=O)C(=O)NC1CCCCC1] |

-continued

| Code | Structure |
|---|---|
| PVA-087 | 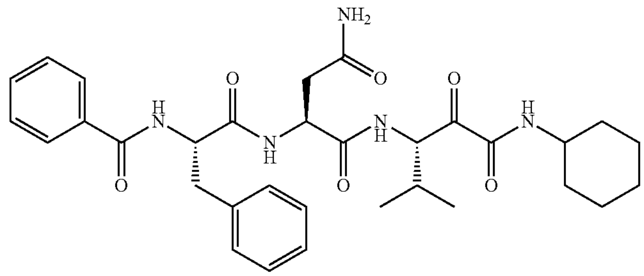 [SMILES: CC(C)[C@H](NC(=O)[C@H](CC(N)=O)NC(=O)[C@H](Cc1ccccc1)NC(=O)c1ccccc1)C(=O)C(=O)NC1CCCCC1] |
| PVA-088 | 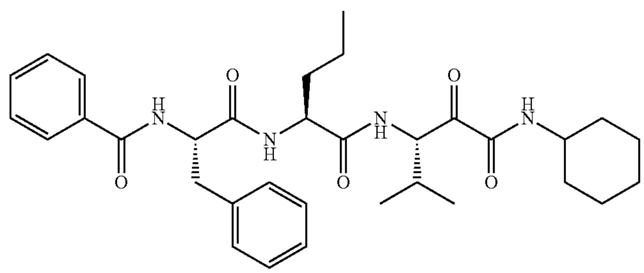 [SMILES: CCC[C@H](NC(=O)[C@H](Cc1ccccc1)NC(=O)c1ccccc1)C(=O)N[C@H](C(=O)C(=O)NC1CCCCC1)C(C)C] |
| PVA-089 | 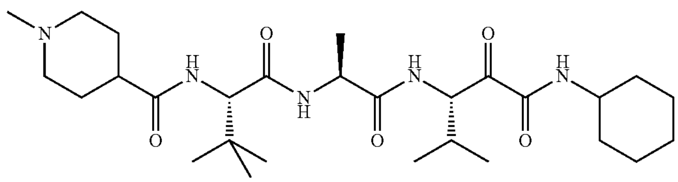 [SMILES: CC(C)[C@H](NC(=O)[C@H](C)NC(=O)[C@@H](NC(=O)C1CCN(C)CC1)C(C)(C)C)C(=O)C(=O)NC1CCCCC1] |
| PVA-090 | 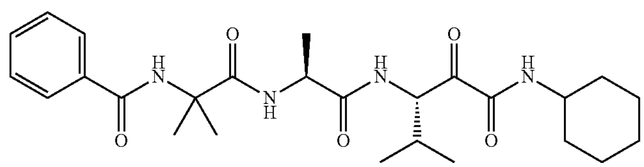 [SMILES: CC(C)[C@H](NC(=O)[C@H](C)NC(=O)C(C)(C)NC(=O)c1ccccc1)C(=O)C(=O)NC1CCCCC1] |
| PVA-091 | 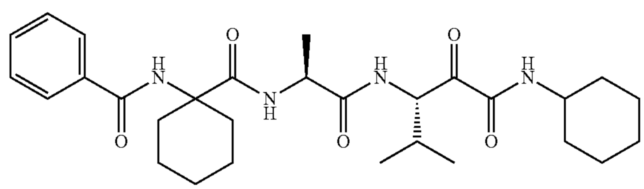 [SMILES: CC(C)[C@H](NC(=O)[C@H](C)NC(=O)C1(NC(=O)c2ccccc2)CCCCC1)C(=O)C(=O)NC1CCCCC1] |
| PVA-092 | 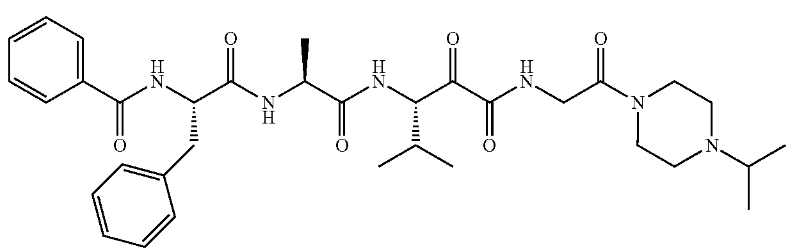 [SMILES: CC(C)[C@H](NC(=O)[C@H](C)NC(=O)[C@H](Cc1ccccc1)NC(=O)c1ccccc1)C(=O)C(=O)NCC(=O)N1CCN(C(C)C)CC1] |
| PVA-093 | 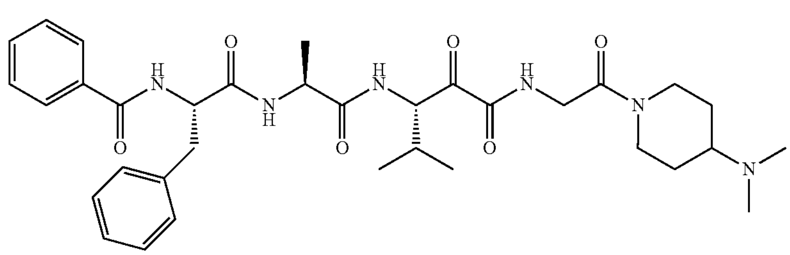 [SMILES: CC(C)[C@H](NC(=O)[C@H](C)NC(=O)[C@H](Cc1ccccc1)NC(=O)c1ccccc1)C(=O)C(=O)NCC(=O)N1CCC(N(C)C)CC1] |

| Code | Structure |
|---|---|
| PVA-094 | 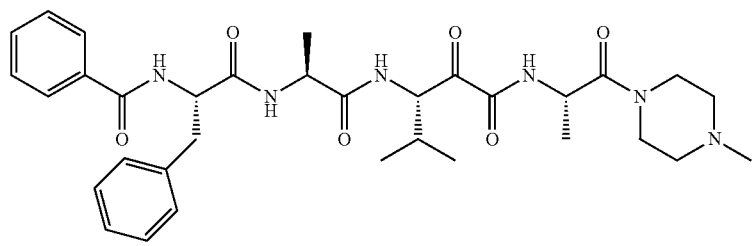 [SMILES: CC(C)[C@H](NC(=O)[C@H](C)NC(=O)[C@H](Cc1ccccc1)NC(=O)c1ccccc1)C(=O)C(=O)N[C@@H](C)C(=O)N1CCN(C)CC1] |
| PVA-095 | 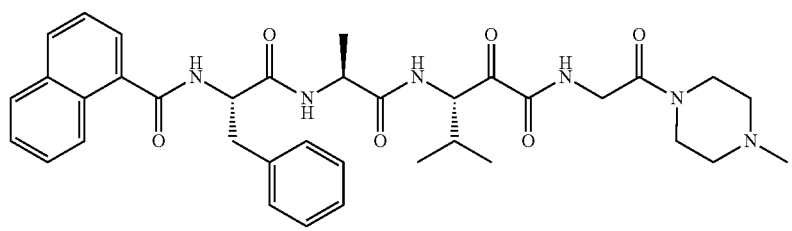 [SMILES: CC(C)[C@H](NC(=O)[C@H](C)NC(=O)[C@H](Cc1ccccc1)NC(=O)c1cccc2ccccc12)C(=O)C(=O)NCC(=O)N1CCN(C)CC1] |
| PVA-096 | 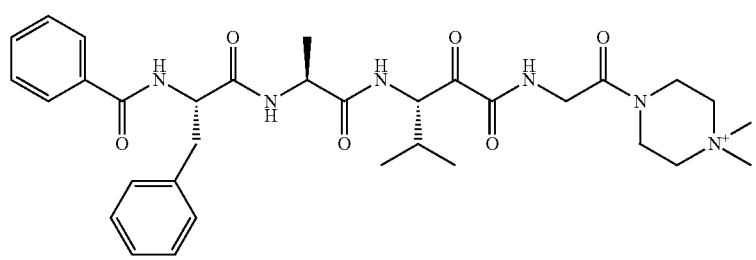 [SMILES: CC(C)[C@H](NC(=O)[C@H](C)NC(=O)[C@H](Cc1ccccc1)NC(=O)c1ccccc1)C(=O)C(=O)NCC(=O)N1CC[N+](C)(C)CC1] |
| PVA-097 | 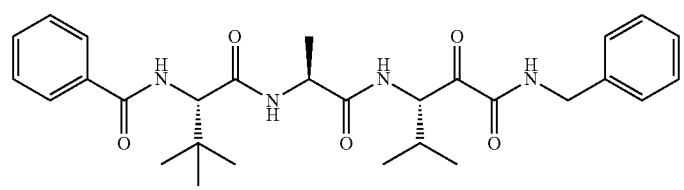 [SMILES: CC(C)[C@H](NC(=O)[C@H](C)NC(=O)[C@@H](NC(=O)c1ccccc1)C(C)(C)C)C(=O)C(=O)NCc1ccccc1] |
| PVA-098 | 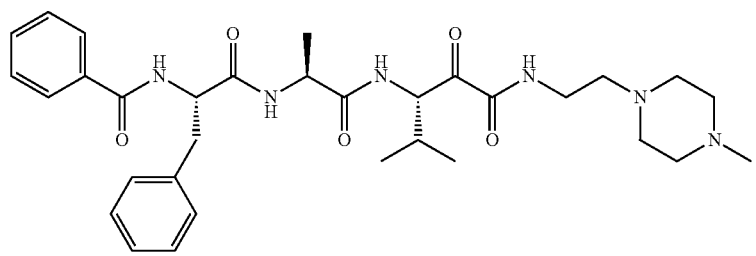 [SMILES: CC(C)[C@H](NC(=O)[C@H](C)NC(=O)[C@H](Cc1ccccc1)NC(=O)c1ccccc1)C(=O)C(=O)NCCN1CCN(C)CC1] |
| PVA-099 | 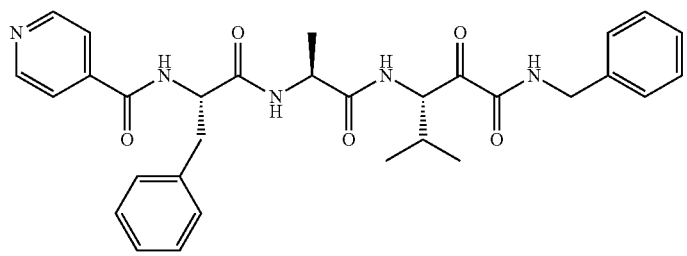 [SMILES: CC(C)[C@H](NC(=O)[C@H](C)NC(=O)[C@H](Cc1ccccc1)NC(=O)c1ccncc1)C(=O)C(=O)NCc1ccccc1] |

-continued

| Code | Structure |
|---|---|
| PVA-100 | 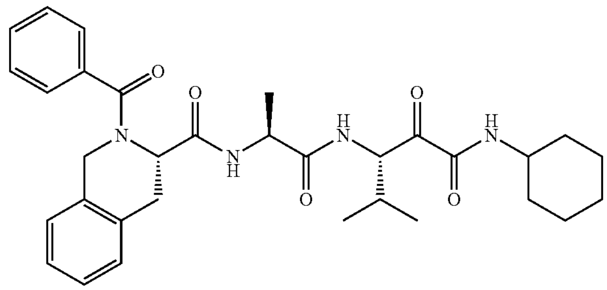 [SMILES: CC(C)[C@H](NC(=O)[C@H](C)NC(=O)[C@@H]1Cc2ccccc2CN1C(=O)c1ccccc1)C(=O)C(=O)NC1CCCCC1] |
| PVA-101 | 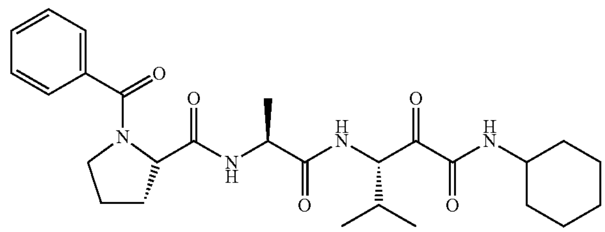 |
| PVA-102 | 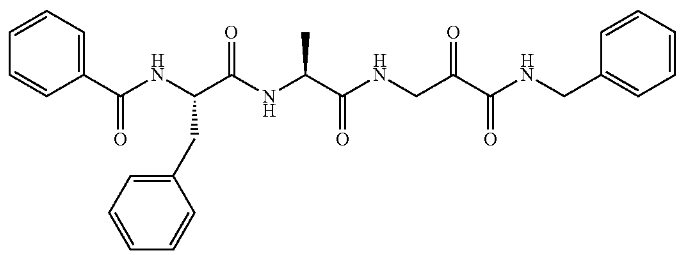 [SMILES: C[C@H](NC(=O)[C@H](Cc1ccccc1)NC(=O)c1ccccc1)C(=O)NCC(=O)C(=O)NCc1ccccc1] |
| PVA-103 | 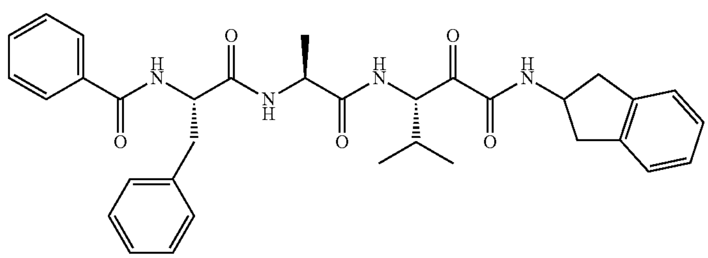 [SMILES: CC(C)[C@H](NC(=O)[C@H](C)NC(=O)[C@H](Cc1ccccc1)NC(=O)c1ccccc1)C(=O)C(=O)NC1Cc2ccccc2C1] |
| PVA-104 | 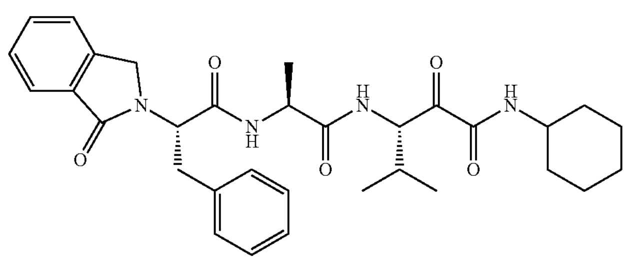 [SMILES: CC(C)[C@H](NC(=O)[C@H](C)NC(=O)[C@H](Cc1ccccc1)N1Cc2ccccc2C1=O)C(=O)C(=O)NC1CCCCC1] |
| PVA-105 | 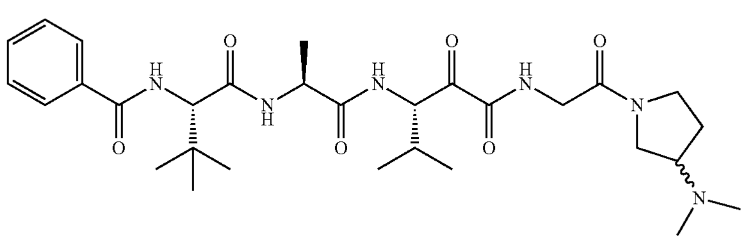 [SMILES: CC(C)[C@H](NC(=O)[C@H](C)NC(=O)[C@@H](NC(=O)c1ccccc1)C(C)(C)C)C(=O)C(=O)NCC(=O)N1CCC(N(C)C)C1] |

| Code | Structure |
|---|---|
| PVA-106 | 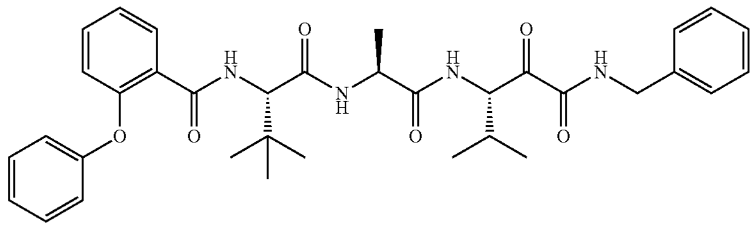 [SMILES: CC(C)[C@H](NC(=O)[C@H](C)NC(=O)[C@@H](NC(=O)c1ccccc1Oc1ccccc1)C(C)(C)C)C(=O)C(=O)NCc1ccccc1] |
| PVA-107 | 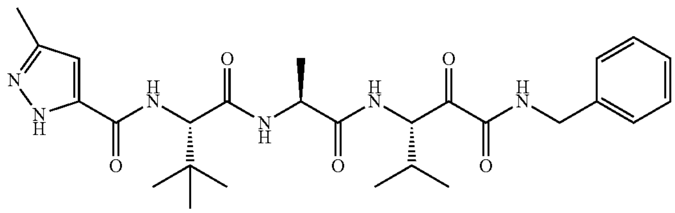 [SMILES: Cc1cc(C(=O)N[C@H](C(=O)N[C@@H](C)C(=O)N[C@H](C(=O)C(=O)NCc2ccccc2)C(C)C)C(C)(C)C)[nH]n1] |
| PVA-108 | 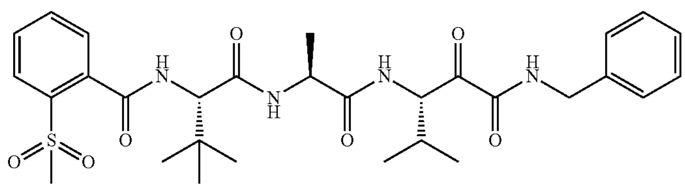 [SMILES: CC(C)[C@H](NC(=O)[C@H](C)NC(=O)[C@@H](NC(=O)c1ccccc1S(C)(=O)=O)C(C)(C)C)C(=O)C(=O)NCc1ccccc1] |
| PVA-109 | 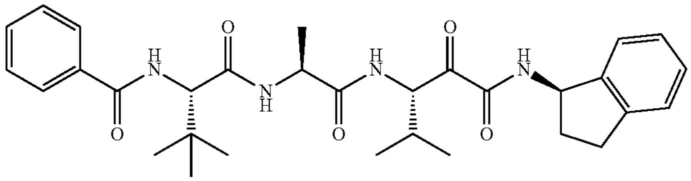 [SMILES: CC(C)[C@H](NC(=O)[C@H](C)NC(=O)[C@@H](NC(=O)c1ccccc1)C(C)(C)C)C(=O)C(=O)N[C@@H]1CCc2ccccc21] |
| PVA-110 | 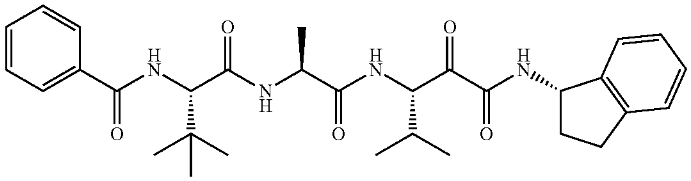 [SMILES: CC(C)[C@H](NC(=O)[C@H](C)NC(=O)[C@@H](NC(=O)c1ccccc1)C(C)(C)C)C(=O)C(=O)N[C@H]1CCc2ccccc21] |
| PVA-111 | 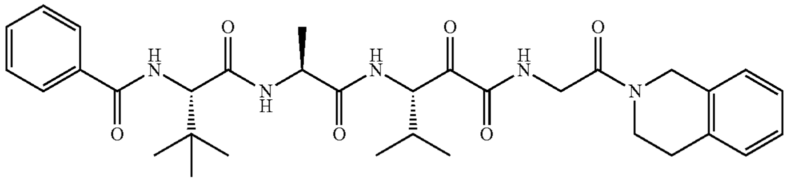 [SMILES: CC(C)[C@H](NC(=O)[C@H](C)NC(=O)[C@@H](NC(=O)c1ccccc1)C(C)(C)C)C(=O)C(=O)NCC(=O)N1CCc2ccccc2C1] |
| PVA-112 | 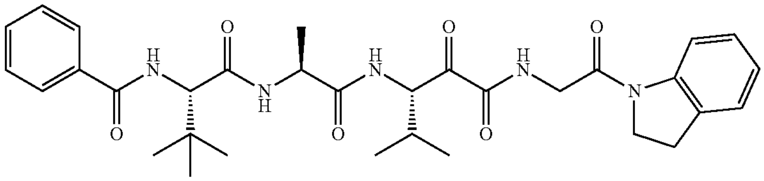 [SMILES: CC(C)[C@H](NC(=O)[C@H](C)NC(=O)[C@@H](NC(=O)c1ccccc1)C(C)(C)C)C(=O)C(=O)NCC(=O)N1CCc2ccccc21] |

| Code | Structure |
|---|---|
| PVA-113 | 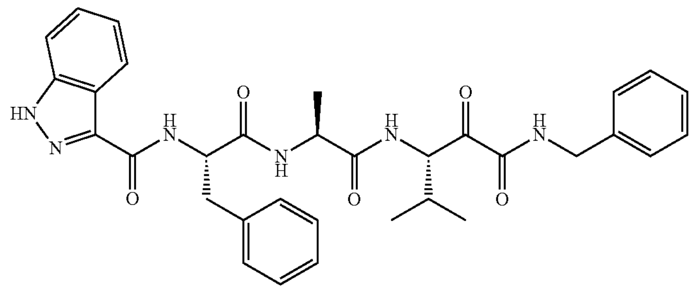 [SMILES: CC(C)[C@H](NC(=O)[C@H](C)NC(=O)[C@H](Cc1ccccc1)NC(=O)c1n[nH]c2ccccc12)C(=O)C(=O)NCc1ccccc1] |
| PVA-114 | 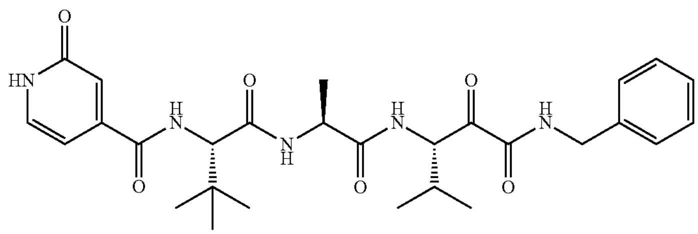 [SMILES: CC(C)[C@H](NC(=O)[C@H](C)NC(=O)[C@@H](NC(=O)c1cc[nH]c(=O)c1)C(C)(C)C)C(=O)C(=O)NCc1ccccc1] |
| PVA-115 | 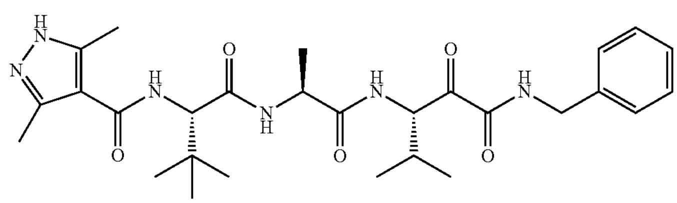 [SMILES: Cc1n[nH]c(C)c1C(=O)N[C@H](C(=O)N[C@@H](C)C(=O)N[C@H](C(=O)C(=O)NCc1ccccc1)C(C)C)C(C)(C)C] |
| PVA-116 | 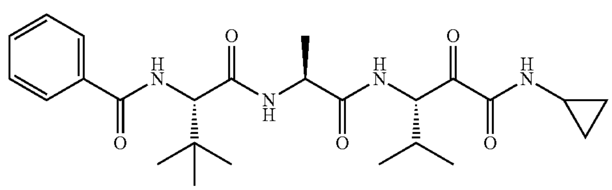 [SMILES: CC(C)[C@H](NC(=O)[C@H](C)NC(=O)[C@@H](NC(=O)c1ccccc1)C(C)(C)C)C(=O)C(=O)NC1CC1] |
| PVA-117 | 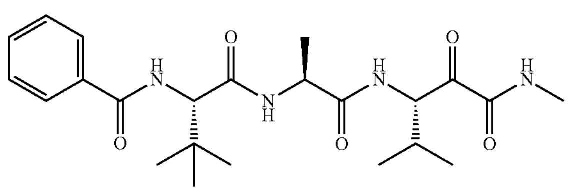 [SMILES: CNC(=O)C(=O)[C@@H](NC(=O)[C@H](C)NC(=O)[C@@H](NC(=O)c1ccccc1)C(C)(C)C)C(C)C] |
| PVA-118 | 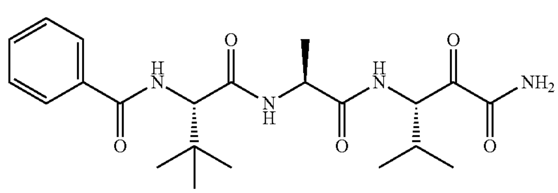 [SMILES: CC(C)[C@H](NC(=O)[C@H](C)NC(=O)[C@@H](NC(=O)c1ccccc1)C(C)(C)C)C(=O)C(N)=O] |
| PVA-119 | 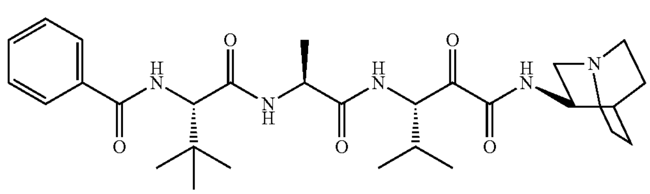 |

| Code | Structure |
|---|---|
| PVA-120 | 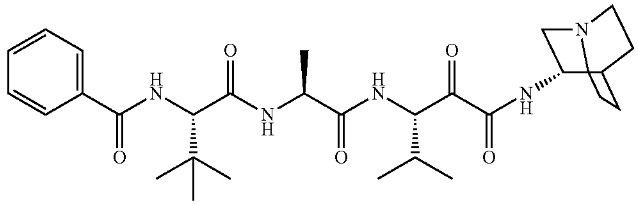 [SMILES: CC(C)[C@H](NC(=O)[C@H](C)NC(=O)[C@@H](NC(=O)c1ccccc1)C(C)(C)C)C(=O)C(=O)N[C@@H]1CN2CCC3CCC312] |
| PVA-121 | 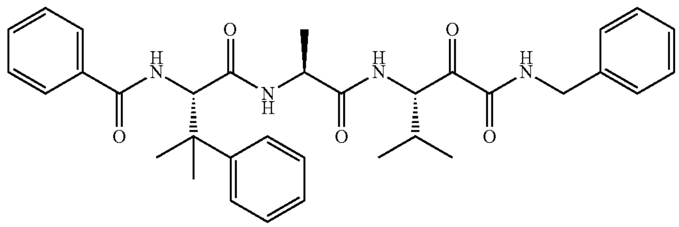 [SMILES: CC(C)[C@H](NC(=O)[C@H](C)NC(=O)[C@@H](NC(=O)c1ccccc1)C(C)(C)c1ccccc1)C(=O)C(=O)NCc1ccccc1] |
| PVA-122 | 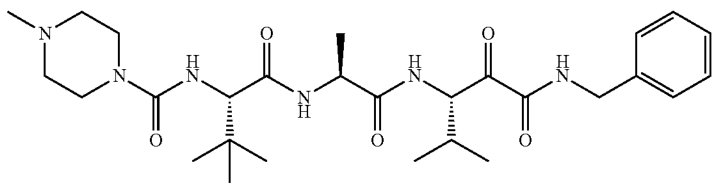 [SMILES: CC(C)[C@H](NC(=O)[C@H](C)NC(=O)[C@@H](NC(=O)N1CCN(C)CC1)C(C)(C)C)C(=O)C(=O)NCc1ccccc1] |
| PVA-123 | 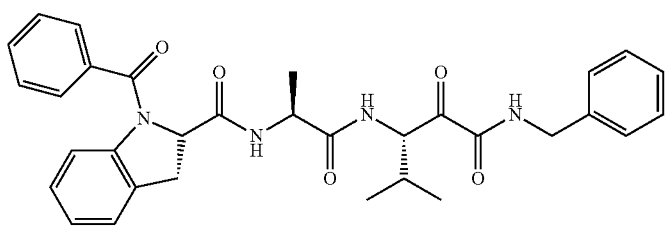 |
| PVA-124 | 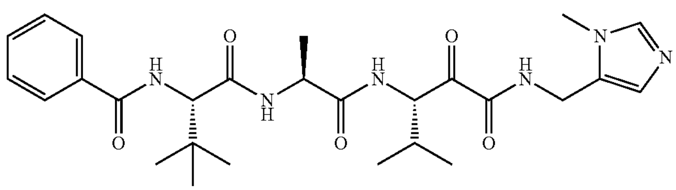 [SMILES: CC(C)[C@H](NC(=O)[C@H](C)NC(=O)[C@@H](NC(=O)c1ccccc1)C(C)(C)C)C(=O)C(=O)NCc1cncn1C] |
| PVA-125 | 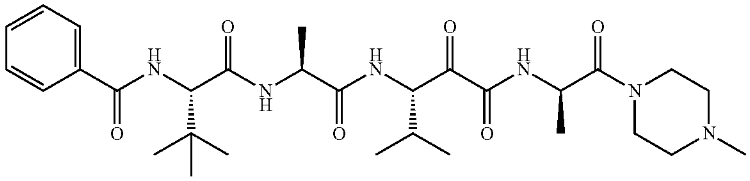 [SMILES: CC(C)[C@H](NC(=O)[C@H](C)NC(=O)[C@@H](NC(=O)c1ccccc1)C(C)(C)C)C(=O)C(=O)N[C@H](C)C(=O)N1CCN(C)CC1] |
| PVA-126 | 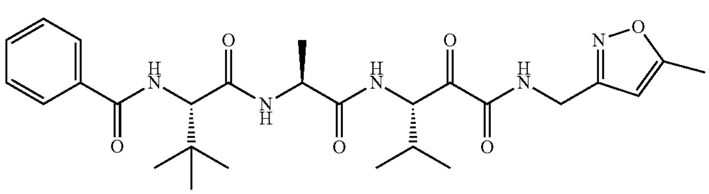 [SMILES: Cc1cc(CNC(=O)C(=O)[C@@H](NC(=O)[C@H](C)NC(=O)[C@@H](NC(=O)c2ccccc2)C(C)(C)C)C(C)C)no1] |

| Code | Structure |
|---|---|
| PVA-127 | 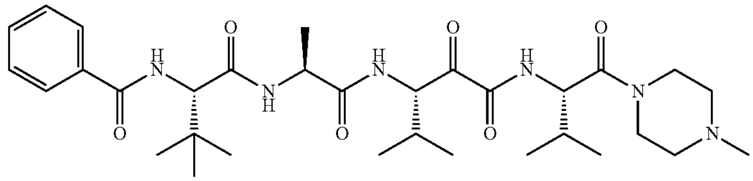 [SMILES: CC(C)[C@H](NC(=O)[C@H](C)NC(=O)[C@@H](NC(=O)c1ccccc1)C(C)(C)C)C(=O)C(=O)N[C@H](C(=O)N1CCN(C)CC1)C(C)C] |
| PVA-128 | 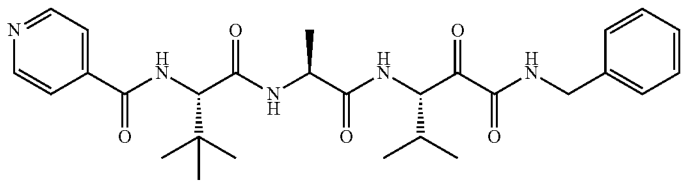 [SMILES: CC(C)[C@H](NC(=O)[C@H](C)NC(=O)[C@@H](NC(=O)c1ccncc1)C(C)(C)C)C(=O)C(=O)NCc1ccccc1] |
| PVA-129 | 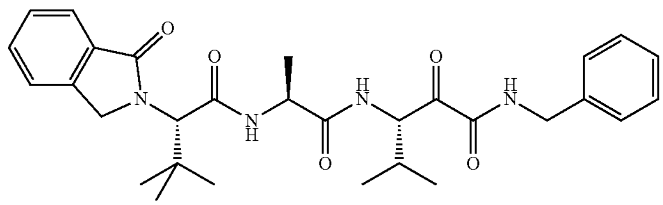 [SMILES: CC(C)[C@H](NC(=O)[C@H](C)NC(=O)[C@@H](N1Cc2ccccc2C1=O)C(C)(C)C)C(=O)C(=O)NCc1ccccc1] |
| PVA-130 | 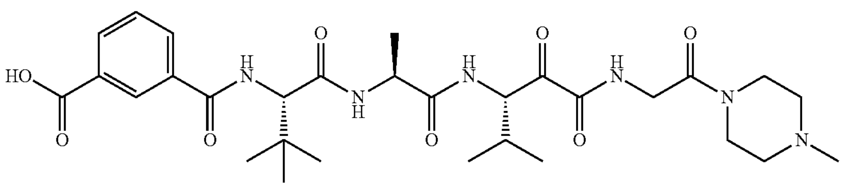 [SMILES: CC(C)[C@H](NC(=O)[C@H](C)NC(=O)[C@@H](NC(=O)c1cccc(C(=O)O)c1)C(C)(C)C)C(=O)C(=O)NCC(=O)N1CCN(C)CC1] |
| PVA-131 | 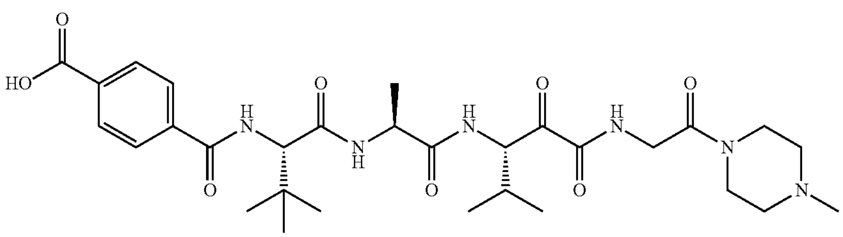 [SMILES: CC(C)[C@H](NC(=O)[C@H](C)NC(=O)[C@@H](NC(=O)c1ccc(C(=O)O)cc1)C(C)(C)C)C(=O)C(=O)NCC(=O)N1CCN(C)CC1] |
| PVA-132 | 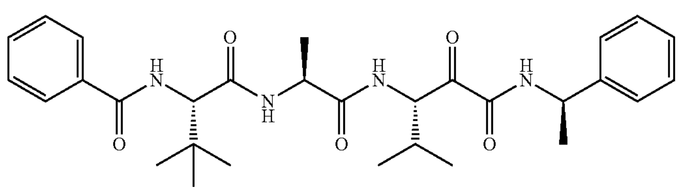 [SMILES: CC(C)[C@H](NC(=O)[C@H](C)NC(=O)[C@@H](NC(=O)c1ccccc1)C(C)(C)C)C(=O)C(=O)N[C@H](C)c1ccccc1] |
| PVA-133 | 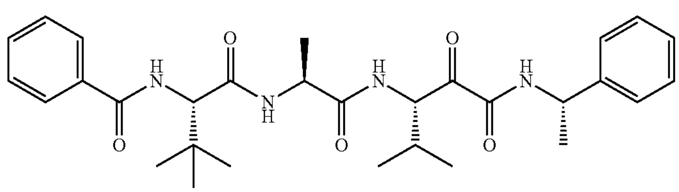 [SMILES: CC(C)[C@H](NC(=O)[C@H](C)NC(=O)[C@@H](NC(=O)c1ccccc1)C(C)(C)C)C(=O)C(=O)N[C@@H](C)c1ccccc1] |
| PVA-134 | 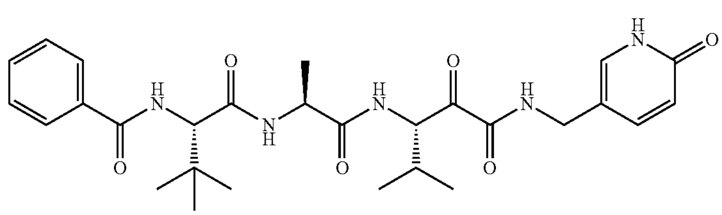 [SMILES: CC(C)[C@H](NC(=O)[C@H](C)NC(=O)[C@@H](NC(=O)c1ccccc1)C(C)(C)C)C(=O)C(=O)NCc1ccc(=O)[nH]c1] |

| Code | Structure |
|---|---|
| PVA-135 | 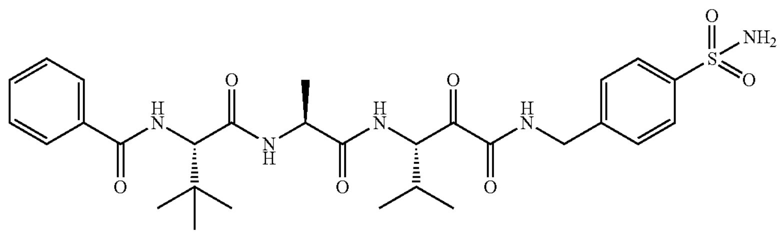 [SMILES: CC(C)[C@H](NC(=O)[C@H](C)NC(=O)[C@@H](NC(=O)c1ccccc1)C(C)(C)C)C(=O)C(=O)NCc1ccc(S(N)(=O)=O)cc1] |
| PVA-136 | 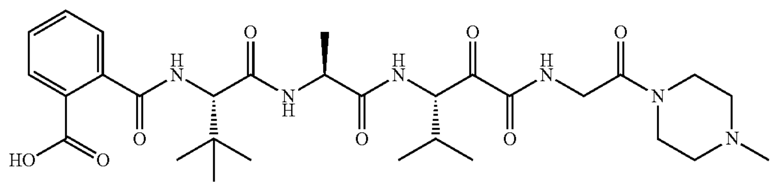 [SMILES: CC(C)[C@H](NC(=O)[C@H](C)NC(=O)[C@@H](NC(=O)c1ccccc1C(=O)O)C(C)(C)C)C(=O)C(=O)NCC(=O)N1CCN(C)CC1] |
| PVA-137 | 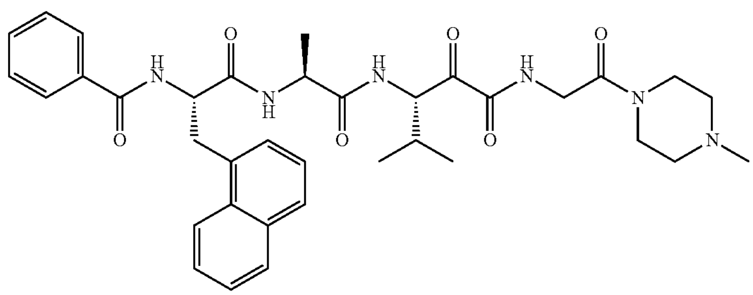 [SMILES: CC(C)[C@H](NC(=O)[C@H](C)NC(=O)[C@H](Cc1cccc2ccccc12)NC(=O)c1ccccc1)C(=O)C(=O)NCC(=O)N1CCN(C)CC1] |
| PVA-138 | 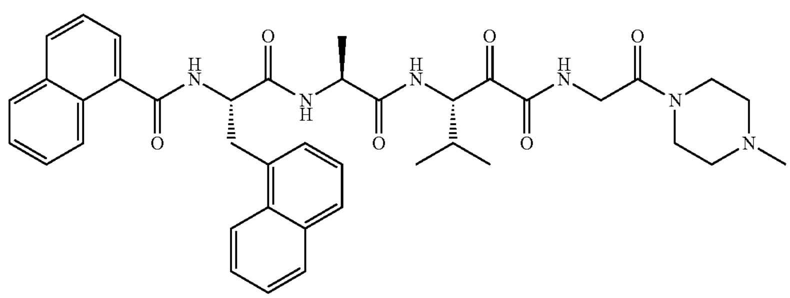 [SMILES: CC(C)[C@H](NC(=O)[C@H](C)NC(=O)[C@H](Cc1cccc2ccccc12)NC(=O)c1cccc2ccccc12)C(=O)C(=O)NCC(=O)N1CCN(C)CC1] |
| PVA-139 | 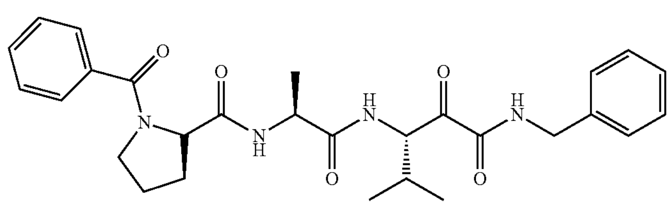 |
| PVA-140 | 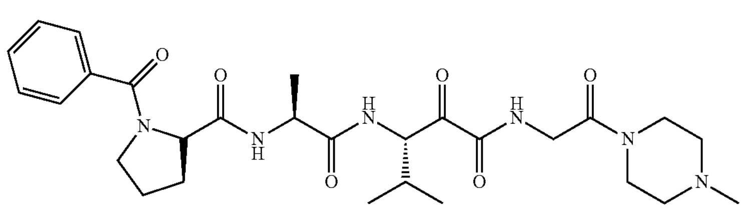 |

-continued

| Code | Structure |
|---|---|
| PVA-141 | 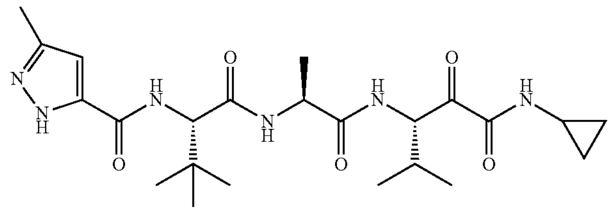 [SMILES: Cc1cc(C(=O)N[C@H](C(=O)N[C@@H](C)C(=O)N[C@H](C(=O)C(=O)NC2CC2)C(C)C)C(C)(C)C)[nH]n1] |
| PVA-142 | 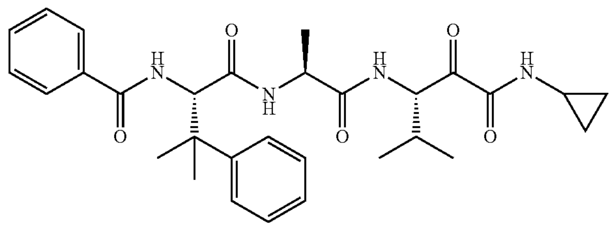 [SMILES: CC(C)[C@H](NC(=O)[C@H](C)NC(=O)[C@@H](NC(=O)c1ccccc1)C(C)(C)c1ccccc1)C(=O)C(=O)NC1CC1] |
| PVA-143 | 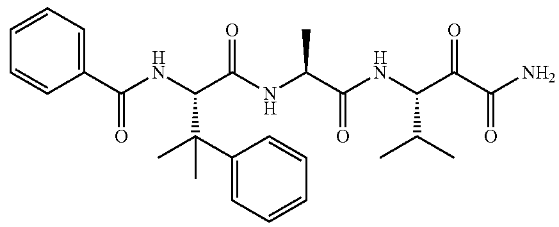 [SMILES: CC(C)[C@H](NC(=O)[C@H](C)NC(=O)[C@@H](NC(=O)c1ccccc1)C(C)(C)c1ccccc1)C(=O)C(N)=O] |
| PVA-144 | 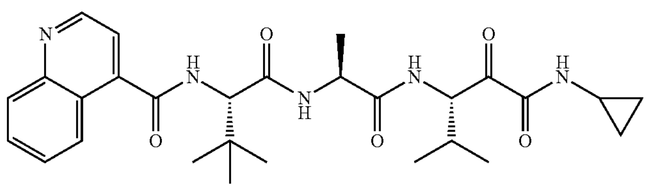 [SMILES: CC(C)[C@H](NC(=O)[C@H](C)NC(=O)[C@@H](NC(=O)c1ccnc2ccccc12)C(C)(C)C)C(=O)C(=O)NC1CC1] |
| PVA-145 | 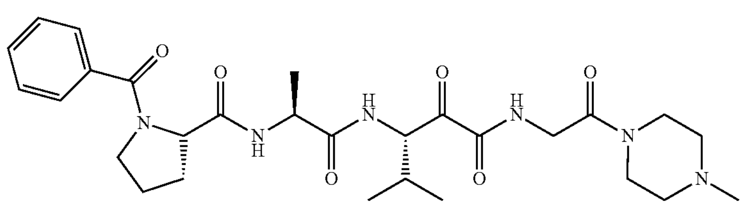 |
| PVA-146 | 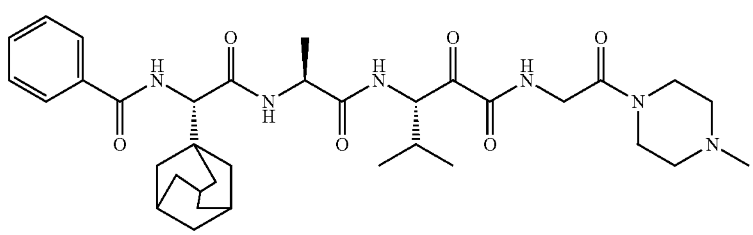 [SMILES: CC(C)[C@H](NC(=O)[C@H](C)NC(=O)[C@@H](NC(=O)c1ccccc1)C12CC3CC(CC(C3)C1)C2)C(=O)C(=O)NCC(=O)N1CCN(C)CC1] |
| PVA-147 | 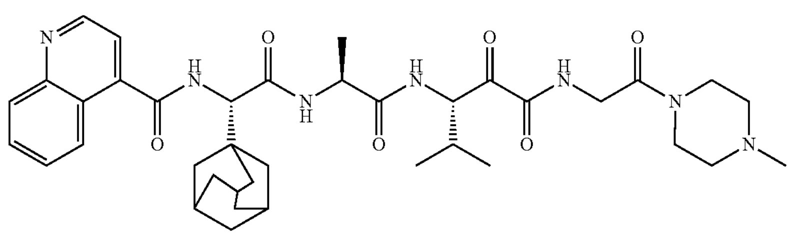 [SMILES: CC(C)[C@H](NC(=O)[C@H](C)NC(=O)[C@@H](NC(=O)c1ccnc2ccccc12)C12CC3CC(CC(C3)C1)C2)C(=O)C(=O)NCC(=O)N1CCN(C)CC1] |

-continued

| Code | Structure |
|---|---|
| PVA-148 | 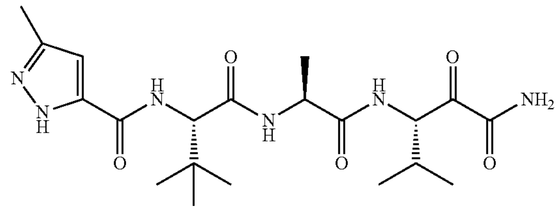 [SMILES: Cc1cc(C(=O)N[C@H](C(=O)N[C@@H](C)C(=O)N[C@H](C(=O)C(N)=O)C(C)C)C(C)(C)C)[nH]n1] |
| PVA-149 | 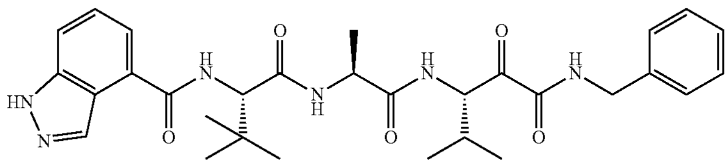 [SMILES: CC(C)[C@H](NC(=O)[C@H](C)NC(=O)[C@@H](NC(=O)c1cccc2[nH]ncc12)C(C)(C)C)C(=O)C(=O)NCc1ccccc1] |
| PVA-150 | 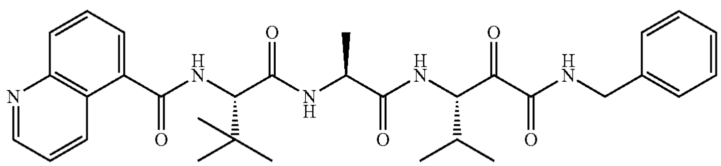 [SMILES: CC(C)[C@H](NC(=O)[C@H](C)NC(=O)[C@@H](NC(=O)c1cccc2ncccc12)C(C)(C)C)C(=O)C(=O)NCc1ccccc1] |
| PVA-151 | 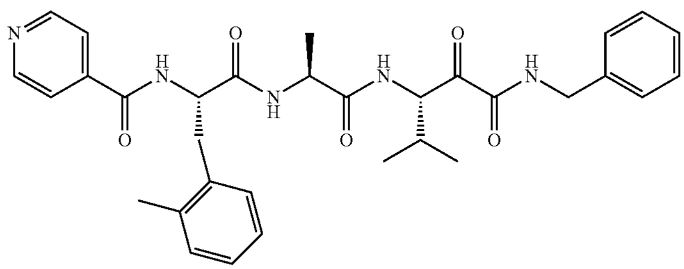 [SMILES: Cc1ccccc1C[C@H](NC(=O)c1ccncc1)C(=O)N[C@@H](C)C(=O)N[C@H](C(=O)C(=O)NCc1ccccc1)C(C)C] |
| PVA-152 | 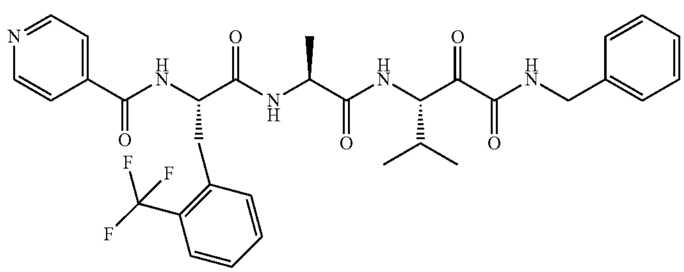 [SMILES: CC(C)[C@H](NC(=O)[C@H](C)NC(=O)[C@H](Cc1ccccc1C(F)(F)F)NC(=O)c1ccncc1)C(=O)C(=O)NCc1ccccc1] |
| PVA-153 | 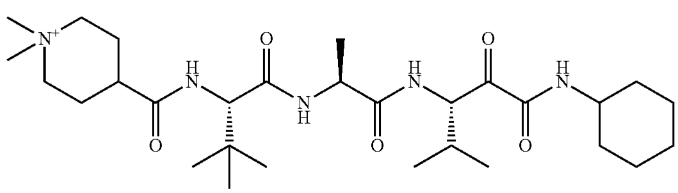 [SMILES: CC(C)[C@H](NC(=O)[C@H](C)NC(=O)[C@@H](NC(=O)C1CC[N+](C)(C)CC1)C(C)(C)C)C(=O)C(=O)NC1CCCCC1] |
| PVA-154 | 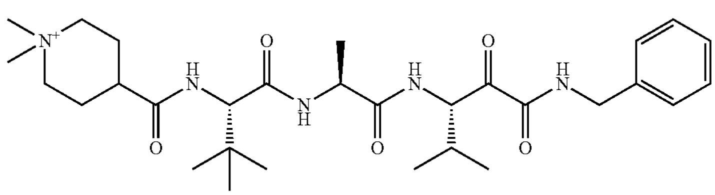 [SMILES: CC(C)[C@H](NC(=O)[C@H](C)NC(=O)[C@@H](NC(=O)C1CC[N+](C)(C)CC1)C(C)(C)C)C(=O)C(=O)NCc1ccccc1] |

-continued
| Code | Structure |
|---|---|
| PVA-155 | 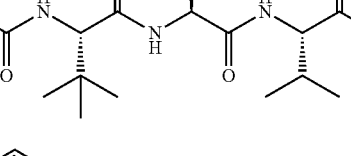 |
| PVA-156 | 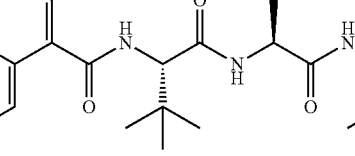 |
| PVA-157 | 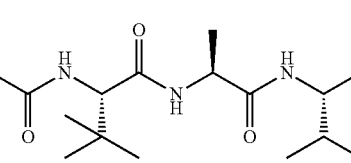 |
| PVA-158 | 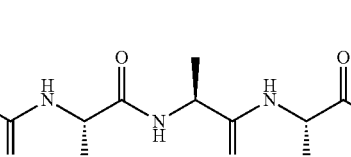 |
| PVA-159 | 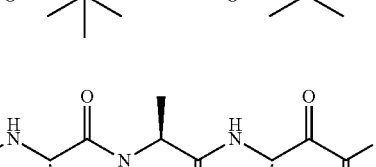 |
| PVA-160 | 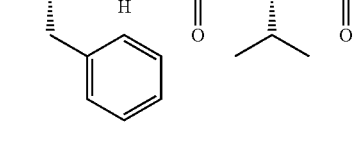 |
| PVA-161 | 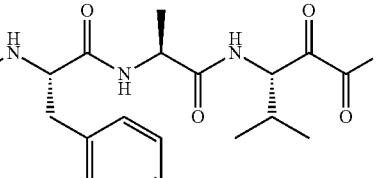 |

| Code | Structure |
|---|---|
| PVA-162 | 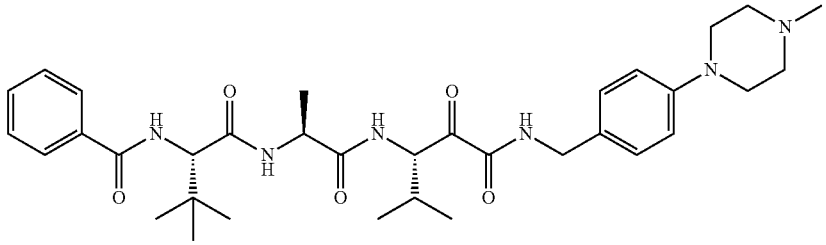 [SMILES: CC(C)[C@H](NC(=O)[C@H](C)NC(=O)[C@@H](NC(=O)c1ccccc1)C(C)(C)C)C(=O)C(=O)NCc1ccc(N2CCN(C)CC2)cc1] |
| PVA-163 | 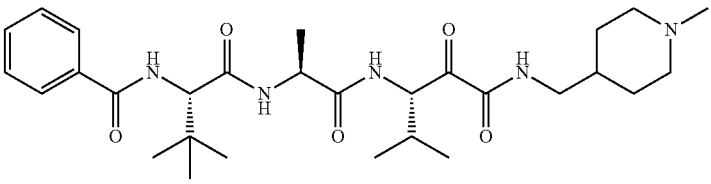 [SMILES: CC(C)[C@H](NC(=O)[C@H](C)NC(=O)[C@@H](NC(=O)c1ccccc1)C(C)(C)C)C(=O)C(=O)NCC1CCN(C)CC1] |
| PVA-164 | 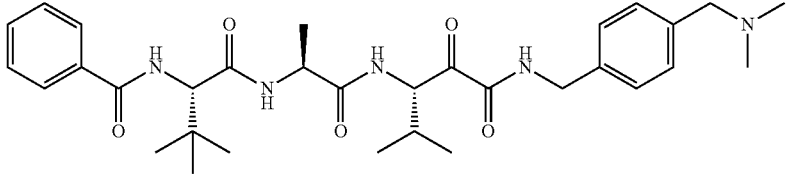 [SMILES: CC(C)[C@H](NC(=O)[C@H](C)NC(=O)[C@@H](NC(=O)c1ccccc1)C(C)(C)C)C(=O)C(=O)NCc1ccc(CN(C)C)cc1] |
| PVA-165 | 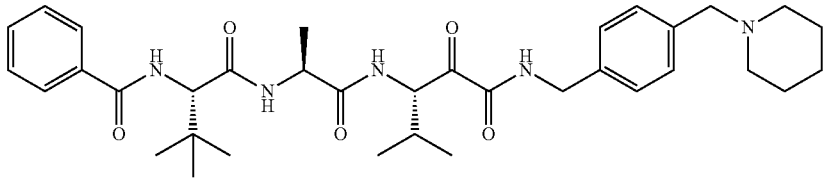 [SMILES: CC(C)[C@H](NC(=O)[C@H](C)NC(=O)[C@@H](NC(=O)c1ccccc1)C(C)(C)C)C(=O)C(=O)NCc1ccc(CN2CCCCC2)cc1] |
| PVA-166 | 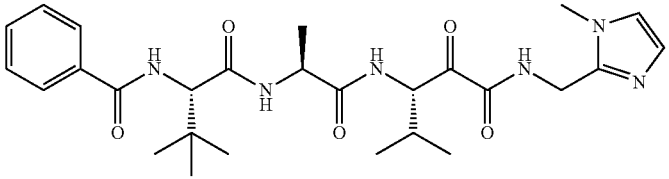 [SMILES: CC(C)[C@H](NC(=O)[C@H](C)NC(=O)[C@@H](NC(=O)c1ccccc1)C(C)(C)C)C(=O)C(=O)NCc1nccn1C] |
| PVA-167 | 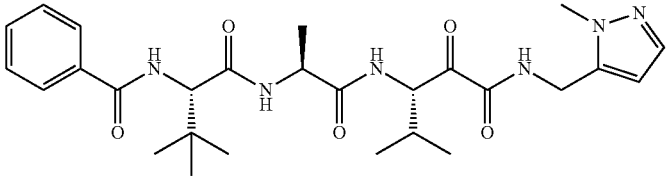 [SMILES: CC(C)[C@H](NC(=O)[C@H](C)NC(=O)[C@@H](NC(=O)c1ccccc1)C(C)(C)C)C(=O)C(=O)NCc1ccnn1C] |
| PVA-168 | 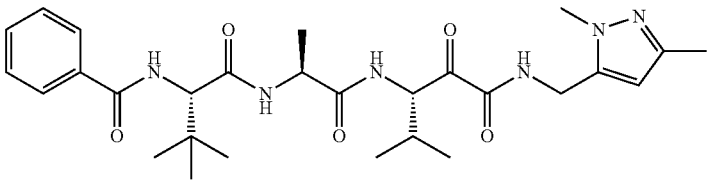 [SMILES: Cc1cc(CNC(=O)C(=O)[C@@H](NC(=O)[C@H](C)NC(=O)[C@@H](NC(=O)c2ccccc2)C(C)(C)C)C(C)C)n(C)n1] |

| Code | Structure |
|---|---|
| PVA-169 | 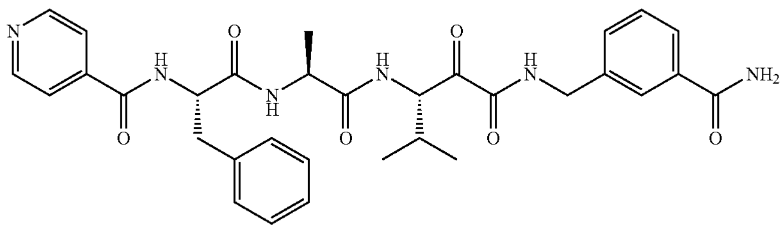 [SMILES: CC(C)[C@H](NC(=O)[C@H](C)NC(=O)[C@H](Cc1ccccc1)NC(=O)c1ccncc1)C(=O)C(=O)NCc1cccc(C(N)=O)c1] |
| PVA-170 | 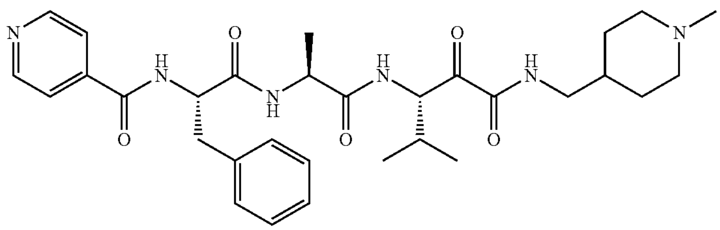 [SMILES: CC(C)[C@H](NC(=O)[C@H](C)NC(=O)[C@H](Cc1ccccc1)NC(=O)c1ccncc1)C(=O)C(=O)NCC1CCN(C)CC1] |
| PVA-171 | 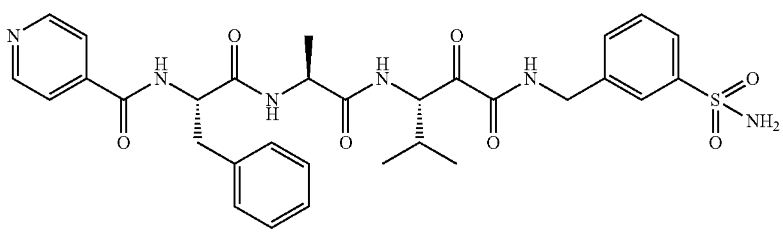 [SMILES: CC(C)[C@H](NC(=O)[C@H](C)NC(=O)[C@H](Cc1ccccc1)NC(=O)c1ccncc1)C(=O)C(=O)NCc1cccc(S(N)(=O)=O)c1] |
| PVA-172 | 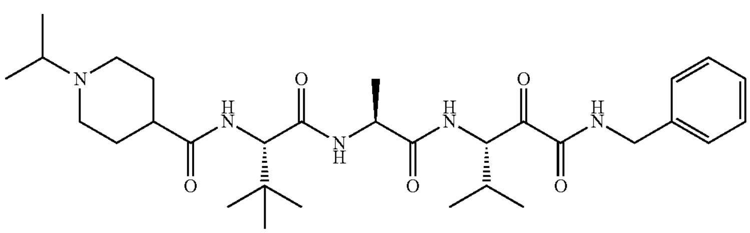 [SMILES: CC(C)[C@H](NC(=O)[C@H](C)NC(=O)[C@@H](NC(=O)C1CCN(C(C)C)CC1)C(C)(C)C)C(=O)C(=O)NCc1ccccc1] |
| PVA-173 | 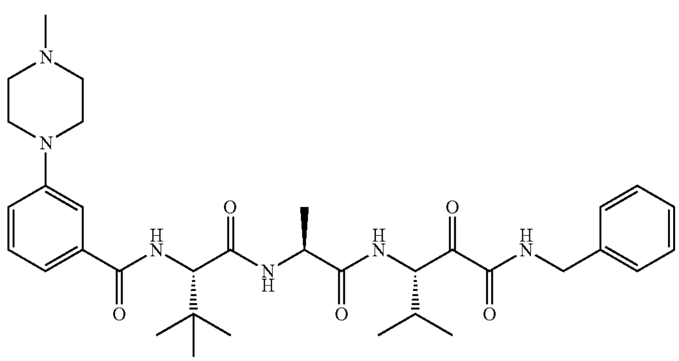 [SMILES: CC(C)[C@H](NC(=O)[C@H](C)NC(=O)[C@@H](NC(=O)c1cccc(N2CCN(C)CC2)c1)C(C)(C)C)C(=O)C(=O)NCc1ccccc1] |
| PVA-174 | 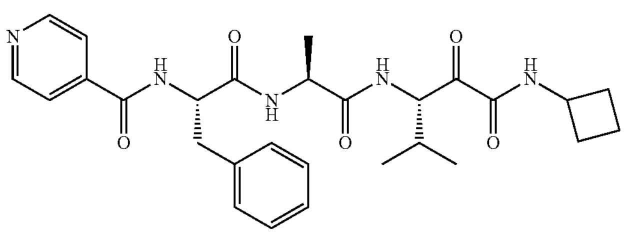 [SMILES: CC(C)[C@H](NC(=O)[C@H](C)NC(=O)[C@H](Cc1ccccc1)NC(=O)c1ccncc1)C(=O)C(=O)NC1CCC1] |

-continued

| Code | Structure |
|---|---|
| PVA-175 | 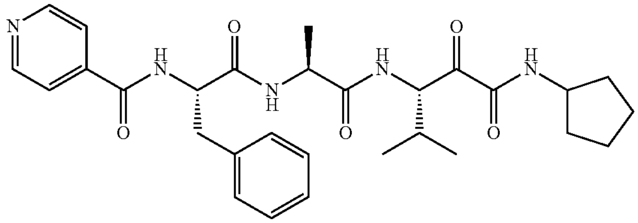 [SMILES: CC(C)[C@H](NC(=O)[C@H](C)NC(=O)[C@H](Cc1ccccc1)NC(=O)c1ccncc1)C(=O)C(=O)NC1CCCC1] |
| PVA-176 | 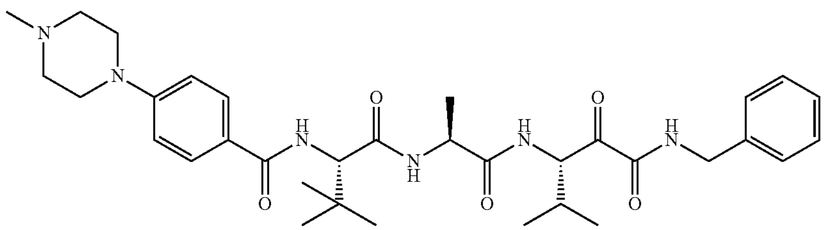 [SMILES: CC(C)[C@H](NC(=O)[C@H](C)NC(=O)[C@@H](NC(=O)c1ccc(N2CCN(C)CC2)cc1)C(C)(C)C)C(=O)C(=O)NCc1ccccc1] |
| PVA-177 | 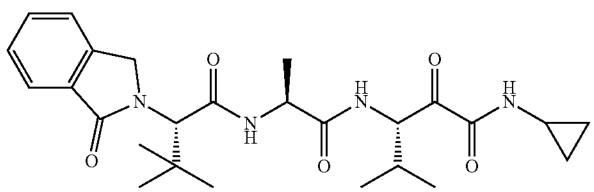 [SMILES: CC(C)[C@H](NC(=O)[C@H](C)NC(=O)[C@@H](N1Cc2ccccc2C1=O)C(C)(C)C)C(=O)C(=O)NC1CC1] |
| PVA-178 | 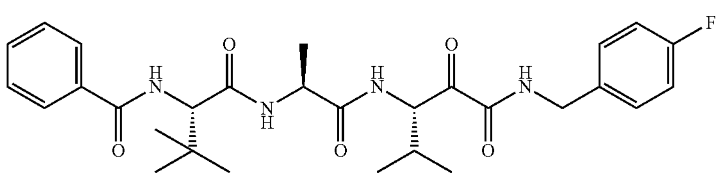 [SMILES: CC(C)[C@H](NC(=O)[C@H](C)NC(=O)[C@@H](NC(=O)c1ccccc1)C(C)(C)C)C(=O)C(=O)NCc1ccc(F)cc1] |
| PVA-179 | 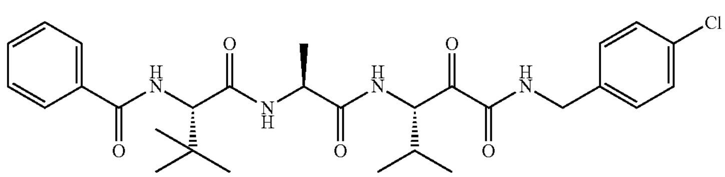 [SMILES: CC(C)[C@H](NC(=O)[C@H](C)NC(=O)[C@@H](NC(=O)c1ccccc1)C(C)(C)C)C(=O)C(=O)NCc1ccc(Cl)cc1] |
| PVA-180 | 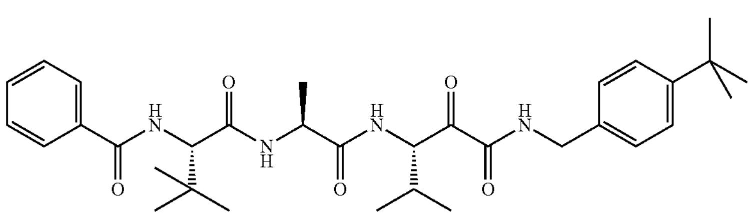 [SMILES: CC(C)[C@H](NC(=O)[C@H](C)NC(=O)[C@@H](NC(=O)c1ccccc1)C(C)(C)C)C(=O)C(=O)NCc1ccc(C(C)(C)C)cc1] |
| PVA-181 | 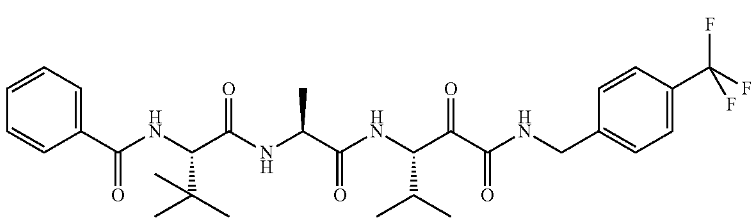 [SMILES: CC(C)[C@H](NC(=O)[C@H](C)NC(=O)[C@@H](NC(=O)c1ccccc1)C(C)(C)C)C(=O)C(=O)NCc1ccc(C(F)(F)F)cc1] |

| Code | Structure |
|---|---|
| PVA-182 | 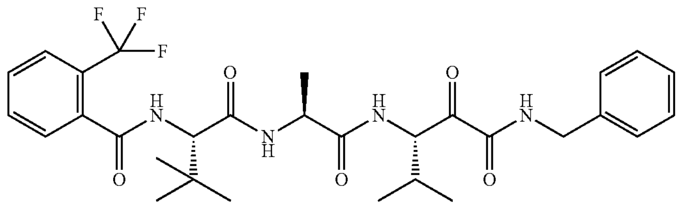 [SMILES: CC(C)[C@H](NC(=O)[C@H](C)NC(=O)[C@@H](NC(=O)c1ccccc1C(F)(F)F)C(C)(C)C)C(=O)C(=O)NCc1ccccc1] |
| PVA-183 | 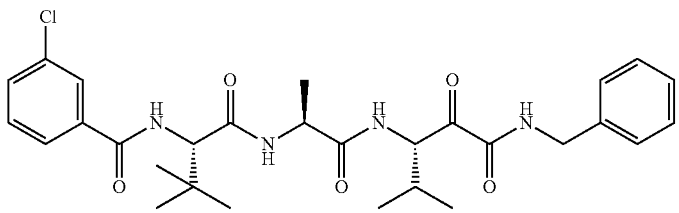 [SMILES: CC(C)[C@H](NC(=O)[C@H](C)NC(=O)[C@@H](NC(=O)c1cccc(Cl)c1)C(C)(C)C)C(=O)C(=O)NCc1ccccc1] |
| PVA-184 | 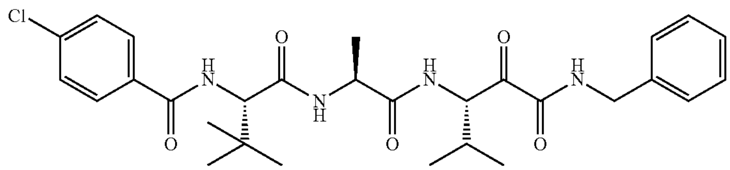 [SMILES: CC(C)[C@H](NC(=O)[C@H](C)NC(=O)[C@@H](NC(=O)c1ccc(Cl)cc1)C(C)(C)C)C(=O)C(=O)NCc1ccccc1] |
| PVA-185 | 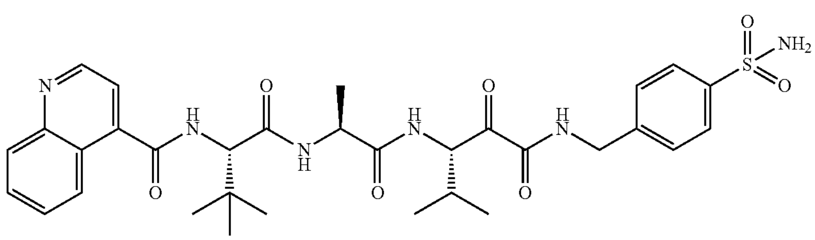 |
| PVA-186 | 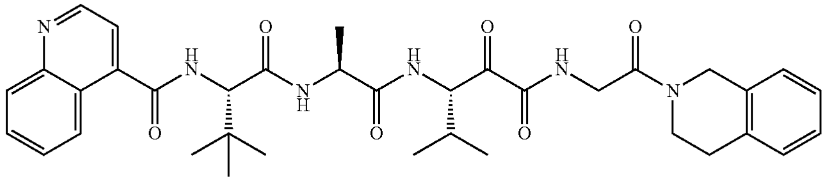 [SMILES: CC(C)[C@H](NC(=O)[C@H](C)NC(=O)[C@@H](NC(=O)c1ccnc2ccccc12)C(C)(C)C)C(=O)C(=O)NCC(=O)N1CCc2ccccc2C1] |
| PVA-187 | 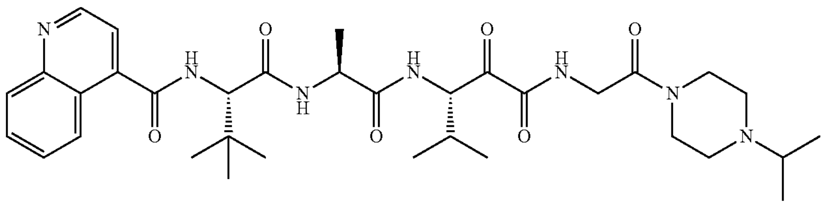 [SMILES: CC(C)[C@H](NC(=O)[C@H](C)NC(=O)[C@@H](NC(=O)c1ccnc2ccccc12)C(C)(C)C)C(=O)C(=O)NCC(=O)N1CCN(C(C)C)CC1] |
| PVA-188 | 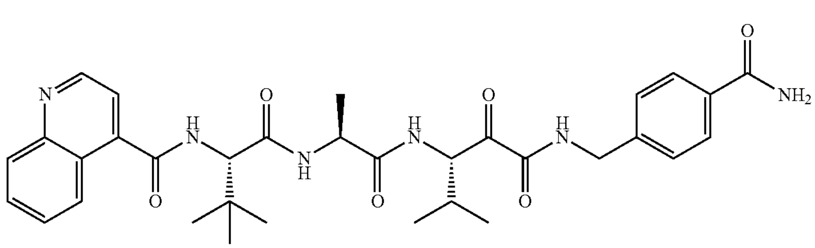 [SMILES: CC(C)[C@H](NC(=O)[C@H](C)NC(=O)[C@@H](NC(=O)c1ccnc2ccccc12)C(C)(C)C)C(=O)C(=O)NCc1ccc(C(N)=O)cc1] |

| Code | Structure |
|---|---|
| PVA-189 | 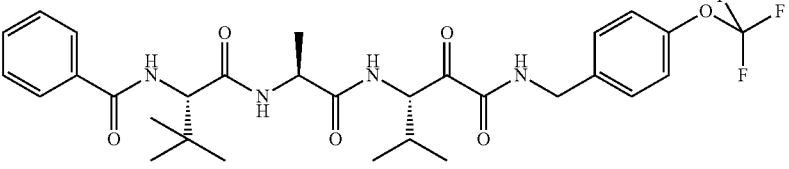 |
| PVA-190 | 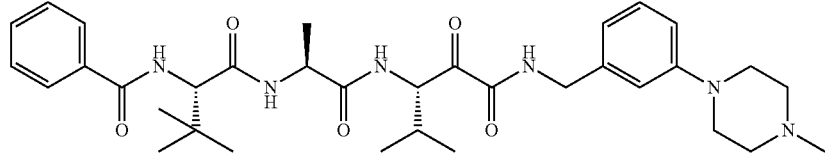 [SMILES: CC(C)[C@H](NC(=O)[C@H](C)NC(=O)[C@@H](NC(=O)c1ccccc1)C(C)(C)C)C(=O)C(=O)NCc1cccc(N2CCN(C)CC2)c1] |
| PVA-191 | 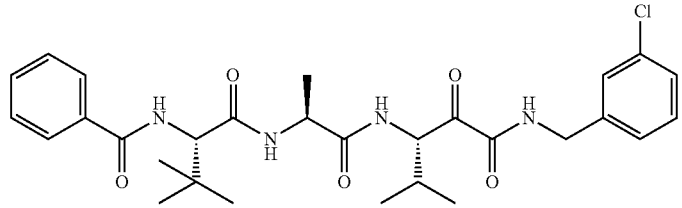 [SMILES: CC(C)[C@H](NC(=O)[C@H](C)NC(=O)[C@@H](NC(=O)c1ccccc1)C(C)(C)C)C(=O)C(=O)NCc1cccc(Cl)c1] |
| PVA-192 | 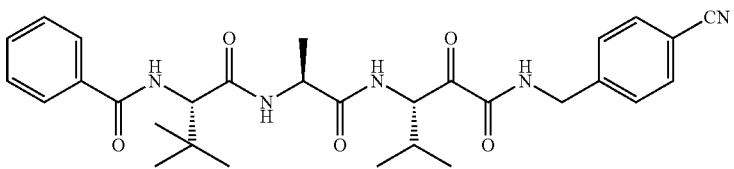 [SMILES: CC(C)[C@H](NC(=O)[C@H](C)NC(=O)[C@@H](NC(=O)c1ccccc1)C(C)(C)C)C(=O)C(=O)NCc1ccc(C#N)cc1] |
| PVA-193 | 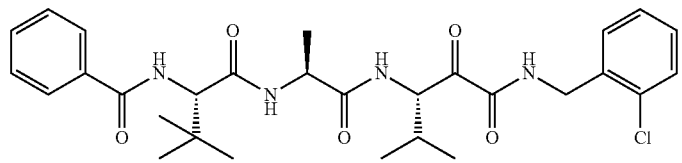 [SMILES: CC(C)[C@H](NC(=O)[C@H](C)NC(=O)[C@@H](NC(=O)c1ccccc1)C(C)(C)C)C(=O)C(=O)NCc1ccccc1Cl] |
| PVA-194 | 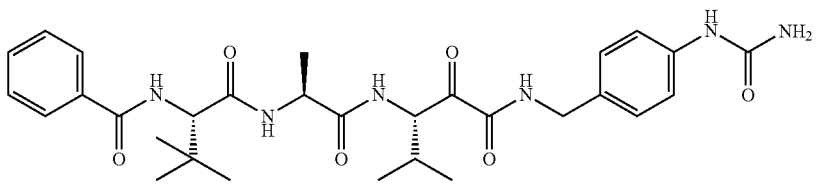 [SMILES: CC(C)[C@H](NC(=O)[C@H](C)NC(=O)[C@@H](NC(=O)c1ccccc1)C(C)(C)C)C(=O)C(=O)NCc1ccc(NC(N)=O)cc1] |
| PVA-195 | 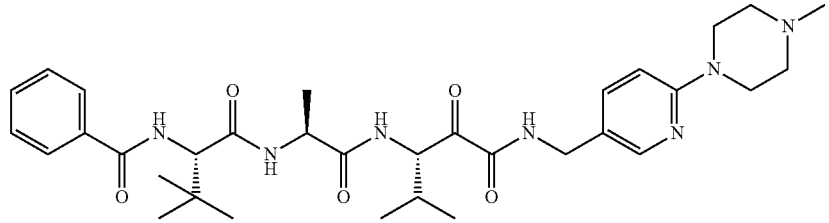 [SMILES: CC(C)[C@H](NC(=O)[C@H](C)NC(=O)[C@@H](NC(=O)c1ccccc1)C(C)(C)C)C(=O)C(=O)NCc1ccc(N2CCN(C)CC2)nc1] |
| PVA-196 | 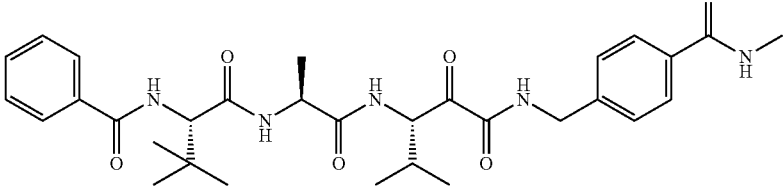 |

| Code | Structure |
|---|---|
| PVA-197 | 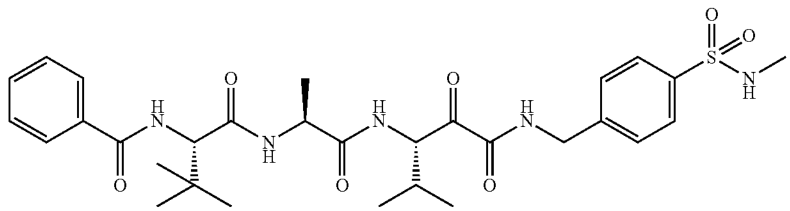 [SMILES: CNS(=O)(=O)c1ccc(CNC(=O)C(=O)[C@@H](NC(=O)[C@H](C)NC(=O)[C@@H](NC(=O)c2ccccc2)C(C)(C)C)C(C)C)cc1] |
| PVA-198 | 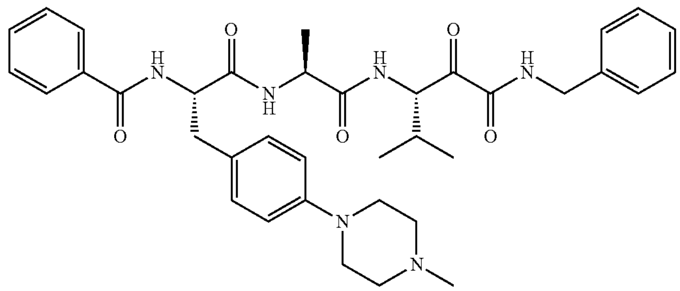 [SMILES: CC(C)[C@H](NC(=O)[C@H](C)NC(=O)[C@H](Cc1ccc(N2CCN(C)CC2)cc1)NC(=O)c1ccccc1)C(=O)C(=O)NCc1ccccc1] |
| PVA-199 | 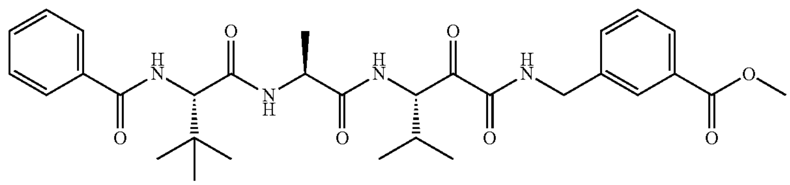 [SMILES: COC(=O)c1cccc(CNC(=O)C(=O)[C@@H](NC(=O)[C@H](C)NC(=O)[C@@H](NC(=O)c2ccccc2)C(C)(C)C)C(C)C)c1] |
| PVA-200 | 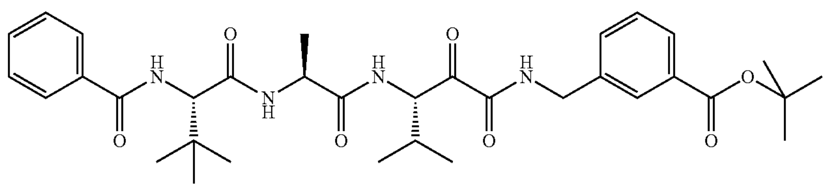 [SMILES: CC(C)[C@H](NC(=O)[C@H](C)NC(=O)[C@@H](NC(=O)c1ccccc1)C(C)(C)C)C(=O)C(=O)NCc1cccc(C(=O)OC(C)(C)C)c1] |
| PVA-201 | 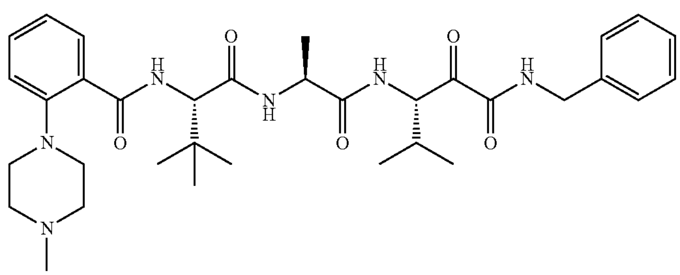 [SMILES: CC(C)[C@H](NC(=O)[C@H](C)NC(=O)[C@@H](NC(=O)c1ccccc1N1CCN(C)CC1)C(C)(C)C)C(=O)C(=O)NCc1ccccc1] |
| PVA-202 | 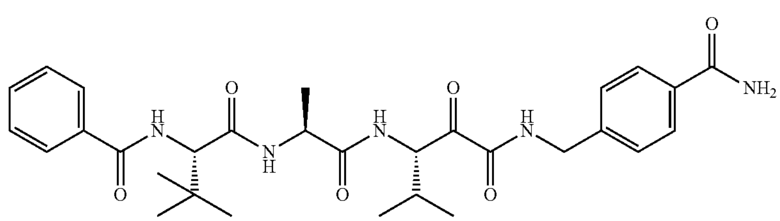 [SMILES: CC(C)[C@H](NC(=O)[C@H](C)NC(=O)[C@@H](NC(=O)c1ccccc1)C(C)(C)C)C(=O)C(=O)NCc1ccc(C(N)=O)cc1] |
| PVA-203 | 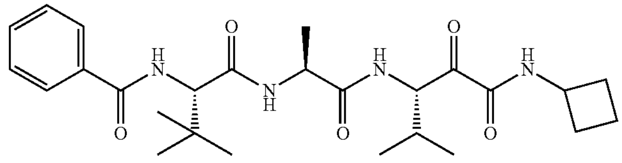 [SMILES: CC(C)[C@H](NC(=O)[C@H](C)NC(=O)[C@@H](NC(=O)c1ccccc1)C(C)(C)C)C(=O)C(=O)NC1CCC1] |

-continued

| Code | Structure |
|---|---|
| PVA-204 | 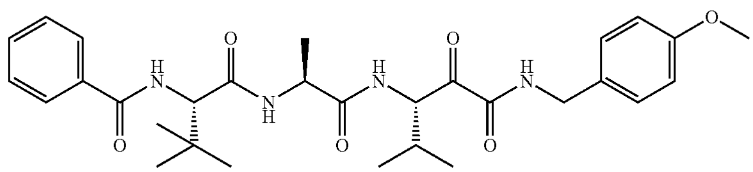 [SMILES: COc1ccc(CNC(=O)C(=O)[C@@H](NC(=O)[C@H](C)NC(=O)[C@@H](NC(=O)c2ccccc2)C(C)(C)C)C(C)C)cc1] |
| PVA-205 | 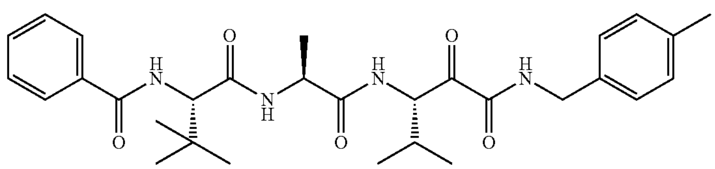 [SMILES: Cc1ccc(CNC(=O)C(=O)[C@@H](NC(=O)[C@H](C)NC(=O)[C@@H](NC(=O)c2ccccc2)C(C)(C)C)C(C)C)cc1] |
| PVA-206 | 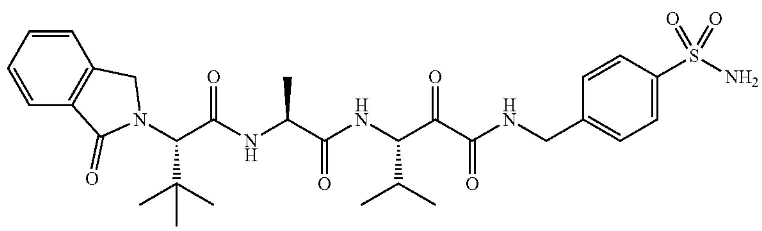 [SMILES: CC(C)[C@H](NC(=O)[C@H](C)NC(=O)[C@@H](N1Cc2ccccc2C1=O)C(C)(C)C)C(=O)C(=O)NCc1ccc(S(N)(=O)=O)cc1] |
| PVA-207 | 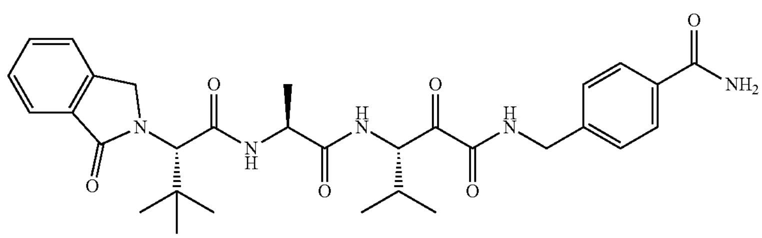 [SMILES: CC(C)[C@H](NC(=O)[C@H](C)NC(=O)[C@@H](N1Cc2ccccc2C1=O)C(C)(C)C)C(=O)C(=O)NCc1ccc(C(N)=O)cc1] |
| PVA-208 | 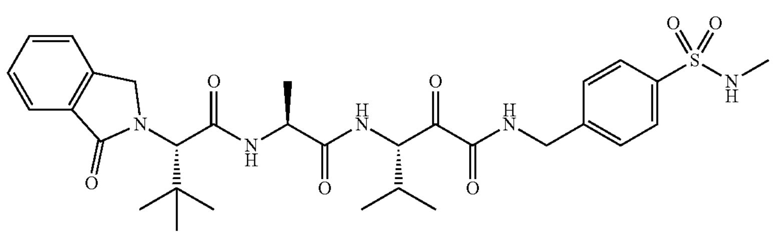 [SMILES: CNS(=O)(=O)c1ccc(CNC(=O)C(=O)[C@@H](NC(=O)[C@H](C)NC(=O)[C@@H](N2Cc3ccccc3C2=O)C(C)(C)C)C(C)C)cc1] |
| PVA-209 | 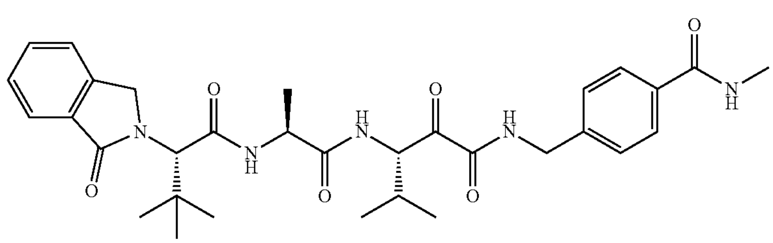 [SMILES: CNC(=O)c1ccc(CNC(=O)C(=O)[C@@H](NC(=O)[C@H](C)NC(=O)[C@@H](N2Cc3ccccc3C2=O)C(C)(C)C)C(C)C)cc1] |
| PVA-210 | 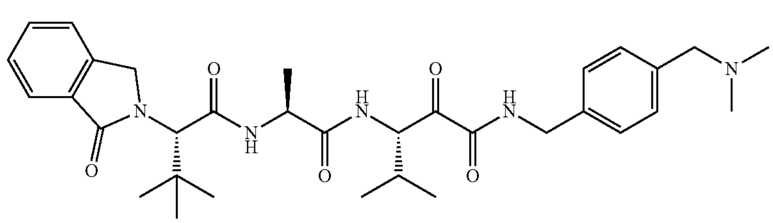 [SMILES: CC(C)[C@H](NC(=O)[C@H](C)NC(=O)[C@@H](N1Cc2ccccc2C1=O)C(C)(C)C)C(=O)C(=O)NCc1ccc(CN(C)C)cc1] |

-continued
| Code | Structure |
|---|---|
| PVA-211 | 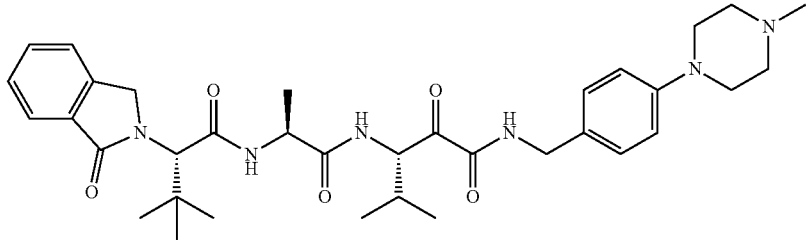 [SMILES: CC(C)[C@H](NC(=O)[C@H](C)NC(=O)[C@@H](N1Cc2ccccc2C1=O)C(C)(C)C)C(=O)C(=O)NCc1ccc(N2CCN(C)CC2)cc1] |
| PVA-212 | 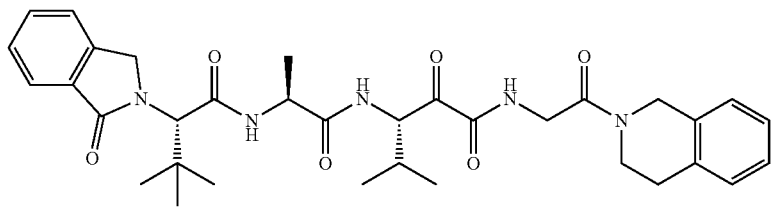 [SMILES: CC(C)[C@H](NC(=O)[C@H](C)NC(=O)[C@@H](N1Cc2ccccc2C1=O)C(C)(C)C)C(=O)C(=O)NCC(=O)N1CCc2ccccc2C1] |
| PVA-213 | 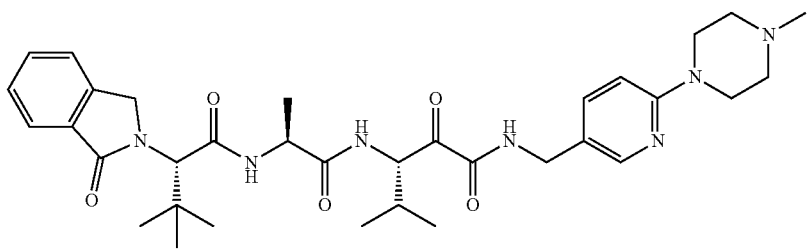 [SMILES: CC(C)[C@H](NC(=O)[C@H](C)NC(=O)[C@@H](N1Cc2ccccc2C1=O)C(C)(C)C)C(=O)C(=O)NCc1ccc(N2CCN(C)CC2)nc1] |
| PVA-214 | 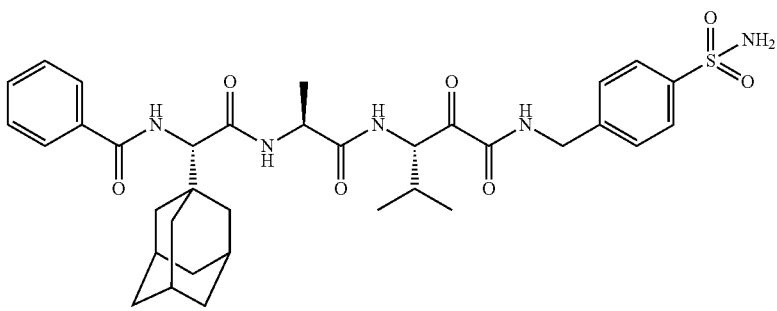 [SMILES: CC(C)[C@H](NC(=O)[C@H](C)NC(=O)[C@@H](NC(=O)c1ccccc1)C12CC3CC(CC(C3)C1)C2)C(=O)C(=O)NCc1ccc(S(N)(=O)=O)cc1] |
| PVA-215 | 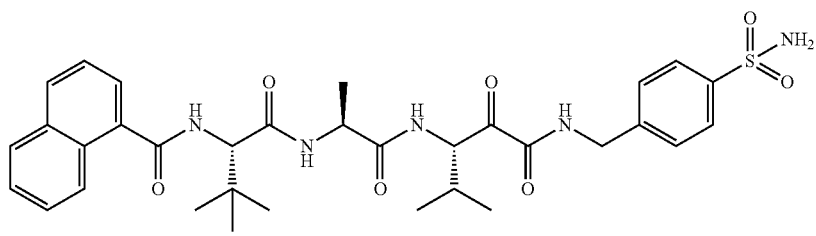 [SMILES: CC(C)[C@H](NC(=O)[C@H](C)NC(=O)[C@@H](NC(=O)c1cccc2ccccc12)C(C)(C)C)C(=O)C(=O)NCc1ccc(S(N)(=O)=O)cc1] |
| PVA-216 | 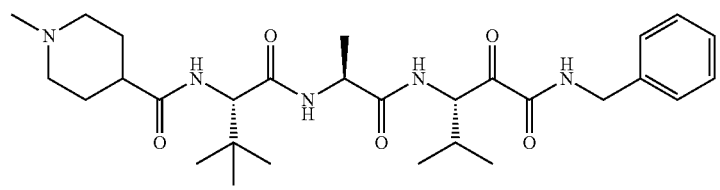 [SMILES: CC(C)[C@H](NC(=O)[C@H](C)NC(=O)[C@@H](NC(=O)C1CCN(C)CC1)C(C)(C)C)C(=O)C(=O)NCc1ccccc1] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $R^1$, $R^2$, $R^3$, $R^4$, $R^5$, $R^6$, $R^7$, $R^8$, $R^9$, $R^{10}$, $R^{11}$, $R^{12}$, $-R^{1A}$, $-R^{2A}$, $-R^{3A}$, $-R^{4A}$, $-R^{5A}$, $-R^{6A}$, $-R^{7A}$, $-R^{7B}$, $-R^{7B1}$, $-R^{7B2}$, $-R^{7BB}$, $-R^{7BB1}$, $-R^{7BB2}$, $-R^{7BB3}$, $-R^{7BB4}$, $-R^{8A}$, $-R^{9A}$, $-R^{10A}$, $-R^{10B}$, $-R^{10C}$, $-R^{10D}$, $-R^{11A}$, $-R^{11B}$, $-R^{Z1}$, $-R^{Z2}$, $-R^{Z3}$, $-R^{Z3A}$, $-R^{Z3B}$, $-R^{Z4}$, $-R^{Z5}$, $-L^Z-$, $-R^{J1}$, $-R^{J2}$, $-R^{J3}$, $-R^{J4}$, $-R^{12A}$, $-R^{X1}$, $-R^{X2}$, $-R^{X3}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to PVA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Geminal Diols, Hemiacetals, and Acetals

It is anticipated that the 2-oxa (—C(=O)—) group of the pyruvamide moiety of the PVA compounds may deliberately or inadvertently be converted entirely or partially to the corresponding geminal diol, hemi-acetal, or acetal upon contact with water, an alcohol, or a mixture of water and an alcohol. Such a transformation may occur, for example during purification (e.g., during recrystallisation from an aqueous or alcoholic solvent). This is illustrated below wherein, for example, each —$R^A$ is independently $C_{1-4}$alkyl, for example, -Me. Furthermore, a cyclic acetal may be formed if a diol is used, for example, ethylene glycol, to produce the corresponding 1,3-dioxolane.

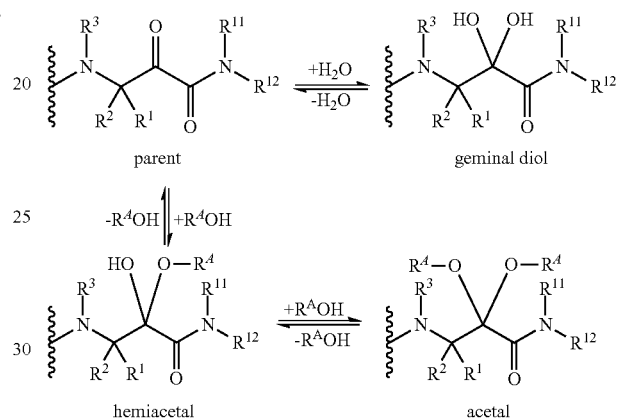

It is anticipated that in aqueous solution any such geminal diols, hemiacetals, and acetals would be present in equilibrium with the parent compound. For the avoidance of doubt, it is intended that, unless otherwise specified, references herein to the PVA compounds also encompass such geminal diol, hemi-acetal, and acetal forms.

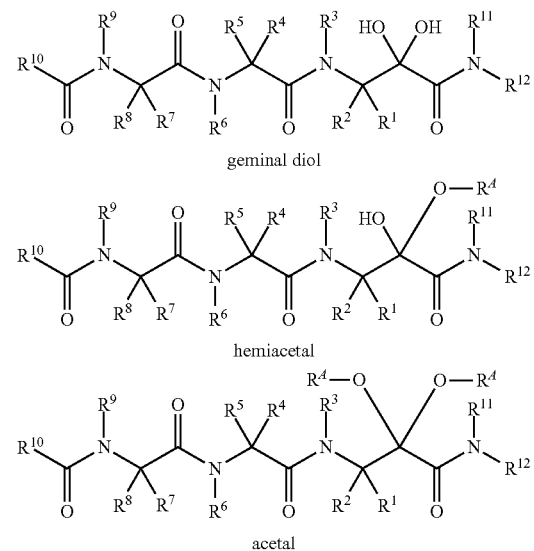

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

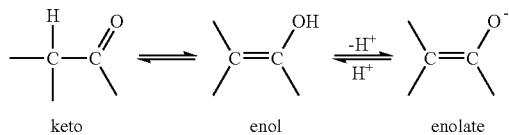

keto    enol    enolate

For example, 1H-pyridin-2-one-5-yl and 2-hydroxyl-pyridin-5-yl (shown below) are tautomers of one another. A reference herein to one is intended to encompass both. See, for example, PVA-084.

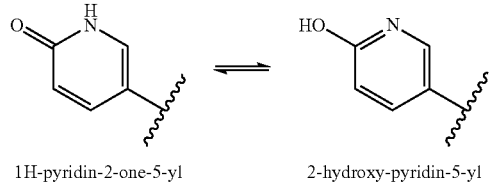 [SMILES: *c1ccc(=O)[nH]c1 ; *c1ccc(O)nc1]

1H-pyridin-2-one-5-yl    2-hydroxy-pyridin-5-yl

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge at al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which upon protonation may become cationic (e.g., —$NH_2$ may become —$NH_3^+$), then a salt may be formed with a suitable anion.

For example, if a parent structure contains a cationic group (e.g., —$NMe_2^+$), or has a functional group which upon protonation may become cationic (e.g., —$NH_2$ may become —$NH_3^+$), then a salt may be formed with a suitable anion. In the case of a quaternary ammonium compound a counter-anion is generally always present in order to balance the positive charge. If, in addition to a cationic group (e.g., —$NMe_2^+$, —$NH_3^+$), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, trifluoroacetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Examples of suitable counter-ions which are especially suitable for quaternary ammonium compounds (e.g., those with a —$NMe_2^+$ group) include 1-adamantane sulfonate, benzenesulfonate, bisulfate, bromide, chloride, iodide, methanesulfonate, methylsulfate, 1,5-napthalene bis sulfonate, 4-nitrobenzenesulfonate, formate, tartrate, tosylate, trifluoroacetate, trifluoromethylsulfonate, sulphate. Again, if the compound also contains a group capable of forming an anion (e.g., —COOH), then an inner salt may be formed.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated, for example, by hydrolysis using water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester, a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Another form of prodrug of the PVA compounds may be one wherein the 2-oxa (C=O) group of the PVA compound is protected, for example, as an acetal or hemiacetal, which is converted, in vivo, to the corresponding 2-oxa group.

Also, some prodrugs are activated enzymatically to yield the active compound, or a compound which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

Chemical Synthesis

Several methods for the chemical synthesis of PVA compounds of the present invention are described herein. These and/or other well known methods may be modified and/or adapted in known ways in order to facilitate the synthesis of additional compounds within the scope of the present invention.

Compounds of Formula (I) may be prepared, for example, by reacting an α-hydroxyamide of Formula (II) with an appropriate oxidising agent, as illustrated in the following scheme. Suitable oxidising agents include, but are not limited to, Dess-Martin periodinane, pyridinium chlorochromate (PCC), tetrapropylammonium perruthenate (TPAP), and the use of Swern or modified Swern conditions, which use DMSO in conjunction with an activating agent such as oxalyl chloride.

Scheme 1

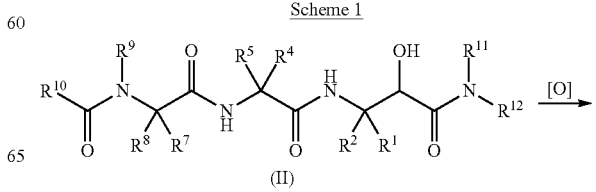

(II)

-continued

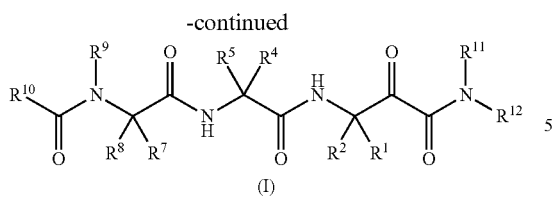

(I)

α-Hydroxyamides of Formula (II) can be prepared by several different routes which are well known in the art. Examples of such methods are described in Arasappan et al., 2009; Barrett et al., 2005; and Zhaozhao et al., 1996. One method for the synthesis of compounds of Formula (II) when $R^{12}$ is H involves the reaction of the corresponding peptidyl aldehyde (III) with an isonitrile using a modified Passerini reaction (see, for example, Marcaccini et al., 2005), as illustrated in the following scheme.

Scheme 2

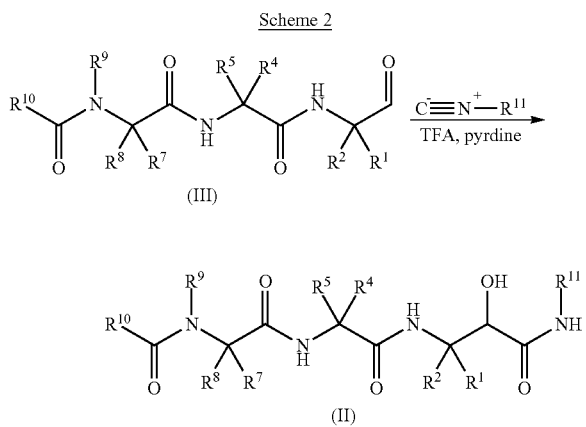

Isonitriles may be prepared using methods known in the art. One method involves the dehydration of the corresponding formamide using reagents such as, but not limited to, p-tosylchloride, thionyl chloride, phosphoryl chloride, and diphosgene.

Alternatively, compounds of Formula (II) may be prepared by reacting a compound of Formula (A) with a compound of Formula (IV) using standard acid-amine coupling conditions, as illustrated in the following scheme. Such conditions are known in the art. A potential side reaction under such conditions can be the epimerisation of the $R^4/R^5$ chiral centre. It is common to avoid such side reactions by carrying out low temperature coupling reactions using a mixed anhydride derived from Formula (A). Mixed anhydrides are commonly generated in situ using, for example, iso-butylchloroformate or ethylchloroformate and a mild base, such as N-methylmorpholine. Such methods are in the art.

Scheme 3

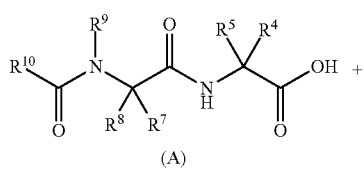

(A)

-continued

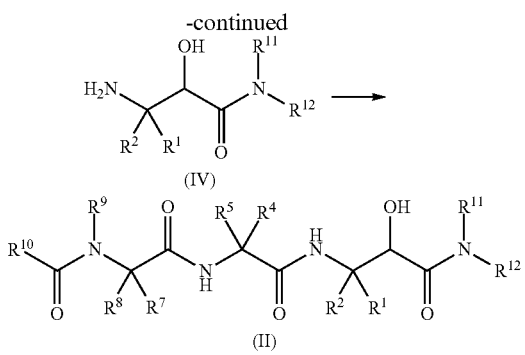

Compounds of Formula (IV) may be prepared in several steps from a suitably protected α-aminoaldehyde. The sequence of reactions involves formation of the corresponding cyanohydrin followed by hydrolysis to generate the corresponding hydroxy acid. The hydroxy acid can be used to generate a range of amides using standard acid-amine coupling reactions, with a compound of Formula (IV) being generated following removal of the nitrogen protecting group.

Suitable nitrogen protecting groups include, but are not limited to, benzyloxycarbonyl (Cbz), t-butoxycarbonyl (Boc), and fluorenylmethyloxycarbonyl (Fmoc). A review of amine protecting groups can be found, for example, in *Protective Groups in Organic Synthesis,* 3rd Ed., (T. Green and P. Wuts; 4th Edition; Wiley-Interscience, 1999), pp. 494-653.

Methods for preparing α-aminoaldehydes include oxidation of the corresponding alcohol or reduction of the corresponding Weinreb amide, both of which can be made from suitably protected α-amino acids using methods known in the art.

Alternatively, compounds of Formula (I) may be prepared by treatment of a triphenylphosphine acetonitrile intermediate of Formula (P) with ozone to generate the corresponding acyl-cyanide in situ, followed by reaction with a suitable amine nucleophile, as illustrated in the following scheme. Triphenylphosphine acetonitrile intermediates may be prepared from the corresponding peptide using conditions analogous to those used in acid-amine coupling reactions. Such conditions include the use of 1-ethyl-3-(3-dimethylaminopropyl)carbodiimide (EDC) with catalytic 4-dimethylaminopyridine (DMAP) and are known in the art.

Scheme 4

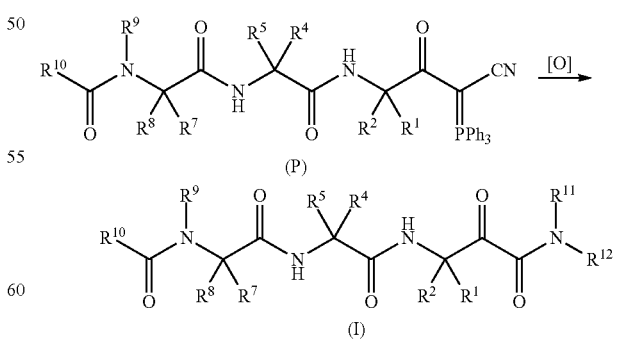

Dipeptide and tripeptide derivatives may be synthesised on a polymeric (e.g., polystyrene resin) using standard resin-based Fmoc coupling methods. The first Fmoc protected amino acid is generally coupled to Wang or 2-chloro-trityl resin. Subsequent amino acids are coupled using standard acid-amine coupling conditions. Suitable conditions include the use of hydroxybenzotriazole (HOBt) with N,N'-diisopropylcarbodiimide (DIC) or 2-(1H-7-azabenzotriazol-1-yl)-1,1,3,3-tetramethyl uronium hexafluorophosphate methanaminium (HATU), O-(Benzotriazol-1-yl)-N,N,N,N-tetramethyluronium tetrafluoroborate (TBTU), O-Benzotriazole-N,N,N',N'-tetramethyl-uronium-hexafluoro-phosphate (HBTU), or benzotriazol-1-yl-oxytripyrrolidinophosphonium hexafluorophosphate (PyBop), with a suitable base such as DIPEA. Further information on the synthesis of peptides on resin may be found, for example, in: Chan and White, *Fmoc Solid Phase Peptide Synthesis: A Practical Approach* (Oxford University Press, 2000).

Alternatively, peptide derivatives can be built up in a sequential fashion using solution chemistry with appropriately protected amino acids using methods known in the art. The use of suitable nitrogen protecting groups such as Boc, Cbz or Fmoc coupled with low temperature mixed-anhydride coupling conditions is commonly used for this purpose.

Compositions

One aspect of the present invention pertains to a composition (e.g., a pharmaceutical composition) comprising a PVA compound, as described herein, and a pharmaceutically acceptable carrier, diluent, or excipient.

In one embodiment, the composition is in the form of a dry powder, for example, suitable for delivery (e.g., administration) using a dry powder inhaler (DPI). Examples of suitable DPIs are well-known in the art. DPI administration may be used to deliver the drug to the lung or the nose.

In one embodiment, the composition is in the form of a suspension, for example, suitable for delivery (e.g., administration) using a nebuliser. This may be used to deliver the drug to the lung or the nose.

In one embodiment, the composition is in the form of a solution or suspension in a liquid propellant, for example, suitable for delivery (e.g., administration) as an aerosol, for example, using a pressurised metered dose inhaler (pMDI). Examples of suitable pMDIs are well-known in the art. Suitable propellants are well-known in the art, and include, for example, dichlorodifluoromethane (CFC-12), trichlorofluoromethane, dichloro-tetrafluoroethane, HFA-134a, HFA-227, HCFC-22, HFA-152, isobutene, and carbon dioxide. This may be used to deliver the drug to the lung or the nose.

In one embodiment, the composition is in the form of an aqueous solution, for example, suitable for delivery (e.g., administration) using a dropper, syringe, metered dose spray pump or atomiser. This may be used to deliver the drug to the nose.

In one embodiment, the composition further comprises one or more (e.g., 1, 2, 3, 4) additional therapeutic agents, as described herein.

Another aspect of the present invention pertains to a method of preparing a composition (e.g., a pharmaceutical composition) comprising admixing a PVA compound, as described herein, and a pharmaceutically acceptable carrier, diluent, or excipient.

Another aspect of the present invention pertains to a method of preparing a composition (e.g., a pharmaceutical composition) comprising admixing a PVA compound, as described herein; one or more (e.g., 1, 2, 3, 4) additional therapeutic agents, as described herein; and a pharmaceutically acceptable carrier, diluent, or excipient.

Uses

The compounds described herein are useful, for example, in the treatment of diseases and disorders that are ameliorated by the inhibition of a dust mite Group 1 peptidase allergen (e.g., Der p 1, Der f 1, Eur m 1), such as, for example, asthma; rhinitis; allergic conjunctivitis; atopic dermatitis; an allergic condition which is triggered by dust mites; an allergic condition which is triggered by a dust mite Group 1 peptidase allergen; and canine atopy.

Use in Methods of Inhibiting a Dust Mite Group 1 Peptidase Allergen

One aspect of the present invention pertains to a method of inhibiting a dust mite Group 1 peptidase allergen (e.g., Der p 1, Der f 1, Eur m 1), in vitro or in vivo, comprising contacting a dust mite Group 1 peptidase allergen with an effective amount of a PVA compound, as described herein.

One aspect of the present invention pertains to a method of inhibiting a dust mite Group 1 peptidase allergen (e.g., Der p 1, Der f 1, Eur m 1) in a cell, in vitro or in vivo, comprising contacting the cell with an effective amount of a PVA compound, as described herein.

Suitable assays for determining inhibition of a dust mite Group 1 peptidase allergen are described herein and/or are known in the art.

Use in Methods of Therapy

Another aspect of the present invention pertains to a PVA compound, as described herein, for use in a method of treatment of the human or animal body by therapy.

Another aspect of the present invention pertains to a PVA compound, as described herein, in combination with one or more (e.g., 1, 2, 3, 4) additional therapeutic agents, as described herein, for use in a method of treatment of the human or animal body by therapy.

Use in the Manufacture of Medicaments

Another aspect of the present invention pertains to use of a PVA compound, as described herein, in the manufacture of a medicament for use in treatment.

In one embodiment, the medicament comprises the PVA compound.

Another aspect of the present invention pertains to use of a PVA compound, as described herein, and one or more (e.g., 1, 2, 3, 4) additional therapeutic agents, as described herein, in the manufacture of a medicament for use in treatment.

In one embodiment, the medicament comprises the PVA compound and the one or more (e.g., 1, 2, 3, 4) additional therapeutic agents.

Methods of Treatment

Another aspect of the present invention pertains to a method of treatment comprising administering to a patient in need of treatment a therapeutically effective amount of a PVA compound, as described herein, preferably in the form of a pharmaceutical composition.

Another aspect of the present invention pertains to a method of treatment comprising administering to a patient in need of treatment a therapeutically effective amount of a PVA compound, as described herein, preferably in the form of a pharmaceutical composition, and one or more (e.g., 1, 2, 3, 4) additional therapeutic agents, as described herein, preferably in the form of a pharmaceutical composition.

Conditions Treated: Diseases and Disorders Mediated by a Dust Mite Group 1 Peptidase Allergen In one embodiment (e.g., of use in methods of therapy, of use in the manufacture of medicaments, of methods of treatment), the treatment is treatment of a disease or disorder that is mediated by a dust mite Group 1 peptidase allergen (e.g., Der p 1, Der f 1, Eur m 1).

Conditions Treated: Diseases and Disorders Ameliorated by the Inhibition of a Dust Mite Group 1 Peptidase Allergen In one embodiment (e.g., of use in methods of therapy, of use in the manufacture of medicaments, of methods of treatment), the treatment is treatment of: a disease or condition that is ameliorated by the inhibition of a dust mite Group 1 peptidase allergen (e.g., Der p 1, Der f 1, Eur m 1).

Conditions Treated: Particular Diseases and Disorders

In one embodiment (e.g., of use in methods of therapy, of use in the manufacture of medicaments, of methods of treatment), the treatment is treatment of: asthma, for example, atopic asthma; allergic asthma; atopic bronchial IgE-mediated asthma; bronchial asthma; extrinsic asthma; allergen-induced asthma; allergic asthma exacerbated by respiratory virus infection; infective asthma; infective asthma caused by bacterial infection; infective asthma caused by fungal infection; infective asthma caused by protozoal infection; or infective asthma caused by viral infection.

In one embodiment (e.g., of use in methods of therapy, of use in the manufacture of medicaments, of methods of treatment), the treatment is treatment of: bronchial hyper-reactivity associated with asthma; or bronchial hyper-responsiveness associated with asthma.

In one embodiment (e.g., of use in methods of therapy, of use in the manufacture of medicaments, of methods of treatment), the treatment is treatment of: airway remodelling associated with an allergic lung disease, for example, airway remodelling associated with asthma.

In one embodiment (e.g., of use in methods of therapy, of use in the manufacture of medicaments, of methods of treatment), the treatment is treatment of: asthma co-presented with a chronic obstructive lung disease, for example, asthma co-presented with emphysema; or asthma co-presented with chronic bronchitis.

In one embodiment (e.g., of use in methods of therapy, of use in the manufacture of medicaments, of methods of treatment), the treatment is treatment of: rhinitis, for example, allergic rhinitis; perennial rhinitis; persistent rhinitis; or IgE-mediated rhinitis.

In one embodiment (e.g., of use in methods of therapy, of use in the manufacture of medicaments, of methods of treatment), the treatment is treatment of: allergic conjunctivitis, for example, IgE-mediated conjunctivitis.

In one embodiment (e.g., of use in methods of therapy, of use in the manufacture of medicaments, of methods of treatment), the treatment is treatment of: atopic dermatitis.

In one embodiment (e.g., of use in methods of therapy, of use in the manufacture of medicaments, of methods of treatment), the treatment is treatment of: an allergic condition which is triggered by dust mites.

In one embodiment (e.g., of use in methods of therapy, of use in the manufacture of medicaments, of methods of treatment), the treatment is treatment of: an allergic condition which is triggered by dust mite Group 1 peptidase allergen (e.g., Der p 1, Der f 1, Eur m 1).

In one embodiment (e.g., of use in methods of therapy, of use in the manufacture of medicaments, of methods of treatment), the treatment is treatment of: canine atopy.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of asthma, reducing the incidence of asthma, reducing the severity of asthma, alleviating the symptoms of asthma, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

Typical examples of combinations for inhaled use in treatment of respiratory disease are fixed combinations of glucocorticoid receptor agonists and beta 2 adrenoceptor agonists. Such a combination product is "Advair" (also known as "Seretide"), which is a fixed combination of fluticasone propionate and salmeterol. Such combinations may be used in dry powder devices, pressurised metered dose inhalers and nebulisers. Many other respiratory agents may be used in fixed combinations in such devices. They may also be administered separately from different devices in different relative doses.

An inhaled combination product will be a fixed combination of a compound described herein with one or more additional agents (in which the ratios are decided on the merits of the individual components and selected from a suitable range by experiment) together with appropriate excipients.

For example, one aspect of the present invention pertains to a compound as described herein, in combination with one or more (e.g., 1, 2, 3, 4) additional therapeutic agents.

Thus, the agents (i.e., the compound described herein, plus one or more other agents) may be administered simultaneously in fixed combination or at different times by individually varying dose schedules from a similar or different inhalation device. The precise dosage regimen of either combination or sequential treatment will be commensurate with the properties of the therapeutic agent(s).

Additional Therapeutic Agents

The PVA compounds described herein may be used in combination with one or more (e.g., 1, 2, 3, 4) additional therapeutic agents, for example, in combination therapy as described herein.

In one embodiment, the one or more additional therapeutic agents are selected from agents used, or likely to be used, in the treatment of a respiratory disease.

In one embodiment, the one or more additional therapeutic agents are selected from: an anti-asthma agent and an anti-allergy agent.

In one embodiment, the one or more additional therapeutic agents are selected from:

a $beta_2$-adrenergic agonist;

an antagonist of the M3 muscarinic receptor;

a dual $beta_2$ adrenoceptor agonist-M3 muscarinic antagonist;

a glucocorticoid receptor agonist;

a leukotriene antagonist;

a 5-lipoxygenase inhibitor;

a cromone;

an immunosuppressant;

an immune response modifier, e.g., an agonist of one or more Toll-Like Receptors (e.g., TLR2, TLR4, TLR7, TLR8, TLR9) or a vaccine;

a xanthine derivative;

a selective phosphodiesterase (PDE) isoenzyme inhibitor, e.g., an inhibitor of PDE4 and/or PDE5;

an inhibitor of certain kinase enzymes, e.g., p38 mitogen-activated protein (MAP) kinase, IkappaB kinase 2 (IKK2), tyrosine-protein kinase (Syk), and phosphoinositide-3 kinase gamma (PI3 Kgamma);

a histamine type 1 receptor antagonist;

a alpha adrenoceptor agonist vasoconstrictor sympathomimetic;

an inhibitor of a matrix metalloprotease;

a modulator of chemokine receptor function;

a cytokine;

a modulator of cytokine function;

an agent which act on a cytokine signalling pathway;

an immunoglobulin;

an immunoglobulin preparation;

an antagonist that modulates immunoglobulin function;

an antibody that modulates immunoglobulin function;

a lung surfactant protein, especially SP-A, SP-D;

an inhibitor of Der p 3, an inhibitor of Der p 6, and an inhibitor of Der p 9.

Use as an Acaricide

The PVA compounds described herein may also be used as an acaricide, e.g., to control the population of, or to kill, mites, e.g., dust mites.

Another aspect of the present invention pertains to a PVA compound, as described herein, for use as an acaricide.

Another aspect of the present invention pertains to a composition comprising a PVA compound, as described herein, for use as an acaricide.

Another aspect of the present invention pertains to an acaricide composition comprising a PVA compound, as described herein.

Another aspect of the present invention pertains to the use of a PVA compound, as described herein, as an acaricide.

Another aspect of the present invention pertains a method of killing mites (e.g., dust mites), comprising exposing said mites to an effective amount of a PVA compound, as described herein.

Another aspect of the present invention pertains a method of controlling (e.g., limiting) a mite (e.g., dust mite) population comprising exposing mites to an effective amount of a PVA compound, as described herein.

Other Uses

The PVA compounds described herein may also be used as cell culture additives to inhibit a dust mite Group 1 peptidase allergen (e.g., Der p 1, Der f 1, Eur m 1).

The PVA compounds described herein may also be used as part of an in vitro assay, for example, in order to determine whether a candidate host is likely to benefit from treatment with the compound in question.

The PVA compounds described herein may also be used as a standard, for example, in an assay, in order to identify other compounds, other dust mite Group 1 peptidase allergen inhibitors, other anti-asthma agents, etc.

Kits

One aspect of the invention pertains to a kit comprising (a) a PVA compound as described herein, or a composition comprising a PVA compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The PVA compound or pharmaceutical composition comprising the PVA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a fetus.

In one preferred embodiment, the subject/patient is a human.

In one preferred embodiment, the subject/patient is a dog.

Formulations

While it is possible for the PVA compound to be administered alone, it is preferable to present it as a pharmaceutical formulation (e.g., composition, preparation, medicament) comprising at least one PVA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one PVA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for administration to the lung (e.g., by inhalation or insufflation therapy using, e.g., an aerosol, e.g., through the mouth) include those presented as a solution or suspension for delivery from a nebuliser; a dry powder for use in an appropriate inhaler device; and an aerosol spray for delivery from a pressurised pack with the use of a suitable propellant, such as dichlorodifluoromethane (CFC-12), trichlorofluoromethane, dichloro-tetrafluoroethane, HFA-134a, HFA-227, HCFC-22, HFA-152, isobutene, carbon dioxide, or other suitable gases. Devices for these methods of delivery are available. Formulations intended for nasal delivery can be administered as aqueous solutions or suspensions, as solutions or suspensions in suitable propellants or as dry powders. Nasal droppers, nebulisers, atomisers, pressurised metered dose inhalers and dry powder inhalers for nasal delivery are available.

For administration by inhalation, the active compound is preferably in the form of microparticles. Suitable microparticles may be prepared by a variety of techniques, including spray-drying, freeze-drying and micronisation.

The microparticles may be formulated with excipients that aid delivery and release. For example, in a dry powder formulation, microparticles may be formulated with large carrier particles that aid the flow, for example, from a dry powder inhaler (DPI) into the lung. Suitable carrier particles are well-known in the art, and include lactose particles; they may have a mass median aerodynamic diameter of >90 µm.

For administration using an aerosol, the active compound may be administered in a manner compatible with the inhaler system used. Suitable aerosol formulation may include, in addition to the active compound, excipients such as, for example, propellant (e.g., Frigen in the case of metered aerosols), surface-active substances, emulsifiers, stabilizers, preservatives, flavourings, fillers (e.g., lactose in the case of powder inhalers) and, if appropriate, one or more additional active compounds.

For the purposes of inhalation of microparticulate formulations, a large number of systems are known with which aerosols of optimum particle size can be generated and administered, using an inhalation technique appropriate for the patient. In addition to the use of adaptors (spacers, expanders) and pear-shaped containers (e.g., Nebulator™, Volumatic™), and automatic devices emitting a puffer spray (e.g., Autohaler™), for metered aerosols, in particular in the case of powdered inhalers, a number of technical solutions are available (e.g., Diskhaler™, Rotadisk™, Turbohaler™). Additionally, the active compound may be delivered in a multi-chamber device, thus allowing for delivery of combination agents.

For administration to the nose or lung, the active compound may also be used when formulated as an aqueous dispersion of nanoparticulates, or as a dry powder nanoparticulate aerosol formulation, or as a propellant-based aerosol formulation. Suitable nanoparticles may be prepared by spray-drying or freeze-drying aqueous nanoparticulate dispersions of drugs. Methods for the preparation of nanoparticulate dispersions of drugs, the preparation of aqueous, dry powder and propellant-based formulations of nanoparticulate drugs and their use in aerosol delivery systems are known (see, e.g., Bosch et al., 2009).

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid and the drug can be administered as an aqueous solution or suspension in a suitable vehicle or propellant, include, for example, nasal spray, nasal drops, or by aerosol administration by nebuliser, by pressurised metered dose inhaler or atomiser, include aqueous or oily preparations of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the PVA compounds, and compositions comprising the PVA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular PVA compound, the route of administration, the time of administration, the rate of excretion of the PVA compound, the duration of the treatment, other drugs, compounds, and/or materials used in combination, the severity of the condition, and the species, sex, age, weight, condition, general health, and prior medical history of the patient. The amount of PVA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the PVA compound is in the range of about 0.5 µg to about 20 mg per kilogram body weight of the subject per day. In practice, for an inhaled agent, the upper limit will be set by the chosen device for delivery. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Abbreviations

Aq., aqueous;
Boc, tert-butoxycarbonyl;
Conc., concentrated;
DCM, dichloromethane;
DIC, diisopropylcarbodiimide;
DIPEA, N,N-diisopropylethylamine;
DMAP, 4-dimethylaminopyridine;
DMF, dimethylformamide;
DMSO, dimethylsulfoxide;
EDC, 1-Ethyl-3-[3-dimethylaminopropyl]carbodiimide;
ELSD, evaporative light scattering detection;
equiv., equivalents;
$Et_2O$, diethyl ether;
EtOAc, ethyl acetate;
Fmoc, fluorenylmethyloxycarbonyl;
h, hours;
HATU, 2-(7-Aza-1H-benzotriazole-1-yl)-1,1,3,3-tetramethyluronium hexafluorophosphate;
HOAt, 1-Hydroxy-7-Azabenzotriazole;
HOBt, N-Hydroxybenzotriazole;
HPLC, high performance liquid chromatography;
LC-MS, liquid chromatography mass spectrometry;
LDA, lithium diisopropylamide;
min, minutes;
MeOH, methanol;
MTBE, methyl-tert-butylether;
NMM, N-methylmorpholine;
NMR, nuclear magnetic resonance;
pet. ether, petroleum ether;
PS-Tosyl chloride, polystyrene supported tosyl chloride;
$R_f$, retention factor;
$R_t$, retention time;
Sat., saturated;
TFA, trifluoroacetic acid;
THF, tetrahydrofuran;
TIPS, triisopropylsilane;
TMS, trimethylsilane;
TBTU, O-(benzotriazol-1-yl)-N,N,N',N'-tetramethyluronium tetrafluoroborate;
UPLC, ultra high performance liquid chromatography;
% v/v, percentage volume to volume;
% w/v percentage weight to volume.

Analytical Methods

Reverse-Phase Preparative LC-MS: Mass-directed purification preparative LC-MS using a preparative C-18 column (Phenomenex Luna C18 (2), 100×21.2 mm, 5 µm).

Analysis of products and intermediates has been carried out using reverse-phase analytical HPLC-MS or UPLC-MS, using the parameters set out below. Purity was typically assessed by diode array at 210-400 nm.

HPLC Analytical Methods:

AnalpH2_MeOH: Phenomenex Luna C18 (2), 3 µm, 50×3.0 mm; A=water+0.1% formic acid; B=MeOH; 45° C.; % B: 0 min 5%, 4.4 min 95%, 5.2 min 95%, 5.21 min 5%, 6.5 min 5%; 1.1 mL/min.

AnalpH2_MeOH_4 min: Phenomenex Luna C18 (2), 3 µm, 50×4.6 mm; A=water+0.1% formic acid; B=MeOH; 45° C.; % B: 0 min 5%, 1 min 37.5%, 3 min 95%, 3.5 min 95%, 3.51 min 5%, 4.5 min 5%; 2.25 mL/min.

AnalpH9_MeOH: Phenomenex Luna C18 (2), 3 µm, 50×4.6 mm; A=aqueous pH9 (water/ammonium bicarb 10 mM); B=MeOH; 45° C.; % B: 0 min 5%, 1 min 37.5%, 3 min 95%, 3.5 min 95%, 3.51 min 5%, 4.5 min 5%; 2.25 mL/min.

Aldehyde_QC_1A: Phenomenex Luna C18 (2), 5 µm, 150×4.6 mm; A=water+0.1% TFA; B=MeCN+0.1% TFA; 55° C.; % B: 0 min 5%, 1 min 5%, 7 min 95%, 10 min 95%, 10.1 min 5%, 13 min 5%; 1.5 mL/min.

Aldehyde_QC_1B: Phenomenex Luna C18 (2), 5 µm, 150×4.6 mm; A=water+0.1% TFA; B=MeCN+0.1% TFA; 55° C.; % B: 0 min 5%, 0.5 min 5%, 7.5 min 95%, 10 min 95%, 10.1 min 5%, 13 min 5%; 1.5 mL/min.

Aldehyde_QC_2: Phenomenex Luna C18 (2), 5 µm, 150×4.6 mm; A=water+0.1% TFA; B=MeCN+0.1% TFA; 50° C.; % B: 0 min 5%, 0.1 min 5%, 8 min 95%, 10.5 min 95%, 10.55 min 5%, 13.5 min 5%; 1.5 mL/min.

Aldehyde_QC (Gemini)_1: Phenomenex Gemini C18, 5 µm, 150×4.6 mm; A=water+0.1% TFA; B=MeCN+0.1% TFA; 55° C.; % B: 0 min 5%, 0.5 min 5%, 7.5 min 95%, 10 min 95%, 10.1 min 5%, 13 min 5%; 1.5 mL/min.

Aldehyde_QC (Gemini)_2: Phenomenex Gemini C18, 5 µm, 150×4.6 mm; A=water+0.1% TFA; B=MeCN+0.1% TFA; 50° C.; % B: 0 min 5%, 0.1 min 5%, 8 min 95%, 10.5 min 95%, 10.55 min 5%, 13.5 min 5%; 1.5 mL/min.

AnalpH2_MeOH_QC: Phenomenex Luna C18 (2), 5 µm, 150×4.6 mm; A=water+0.1% formic acid; B=MeOH; 35° C.; % B: 0 min 5%, 0.5 min 5%, 7.5 min 95%, 10 min 95%, 10.1 min 5%, 13.0 min 5%; 1.5 mL/min.

AnalpH9_MeOH_QC. Phenomenex Luna C18 (2), 5 µm, 150×4.6 mm; A=aqueous pH 9 (water/ammonium bicarb 10 mM); B=MeOH; 35° C.; % B: 0 min 5%, 0.5 min 5%, 7.5 min 95%, 10 min 95%, 10.1 min 5%, 13 min 5%; 1.5 mL/min.

AnalpH_2QC: Phenomenex Luna C18 (2), 5 µm, 150×4.6 mm; A=water+0.1% formic acid; B=acetonitrile+0.1% formic acid; 30° C.; % B: 0 min 5%, 1 min 5%, 7 min 95%, 10 min 95%, 10.1 min 5%, 13 min 5%; 1.5 mL/min.

AnalpH2_A1B1_QC. Phenomenex Gemini C18, 5 µm, 150×4.6 mm; A=water+0.1% formic acid; B=acetonitrile+0.1% formic acid; 40° C.; % B: 0 min 5%, 0.5 min 5%, 7.5 min 95%, 10 min 95%, 10.1 min 5%, 13 min 5%; 1.5 mL/min.

UPLC Analytical Methods:

Method_2_Bic: Acquity UPLC BEH C-8, 1.7 µm, 100×2.1 mm; 40° C.; A=0.005 M ammonium bicarbonate (aq.); B=acetonitrile; % B: 0 min 30%, 4 min 80%, 6 min 80%, 6.1 min 30%; 0.3 mL/min.

Method_2_TFA_UPLC_2: Acquity UPLC BEH C18 1.7 µm, 100×2.1 mm; 25° C.; A=water+0.025% TFA; B=acetonitrile+0.025% TFA; % B: 0 min 30%, 4 min 80%, 6 min 80%, 6.1 min 30%; 0.4 mL/min.

Method_4_TFA_UPLC_2: Acquity UPLC BEH C18 1.7 µm, 100×2.1 mm; 25° C.; A=water+0.025% TFA; B=acetonitrile+0.025% TFA; % B: 0 min 10%, 4 min 80%, 6 min 80%, 6.1 min 10%; 0.3 mL/min.

A General Approach for the Synthesis of PVA Compounds (I)

Some general methods for the synthesis of PVA compounds of the present invention are illustrated in the following scheme.

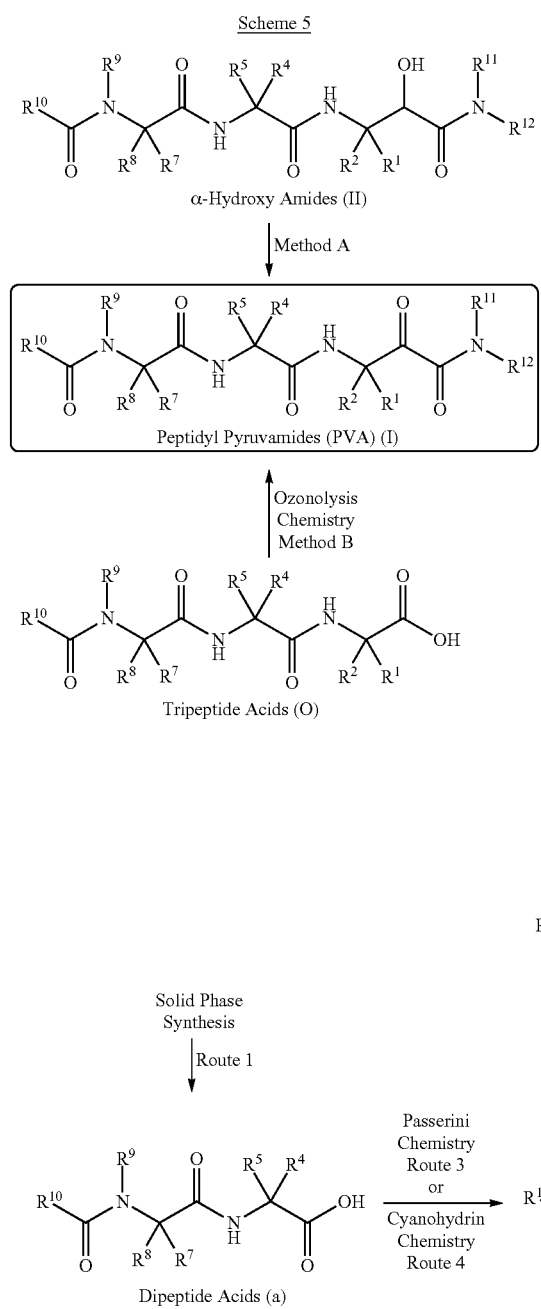

Method a Synthesis of PVA Compounds Via Oxidation of α-Hydroxy Amides (II)

Typical Procedure

To a stirred solution of the corresponding α-hydroxyamide (II) (1 equiv.) in dry DCM (1 mL/25-250 mg of alcohol) and optionally dry DMF (10-35% v/v depending upon solubility) at ambient temperature was added Dess-Martin periodinane (1.6 equiv.) in portions. The reaction mixture was stirred at ambient temperature and monitored by LC-MS until full conversion to product pyruvamide had occurred (typically 1 h to 1 day). Where necessary, additional Dess-Martin periodinane was added to complete the oxidation. The reaction mixture was quenched by addition of sat. (aq.) $NaHCO_3$ (1 volume) and (aq.) $Na_2S_2O_3$ (10% w/v). The mixture was stirred for approximately 30 min, diluted with EtOAc (10 volumes) and washed with sat. (aq.) $NaHCO_3$ (2×5 volumes), deionised water (5 volumes) and brine (5 volumes). The organic layer was subsequently dried over $MgSO_4$ and evaporated. Purification by reverse-phase preparative UPLC was generally followed by lyophilisation to give the desired peptidyl pyruvamide (I).

In some instances especially where the PVA compounds were water soluble, the DMP oxidation was concentrated without work-up, the residue was dissolved in DMSO and directly subjected to purification by reverse-phase preparative HPLC.

Alternatively the reaction could be carried out directly in DMSO in some instances.

Some general methods for the synthesis of α-hydroxy amides of formula (II) are illustrated in the following scheme.

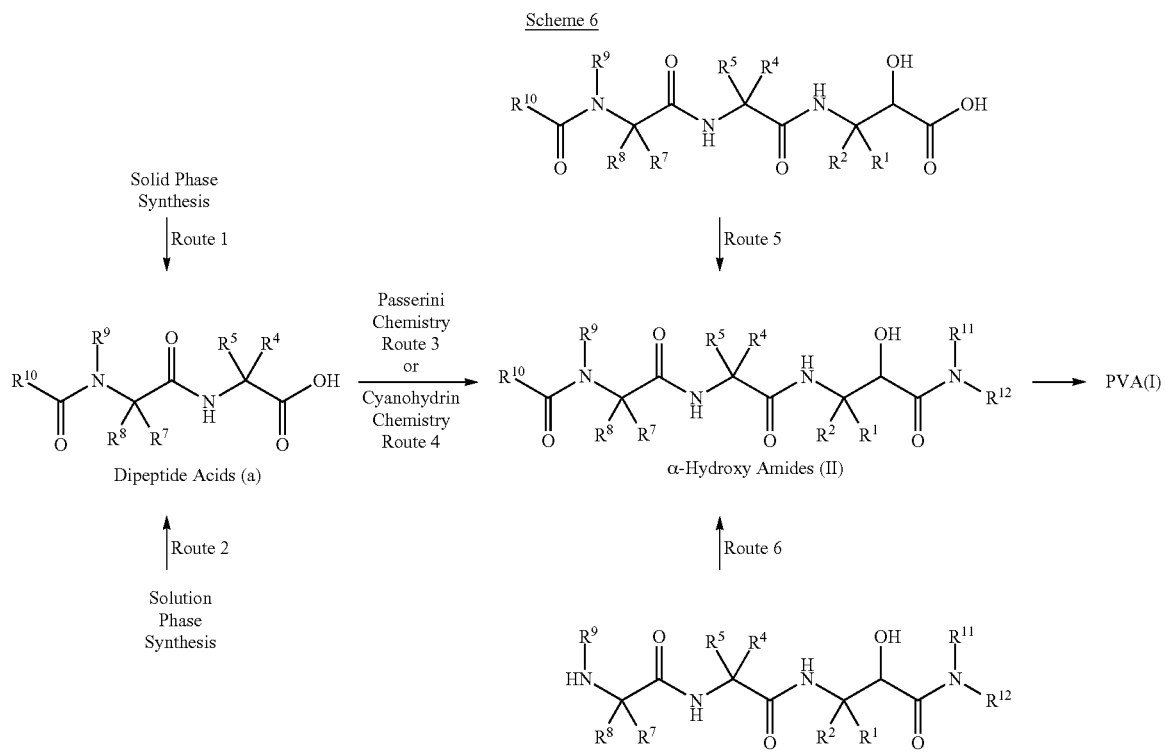

Routes 3 and 4 require the synthesis of dipeptide intermediates (A). Some routes to the synthesis of these compounds and specific examples prepared by these routes are outlined below.

Synthesis of Dipeptide Intermediates (A)

Route 1: Dipeptide Intermediates (A) Via Solid Phase Peptide Synthesis

Scheme 7

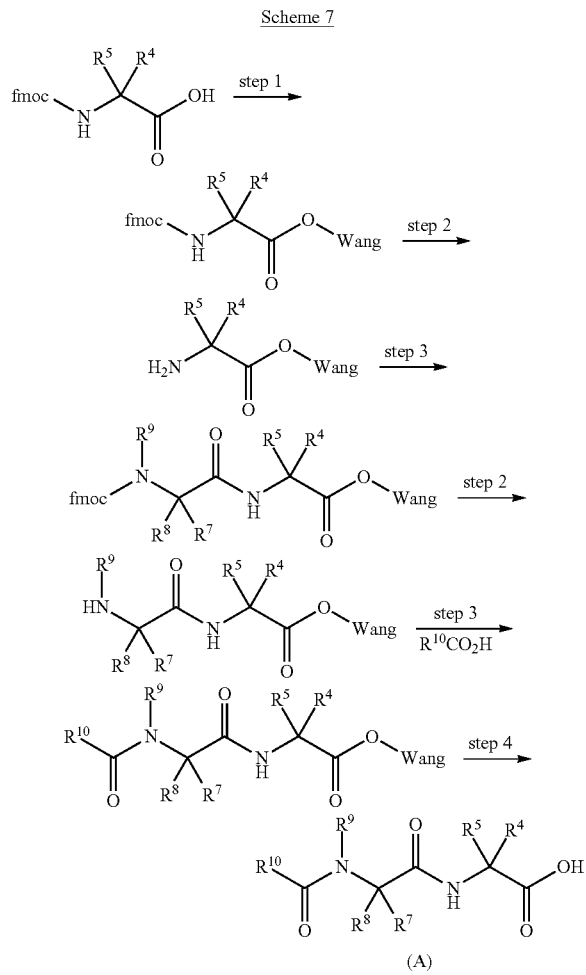

Peptides were synthesised on Wang resin using standard amide coupling procedures (see., e.g., Chan, W. C. and White, P. D., *Fmoc Solid Phase Peptide Synthesis A Practical Approach*, Oxford University Press, 2000). Fmoc-amino acids were purchased from commercial suppliers (e.g., Advanced Chemtech, Bachem, NovaBiochem or Polypeptide). Peptide grade DMF, which is free of dimethylamine, was used for peptide couplings to prevent any unwanted removal of Fmoc groups. Kaiser tests were used to indicate successful coupling of Fmoc-amino acids.

Typical Procedure

Step 1—Coupling of First Amino Acid to Wang Resin:

Wang resin was swollen with an appropriate volume of DMF then drained under vacuum. The Fmoc-amino acid (6 equiv.) was added followed by an appropriate volume of DMF (5 mL/g of resin), sufficient to cover the resin and peptide, and this mixture was shaken for 30 min. After that time, DIC (3 equiv.) and DMAP (catalytic) were added and the mixture was shaken for 4-5 h. The resin was drained under vacuum, washed with DCM and MeOH then re-swollen with DCM. Successful coupling could be indicated by carrying out step 2 on a small portion of the resin and performing a Kaiser test to indicate the presence of a free $NH_2$ group. In general, the exact amount of amino acid attached to the resin was not quantified and subsequent reactions were performed on the basis of the maximum loading as indicated from the supplier. For amino acids that were purchased pre-attached to Wang resin, approximate loadings are supplied by the supplier and these were used for calculating amounts of reagent for subsequent steps.

Step 2—Fmoc-Deprotection:

The resin was shaken with an appropriate volume of 20% v/v piperidine in DMF (5 mL/g resin) for 1 h then washed with DMF, DCM, MeOH and re-swollen with DCM. A positive Kaiser Test (blue colour) indicates the presence of a free $NH_2$ group.

Step 3—Amide Coupling:

The resin was shaken in an appropriate volume of DMF (~5 mL/g resin) with the appropriate Fmoc-amino acid (2 equiv.) or capping group $R_{10}CO_2H$ (2 equiv.), TBTU (2 equiv.) and DIPEA (4 equiv. or 6 equiv. if, e.g., HCl salt is used) for 4-5 h. After that time, the resin was drained under vacuum, washed with DMF, DCM, MeOH and re-swollen with DCM. A negative Kaiser test (no colour change) indicates that all of the free amino sites have coupled. If the solution remained blue, step 3 was repeated.

Steps 2 and 3 were repeated for the coupling of additional amino acids and capping groups as necessary.

Step 4—Resin Cleavage:

The resin was shaken with the cleavage solution consisting of 95% TFA, 2.5% TIPS and 2.5% water (10 mL/g of resin) for 90 min, and then drained into an appropriate vessel. The resin was washed with DCM under vacuum filtration. The solvent was subsequently evaporated under vacuum, then azeotroped with toluene to remove any residual water or triturated with iso-hexane and diethyl ether or MTBE to leave the crude product residue. The resulting peptide (A) was either used crude or further purified by trituration with $Et_2O$, flash column chromatography or reverse-phase preparative HPLC.

Dipeptide Intermediates (A) Prepared by Route 1

| Compound | Code | Analytical Data | Yield |
|---|---|---|---|
| [structure] | A1 | AnalpH2_MeOH; Rt = 2.96 min; m/z 341 (MH⁺); white solid | 2.6 g, 60% |

| Compound | Code | Analytical Data | Yield |
|---|---|---|---|
| (benzoyl-Phe-Ala-OH structure) | A2 | AnalpH2_MeOH; Rt = 3.78 min; m/z 341 (MH⁺); white solid | 1.09 g, 17% |
| (biphenyl-carbonyl-Phe-Ala-OH structure) | A3 | AnalpH2_MeOH; Rt = 4.54 min; m/z 417 (MH⁺); pale pink solid | 318 mg, 40% |
| (isonicotinoyl-Phe-Ala-OH structure) | A4 | AnalpH2_MeOH; Rt = 3.04 min; m/z 342 (MH⁺); pale orange solid | 368 mg, 57% |
| (3-phenoxybenzoyl-Phe-Ala-OH structure) | A5 | AnalpH2_MeOH; Rt = 4.54 min; m/z 433 (MH⁺); white solid | 378 mg, 46% |
| (benzoyl-tLeu-Ala-OH structure) | A6 | AnalpH2_MeOH; Rt = 3.59 min; m/z 307 (MH⁺); white solid | 105 mg, 80% |
| (benzoyl-(4-F-Phe)-Ala-OH structure) | A7 | AnalpH2_MeOH; Rt = 3.85 min; m/z 359 (MH⁺); white solid | 171 mg, 49% |

| Compound | Code | Analytical Data | Yield |
|---|---|---|---|
| (structure: benzamide-Phe(3,4-diF)-Ala-OH) | A8 | AnalpH2_MeOH; Rt = 3.98 min; m/z 377 (MH⁺); white solid | 269 mg, 73% |
| (structure: benzamide-(indanyl)Gly-Ala-OH) | A9 | AnalpH2_MeOH; Rt = 4.12 min; m/z 367 (MH⁺); white solid | 213 mg, 60% |
| (structure: benzamide-Phe(2-F)-Ala-OH) | A10 | AnalpH2_MeOH; Rt = 3.78 min; m/z 359 (MH⁺); white solid | 183 mg, 52% |
| (structure: benzamide-Phe(3-F)-Ala-OH) | A11 | AnalpH2_MeOH; Rt = 3.85 min; m/z 359 (MH⁺); white solid | 190 mg, 54% |
| (structure: benzamide-(2-naphthyl)Ala-Ala-OH) | A12 | AnalpH2_MeOH; Rt = 4.23 min; m/z 391 (MH⁺); white solid | 160 mg, 42% |

-continued

| Compound | Code | Analytical Data | Yield |
|---|---|---|---|
| (structure) | A13 | AnalpH2_MeOH; Rt = 4.49 min; m/z 417 (MH+); white solid | 307 mg, 75% |
| (structure) | A14 | AnalpH2_MeOH; Rt = 4.26 min; m/z 391 (MH+); white solid | 317 mg, 83% |
| (structure) | A15 | AnalpH2_MeOH_4 min; Rt = 1.12 min; m/z 342 (MH+); white solid | 105 mg, 31% |
| (structure) | A16 | AnalpH2_MeOH_4 min; Rt = 1.77 min; m/z 308 (MH+); white foam | 427 mg, 72% |
| (structure) | A17 | AnalpH2_MeOH_4 min; Rt = 1.51 min; m/z 440 (MH+); white solid | 154 mg, 13% |
| (structure) | A18 | AnalpH2_MeOH_4 min; Rt = 2.16 min; m/z 393 (MH+); white solid | 408 mg, 73% |

-continued

| Compound | Code | Analytical Data | Yield |
|---|---|---|---|
| | A19 | AnalpH2_MeOH_4 min; Rt = 2.38 min; m/z 384 (MH+); white solid | 140 mg, 57% |
| | A20 | AnalpH2_MeOH_4 min; Rt = 2.24 min; m/z 393 (MH+); white solid | 328 mg, 60% |
| | A21 | AnalpH2_MeOH_4 Min; Rt = 2.90 min; m/z 436 (MH+); white solid | 267 mg, 53% |
| | A22 | AnalpH2_MeOH_4 min; Rt = 2.53 min; m/z 398 (MH+); white solid | 88 mg, 15% |
| | A23 | AnalpH2_MeOH_4 min; Rt = 2.74 min; m/z 357 (MH+); white solid | 187 mg, 37% |
| | A24 | AnalpH2_MeOH_4 min; Rt = 2.38 min; m/z 364 (MH+); white solid | 245 mg, 48% |
| | A25 | AnalpH2_MeOH_4 min; Rt = 2.13 min; m/z 309 (MH+); white solid | 233 mg, 53% |

-continued

| Compound | Code | Analytical Data | Yield |
|---|---|---|---|
| (structure) | A26 | AnalpH2_MeOH_4 min; Rt = 2.18 min; m/z 399 (MH+); white solid | 58 mg, 5% |
| (structure) | A27 | AnalpH2_MeOH_4 min; Rt = 2.13 min; m/z 399 (MH+); white solid | 62 mg, 5% |
| (structure) | A28 | AnalpH2_MeOH_4 min; Rt = 2.08 min; m/z 365 (MH+); white solid | 405 mg, 78% |
| (structure) | A29 | AnalpH2_MeOH_4 min; Rt = 2.02 min; m/z 365 (MH+); white solid | 323 mg, 63% |
| (structure) | A30 | AnalpH2_MeOH_4 min; Rt = 1.52 min; m/z 454 (MH+); cream solid | 180 mg, 15% |
| (structure) | A31 | AnalpH2_MeOH_4 min; Rt = 3.08 min; m/z 385 (MH+); white solid | 100 mg, 20% |
| (structure) | A32 | AnalpH2_MeOH_4 min; Rt = 2.20 min; m/z 427 (MH+); white solid | 111 mg, 17% |

-continued

| Compound | Code | Analytical Data | Yield |
|---|---|---|---|
| (structure: morpholine-pyridine-CONH-Phe-Ala-OH) | A33 | AnalpH2_MeOH_4 min; Rt = 2.30 min; m/z 427 (MH+); colourless oil | 66 mg, 10% |
| (structure: naphthyl-CONH-(naphthylmethyl-CH)-CONH-Ala-OH) | A34 | AnalpH2_MeOH_4 Min; RT 3.08 min; m/z 441 (MH+); white solid | 221 mg, 44% |
| (structure: benzoyl-Phe-Nva-OH) | A35 | AnalpH2_MeOH_4 min; Rt = 2.76 min; m/z 369 (MH+); white solid | 165 mg, 35% |
| (structure: N-methylpiperidine-4-CO-NH-CH(tBu)-CO-NH-Ala-OH) | A36 | AnalpH2_MeOH_4 min; Rt = 0.71/0.84 min; m/z 328 (MH+); transleucerit solid | 383 mg, 17% |

Route 2: Dipeptide Intermediates (A) Via Solution Phase Peptide Synthesis

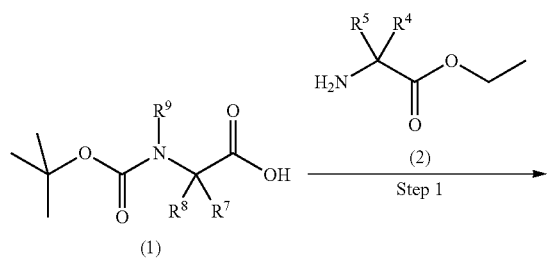

Scheme 8

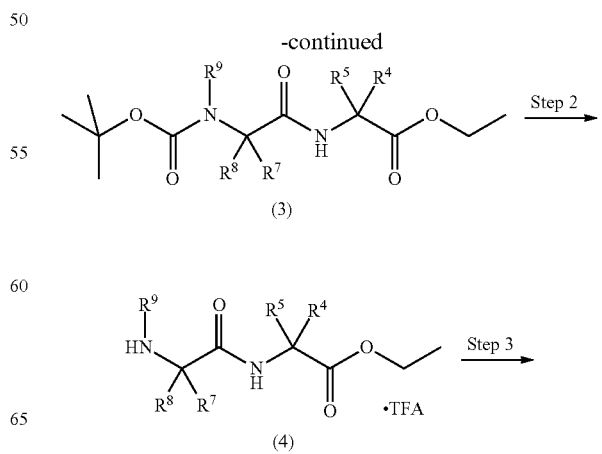

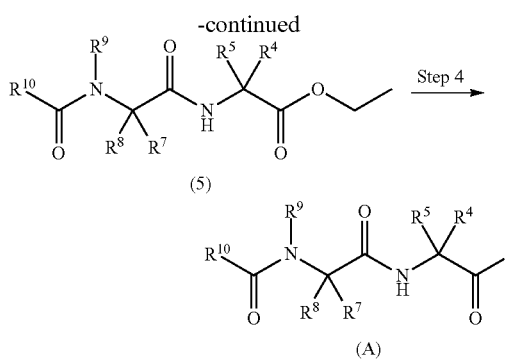

Typical Procedure

Step 1—Synthesis of Boc-Amino Dipeptide Ethyl Esters (3):

A solution of compound (1) (1 equiv.) in THF (~1 g/10 mL) was treated with iso-butyl chloroformate (1.05 equiv.) at −40° C., and NMM (1 equiv.), and stirred at −40° C. for 30 min. A solution of compound (2) (1.1 equiv.) in a DMF and THF (~1 g/4 mL, 1:1) mixture was added to the above reaction mixture at −40° C. followed by addition of NMM (1 equiv.). The resulting mixture was stirred at −40° C. for 2 h. The precipitated salts were filtered and washed with EtOAc. The combined filtrate was washed with 10% w/v citric acid solution, 5% w/v NaHCO$_3$ solution, brine solution, dried over Na$_2$SO$_4$, filtered and concentrated in vacuo to give a crude residue. This was generally purified by flash chromatography on silica or by reverse-phase preparative HPLC to give the desired compound (3).

Step 2—Synthesis of Amino Dipeptide Ethyl Esters (4):

A solution of compound (3) (1 equiv.) in DCM (1 g/10 mL) was treated with TFA (5 equiv.) at 0° C. and stirred at room temperature for 16 h. The volatiles were concentrated and the residue was triturated with Et$_2$O (150 mL) to obtain the desired compound (4).

Alternatively this reaction can be carried out by dissolving the Boc-protected compound (3) in DCM and stirring with ~10 equiv of 4 N HCl in dioxane for up to 18 hours.

Step 3—Synthesis of Amido Dipeptide Ethyl Esters (5):

Step 3 can be carried out using a variety of amide coupling conditions, well known to those in the art. These include the reaction of the corresponding carboxylic acid with compound of formula (4) in the presence of reagents such as HATU, TBTU or EDC/HOBt and a tertiary amine base such as DIPEA in solvents such as DCM or DMF. Alternatively the corresponding acid chloride can be used in the presence of a tertiary amine base in solvents such as DCM.

One typical procedure is as follows:

Synthesis of (S)-2-((S)-2-Benzoylamino-3-phenyl-propionylamino)-propionic acid ethyl ester (for A1)

To a solution of (S)-2-((S)-2-Amino-3-phenyl-propionylamino)-propionic acid ethyl ester.trifluoroacetate salt (10 g, 37.9 mmol) and DIPEA (19.5 mL, 113.6 mmol) in DCM (100 mL) was added benzoyl chloride (4.0 mL, 34.1 mmol) at −20° C. and stirred at −20° C. for 1 h. The reaction mixture was filtered to remove salts and the filtrate was washed with 10% citric acid solution (2×50 mL), 5% NaHCO$_3$ solution (2×50 mL) and brine solution (50 mL) respectively, dried over Na$_2$SO$_4$, filtered and concentrated in vacuo to give a residue that was dissolved in CHCl$_3$ (20 mL) and triturated with n-pentane. The precipitated solid was filtered and washed with a mixture of Et$_2$O and n-pentane (50 mL, 1:1), then dried to obtain (S)-2-((S)-2-Benzoylamino-3-phenyl-propionylamino)-propionic acid ethyl ester (6.5 g, 47%) as a white solid. R$_f$: 0.8 (10% MeOH/CHCl$_3$); $^1$H NMR (400 MHz, DMSO-d$_6$): δ 8.60-8.55 (1H, m), 7.76 (2H, d, J=6.8 Hz), 7.52-7.35 (5H, m), 7.27 (2H, t, J=7.6 Hz), 7.18 (1H, t, J=7.6 Hz), 4.80-4.70 (1H, m), 4.30-4.22 (1H, m), 4.07 (2H, q), 3.11 (1H, dd, J=4, 14 Hz), 3.01-2.98 (1H, m), 1.34 (3H, d, J=7.2 Hz), 1.18 (3H, t, J=6.8 Hz); m/z 369 (MH)$^+$.

Step 4—Synthesis of Capped Dipeptides (A):

To a solution of compound (5) (1 equiv.) in THF (6 volumes) and H$_2$O (6 volumes) was added LiOH.H$_2$O (4 equiv.) at 0° C. The reaction mixture was stirred for 2 h. The volatiles (THF) were removed from the reaction mixture and the aqueous phase was adjusted to pH ~3 with 10% w/v citric acid solution or 1M HCl. If a solid precipitated this was collected by filtration, washed with H$_2$O and n-pentane and dried to obtain the corresponding capped dipeptide intermediate (A). Alternatively the acidified aqueous layer was extracted with EtOAc×3 and the combined organics dried over MgSO$_4$ and evaporated to give the crude product. In some instances this was further purified by flash chromatography on silica or by reverse-phase preparative HPLC.

Dipeptide Intermediates (A) Prepared by Route 2

| Compound | Code | Analytical Data | Yield |
|---|---|---|---|
| (structure) | A1 | Method_2_Bic; Rt = 1.01 min; m/z 339 (M − H)$^{-1}$; white solid | 4.5 g, 22% |
| (structure) | A6 | Method_2_TFA_UPLC_2; Rt = 1.54 min; m/z 307 (MH$^+$); white solid | 2.0 g, 16% |

-continued

| Compound | Code | Analytical Data | Yield |
|---|---|---|---|
| (structure) | A16 | Method_2_TFA_UPLC_2; Rt = 1.78 mins; m/z 336 (MH$^+$); off white solid | 2.8 g, 19% |
| (structure) | A23 | R$_f$: 0.2 (10% MeOH—CHCl$_3$); m/z 357 (MH)$^+$; white solid | 3.0 g, 43% |
| (structure) | A31 | AnalpH2_MeOH_4 Min; Rt = 3.12 min; m/z 385 (MH$^+$); cream solid | 3.0 g, 49% |
| (structure) | A37 | AnalpH2_MeOH_4 Min; Rt = 2.40 min; m/z 410 (MH$^+$); white solid | 212 mg, 35% |
| (structure) | A38 | Method_4_TFA_UPLC_2; Rt = 2.40 min; m/z 307 (M − H)$^-$; white solid | 220 mg, 8% |
| (structure) | A39 | AnalpH2_MeOH_4 Min; Rt = 2.75 min; m/z 407 (MH)$^+$; white solid | 240 mg, 8% |
| (structure) | A40 | Method_4_TFA_UPLC_2; Rt = 1.90 min; m/z 324 (MH$^+$); white solid | 300 mg, 13% |

-continued

| Compound | Code | Analytical Data | Yield |
|---|---|---|---|
| (quinoline-4-carbonyl-tLeu-Ala-OH structure) | A41 | AnalpH2_MeOH_4 min; Rt = 2.25 min; m/z 357 (MH+); white solid | 257 mg, 13% |
| (isoquinoline-3-carbonyl-tLeu-Ala-OH structure) | A42 | AnalpH2_MeOH_4 min; Rt = 2.20 min; m/z 358 (MH+); white solid | 150 mg, 16% |
| (3-((1-methylimidazol-2-yl)methoxy)benzoyl-tLeu-Ala-OH structure) | A43 | AnalpH2_MeOH_4 min; Rt = 1.49 min; m/z 417 (MH+); white solid | Used crude |
| (4-(2-pyrrolidin-1-ylethoxy)benzoyl-tLeu-Ala-OH structure) | A44 | AnalpH2_MeOH_4 min; Rt = 1.20 min; m/z 420 (MH+); translucent solid | Used crude |
| (4-((1-methylimidazol-2-yl)methoxy)benzoyl-tLeu-Ala-OH structure) | A45 | AnalpH2_MeOH_4 min; Rt = 1.42 min; m/z 417 (MH+); translucent solid | Used crude |
| (benzoyl-Aib-Ala-OH structure) | A46* | $^1$H NMR (400 MHz, DMSO-$d_6$): δ 12.04 (1H, br, s), 8.19 (1H, s), 7.83 (2H, d, J = 6.4 Hz), 7.70 (1H, d, J = 7.2 Hz), 7.54-7.48 (1H, m), 7.48-7.41 (2H, m), 4.25-4.16 (1H, m), 1.46 (3H, s), 1.44 (3H, s), 1.22 (3H, d, J = 7.2 Hz); m/z 279 (MH+); white solid | — |
| (benzoyl-1-aminocyclohexanecarbonyl-Ala-OH structure) | A47* | $^1$H NMR (400 MHz, DMSO-$d_6$): δ 7.92 (1H, s), 7.83 (2H, d, J = 7.2 Hz), 7.57-7.52 (2H, m), 7.47 (2H, t, J = 7.6 Hz), 4.25-4.16 (1H, m), 2.67-2.54 (2H, m), 2.25-2.15 (2H, m), 1.80-1.67 (2H, m), 1.60-1.41 (4H, m), 1.22 (3H, d, J = 7.2 Hz); m/z 319 (MH+); white solid | — |

| Compound | Code | Analytical Data | Yield |
|---|---|---|---|
| [structure] | A48* | ¹H NMR (400 MHz, DMSO-$d_6$): δ 8.80 (1H, br, s), 7.76 (1H, br s), 4.01 (1H, d, J = 9.6 Hz), 3.70-3.61 (1H, m), 3.49-3.41 (2H, m), 3.30-3.21 (2H, m), 3.11 (3H, s), 3.02 (3H, s), 2.65-2.55 (1H, m), 2.03-1.88 (4H, m), 1.11 (3H, d, J = 6.4 Hz), 0.93 (9H, s); white solid | 400 mg, 5% |
| [structure] | A49 | ¹H NMR (400 MHz, DMSO-$d_6$): δ 8.50 (1H, d, J = 8.4 Hz), 8.41 (1H, d, J = 7.2 Hz), 7.82-7.78 (2H, m), 7.54-7.40 (3H, m), 7.30-7.25 (2H, m), 6.93-6.87 (2H, m), 4.72-4.64 (1H, m), 4.30-4.21 (1H, m), 3.73 (2H, d, J = 12.4 Hz), 3.47-3.40 (2H, m), 3.15-2.90 (6H, m), 2.77 (3H, d, J = 3.6 Hz), 1.31 (3H, d, J = 7.2 Hz); pale yellow gummy liquid | 150 mg, 15% |
| [structure] | A50 | $R_f$: 0.1 (10% MeOH/CHCl₃); m/z 329 (MH⁺) | 450 mg, 18% |
| [structure] | A51 | ¹H NMR (400 MHz, DMSO-$d_6$): 8.75 (1H, d, J = 8.8 Hz), 8.34 (1H, d, J = 6.8 Hz), 7.96 (1H, d, J = 8 Hz), 7.92 (1H, d, J = 8 Hz), 7.70 (1H, d, J = 8 Hz), 7.53-7.47 (2H, m), 7.44-7.37 (4H, m), 7.31 (2H, t, J = 7.6 Hz), 7.27-7.23 (1H, m), 4.90-4.81 (1H, m), 4.24-4.13 (1H, m), 3.21 (1H, dd, J = 3.2, 14.1 Hz), 2.86 (1H, dd, J = 14.1, 11.6 Hz), 1.34 (3H, d, J = 7.2 Hz); white solid | 1.6 g, 43% |
| [structure] | A52 | ¹H NMR (400 MHz, DMSO-$d_6$): 12.56 (1H, brs), 8.90 (1H, d, J = 8.8 Hz), 8.69 (2H, d, J = 5.8 Hz), 8.53 (1H, d, J = 7.2 Hz), 7.67 (2H, d. J = 5.8 Hz), 7.37 (2H, d, J = 7.5 Hz), 7.25 (2H, t, J = 7.5 Hz), 7.16 (1H, t, J = 7.5 Hz), 4.79-4.73 (1H, m), 4.30-4.19 (1H, m), 3.15 (1H, dd, J = 14.1, 3.3 Hz), 2.95 (1H, dd, J = 14.1, 11.6 Hz), 1.33 (3H, d, J = 7.2 Hz); white solid | 2.0 g, 30% |

-continued
| Compound | Code | Analytical Data | Yield |
|---|---|---|---|
| 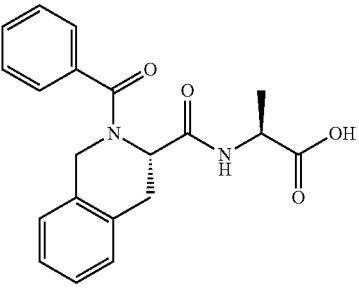 [SMILES: C[C@H](NC(=O)[C@@H]1Cc2ccccc2CN1C(=O)c1ccccc1)C(=O)O] | A53 | AnalpH2_MeOH_4 Min; Rt = 2.53 min; m/z 353 (MH+); white solid | 180 mg, 7% |
| 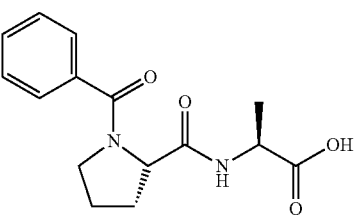 | A54 | AnalpH2_MeOH_4 Min; Rt = 1.80 min; m/z 291 (MH+); white solid | 957 mg, 36% |
| 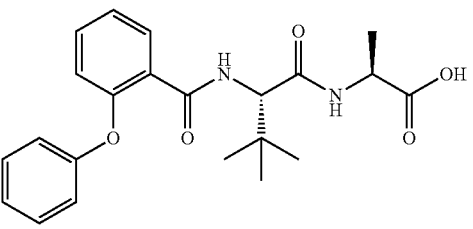 [SMILES: C[C@H](NC(=O)[C@@H](NC(=O)c1ccccc1Oc1ccccc1)C(C)(C)C)C(=O)O] | A55 | $R_f$: 0.4 (15% MeOH/CHCl$_3$); m/z 399 (MH)+; white solid | 600 mg, 32% |
| 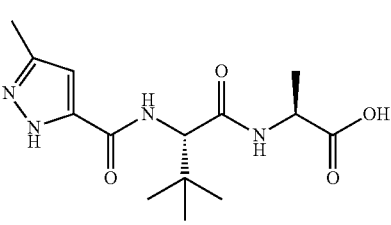 [SMILES: Cc1cc(C(=O)N[C@H](C(=O)N[C@@H](C)C(=O)O)C(C)(C)C)[nH]n1] | A56 | $R_f$: 0.5 (10:89:1, MeOH:CHCl$_3$:AcOH); m/z 311 (MH)+; off-white solid | 750 mg, 39% |
| 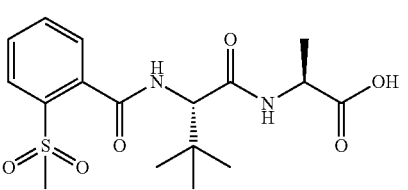 [SMILES: C[C@H](NC(=O)[C@@H](NC(=O)c1ccccc1S(C)(=O)=O)C(C)(C)C)C(=O)O] | A57 | $R_f$: 0.3 (15% MeOH/CHCl$_3$); m/z 385 (MH)+; white solid | 500 mg, 29% |
| 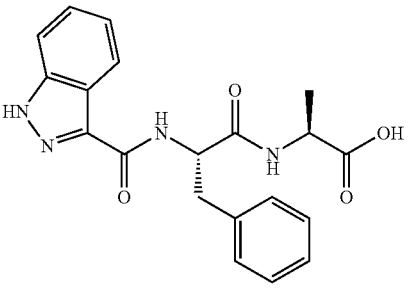 [SMILES: C[C@H](NC(=O)[C@H](Cc1ccccc1)NC(=O)c1n[nH]c2ccccc12)C(=O)O] | A58 | AnalpH2_MeOH_4 min; Rt = 2.60 mins; m/z 379 ((M − H)−); pale yellow solid | 488 mg, 28% |

-continued

| Compound | Code | Analytical Data | Yield |
|---|---|---|---|
| (structure) | A59 | R$_f$: 0.6 (50% MeOH/CHCl$_3$). m/z 324 (MH)$^+$; off-white solid | 300 mg, 13% |
| (structure) | A60 | R$_f$: 0.4 (10:89:1, MeOH:CHCl$_3$:AcOH). m/z 323 (M − H)$^-$; off-white solid | 700 mg, 25% |
| (structure) | A61 | AnalpH2_MeOH_4 Min; Rt = 2.37 min; m/z 339 (MH$^+$); white solid | 80 mg, 6% |
| (structure) | A62 | R$_f$: 0.5 (20% MeOH—CHCl$_3$); m/z 391 (MH)$^+$; white solid | 1.4 g, 23% |
| (structure) | A63 | AnalpH2_MeOH_4 Min; RT = 1.91 min; m/z 291 (MH$^+$); white solid. | 142 mg, 27% |
| (structure) | A64 | R$_f$: 0.6 (20% MeOH/CHCl$_3$); m/z 369 (MH)$^+$; white solid | 220 mg, 24% from BB17 |

| Compound | Code | Analytical Data | Yield |
|---|---|---|---|
| 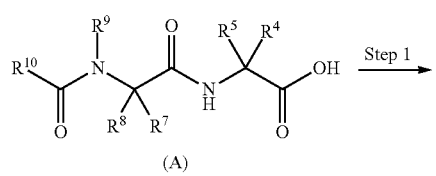 | A65 | AnalpH2_MeOH_4 Min; Rt = 2.87 min; m/z 355 (MH)+; white solid | 317 mg, 50% |

*The following compounds were prepared using solution phase chemistry using a variation of the scheme outlined in Route 2.

For compounds (A46) and (A47) the α-disubstituted amino acid was first converted to its ethyl ester (SOCl$_2$, ethanol) which was in turn converted to the corresponding benzamide. This was subsequently coupled with intermediate (2) as depicted in Scheme 8, and then hydrolysed in an analogous fashion to give the corresponding dipeptide acid (A).

For compound (A48) (S)-2-((S)-2-Amino-3,3-dimethyl-butyrylamino)-propionic acid ethyl ester was coupled with 1-Methyl-piperidine-4-carboxylic acid using isobutylchloroformate and N-methylmorpholine in DMF to give (S)-2-{(S)-3,3-Dimethyl-2-[(1-methyl-piperidine-4-carbonyl)-amino]-butyrylamino}-propionic acid ethyl ester. This was then quaternised with MeI in DCM-acetone and subsequently hydrolysed using an hydroxide resin such as Ambersep 900-OH resin.

For compound (A49) the compounds of formula (1) was first prepared as follows. Boc-p-bromo-Phe-ON was first converted to its methyl ester using diazomethane under standard conditions. The bromo group was then displaced with 4-methylpiperazine under Buchwald-Hartwig type conditions (Pd$_2$(dba)$_3$, DavePhos, CsCO$_3$, THF reflux, for 16 h). Finally hydrolysis of the methyl ester using hydroxide resin Ambersep 900 OH in THF over 48 h gave Boc-p-(4-methylpiperazin-1-yl)-Phe-OH (formula (I)), which was used to synthesise the desired compound A49 as outlined in Scheme 8.

For compound (A50) a solution of (S)-2-((S)-2-Amino-3,3-dimethyl-butyrylamino)-propionic add ethyl ester in a 1:1 mixture of DCM and 5% aq NaHCO$_3$ was treated with triphosgene to generate the corresponding isocyanate. This was subsequently reacted with 1-methylpiperazine to generate the urea, which was subsequently hydrolysed with LiOH in THF/H$_2$O to give the desired compound (A50).

Route 3: Synthesis of PVA Compounds (I) Using Passerini Chemistry

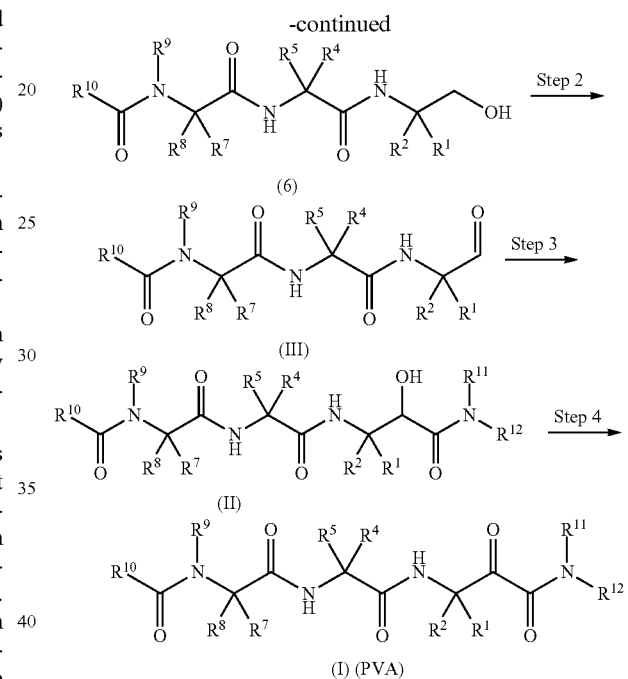

Typical Procedure

Step 1—Synthesis of Peptidyl Alcohols (6)

To a solution of acid (A) (1 equiv.) in THF (25-50 mg/mL) and optionally DMF (0.05-0.25 volumes) at −40° C. was added NMM (3.1 equiv.) and iso-butyl chloroformate (1.1 equiv.). The reaction mixture was stirred at −40° C. for approximately 30 min (extent of formation of the mixed anhydride can be monitored by quenching an aliquot of the reaction mixture in, e.g., excess pyrrolidine and analysing extent of amide formation by LC-MS). A solution of the amino alcohol (1.1 equiv.) in THF or DMF (0.1 volumes) was added dropwise. The reaction was stirred at −40° C. for approximately 1 h until complete as measured by LC-MS. Additional amino alcohol could be added if required. The reaction mixture was allowed to warm to ambient temperature. The resulting mixture was diluted with EtOAc (10 volumes) and sat. aq. NaHCO$_3$ (10 volumes). The layers were separated and the aqueous layer extracted with EtOAc (2×10 volumes). The combined organic phases were washed with water (3×10 volumes) and brine (10 volumes) and concentrated under vacuum. The resulting alcohol (6) was either used directly or purified by flash column chromatography on silica or by reverse-phase preparative HPLC.

Step 2—Synthesis of Peptidyl Aldehydes (III)

To a stirred solution of the corresponding alcohol (6) (1 equiv.) in dry DCM (1 mL/15-200 mg of alcohol) and optionally dry DMF (10-100% v/v depending upon solubility) at ambient temperature was added Dess-Martin periodinane (2 equiv.) in portions. The reaction mixture was stirred at ambient temperature and monitored by LC-MS until full conversion to product aldehyde had occurred (typically 1 h to 1 day). Where necessary, more Dess-Martin periodinane was added to complete the oxidation. The reaction mixture was quenched by addition of sat. (aq.) NaHCO$_3$ (1 volume) and (aq.) Na$_2$S$_2$O$_3$ (10% w/v). The mixture was stirred for approximately 30 min, diluted with EtOAc (10 volumes) and washed with sat. (aq.) NaHCO$_3$ (2×5 volumes), deionised water (5 volumes) and brine (5 volumes). The organic layer was subsequently dried over MgSO$_4$ and evaporated to give the desired compound which was optionally used 'as is' or purified by reverse-phase preparative HPLC (a H$_2$O+0.1% TFA:MeCN+0.1% TFA gradient at 50° C. was used for preparative HPLC) followed by lyophilisation to give the desired compound (III).

Step 3—Synthesis of Peptidyl α-Hydroxyamides (II)

To a stirred solution of the corresponding aldehyde (III) (1 equiv.) in dry DCM (1 mL/10-50 mg of aldehyde) and optionally dry DMF (10-35% v/v depending upon solubility) at 0° C. was added appropriate isocyanide (1.1 equiv.) then pyridine (4 equiv.) followed by dropwise addition of trifluoroacetic acid (2 equiv.). The reaction mixture was stirred at 0° C. for 10 min and then allowed to warm to ambient temperature. The reaction was monitored by LC-MS until full conversion to product α-hydroxyamides and/or α-hydroxyamide trifluoroacetate esters had occurred (typically 0.5-1 day). Where necessary, additional isocyanide was added to complete the reaction. The reaction mixture was evaporated in vacuo, diluted with EtOAc (5 volumes) and quenched by addition of sat. (aq.) NaHCO$_3$ (1 volume). The mixture was stirred for approximately 30 min and was washed with sat. (aq.) NaHCO$_3$ (2×5 volumes) and brine (5 volumes).

The organic layer was subsequently dried over MgSO$_4$ and evaporated and was used as is or purified by preparative HPLC to give the desired compound (II).

Step 4—Synthesis of PVA Compounds (1)

See Method A

PVA Compounds Prepared by Route 3

| Compound | Code Int. | Analytical Data | Yield |
|---|---|---|---|
|  | PVA-A1 001 | Aldehyde QC_2; Rt 7.70 min; m/z 563 (MH$^+$); white solid | 76 mg, 7% |
|  | PVA-A1 002 | Aldehyde_QC (Gemini)_1; Rt 6.91 min; m/z 585 (MH$^+$); white solid | 3 mg, 2% |
|  | PVA-A1 003 | Aldehyde QC (Gemini)_1; Rt 6.82 min; m/z 549 (MH$^+$); white solid | 11 mg, 26% |

-continued

| Compound | Code Int. | Analytical Data | Yield |
|---|---|---|---|
| (structure) | PVA-A1 004 | Aldehyde QC (Gemini)_1; Rt 6.53 min; m/z 523 (MH$^+$); white solid | 9 mg, 7% |
| (structure) | PVA-A1 005 | Aldehyde QC (Gemini)_1; Rt 6.76 min; m/z 571 (MH$^+$); white solid | 2 mg, 1% |
| (structure) | PVA-A1 008 | Aldehyde QC (Gemini)_1; Rt 6.97 min; m/z 563 (MH$^+$); white solid | 8 mg, 8% |
| (structure) | PVA-A1 009 | Aldehyde QC (Gemini)_1; Rt 6.53 min; m/z 557 (MH$^+$); white solid | 8 mg, 6% |
| (structure) | PVA-A1 010 | Aldehyde QC (Gemini)_1; Rt 6.65 min; m/z 571 (MH$^+$); white solid | 5 mg, 3% |
| (structure) | PVA-A1 011 | Aldehyde QC (Gemini)_1; Rt 6.65 min; m/z 561 (MH$^+$); white solid | 4 mg, 3% |

| Compound | Code Int. | Analytical Data | Yield |
|---|---|---|---|
| | PVA-012 | A1 | Aldehyde QC (Gemini)_1; Rt 6.55 min; m/z 573 (MH+); beige solid | 6 mg, 4% |
| | PVA-013 | A1 | Aldehyde QC (Gemini)_1; Rt 6.69 min; m/z 592 (MH+); beige solid | 2 mg, 1% |
| | PVA-015 | A1 | Aldehyde QC (Gemini)_1; Rt 6.31 min; m/z 509 (MH+); white solid | 1 mg, 1% |
| | PVA-016 | A1 | Aldehyde QC (Gemini)_1; Rt 6.83 min; m/z 571 (MH+); white solid | 1 mg, 1% |
| | PVA-019 | A3 | Aldehyde QC_1B; Rt 8.28 min; m/z 625 (MH+); white solid | 8 mg, 14% |
| | PVA-020 | A4 | Aldehyde QC_1B; Rt 5.62 min; m/z 550 (MH+); white solid | 14 mg, 9% |

| Compound | Code Int. | Analytical Data | Yield |
|---|---|---|---|
| | PVA-021 | A5 | Aldehyde QC (Gemini)_1; Rt 7.66 min; m/z 641 (MH+); white solid | 3 mg, 3% |
| | PVA-026 | A6 | Aldehyde QC_2; Rt 7.38 min; m/z 515 (MH+); white solid | 17 mg, 10% |
| | PVA-027 | A7 | Aldehyde QC_2; Rt 7.49 min; m/z 567 (MH+); white solid | 12 mg, 6% |
| | PVA-028 | A8 | Aldehyde QC_2; Rt 7.60 min; m/z 585 (MH+); white solid | 8 mg, 3% |
| | PVA-029 | A9 | Aldehyde QC_2; Rt 7.80 min; m/z 575 (MH+); white solid | 11 mg, 7% |
| | PVA-030 | A10 | Aldehyde QC_2; Rt 7.48 min; m/z 567 (MH+); white solid | 2 mg, 4% |

-continued

| Compound | Code Int. | Analytical Data | Yield |
|---|---|---|---|
| [structure with 3-fluorobenzyl side chain, cyclohexyl amide] | PVA-A11 031 | Aldehyde QC_2; Rt 7.50 min; m/z 567 (MH$^+$); white solid | 1 mg, 1% |
| [structure with 2-naphthylmethyl side chain, benzyl amide] | PVA-A12 032 | Aldehyde QC_2; Rt 7.57 min; m/z 607 (MH$^+$); pale yellow solid | 4 mg, 3% |
| [structure with biphenylmethyl side chain, benzyl amide] | PVA-A13 033 | Aldehyde QC_2; Rt 7.84 min; m/z 633 (MH$^+$); white solid | 2 mg, 1% |
| [structure with 1-naphthylmethyl side chain, benzyl amide] | PVA-A14 034 | Aldehyde QC_2; Rt 7.60 min; m/z 607 (MH$^+$); white solid | 1 mg, 1% |
| [structure with isonicotinoyl cap, benzyl side chain, benzyl amide] | PVA-A4 035 | Aldehyde QC_2; Rt 5.36 min; m/z 558 (MH$^+$); white solid | 4 mg, 2% |

-continued
| Compound | Code Int. | Analytical Data | Yield |
|---|---|---|---|
| 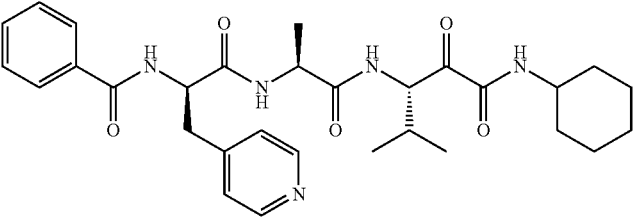 [SMILES: CC(C)[C@H](NC(=O)[C@H](C)NC(=O)[C@@H](Cc1ccncc1)NC(=O)c1ccccc1)C(=O)C(=O)NC1CCCCC1] | PVA-036 | A15 | Aldehyde QC_2; Rt 5.32 min; m/z 550 (MH+); white solid | 14 mg, 10% |
| 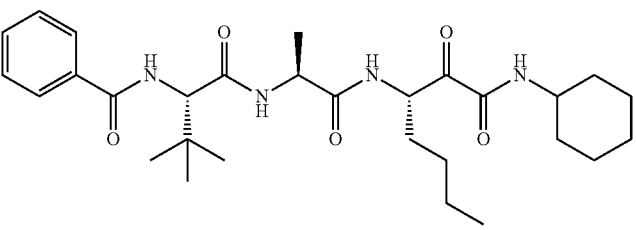 [SMILES: CCCC[C@H](NC(=O)[C@H](C)NC(=O)[C@@H](NC(=O)c1ccccc1)C(C)(C)C)C(=O)C(=O)NC1CCCCC1] | PVA-037 | A6 | Aldehyde QC_2; Rt 7.76 min; m/z 529 (MH+); white solid | 15 mg, 16% |
| 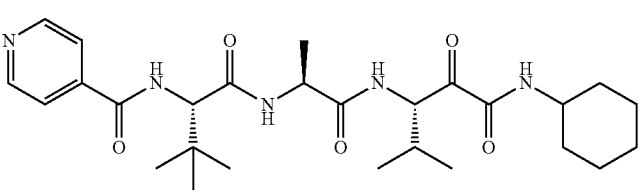 [SMILES: CC(C)[C@H](NC(=O)[C@H](C)NC(=O)[C@@H](NC(=O)c1ccncc1)C(C)(C)C)C(=O)C(=O)NC1CCCCC1] | PVA-038 | A16 | Aldehyde QC_2; Rt 5.54 min; m/z 516 (MH+); white solid | 15 mg, 9% |
| 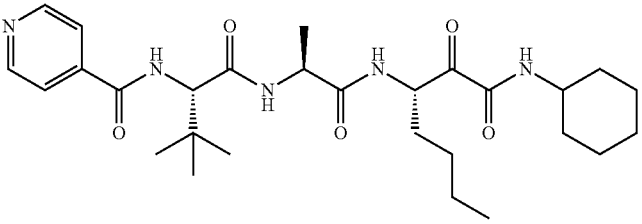 [SMILES: CCCC[C@H](NC(=O)[C@H](C)NC(=O)[C@@H](NC(=O)c1ccncc1)C(C)(C)C)C(=O)C(=O)NC1CCCCC1] | PVA-039 | A16 | Aldehyde QC_2; Rt 5.90 min; m/z 530 (MH+); white solid | 14 mg, 11% |
| 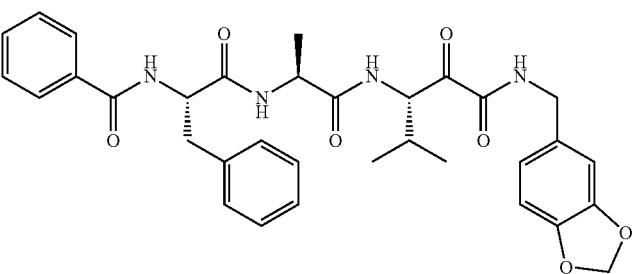 [SMILES: CC(C)[C@H](NC(=O)[C@H](C)NC(=O)[C@H](Cc1ccccc1)NC(=O)c1ccccc1)C(=O)C(=O)NCc1ccc2c(c1)OCO2] | PVA-041 | A1 | Aldehyde QC_2; Rt 6.94 min; m/z 601 (MH+); cream solid | 7 mg, 6% |
| 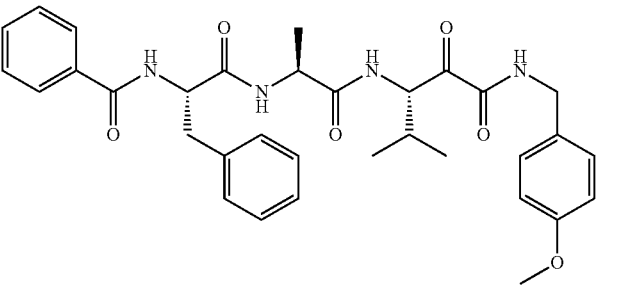 [SMILES: COc1ccc(CNC(=O)C(=O)[C@@H](NC(=O)[C@H](C)NC(=O)[C@H](Cc2ccccc2)NC(=O)c2ccccc2)C(C)C)cc1] | PVA-042 | A1 | Aldehyde QC_2; Rt 7.02 min; m/z 587 (MH+); cream solid | 8 mg, 6% |

-continued
| Compound | Code Int. | Analytical Data | Yield |
|---|---|---|---|
| 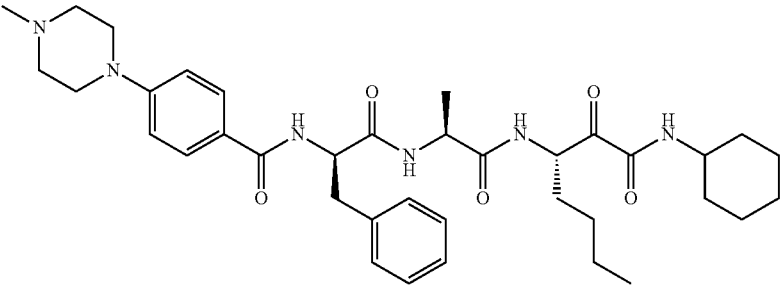 [SMILES: CCCC[C@H](NC(=O)[C@H](C)NC(=O)[C@@H](Cc1ccccc1)NC(=O)c1ccc(N2CCN(C)CC2)cc1)C(=O)C(=O)NC1CCCCC1] | PVA-043 | A17 | Aldehyde QC_2; Rt 5.81 min; m/z 661 (MH+); white solid | 2 mg, 1% |
| 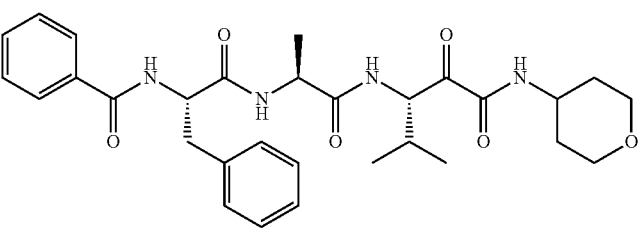 [SMILES: CC(C)[C@H](NC(=O)[C@H](C)NC(=O)[C@H](Cc1ccccc1)NC(=O)c1ccccc1)C(=O)C(=O)NC1CCOCC1] | PVA-044 | A1 | Aldehyde QC_2; Rt 6.20 min; m/z 551 (MH+); white solid | 8 mg, 7% |
| 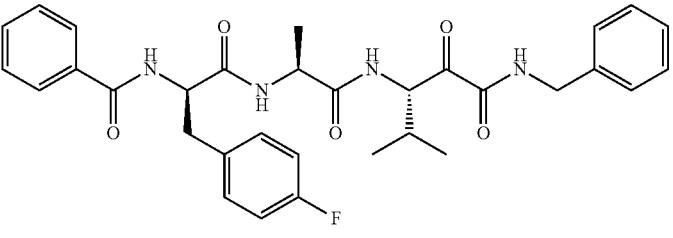 [SMILES: CC(C)[C@H](NC(=O)[C@H](C)NC(=O)[C@@H](Cc1ccc(F)cc1)NC(=O)c1ccccc1)C(=O)C(=O)NCc1ccccc1] | PVA-045 | A7 | Aldehyde QC_2; Rt 7.14 min; m/z 575 (MH+); white solid | 13 mg, 11% |
| 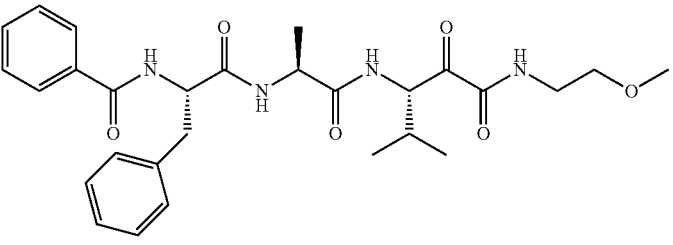 [SMILES: COCCNC(=O)C(=O)[C@@H](NC(=O)[C@H](C)NC(=O)[C@H](Cc1ccccc1)NC(=O)c1ccccc1)C(C)C] | PVA-046 | A1 | Aldehyde QC_2; Rt 6.18 min; m/z 525 (MH+); white solid | 8 mg, 9% |
| 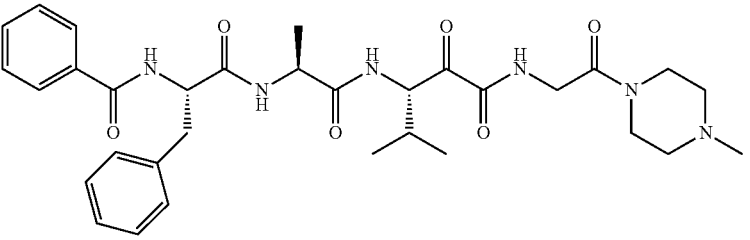 [SMILES: CC(C)[C@H](NC(=O)[C@H](C)NC(=O)[C@H](Cc1ccccc1)NC(=O)c1ccccc1)C(=O)C(=O)NCC(=O)N1CCN(C)CC1] | PVA-047 | A1 | Aldehyde QC_2; Rt 4.86 min; m/z 607 (MH+); white solid | 16 mg, 14% |
| 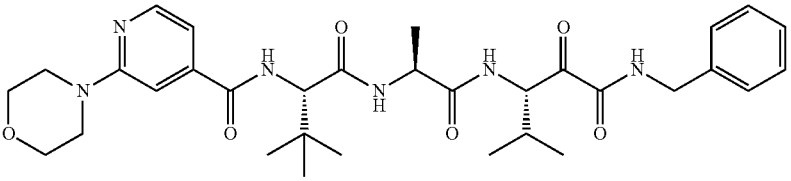 [SMILES: CC(C)[C@H](NC(=O)[C@H](C)NC(=O)[C@@H](NC(=O)c1ccnc(N2CCOCC2)c1)C(C)(C)C)C(=O)C(=O)NCc1ccccc1] | PVA-048 | A18 | Aldehyde QC_2; Rt 5.42 min; m/z 609 (MH+); white solid | 7 mg, 6% |

-continued

| Compound | Code Int. | Analytical Data | Yield |
|---|---|---|---|
| | PVA-049 | A20 Aldehyde QC_2; Rt 5.75 min; m/z 601 (MH+); white solid | 8 mg, 17% |
| | PVA-050 | A22 Aldehyde QC_2; Rt 7.06 min; m/z 606 (MH+); white solid | 8 mg, 12% |
| | PVA-051 | A22 Aldehyde QC_2; Rt 6.73 min; m/z 614 (MH+); white solid | 3 mg, 4% |
| | PVA-052 | A23 Aldehyde QC_2; Rt 7.82 min; m/z 565 (MH+); white solid | 30 mg, 30% |
| | PVA-053 | A24 Aldehyde QC_2; Rt 7.06 min; m/z 572 (MH+); white solid | 21 mg, 26% |
| | PVA-054 | A25 Aldehyde QC_2; Rt 6.92 min; m/z 517 (MH+); white solid | 27 mg, 37% |
| | PVA-055 | A6 Aldehyde QC_2; Rt 4.75 min; m/z 573 (MH+); white solid | 9 mg, 3% |

-continued

| Compound | Code Int. | Analytical Data | Yield |
|---|---|---|---|
| 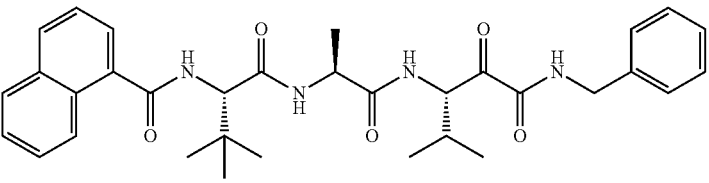 [SMILES: CC(C)[C@H](NC(=O)[C@H](C)NC(=O)[C@@H](NC(=O)c1cccc2ccccc12)C(C)(C)C)C(=O)C(=O)NCc1ccccc1] | PVA-056 | A23 Aldehyde QC_2; Rt 7.47 min; m/z 573 (MH+); white solid | 17 mg, 17% |
| 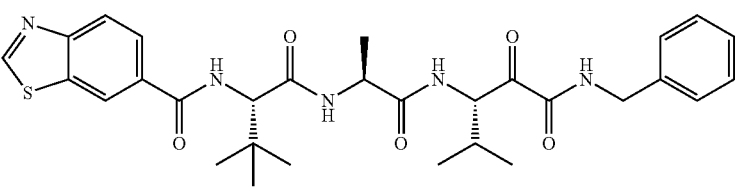 [SMILES: CC(C)[C@H](NC(=O)[C@H](C)NC(=O)[C@@H](NC(=O)c1ccc2ncsc2c1)C(C)(C)C)C(=O)C(=O)NCc1ccccc1] | PVA-057 | A24 Aldehyde QC_2; Rt 6.72 min; m/z 580 (MH+); white solid | 12 mg, 11% |
| 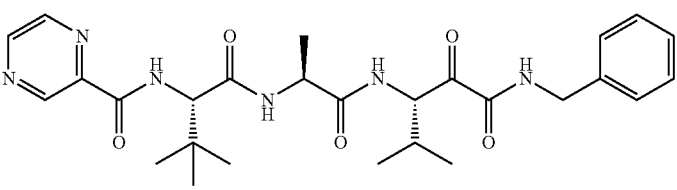 | PVA-058 | A25 Aldehyde QC_2; Rt 6.56 min; m/z 525 (MH+); white solid | 10 mg, 91% |
| 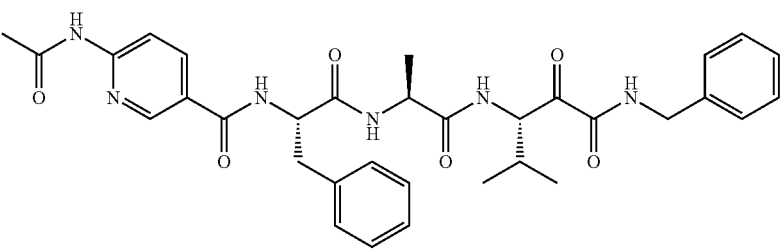 [SMILES: CC(=O)Nc1ccc(C(=O)N[C@@H](Cc2ccccc2)C(=O)N[C@@H](C)C(=O)N[C@H](C(=O)C(=O)NCc2ccccc2)C(C)C)cn1] | PVA-059 | A26 Aldehyde QC_2; Rt 6.06 min; m/z 615 (MH+); white solid | 1 mg, 1% |
| 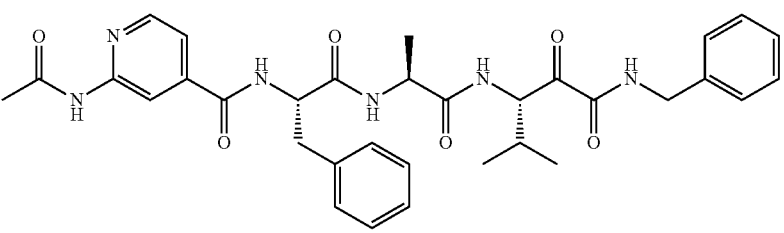 [SMILES: CC(=O)Nc1cc(C(=O)N[C@@H](Cc2ccccc2)C(=O)N[C@@H](C)C(=O)N[C@H](C(=O)C(=O)NCc2ccccc2)C(C)C)ccn1] | PVA-060 | A27 Aldehyde QC_2; Rt 5.98 min; m/z 615 (MH+); white solid | 1 mg, 1% |
| 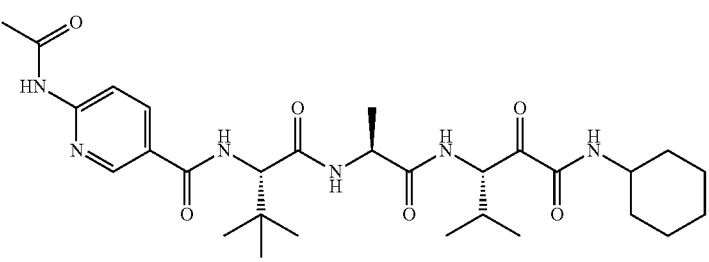 [SMILES: CC(=O)Nc1ccc(C(=O)N[C@H](C(=O)N[C@@H](C)C(=O)N[C@H](C(=O)C(=O)NC2CCCCC2)C(C)C)C(C)(C)C)cn1] | PVA-061 | A28 Aldehyde QC_2; Rt 6.23 min; m/z 573 (MH+); white solid | 27 mg, 19% |
| 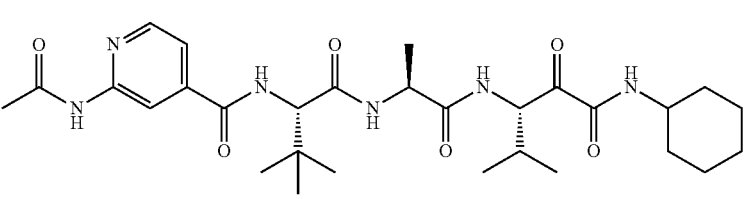 [SMILES: CC(=O)Nc1cc(C(=O)N[C@H](C(=O)N[C@@H](C)C(=O)N[C@H](C(=O)C(=O)NC2CCCCC2)C(C)C)C(C)(C)C)ccn1] | PVA-062 | A29 Aldehyde QC_2; Rt 6.13 min; m/z 573 (MH+); white solid | 20 mg, 15% |

-continued
| Compound | Code Int. | Analytical Data | Yield |
|---|---|---|---|
| 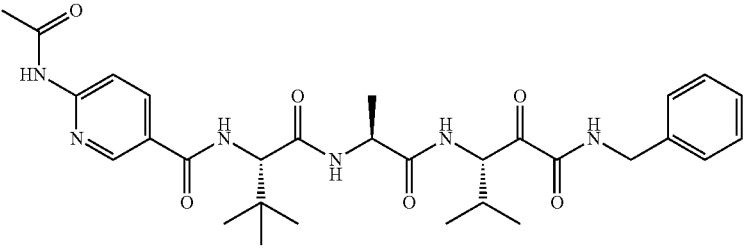 [SMILES: CC(=O)Nc1ccc(C(=O)N[C@H](C(=O)N[C@@H](C)C(=O)N[C@H](C(=O)C(=O)NCc2ccccc2)C(C)C)C(C)(C)C)cn1] | PVA-A28 063 | Aldehyde QC_2; Rt 5.92 min; m/z 581 (MH$^+$); white solid | 14 mg, 81% |
| 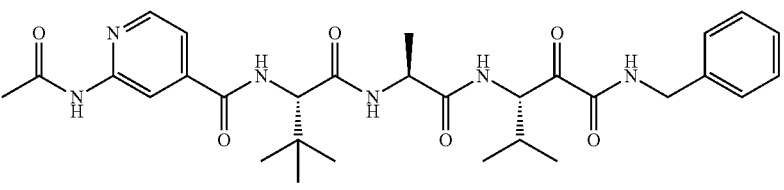 [SMILES: CC(=O)Nc1cc(C(=O)N[C@H](C(=O)N[C@@H](C)C(=O)N[C@H](C(=O)C(=O)NCc2ccccc2)C(C)C)C(C)(C)C)ccn1] | PVA-A29 064 | Aldehyde QC_2; Rt 5.83 min; m/z 581 (MH$^+$); white solid | 10 mg, 7% |
| 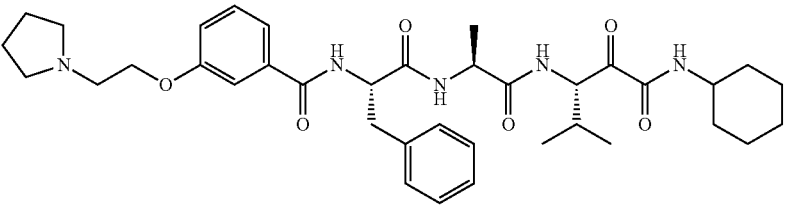 [SMILES: CC(C)[C@H](NC(=O)[C@H](C)NC(=O)[C@H](Cc1ccccc1)NC(=O)c1cccc(OCCN2CCCC2)c1)C(=O)C(=O)NC1CCCCC1] | PVA-A30 065 | Aldehyde QC_2; Rt 5.85 min; m/z 662 (MH$^+$); white solid | 3 mg, 5% |
| 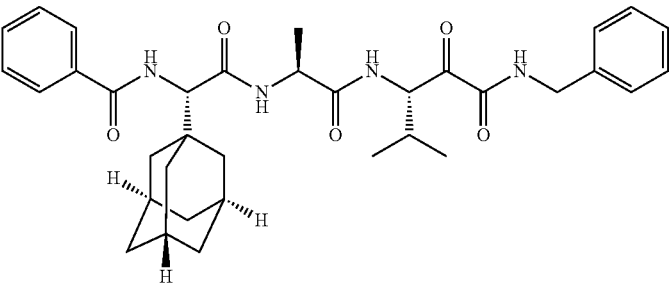 [SMILES: CC(C)[C@H](NC(=O)[C@H](C)NC(=O)[C@@H](NC(=O)c1ccccc1)C12C[C@H]3C[C@@H](C1)C[C@@H](C2)C3)C(=O)C(=O)NCc1ccccc1] | PVA-A31 066 | Aldehyde QC_2; Rt 8.04 min; m/z 601 (MH$^+$), white solid | 4 mg, 2% |
| 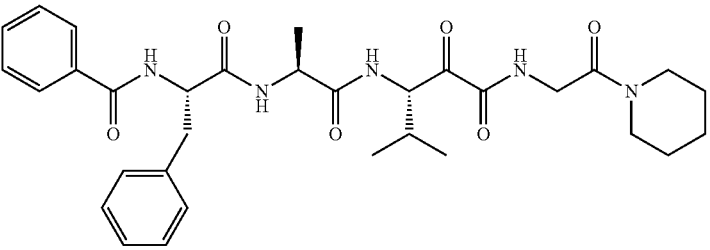 [SMILES: CC(C)[C@H](NC(=O)[C@H](C)NC(=O)[C@H](Cc1ccccc1)NC(=O)c1ccccc1)C(=O)C(=O)NCC(=O)N1CCCCC1] | PVA-A1 067 | Aldehyde QC_2; Rt 6.56 min; m/z 592 (MH$^+$), cream solid | 20 mg, 12% |
| 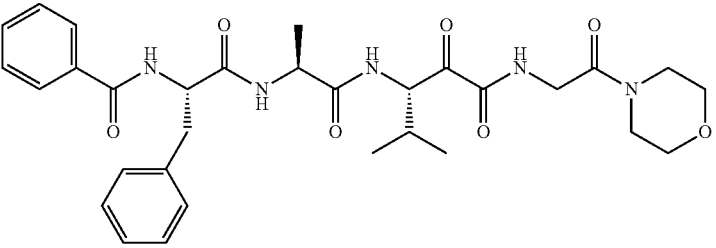 [SMILES: CC(C)[C@H](NC(=O)[C@H](C)NC(=O)[C@H](Cc1ccccc1)NC(=O)c1ccccc1)C(=O)C(=O)NCC(=O)N1CCOCC1] | PVA-A1 068 | Aldehyde QC_2; Rt 5.83 min; m/z 594 (MH$^+$), cream solid | 8 mg, 5% |

-continued

| Compound | Code Int. | Analytical Data | Yield |
|---|---|---|---|
| 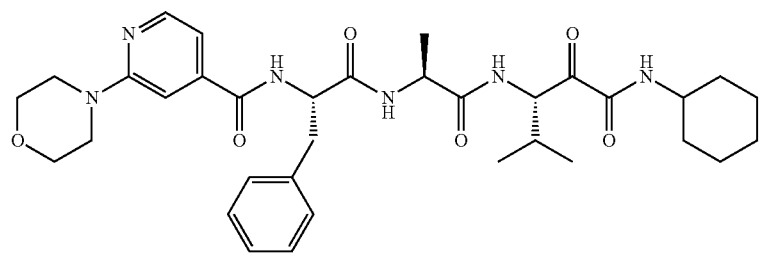 [SMILES: CC(C)[C@H](NC(=O)[C@H](C)NC(=O)[C@H](Cc1ccccc1)NC(=O)c1ccnc(N2CCOCC2)c1)C(=O)C(=O)NC1CCCCC1] | PVA-069 A32 | AnalpH2_MeOH_QC; Rt 8.32 min; m/z 635 (MH$^+$), white solid | 10 mg, 6% |
| 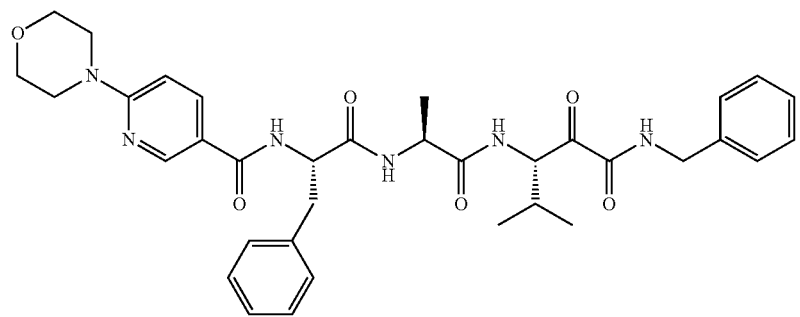 [SMILES: CC(C)[C@H](NC(=O)[C@H](C)NC(=O)[C@H](Cc1ccccc1)NC(=O)c1ccc(N2CCOCC2)nc1)C(=O)C(=O)NCc1ccccc1] | PVA-070 A33 | AnalpH2_MeOH_QC; Rt 8.01 min; m/z 643 (MH$^+$), white solid | 1 mg, 1% |
| 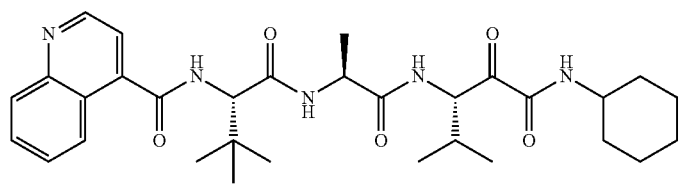 | PVA-071 A41 | Aldehyde QC_2; Rt 5.98 min; m/z 566 (MH$^+$), white solid | 29 mg, 23% |
| 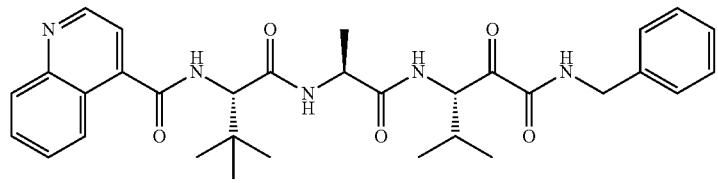 | PVA-072 A41 | Aldehyde QC_2; Rt 5.70 min; m/z 574 (MH$^+$), white solid | 32 mg, 26% |
| 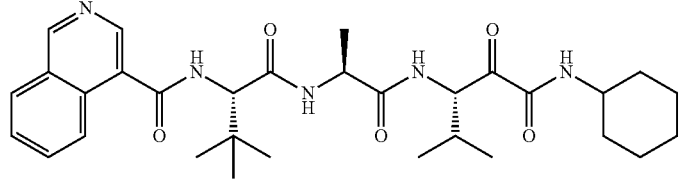 [SMILES: CC(C)[C@H](NC(=O)[C@H](C)NC(=O)[C@@H](NC(=O)c1cncc2ccccc12)C(C)(C)C)C(=O)C(=O)NC1CCCCC1] | PVA-073 A42 | Aldehyde QC_2; Rt 5.81 min; m/z 566 (MH$^+$), white solid | 30 mg, 31% |
| 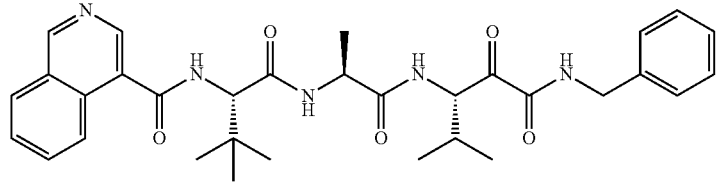 [SMILES: CC(C)[C@H](NC(=O)[C@H](C)NC(=O)[C@@H](NC(=O)c1cncc2ccccc12)C(C)(C)C)C(=O)C(=O)NCc1ccccc1] | PVA-074 A42 | Aldehyde QC_2; Rt 5.55 min; m/z 575 (MH$^+$), white solid | 11 mg, 11% |
| 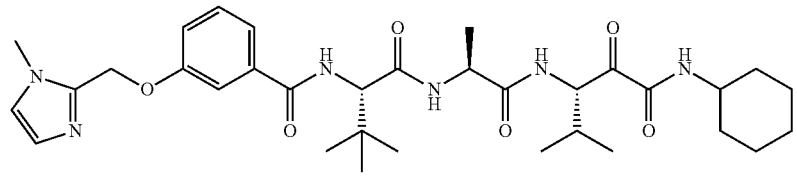 [SMILES: CC(C)[C@H](NC(=O)[C@H](C)NC(=O)[C@@H](NC(=O)c1cccc(OCc2nccn2C)c1)C(C)(C)C)C(=O)C(=O)NC1CCCCC1] | PVA-075 A43 | Aldehyde QC_2; Rt 5.74 min; m/z 625 (MH$^+$), white solid | 9 mg, 11% |

-continued
| Compound | Code Int. | Analytical Data | Yield |
|---|---|---|---|
| 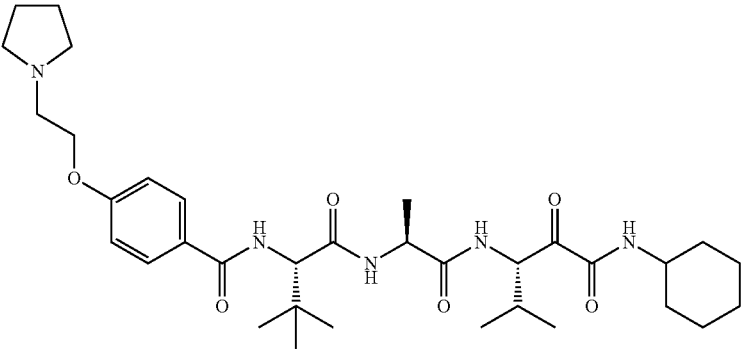 [SMILES: CC(C)[C@H](NC(=O)[C@H](C)NC(=O)[C@@H](NC(=O)c1ccc(OCCN2CCCC2)cc1)C(C)(C)C)C(=O)C(=O)NC1CCCCC1] | PVA-076 A44 | Aldehyde QC_2; Rt 5.73 min; m/z 628 (MH+), white solid | 4 mg, 1% |
| 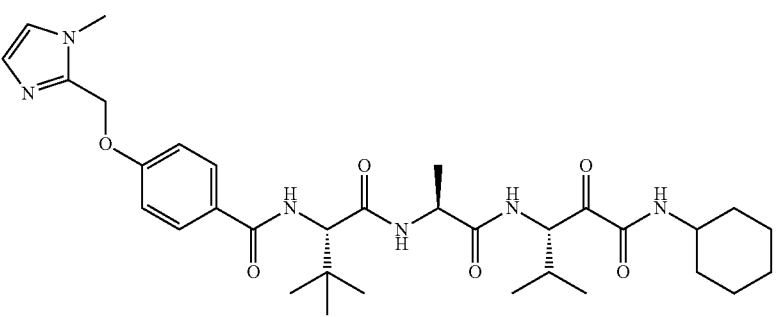 [SMILES: CC(C)[C@H](NC(=O)[C@H](C)NC(=O)[C@@H](NC(=O)c1ccc(OCc2nccn2C)cc1)C(C)(C)C)C(=O)C(=O)NC1CCCCC1] | PVA-077 A45 | Aldehyde QC_2; Rt 5.68 min; m/z 625 (MH+), white solid | 6 mg, 1% |
| 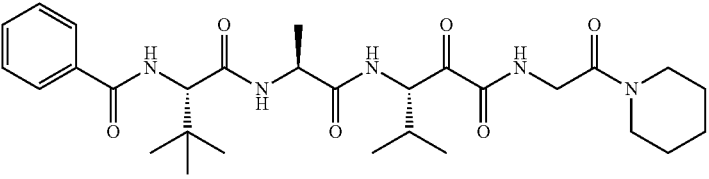 [SMILES: CC(C)[C@H](NC(=O)[C@H](C)NC(=O)[C@@H](NC(=O)c1ccccc1)C(C)(C)C)C(=O)C(=O)NCC(=O)N1CCCCC1] | PVA-078 A6 | Aldehyde QC_2; Rt 6.49 min; m/z 558 (MH+), white solid | 8 mg, 5% |
| 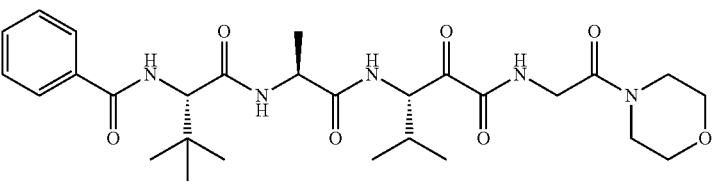 [SMILES: CC(C)[C@H](NC(=O)[C@H](C)NC(=O)[C@@H](NC(=O)c1ccccc1)C(C)(C)C)C(=O)C(=O)NCC(=O)N1CCOCC1] | PVA-079 A6 | Aldehyde QC_2; Rt 5.72 min; m/z 560 (MH+), white solid | 5 mg, 3% |
| 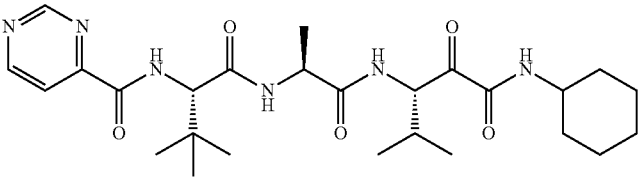 [SMILES: CC(C)[C@H](NC(=O)[C@H](C)NC(=O)[C@@H](NC(=O)c1ccncn1)C(C)(C)C)C(=O)C(=O)NC1CCCCC1] | PVA-082 A38 | Aldehyde QC_2; Rt 6.90 min; m/z 517 (MH+), white solid | 2 mg, 1% |
| 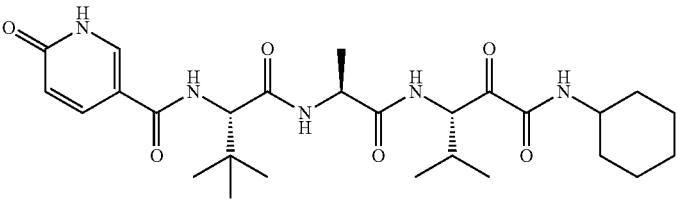 [SMILES: CC(C)[C@H](NC(=O)[C@H](C)NC(=O)[C@@H](NC(=O)c1ccc(=O)[nH]c1)C(C)(C)C)C(=O)C(=O)NC1CCCCC1] | PVA-084 A40 | Aldehyde QC_2; Rt 5.90 min; m/z 532 (MH+), white solid | 1 mg, 2% |

-continued

| Compound | Code Int. | Analytical Data | Yield |
|---|---|---|---|
| 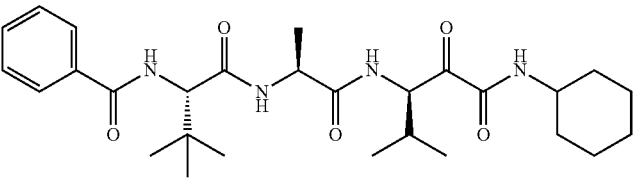 [SMILES: CC(C)[C@@H](NC(=O)[C@H](C)NC(=O)[C@@H](NC(=O)c1ccccc1)C(C)(C)C)C(=O)C(=O)NC1CCCCC1] | PVA-085 | A6 Aldehyde QC_2; Rt 7.42 min; m/z 515 (MH+), white solid | 88 mg, 27% |
| 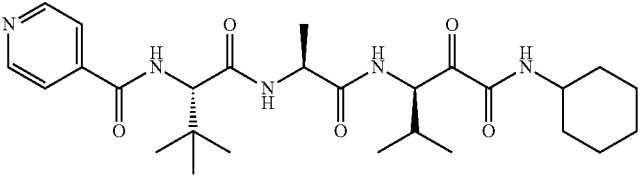 [SMILES: CC(C)[C@@H](NC(=O)[C@H](C)NC(=O)[C@@H](NC(=O)c1ccncc1)C(C)(C)C)C(=O)C(=O)NC1CCCCC1] | PVA-086 | A16 Aldehyde QC_2; Rt 5.52 min; m/z 516 (MH+), white solid | 5 mg, 3% |
| 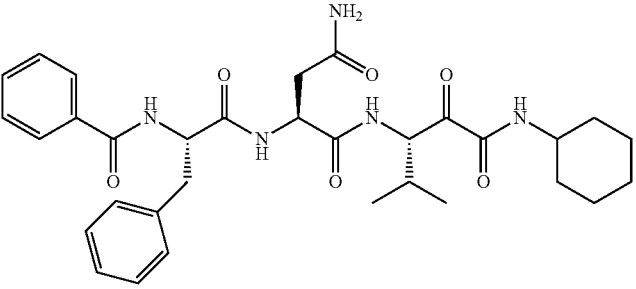 [SMILES: CC(C)[C@H](NC(=O)[C@H](CC(N)=O)NC(=O)[C@H](Cc1ccccc1)NC(=O)c1ccccc1)C(=O)C(=O)NC1CCCCC1] | PVA-087 | A19 Aldehyde QC_1B; Rt 6.73 min; m/z 592 (MH+), white solid | 16 mg, 7% |
| 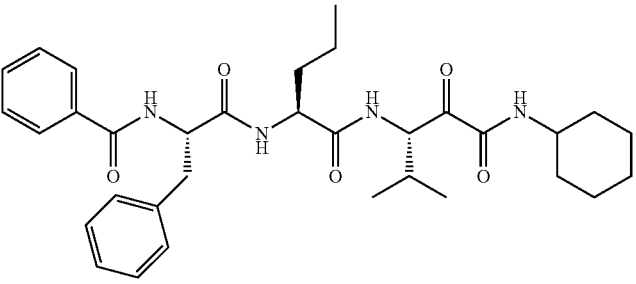 [SMILES: CCC[C@H](NC(=O)[C@H](Cc1ccccc1)NC(=O)c1ccccc1)C(=O)N[C@H](C(=O)C(=O)NC1CCCCC1)C(C)C] | PVA-088 | A35 Aldehyde QC_1B; Rt 7.76 min; m/z 577 (MH+), white solid | 25 mg, 20% |
| 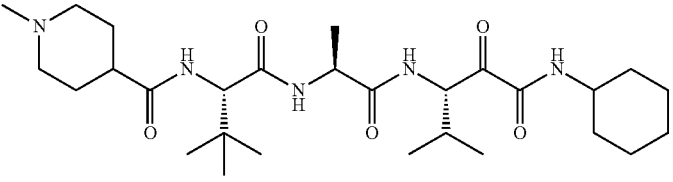 [SMILES: CC(C)[C@H](NC(=O)[C@H](C)NC(=O)[C@@H](NC(=O)C1CCN(C)CC1)C(C)(C)C)C(=O)C(=O)NC1CCCCC1] | PVA-089 | A36 Aldehyde QC_2; Rt 5.26 min; m/z 536 (MH+), white solid | 10 mg, 8% |
| 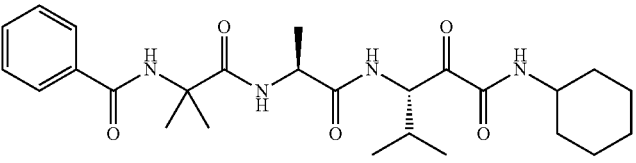 [SMILES: CC(C)[C@H](NC(=O)[C@H](C)NC(=O)C(C)(C)NC(=O)c1ccccc1)C(=O)C(=O)NC1CCCCC1] | PVA-090 | A46 Aldehyde QC_2; Rt 6.81 min; m/z 487 (MH+), white solid | 23 mg, 4% |
| 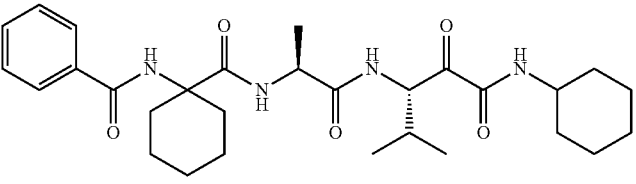 [SMILES: CC(C)[C@H](NC(=O)[C@H](C)NC(=O)C1(NC(=O)c2ccccc2)CCCCC1)C(=O)C(=O)NC1CCCCC1] | PVA-091 | A47 Aldehyde QC_2; Rt 7.50 min; m/z 527 (MH+), white solid | 8 mg, 2% |

| Compound | Code | Int. | Analytical Data | Yield |
|---|---|---|---|---|
| | PVA-100 | A53 | Aldehyde QC (Gemini)_2; Rt 6.09 min; m/z 561 (MH+), white solid | 5 mg, 1.6% |
| | PVA-101 | A54 | Aldehyde QC_(Gemini)_2; Rt 5.31 min; m/z 499 (MH+), white solid | 8 mg, 0.5% |
| | PVA-104 | BB20 | Aldehyde QC _1B; Rt 7.38, min; m/z 561 (MH+), white solid | 3 mg, 3% |
| | PVA-145 | A54 | Aldehyde QC_2; Rt 3.99 min; m/z 557 (MH+); yellow solid | 10 mg, 1% |

Routes 4, 5 and 6

All compounds made via routes 4, 5 and 6 utilised the common intermediates 12A and/or 12B.

Synthesis of β-Amino-α-hydroxyamide Intermediates (12A and 12B)*

Scheme 10

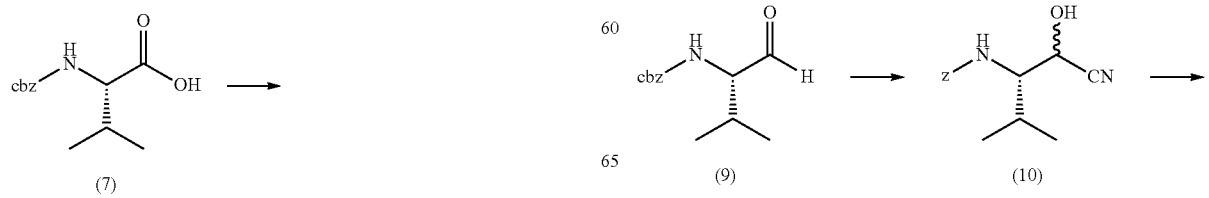

-continued

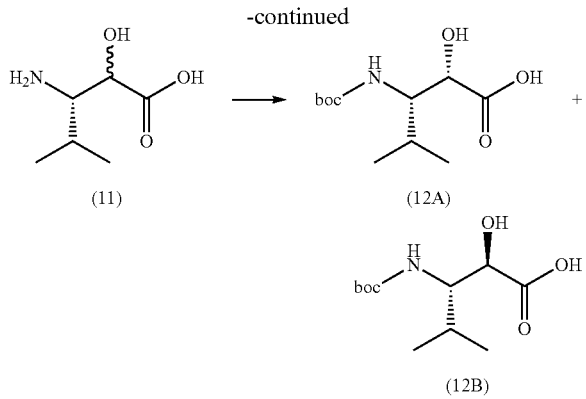

(*) Note that although 12A and 12B could be isolated as separate compounds, no attempt was made to unambiguously characterise the stereocentres alpha to the carboxylic acid therefore the structures have been drawn as is simply to clarify that they are two diastereomers. For simplicity when 12A is used it will be drawn as above with the alpha chiral centre having the (S) configuration.

Synthesis of [(S)-1-(Methoxy-methyl-carbamoyl)-2-methyl-propyl]-carbamic acid benzyl ester (8)

To (S)-2-benzyloxycarbonylamino-3-methyl-butyric acid (7) (50.0 g, 199 mmol), N-methoxymethylamine hydrochloride (38.8 g, 398 mmol) and EDC.HCl (47.7 g, 249 mmol) in DCM (500 mL) was added DIPEA (87 mL, 497 mmol) and the reaction mixture stirred at ambient temperature for 20 h, after which time the reaction mixture was diluted with DCM (200 mL), washed with 1M HCl (aq) (3×200 mL), 1M NaOH (aq) (200 mL), sat. NaHCO$_3$ (aq) (200 mL) and brine (300 mL). The organic layer was dried over MgSO$_4$, filtered and the solvent removed under vacuum to give the desired compound as a colourless oil (51.2 g, 87%); (AnalpH2_MeOH_4 min) R$_t$ 2.76 min; m/z 295 (MH)$^+$.

Synthesis of ((S)-1-Formyl-2-methyl-propyl)-carbamic acid benzyl ester (9)

To a solution of [(S)-1-(Methoxy-methyl-carbamoyl)-2-methyl-propyl]-carbamic acid benzyl ester (8) (33 g, 112 mmol) in dry THF (300 mL) at −30 to −40° C. was added LiAlH$_4$ (4.3 g, 113 mmol) portion wise over a period of 45 min. The reaction mixture was warmed to 0° C. and stirred at this temperature for 2 h. The reaction mixture was quenched with 1 M KHSO$_4$ (330 mL) at 0° C. then 10% w/v Rochelle's salt (aq) (330 mL) was added and the mixture stirred for 20 minutes, then extracted with EtOAc (2×700 mL). The combined organic phases were washed with 10% w/v Rochelle's salt (aq) (330 mL) and brine (450 mL), dried over MgSO$_4$, filtered and concentrated under vacuum to obtain the desired aldehyde as a clear oil (26.3 g) (AnalpH2_MeOH_4 min) R$_t$ 2.59 min; m/z 236 (MH)$^+$. (This was used without further purification in the next step.)

Synthesis of ((S)-2-Cyano-2-hydroxy-1-isopropyl-ethyl)-carbamic acid benzyl ester (10)

To a stirred solution of ((S)-1-Formyl-2-methyl-propyl)-carbamic acid benzyl ester (9) (26.0 g, 110 mmol) in MeOH (150 mL) at 0° C. was added a solution of NaHSO$_3$ (11.9 g, 114 mmol) in H$_2$O (230 mL) and the mixture was stirred at 0° C. for 2.5 h. The resulting mixture was added to a solution of NaCN (8.5 g, 174 mmol) in H$_2$O (150 mL) and EtOAc (450 mL) at 0° C. and stirred at ambient temperature for 20 h. The EtOAc layer was separated and the aqueous layer was extracted with EtOAc (2×500 mL). The combined organic extracts were washed with brine (400 mL), dried (MgSO$_4$) and concentrated to give the desired cyanohydrin (29.7 g, crude, a ~1:1 mixture of diastereoisomers) as a clear gummy liquid (AnalpH2_MeOH_4 min) R$_t$ 2.44 min, 2.48 min; m/z 280 [M+H$_2$O]$^+$. (The mixture was used without further purification in the next step.)

Synthesis of (S)-3-Amino-2-hydroxy-4-methyl-pentanoic acid (11)

To a solution of ((S)-2-Cyano-2-hydroxy-1-isopropyl-ethyl)-carbamic acid benzyl ester (10) (5.1 g, 19.5 mmol) in 1,4-dioxane (90 mL) was added conc. HCl (90 mL) and anisole (1.5 equiv.) and the mixture was heated to 110° C. for 18 h. The reaction mixture was cooled to ambient temperature and concentrated under vacuum to remove the dioxane. The mixture was then washed with EtOAc and the residue further concentrated under vacuum at 40° C. to remove the conc HCl. Any residual water was removed by azeotroping with toluene. The residue was washed with Et$_2$O (2×50 mL) to afford hydroxyl acid (11) as a gummy solid (crude, mixture of diastereoisomers). $^1$H NMR (400 MHz, DMSO-d$_6$): δ 8.20 (1H, brs), 7.96 (1H, brs), 4.42 (1H, d J=3.0 Hz), 4.17 (1H, d J=4.0 Hz), 3.17-3.05 (2H, m), 1.98-1.86 (2H, m), 0.96-0.86 (6H, m); m/z 148 (MH)$^+$.

Synthesis of (S)-3-tert-Butoxycarbonylamino-2-hydroxy-4-methyl-pentanoic acid (12)

To a solution of (S)-3-Amino-2-hydroxy-4-methyl-pentanoic acid (11) (assume 19.5 mmol) in MeOH (100 mL) was added triethylamine (9.0 mL, 64 mmol). Di-tert-butyl dicarbonate (4.7 g 1.1 eq) was added portionwise and the reaction mixture was stirred at ambient temperature for 20 h. The reaction mixture was concentrated in vacuo and the residue was dissolved in EtOAc (100 mL) and 1N NaOH (aq) (75 mL). The organic phase was separated and the aqueous phase washed further with EtOAc (2×100 ml) to remove any non-polar/non-acidic impurities. The aqueous layer was then acidified (pH ~2) with 2 N HCl and extracted with EtOAc (3×100 mL). The combined organic phases were dried (MgSO$_4$) and concentrated under vacuum to give a white waxy solid. This could be further purified on a Biotage Isolute (IST)-NH2 cartridge (25 g/150 mL). The cartridge was first equilibrated with MeOH (75 mL), MeCN (75 mL) and ethyl acetate (75 mL). The crude mixture was then loaded onto the cartridge in 5% MeOH/ethylacetate (50 mL), then washed with ethyl acetate (2×75 mL) and MeCN (75 mL). The desired mixture of diastereomeric acids was then eluted from the cartridge by washing with MeCN containing 1% formic acid (350 mL). A 1:1 mixture of the desired compounds were obtained as a white solid (1.5 g, 31%) following evaporation of the solvent under vacuum.

Alternatively the single diasteromer 12A could be isolated by dissolving crude material in CHCl$_3$ and triturating with n-pentane, to afford isomer 12A as a precipitate that could be collected by filtration.

The filtrate could be concentrated to afford the other diastereoisomer (12B) gummy brown solid which may be further purified by flash chromatography on silica (gradient 1% MeOH/CHCl$_3$ to 10% MeOH/CHCl$_3$). No attempt was made to unambiguously characterise the stereocenters positioned alpha to the carboxylic acid.

(12A): $^1$H NMR (400 MHz, DMSO-$d_6$): δ 12.4 (1H, s br), 6.46 (1H, d, J=10 Hz), 5.38 (1H, br s), 3.83 (1H, d, J=6.8 Hz), 3.65-3.59 (1H, m), 1.99-1.91 (1H, m), 1.36 (9H, s), 0.81-0.76 (6H, m); m/z: 246 [M−H]$^−$.

(12B): $^1$H NMR (400 MHz, DMSO-$d_6$): δ 12.44 (1H, s br), 6.21 (1H, d, J=10 Hz), 4.95 (1H, br s), 4.11 (1H, d, J=1.6 Hz), 3.53-3.47 (1H, m), 1.74 (1H, m), 1.35 (9H, s), 0.91-0.83 (6H, m); m/z: 246 [M−H]$^−$.

Alternatively 12A and 12B could be synthesised according to the following procedure:

To a solution of hydroxyl acid (11) (2×11.5 g,) in 1 N aqueous NaOH solution (100 mL) was added a solution of di-tert-butyl dicarbonate (0.8 equiv.) in 1,4-dioxane (100 mL) at 0° C. and stirred at ambient temperature for 16 h. The reaction mixture was concentrated in vacuo and the residue was dissolved in H$_2$O and washed with Et$_2$O (2×100 mL) to remove any non-polar impurities. The aqueous layer was cooled to 0° C. and acidified (pH ~2) with 1 N HCl and extracted with 10% MeOH/CHCl$_3$ (2×500 mL). The combined organic phases were washed with brine (200 mL), dried (Na$_2$SO$_4$) and concentrated under vacuum to give a crude mixture of diastereomeric alcohols (12A) and (12B) which could be further purified as described above.

In some instances the mixture the diastereomeric alcohols (12A) and (12B) was used or alternatively (12A) or (12B) were used as single diastereomers to enable the subsequent products to be characterised more readily.

Synthesis of PVA Compounds (I) Via Route 4

Scheme 11

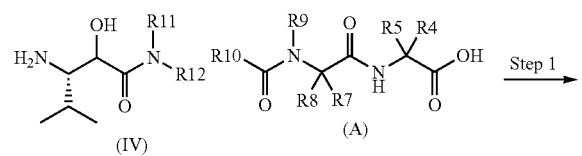

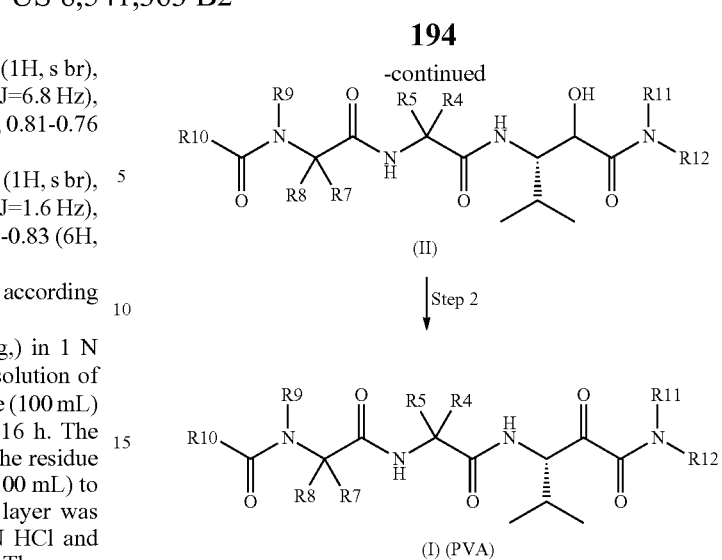

Typical Procedure

Step 1—Synthesis of Capped Peptidyl α-Hydroxyamides (II)

To a solution of (A) (375 mg, 1 equiv.) in THF (5 mL) was added iso-butyl chloroformate (0.15 mL, 1 equiv.), NMM (2.5 equiv.) at −40° C. After 40 min, a solution of compound (IV) (1 equiv.) in THF (2 mL) was added and stirred at −40° C. for 3 h. The reaction mixture was diluted with EtOAc (20 mL) and filtered. The filtrate was washed with (aq.) 5% NaHCO$_3$ solution (10 mL), brine solution (10 mL), dried (Na$_2$SO$_4$), and concentrated in vacuo. The residue was typically purified by reverse-phase preparative HPLC to afford the desired compound (II).

Step 2—Synthesis of PVA Compounds (1)

See Method A

PVA Compounds Prepared by Route 4

| Compound | Int Code (A) | Analytical Data | Yield |
|---|---|---|---|
| (structure) | PVA-A1 080 | Aldehyde QC_2; Rt 6.96 min; m/z 615 (MH$^+$); white solid | 11 mg, 13% |
| (structure) | PVA-A1 081 (*) | Aldehyde QC_2; Rt 6.27 min; m/z 601 (MH$^+$); white solid | 27 mg, 6% |

-continued
| Compound | Int Code (A) | Analytical Data | Yield |
|---|---|---|---|
| 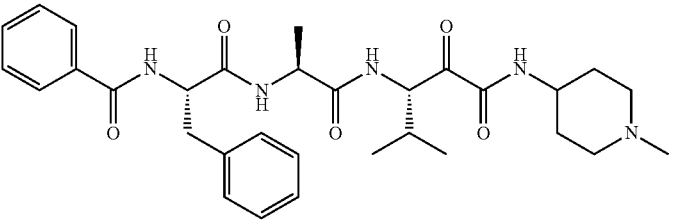 [SMILES: CC(C)[C@H](NC(=O)[C@H](C)NC(=O)[C@H](Cc1ccccc1)NC(=O)c1ccccc1)C(=O)C(=O)NC1CCN(C)CC1] | PVA-083 | A1 Aldehyde QC_2; Rt 4.98 min; m/z 564 (MH+); white solid | 27 mg, 10% |
| 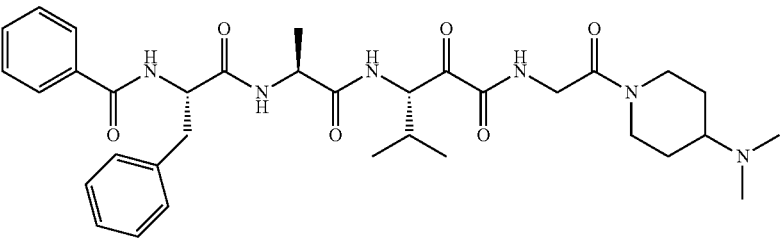 | PVA-093 | A1 AnalpH9_MeOH_QC; Rt 7.80 min; m/z 651 (MH+); white solid | 23 mg, 32% |
| 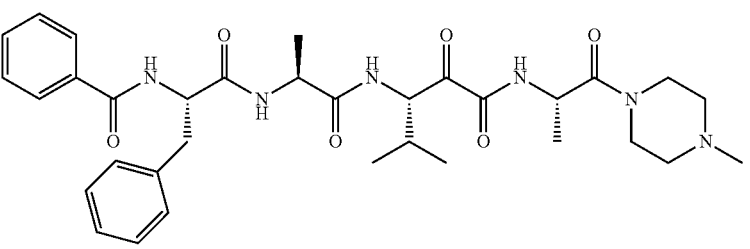 [SMILES: CC(C)[C@H](NC(=O)[C@H](C)NC(=O)[C@H](Cc1ccccc1)NC(=O)c1ccccc1)C(=O)C(=O)N[C@@H](C)C(=O)N1CCN(C)CC1] | PVA-094 | A1 AnalpH9_MeOH_QC; Rt 7.65 min; m/z 621 (MH+); white solid | 62 mg, 40% |
| 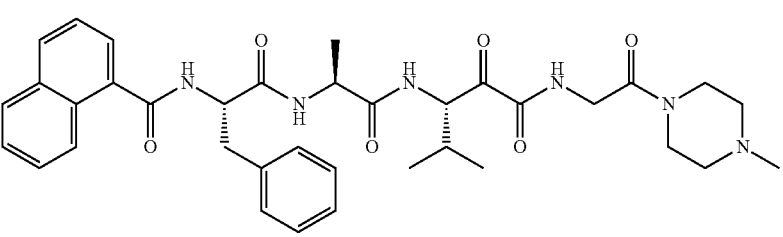 [SMILES: CC(C)[C@H](NC(=O)[C@H](C)NC(=O)[C@H](Cc1ccccc1)NC(=O)c1cccc2ccccc12)C(=O)C(=O)NCC(=O)N1CCN(C)CC1] | PVA-095 | A51 Aldehyde QC_2; Rt 5.33 min; m/z 657 (MH+); white solid | 30 mg, 18% |
| 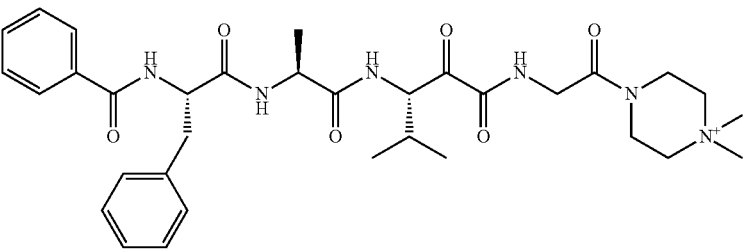 [SMILES: CC(C)[C@H](NC(=O)[C@H](C)NC(=O)[C@H](Cc1ccccc1)NC(=O)c1ccccc1)C(=O)C(=O)NCC(=O)N1CC[N+](C)(C)CC1] | PVA-096 | A1 Aldehyde QC_2; Rt 4.84 min; m/z 621 (M+); white solid | 40 mg, 37% |
| 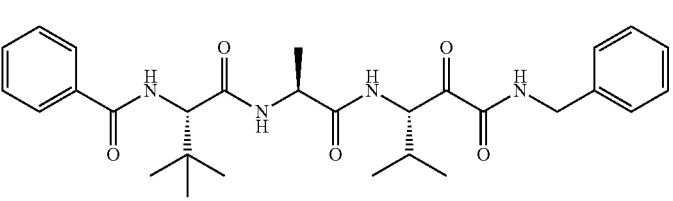 [SMILES: CC(C)[C@H](NC(=O)[C@H](C)NC(=O)[C@@H](NC(=O)c1ccccc1)C(C)(C)C)C(=O)C(=O)NCc1ccccc1] | PVA-097 | A6 Aldehyde QC_2; Rt 7.07 min; m/z 523 (MH+); white solid | 170 mg, 50% |

-continued
| Compound | Int Code (A) | Analytical Data | Yield |
|---|---|---|---|
| 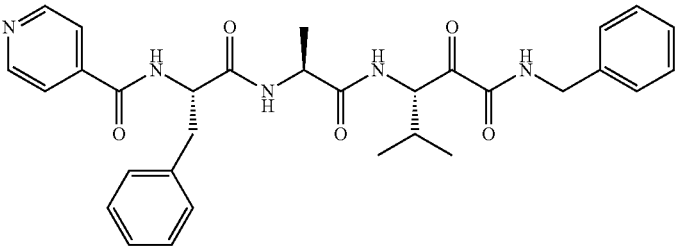 [SMILES: CC(C)[C@H](NC(=O)[C@H](C)NC(=O)[C@H](Cc1ccccc1)NC(=O)c1ccncc1)C(=O)C(=O)NCc1ccccc1] | PVA-099 | A52 Aldehyde QC_2; Rt 5.41 min; m/z 558 (MH+); white solid | 137 mg, 12% |
| 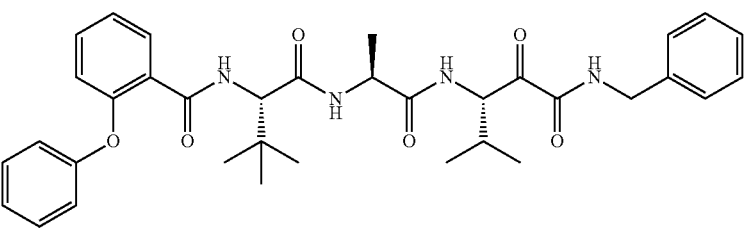 [SMILES: CC(C)[C@H](NC(=O)[C@H](C)NC(=O)[C@@H](NC(=O)c1ccccc1Oc1ccccc1)C(C)(C)C)C(=O)C(=O)NCc1ccccc1] | PVA-106 | A55 Aldehyde QC_2; Rt 8.05 min; m/z 615 (MH+); white solid | 35 mg, 24% |
| 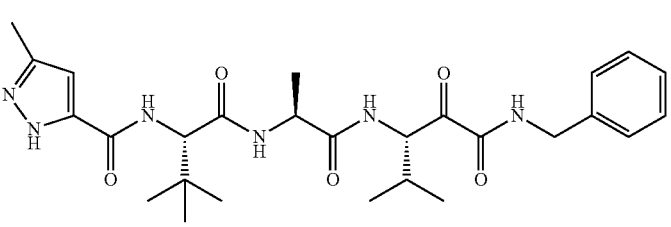 [SMILES: Cc1cc(C(=O)N[C@H](C(=O)N[C@@H](C)C(=O)N[C@H](C(=O)C(=O)NCc2ccccc2)C(C)C)C(C)(C)C)[nH]n1] | PVA-107 | A56 Aldehyde QC_2; Rt 6.25 min; m/z 527 (MH+); white solid | 20 mg, 12% |
| 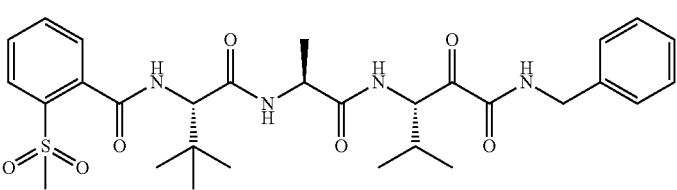 [SMILES: CC(C)[C@H](NC(=O)[C@H](C)NC(=O)[C@@H](NC(=O)c1ccccc1S(C)(=O)=O)C(C)(C)C)C(=O)C(=O)NCc1ccccc1] | PVA-108 | A57 Aldehyde QC_2; Rt 6.63 min; m/z 601 (MH+); white solid | 28 mg, 21% |
| 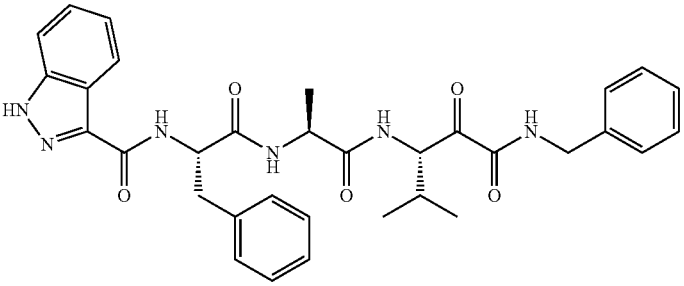 [SMILES: CC(C)[C@H](NC(=O)[C@H](C)NC(=O)[C@H](Cc1ccccc1)NC(=O)c1n[nH]c2ccccc12)C(=O)C(=O)NCc1ccccc1] | PVA-113 | A58 Aldehyde QC_2; Rt 6.96 min; m/z 597 (MH+); pale yellow solid | 58 mg, 50% |
| 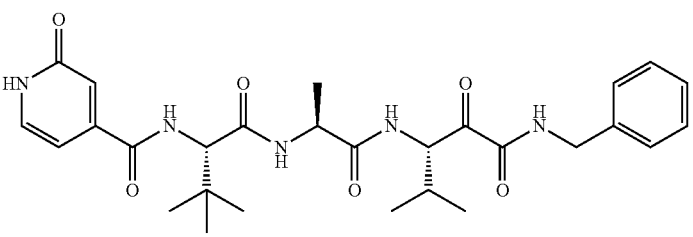 [SMILES: CC(C)[C@H](NC(=O)[C@H](C)NC(=O)[C@@H](NC(=O)c1cc[nH]c(=O)c1)C(C)(C)C)C(=O)C(=O)NCc1ccccc1] | PVA-114 | A59 Aldehyde QC_2; Rt 5.56 min; m/z 540 (MH+); white solid | 24 mg, 7.5% |

-continued

| Compound | Int Code (A) | Analytical Data | Yield |
|---|---|---|---|
| 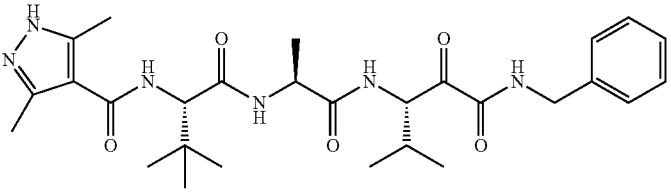 [SMILES: Cc1n[nH]c(C)c1C(=O)N[C@H](C(=O)N[C@@H](C)C(=O)N[C@H](C(=O)C(=O)NCc1ccccc1)C(C)C)C(C)(C)C] | PVA-115 | A60 Aldehyde QC_2; Rt 5.82 min; m/z 541 (MH$^+$); white solid | 30 mg, 11% |
| 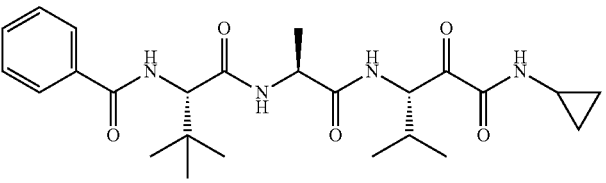 [SMILES: CC(C)[C@H](NC(=O)[C@H](C)NC(=O)[C@@H](NC(=O)c1ccccc1)C(C)(C)C)C(=O)C(=O)NC1CC1] | PVA-116 | A6 Aldehyde QC_2; Rt 6.33 min; m/z 473 (MH$^+$); white solid | 184 mg, 51% |
| 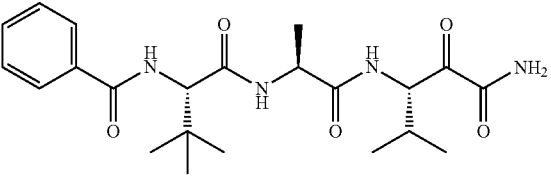 [SMILES: CC(C)[C@H](NC(=O)[C@H](C)NC(=O)[C@@H](NC(=O)c1ccccc1)C(C)(C)C)C(=O)C(N)=O] | PVA-118 | A6 Aldehyde QC_2; Rt 5.61 min; m/z 433 (MH$^+$); white solid | 35 mg 6% |
| 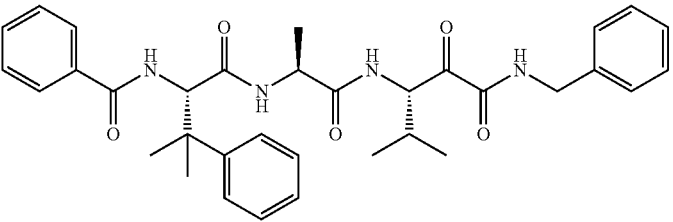 [SMILES: CC(C)[C@H](NC(=O)[C@H](C)NC(=O)[C@@H](NC(=O)c1ccccc1)C(C)(C)c1ccccc1)C(=O)C(=O)NCc1ccccc1] | PVA-121 | A64 Aldehyde QC_2; Rt 7.55 min; m/z 585 (MH$^+$); white solid | 40 mg, 27% |
| 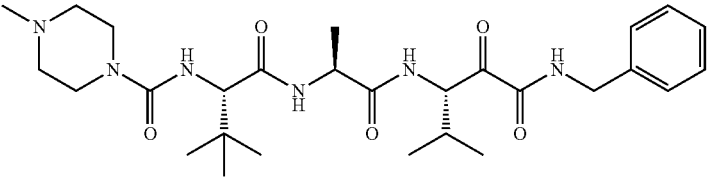 | PVA-122 | A50 Aldehyde QC_2; Rt 4.90 min; m/z 545 (MH$^+$); white solid | 31 mg, 8% |
| 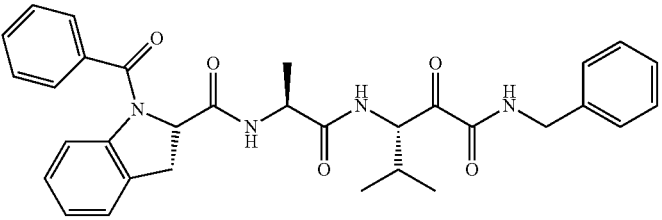 | PVA-123 | A61 Aldehyde QC_2; Rt 7.03 min; m/z 555 (MH$^+$); white solid | 3 mg, 4% |
| 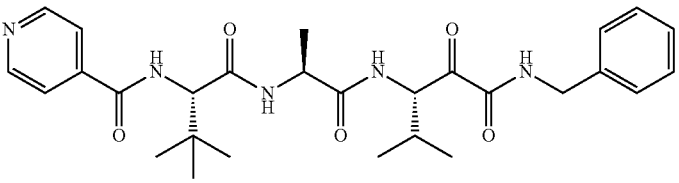 [SMILES: CC(C)[C@H](NC(=O)[C@H](C)NC(=O)[C@@H](NC(=O)c1ccncc1)C(C)(C)C)C(=O)C(=O)NCc1ccccc1] | PVA-128 | A16 Aldehyde QC_2; Rt 5.23 min; m/z 524 (MH$^+$); white solid | 99 mg, 15% |

-continued

| Compound | Int Code (A) | Analytical Data | Yield |
|---|---|---|---|
| (structure) | PVA-129 | BB19 Aldehyde QC_2; Rt 7.25 min; m/z 535 (MH⁺); white solid | 276 mg, 47% |
| (structure) | PVA-136 (†) | A39 AnalpH9_MeOH_QC; Rt 5.81 min; m/z 617 (MH⁺); white solid | 110 mg, 35% |
| (structure) | PVA-137 | A62 Aldehyde QC_2; Rt 5.33 min; m/z 657 (MH⁺); white solid | 89 mg, 53% |
| (structure) | PVA-138 | A34 Aldehyde QC_2; Rt 5.68 min; m/z 707 (MH⁺); white solid | 85 mg, 53% |
| (structure) | PVA-139 | A63 Aldehyde_QC (Gemini)_2,; Rt 5.33 min; m/z 507 (MH⁺); white solid | 53 mg, 48% |
| (structure) | PVA-140 | A63 Aldehyde_QC (Gemini)_2; Rt 3.32 min; m/z 557 (MH⁺); pale yellow solid | 45 mg, 25% |

| Compound | Int Code (A) | Analytical Data | Yield |
|---|---|---|---|
| (structure) | PVA-141 | A56 | ¹H NMR (400 MHz, DMSO-d$_6$): δ 12.96 (1H, s), 8.75 (1H, d, J = 4.8 Hz), 8.37 (1H, d, J = 6.8 Hz), 8.02 (1H, d, J = 7.2 Hz), 7.45 (1H, d, J = 9.6 Hz), 6.37 (1H, s), 5.00 (1H, t, J = 6.2 Hz), 4.47-4.37 (2H, m), 2.77-2.69 (1H, m), 2.25 (3H, s), 2.22-2.10 (1H, m), 1.18 (1H, d, J = 7.2 Hz), 0.92-0.76 (15H, m), 0.70-0.61 (2H, m), 0.60-0.52 (2H, m); m/z 477 (MH$_+$); white solid | 9 mg, 3% |
| (structure) | PVA-142 | A64 | ¹H NMR (400 MHz, DMSO-d$_6$): δ 8.76 (1H, d, J = 4.4 Hz), 8.16 (1H, d, J = 6.8 Hz), 8.08 (1H, d, J = 8 Hz), 7.69 (1H, d, J = 9.3 Hz), 7.51-7.34 (7H, m), 7.27 (2H, t, J = 7.6 Hz), 7.16-7.10 (1H, m), 5.03 (1H, dd, J = 7.7, 5.3 Hz), 4.91 (1H, d, J = 9.3 Hz), 4.47-4.41 (1H, m), 2.79-2.71 (1H, m), 2.24-2.14 (1H, m), 1.46 (3H, s), 1.45 (3H, s) 1.22 (3H, d, J = 6.9 Hz), 0.90 (3H, d, J = 7.0 Hz), 0.80 (3H, d, J = 7.0 Hz), 0.69-0.63 (2H, m), 0.59-0.53 (2H, m); m/z 535 (MH$^+$); white solid | 20 mg, 18% |

-continued

| Compound | Int Code (A) | Analytical Data | Yield |
|---|---|---|---|
| (structure) | PVA-143 | A64 | ¹H NMR (400 MHz, DMSO-d$_6$): δ 8.16 (1H, d, J = 6.8 Hz), 8.10-8.02 (2H, m), 7.77 (1H, s), 7.69 (1H, d, J = 9.6 Hz), 7.51-7.34 (7H, m), 7.29-7.21 (2H, m), 7.15-7.10 (1H, m), 5.05 (1H, dd, J = 7.9, 5.4 Hz), 4.91 (1H, d, J = 9.6 Hz), 4.47-4.41 (1H, m), 2.24-2.15 (1H, m), 1.46 (3H, s), 1.45 (3H, s), 1.22 (3H, d, J = 7.2 Hz), 0.90 (3H, d, J = 6.4 Hz), 0.81 (3H, d, J = 6.8 Hz); m/z 493 (MH⁺); white solid | 22 mg, 22% |
| (structure) | PVA-144 | A41 | Aldehyde QC_2; Rt 4.89 min; m/z 524 (MH⁺); white solid | 130 mg, 13% |
| (structure) | PVA-146 | A31 | Aldehyde QC_2; Rt 5.57 min; m/z 651 (MH⁺); white solid | 17 mg, 70% |
| (structure) | PVA-147 | A21 | Aldehyde QC_2; Rt 4.58 min; m/z 702 (MH⁺); white solid | 35 mg, 8% |

-continued

| Compound | Int Code (A) | Analytical Data | Yield |
|---|---|---|---|
| 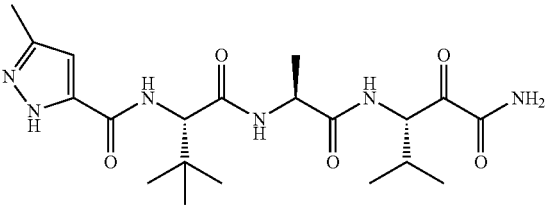 [SMILES: Cc1cc(C(=O)N[C@H](C(=O)N[C@@H](C)C(=O)N[C@H](C(=O)C(N)=O)C(C)C)C(C)(C)C)[nH]n1] | PVA-148 | A56 | ¹H NMR (400 MHz, DMSO-d₆): δ 12.94 (1H, s), 8.34 (1H, d, J = 6.8 Hz), 8.01 (1H, s), 7.95 (1H, d, J = 7.6 Hz), 7.73 (1H, s), 6.37 (1H, s), 5.03 (1H, dd, J = 7.8, 5.3 Hz), 4.47-4.41 (1H, m), 2.26 (3H, s), 2.25-2.14 (1H, m), 1.19 (3H, d, J = 6.8 Hz), 0.97-0.86 (12H, m) 0.82 (3H, d, J = 7.0 Hz); m/z 435 (M − H)⁻ cream solid | 11 mg, 10% |
| 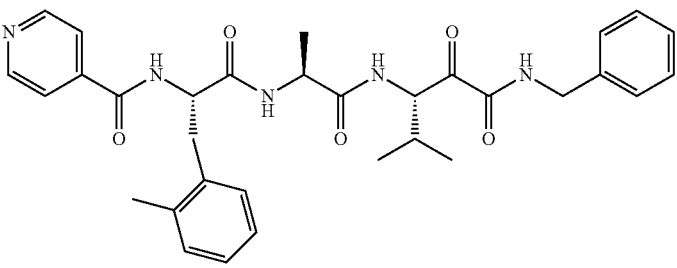 [SMILES: Cc1ccccc1C[C@H](NC(=O)c1ccncc1)C(=O)N[C@@H](C)C(=O)N[C@H](C(=O)C(=O)NCc1ccccc1)C(C)C] | PVA-151 | A65 | Aldehyde QC_2; Rt 5.61 min; m/z 572 (MH⁺); white solid | 33 mg 4% |
| 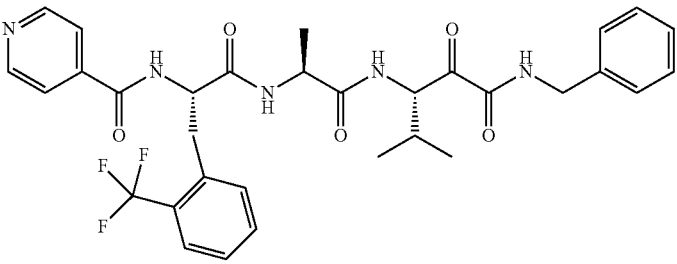 [SMILES: CC(C)[C@H](NC(=O)[C@H](C)NC(=O)[C@H](Cc1ccccc1C(F)(F)F)NC(=O)c1ccncc1)C(=O)C(=O)NCc1ccccc1] | PVA-152 | A37 | Aldehyde QC_2; Rt 5.87 min; m/z 626 (MH⁺); white solid | 51 mg 16% |
| 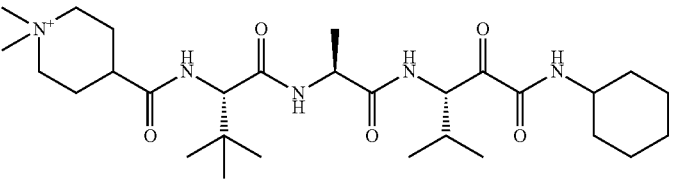 [SMILES: CC(C)[C@H](NC(=O)[C@H](C)NC(=O)[C@@H](NC(=O)C1CC[N+](C)(C)CC1)C(C)(C)C)C(=O)C(=O)NC1CCCCC1] | PVA-153 | A48 | Aldehyde QC_2; Rt 5.21 min; m/z 550 (M⁺); white solid | 16 mg, 17% |
| 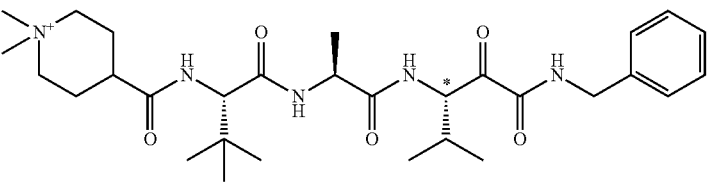 [SMILES: CC(C)[C@H](NC(=O)[C@H](C)NC(=O)[C@@H](NC(=O)C1CC[N+](C)(C)CC1)C(C)(C)C)C(=O)C(=O)NCc1ccccc1] | PVA-154 | A48 | Aldehyde QC_2; Rt 4.96 min; m/z 558 (M⁺); white solid | 19 mg, 20% |
| 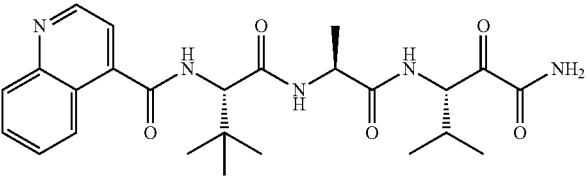 [SMILES: CC(C)[C@H](NC(=O)[C@H](C)NC(=O)[C@@H](NC(=O)c1ccnc2ccccc12)C(C)(C)C)C(=O)C(N)=O] | PVA-156 | A41 | Aldehyde QC_2; Rt 4.26 min; m/z 484 (MH⁺); white solid | 15 mg 2% |

-continued
| Compound | Int Code (A) | Analytical Data | Yield |
|---|---|---|---|
| 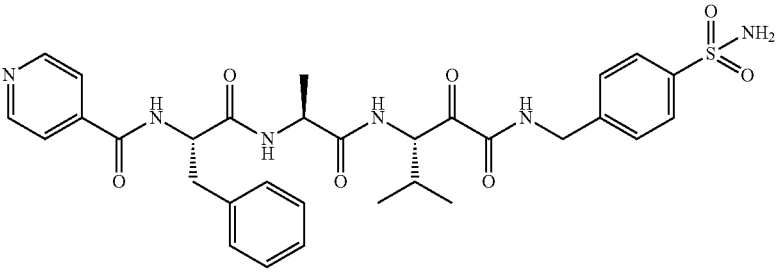 [SMILES: CC(C)[C@H](NC(=O)[C@H](C)NC(=O)[C@H](Cc1ccccc1)NC(=O)c1ccncc1)C(=O)C(=O)NCc1ccc(S(N)(=O)=O)cc1] | PVA-161 | A52 AnalpH9_MeOH_QC; Rt 6.75 min; m/z 637 (MH+); white solid | 32 mg, 20% |
| 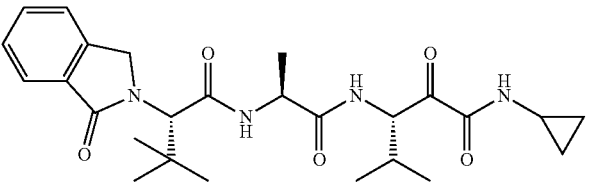 [SMILES: CC(C)[C@H](NC(=O)[C@H](C)NC(=O)[C@@H](N1Cc2ccccc2C1=O)C(C)(C)C)C(=O)C(=O)NC1CC1] | PVA-177 | BB19 AnalpH2_MeOH_QC; Rt 8.03 min; m/z 485 (MH+); white solid | 109 mg, 18% |
| 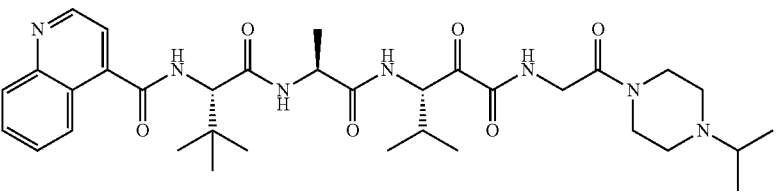 [SMILES: CC(C)[C@H](NC(=O)[C@H](C)NC(=O)[C@@H](NC(=O)c1ccnc2ccccc12)C(C)(C)C)C(=O)C(=O)NCC(=O)N1CCN(C(C)C)CC1] | PVA-187 | A41 Aldehyde QC_2; Rt 3.94 min; m/z 652(MH+); white solid | 106 mg, 35% |
| 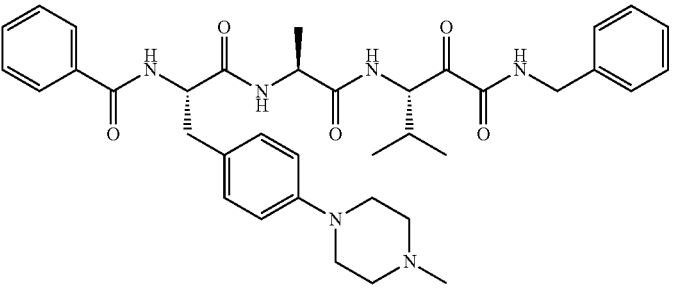 [SMILES: CC(C)[C@H](NC(=O)[C@H](C)NC(=O)[C@H](Cc1ccc(N2CCN(C)CC2)cc1)NC(=O)c1ccccc1)C(=O)C(=O)NCc1ccccc1] | PVA-198 | A49 Aldehyde QC_2; Rt 5.27 min; m/z 655 (MH+); pale yellow solid | 1 mg, 1% |
| 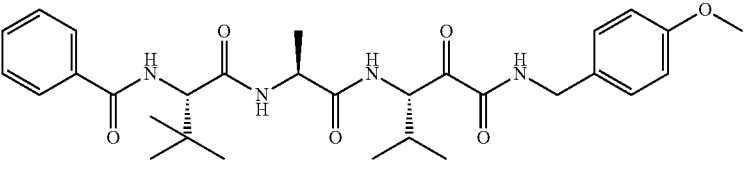 [SMILES: COc1ccc(CNC(=O)C(=O)[C@@H](NC(=O)[C@H](C)NC(=O)[C@@H](NC(=O)c2ccccc2)C(C)(C)C)C(C)C)cc1] | PVA-204 | A6 AnalpH2_MeOH_QC; Rt 7.02 min; m/z 553(MH+); white solid | 59 mg, 29% |
| 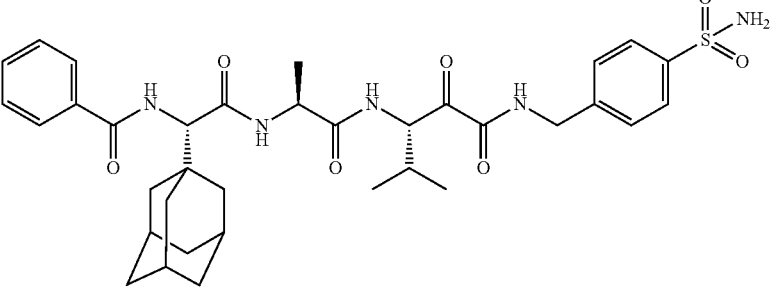 | PVA-214 | A31 Aldehyde QC_2; Rt 6.93 min; m/z 680(MH+); white solid | 52 mg, 26% |

| Compound | Int Code (A) | Analytical Data | Yield |
|---|---|---|---|
| 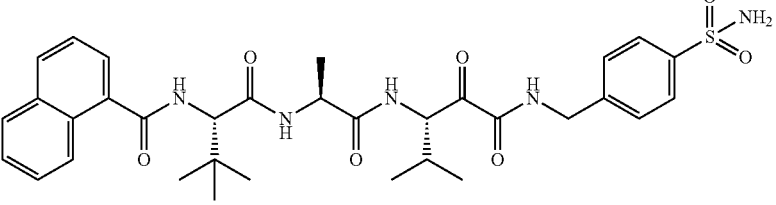 | PVA-215 | A23 Aldehyde QC_2; Rt 6.43 min; m/z 652(MH$^+$); white solid | 77 mg, 39% |

(*) Involves an additional hydrolysis step. See conversion of (BB21) to (BB22).
(†) Involves an additional deprotection of tBu group with TFA and triisopropylsilane in DCM prior to oxidation with Dess-Martin Periodinane.

In addition to dipeptide intermediates (A) all of the above compounds synthesised by Route 4 used α-Hydroxyamides intermediates of formula (IV).

Synthesis of α-Hydroxyamides (IV)

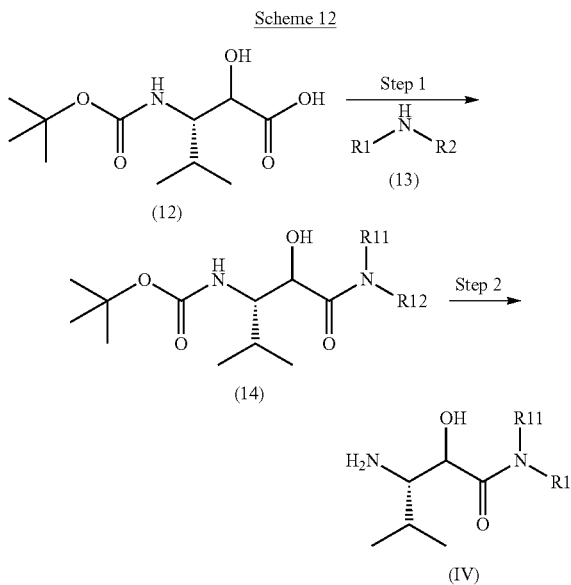

Typical Procedures

Step 1—Synthesis of Boc-β-Amino-α-Hydroxyamides (14)

To a solution of (12A) (1.0 equiv.) in DMF or DCM (1 g/5 mL) was added EDC.HCl (1.2 equiv.), HOBt (1.1 equiv.) and DIPEA (1.5 equiv.) then amine (13) (1.1-2 equiv.) was added either neat or dissolved in an appropriate solvent such as DCM or DMF at 0° C., and the reaction mixture stirred at ambient temperature for 16 h. The reaction mixture was concentrated in vacuo and the residue was dissolved in EtOAc (50 mL), washed with (aq.) 5% w/v NaHCO$_3$ solution (10 mL), brine (2×20 mL), dried (Na$_2$SO$_4$) and concentrated. The residue was generally purified by flash column chromatography on silica gel or by reverse-phase preparative HPLC to afford the desired compound (14).

In some instances EDC and HOBT could be replaced with other amide coupling reagents such as HATU. The Boc-β-amino-α-hydroxyamides could also be formed by reacting the hydroxyl acid (12A) and or (12B)) with diphosgene to form intermediate 1,3-dioxolane-2,4-diones which could be ring opened with the requisite amines to afford the hydroxyamides.

Step 2—Synthesis of β-Amino-α-Hydroxyamides (26)

A solution of compound (14) (1 equiv.) in DCM (~100 mg/mL) was treated with TFA (6 equiv.) at 0° C. and allowed to stir at ambient temperature. After 3 h, the reaction mixture was concentrated and the residue was washed with Et$_2$O and dried under vacuum to obtain compound (IV) which was used in the next step without further purification.

Alternatively, the deprotection was carried out by treating the Boc β-amino-α-hydroxyamides with a solution of 4M HCl in dioxane after dissolving the compound in DCM.

Route 5: Synthesis of PVA Compounds (I) Via Tri-Peptide Hydroxy Acid

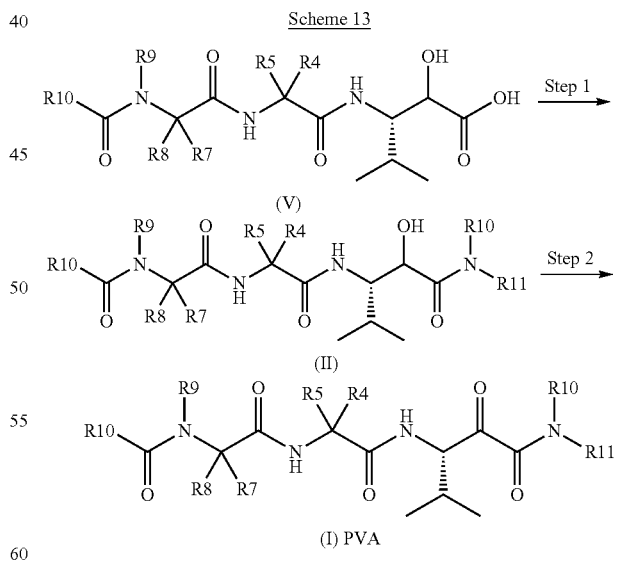

Typical Procedure
Step 1:
This was typically carried out using a standard acid amine coupling reaction in analogous fashion to Step 1/Route 4.
Step 2—Synthesis of PVA Compounds (1):
See Method A.

PVA Compounds Prepared by Route 5

| Compound | Code | Analytical Data | Yield |
|---|---|---|---|
| | PVA-092 | Aldehyde_QC_2; Rt = 5.05 min; m/z 635 (MH$^+$); white solid | 10 mg, 15% |
| | PVA-098 | Aldehyde QC_2; Rt 4.70 min; m/z 593 (MH$^+$); white solid | 19 mg, 19% |
| | PVA-103 | Aldehyde_QC (Gemini)_2; Rt 6.13 min; m/z 583 (MH$^+$); white solid | 3 mg, 2% |
| | PVA-105 | Aldehyde QC_2; Rt 4.69 min; m/z 587 (MH$^+$); white solid | 14 mg, 18% |
| | PVA-109 | Aldehyde QC_2; Rt 7.50 min; m/z 549 (MH$^+$); white solid | 21 mg, 34% |
| | PVA-110 | Aldehyde QC_2; Rt 7.50 min; m/z 549 (MH$^+$); white solid | 20 mg, 21% |
| | PVA-111 | Aldehyde QC_2; Rt 6.93 min; m/z 606 (MH$^+$); white solid | 84 mg, 31% |

-continued

| Compound | Code | Analytical Data | Yield |
|---|---|---|---|
| (structure) | PVA-112 | Aldehyde QC_2; Rt 7.03 min; m/z 592 (MH+); white solid | 21 mg, 34% |
| (structure) | PVA-117 | Aldehyde QC_2; Rt 5.91 min; m/z 447 (MH+); white solid | 10 mg, 26% |
| (structure) | PVA-119 | Aldehyde QC_2; Rt 4.85 min; m/z 542 (MH+); white solid | 16 mg, 33%, |
| (structure) | PVA-120 | Aldehyde QC_2; Rt 4.90 min; m/z 542 (MH+); white solid | 18 mg, 36% |
| (structure) | PVA-124 | Aldehyde QC_2; Rt 4.81 min; m/z 527 (MH+); white solid | 13 mg, 17% |
| (structure) | PVA-125 | Aldehyde QC_2; Rt 4.75 min; m/z 587 (MH+); white solid | 9 mg, 11% |
| (structure) | PVA-126 | Aldehyde QC_2; Rt 6.42 min; m/z 528 (MH+); white solid | 11 mg, 18% |
| (structure) | PVA-127 | Aldehyde QC_2; Rt 5.23 min; m/z 615 (MH+); white solid | 15 mg, 20% |

-continued

| Compound | Code | Analytical Data | Yield |
|---|---|---|---|
| | PVA-132 | Aldehyde_QC (Gemini)_2; Rt 6.04 min; m/z 537 (MH+); white solid | 14 mg, 24% |
| | PVA-133 | Aldehyde_QC (Gemini)_2, TFA; Rt 6.05 min; m/z 537 (MH+); white solid | 17 mg, 27% |
| | PVA-134 | Aldehyde_QC (Gemini)_2; Rt 4.57 min; m/z 540 (MH+); white solid | 5 mg, 8% |
| | PVA-135 | Aldehyde QC_2; Rt 5.98 min; m/z 601 (MH+); white solid | 3 mg, 4% |
| | PVA-155 | Aldehyde QC_2; Rt 5.84 min; m/z 566 (MH+); white solid | 1 mg 0.3% |
| | PVA-158 | Aldehyde QC_2; Rt 5.41 min; m/z 513 (MH+); white solid | 8 mg 3% |
| | PVA-159 | Aldehyde QC_2; Rt 5.37 min; m/z 588 (MH+); white solid | 2 mg, 4% |

-continued

| Compound | Code | Analytical Data | Yield |
|---|---|---|---|
| 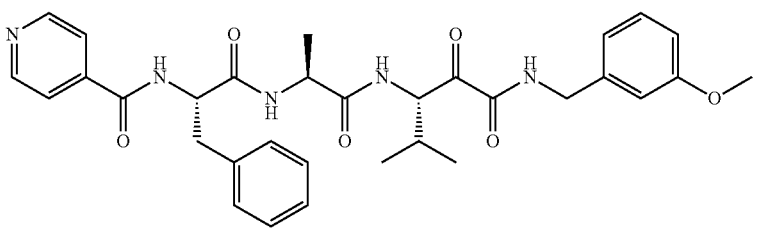 [SMILES: COc1cccc(CNC(=O)C(=O)[C@@H](NC(=O)[C@H](C)NC(=O)[C@H](Cc2ccccc2)NC(=O)c2ccncc2)C(C)C)c1] | PVA-160 | Aldehyde QC_2; Rt 5.42 min; m/z 588 (MH+); white solid | 8 mg, 15% |
| 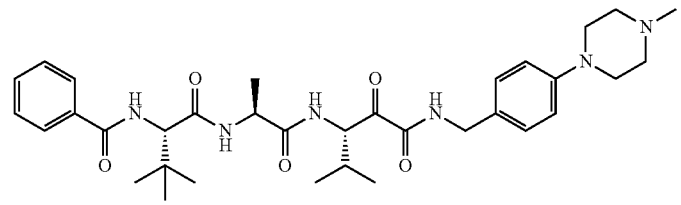 [SMILES: CC(C)[C@H](NC(=O)[C@H](C)NC(=O)[C@@H](NC(=O)c1ccccc1)C(C)(C)C)C(=O)C(=O)NCc1ccc(N2CCN(C)CC2)cc1] | PVA-162 | Analph9_MeOH_QC; Rt 8.15 min; m/z 621 (MH+); white solid | 8 mg 7% |
| 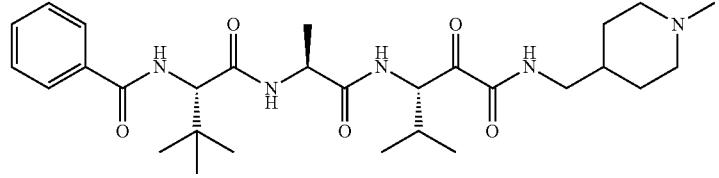 [SMILES: CC(C)[C@H](NC(=O)[C@H](C)NC(=O)[C@@H](NC(=O)c1ccccc1)C(C)(C)C)C(=O)C(=O)NCC1CCN(C)CC1] | PVA-163 | Analph9_MeOH_QC_2; Rt 8.01 min; m/z 544 (MH+); white solid | 6 mg 7% |
| 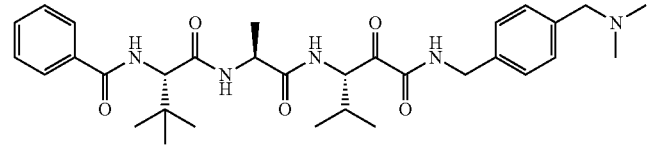 [SMILES: CC(C)[C@H](NC(=O)[C@H](C)NC(=O)[C@@H](NC(=O)c1ccccc1)C(C)(C)C)C(=O)C(=O)NCc1ccc(CN(C)C)cc1] | PVA-164 | Analph9_MeOH_QC_2; Rt 8.24 min; m/z 581 (MH+); white solid | 4 mg 4% |
| 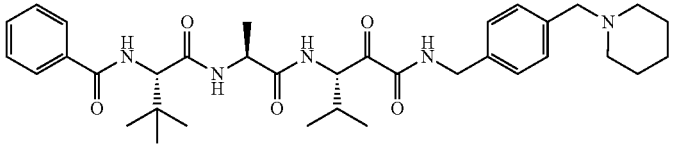 [SMILES: CC(C)[C@H](NC(=O)[C@H](C)NC(=O)[C@@H](NC(=O)c1ccccc1)C(C)(C)C)C(=O)C(=O)NCc1ccc(CN2CCCCC2)cc1] | PVA-165 | Analph9_MeOH_QC_2; Rt 8.72 min; m/z 620 (MH+); white solid; | 12 mg 11% |
| 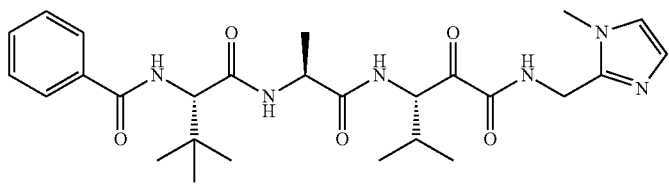 [SMILES: CC(C)[C@H](NC(=O)[C@H](C)NC(=O)[C@@H](NC(=O)c1ccccc1)C(C)(C)C)C(=O)C(=O)NCc1nccn1C] | PVA-166 | Analph9_MeOH_QC_2; Rt 7.66 min; m/z 528 (MH+); white solid | 4 mg 4% |
| 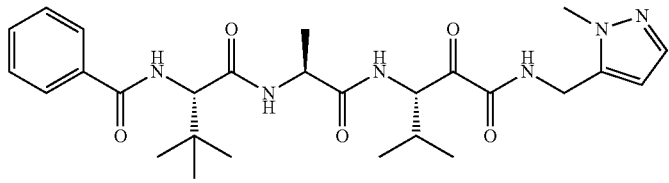 [SMILES: CC(C)[C@H](NC(=O)[C@H](C)NC(=O)[C@@H](NC(=O)c1ccccc1)C(C)(C)C)C(=O)C(=O)NCc1ccnn1C] | PVA-167 | Analph9_MeOH_QC_2; Rt 7.67 min; m/z 527 (MH+); white solid | 9 mg 10% |
| 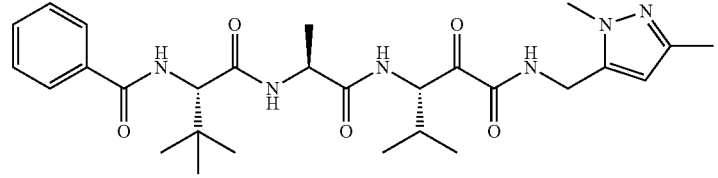 [SMILES: Cc1cc(CNC(=O)C(=O)[C@@H](NC(=O)[C@H](C)NC(=O)[C@@H](NC(=O)c2ccccc2)C(C)(C)C)C(C)C)n(C)n1] | PVA-168 | Analph9_MeOH_QC_2; Rt 7.85 min; m/z 542 (MH+); white solid | 10 mg 10% |

-continued

| Compound | Code | Analytical Data | Yield |
|---|---|---|---|
| (structure) | PVA-169 | AnalpH9_MeOH_QC; Rt 6.93 mins; m/z 601 (MH+); white solid | 5 mg, 10% |
| (structure) | PVA-170 | AnalpH9_MeOH_QC; Rt 7.39 min; m/z 579 (MH+); white solid | 5 mg, 11% |
| (structure) | PVA-171 | AnalpH9_MeOH_QC; Rt 6.82 min; m/z 637 (MH+); white solid | 9 mg, 11% |
| (structure) | PVA-174 | Aldehyde QC_2; Rt 5.08 min; m/z 522 (MH+); white solid | 22 mg, 45% |
| (structure) | PVA-175 | Aldehyde QC_2; Rt 5.33 min; m/z 536 (MH+); white solid | 19 mg, 36% |
| (structure) | PVA-178 | Aldehyde QC_2; Rt 7.10 min; m/z 541 (MH+); white solid | 9 mg 16% |
| (structure) | PVA-179 | Aldehyde QC_2; Rt 7.42 min; m/z 557, 559 (MH+); white solid | 10 mg 19% |

-continued

| Compound | Code | Analytical Data | Yield |
|---|---|---|---|
| | PVA-180 | Aldehyde QC_2; Rt 8.13 min; m/z 579 (MH+); white solid | 12 mg 21% |
| | PVA-181 | Aldehyde QC_2; Rt 7.56 min; m/z 591 (MH+); white solid | 9 mg 15% |
| | PVA-185 | Aldehyde QC_2; Rt 4.73 min; m/z 653 (MH+); white solid | 7 mg, 13% |
| | PVA-186 | Aldehyde QC_2; Rt 5.64 min; m/z 657 (MH+); white solid | 6 mg, 3%, |
| | PVA-188 | Aldehyde QC_2; Rt 4.55 min; m/z 617 (MH+); white solid | 10 mg, 19% |
| | PVA-189 | Aldehyde QC_2; Rt 7.67 min; m/z 607 (MH+); white solid | 9 mg 16% |
| | PVA-190 | Aldehyde QC_2; Rt 5.29 min; m/z 621 (MH+); white solid | 1 mg 2% |
| | PVA-191 | Aldehyde QC_2; Rt 7.41 min; m/z 557, 559 (MH+); white solid | 3 mg 6% |

-continued

| Compound | Code | Analytical Data | Yield |
|---|---|---|---|
| (structure) | 192 | Aldehyde QC_2; Rt 6.76 min; m/z 548 (MH$^+$); white solid | 3 mg 5% |
| (structure) | PVA-193 | Aldehyde QC_2; Rt 7.39 min; m/z 557, 559 (MH$^+$); white solid | 4 mg 8% |
| (structure) | PVA-194 | Analph2_MeOH_QC_2; Rt 7.57 min; m/z 581 (MH$^+$); cream solid | 1 mg 2% |
| (structure) | PVA-195 | Aldehyde QC_2; Rt 4.59 min; m/z 622 (MH$^+$); white solid | 3 mg 4% |
| (structure) | PVA-196 | Aldehyde QC_2; Rt 5.96 min; m/z 580 (MH$^+$); white solid | 2 mg 3% |
| (structure) | PVA-197 | Analph2_MeOH_QC_2; Rt 7.67 min; m/z 616 (MH$^+$); white solid | 2 mg 2% |
| (structure) | PVA-199 | Analph2_MeOH_QC_2; Rt 8.23 min; m/z 581 (MH$^+$); white solid | 13 mg 20% |
| (structure) | PVA-200 | Analph2_MeOH_QC_2; Rt 8.71 min; m/z 623 (MH$^+$); white solid | 12 mg 18% |

-continued

| Compound | Code | Analytical Data | Yield |
|---|---|---|---|
| 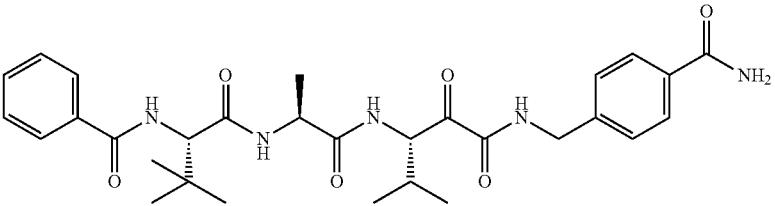 [SMILES: CC(C)[C@H](NC(=O)[C@H](C)NC(=O)[C@@H](NC(=O)c1ccccc1)C(C)(C)C)C(=O)C(=O)NCc1ccc(C(N)=O)cc1] | PVA-202 | Analph2_MeOH_QC_2; Rt 7.55 min; m/z 566 (MH⁺); white solid | 1 mg 2 % |
| 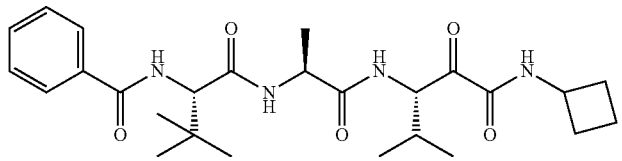 [SMILES: CC(C)[C@H](NC(=O)[C@H](C)NC(=O)[C@@H](NC(=O)c1ccccc1)C(C)(C)C)C(=O)C(=O)NC1CCC1] | PVA-203 | Analph2_MeOH_QC_2; Rt 8.71 min; m/z 487 (MH⁺); white solid | 2 mg 4% |
| 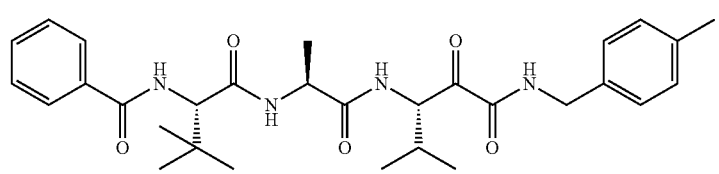 [SMILES: Cc1ccc(CNC(=O)C(=O)[C@@H](NC(=O)[C@H](C)NC(=O)[C@@H](NC(=O)c2ccccc2)C(C)(C)C)C(C)C)cc1] | PVA-205 | Analph9_MeOH_QC_2; Rt 8.41 min; m/z 537 (MH⁺); cream solid | 3 mg 4% |
| 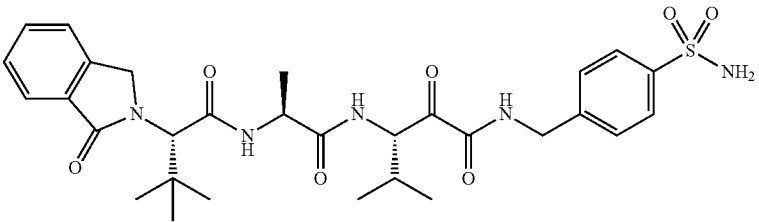 [SMILES: CC(C)[C@H](NC(=O)[C@H](C)NC(=O)[C@@H](N1Cc2ccccc2C1=O)C(C)(C)C)C(=O)C(=O)NCc1ccc(S(N)(=O)=O)cc1] | PVA-206 | Analph2_MeOH_QC_2; Rt 7.63 min; m/z 614 (MH⁺); white solid | 13 mg 6% |
| 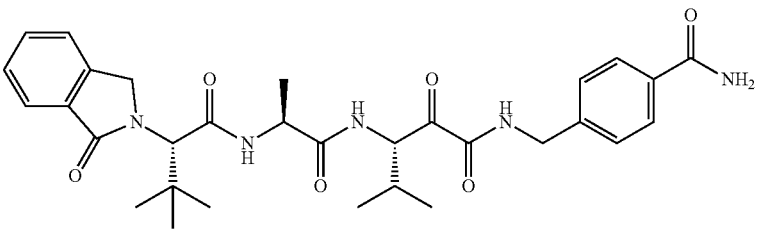 [SMILES: CC(C)[C@H](NC(=O)[C@H](C)NC(=O)[C@@H](N1Cc2ccccc2C1=O)C(C)(C)C)C(=O)C(=O)NCc1ccc(C(N)=O)cc1] | PVA-207 | Aldehyde Q_2; Rt 5.88 min; m/z 578 (MH⁺); white solid | 1 mg, 1% |
| 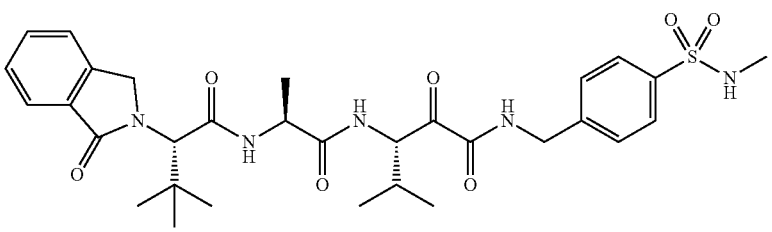 [SMILES: CNS(=O)(=O)c1ccc(CNC(=O)C(=O)[C@@H](NC(=O)[C@H](C)NC(=O)[C@@H](N2Cc3ccccc3C2=O)C(C)(C)C)C(C)C)cc1] | PVA-208 | Aldehyde QC_2; Rt 6.43 min; m/z 628 (MH⁺); white solid | 1 mg, 2% |
| 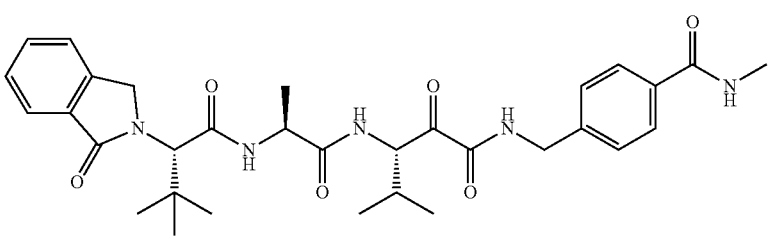 [SMILES: CNC(=O)c1ccc(CNC(=O)C(=O)[C@@H](NC(=O)[C@H](C)NC(=O)[C@@H](N2Cc3ccccc3C2=O)C(C)(C)C)C(C)C)cc1] | PVA-209 | Analph2_MeOH_QC_2; Rt 7.85 min; m/z 592 (MH⁺); white solid | 14 mg 6% |

| Compound | Code | Analytical Data | Yield |
|---|---|---|---|
| 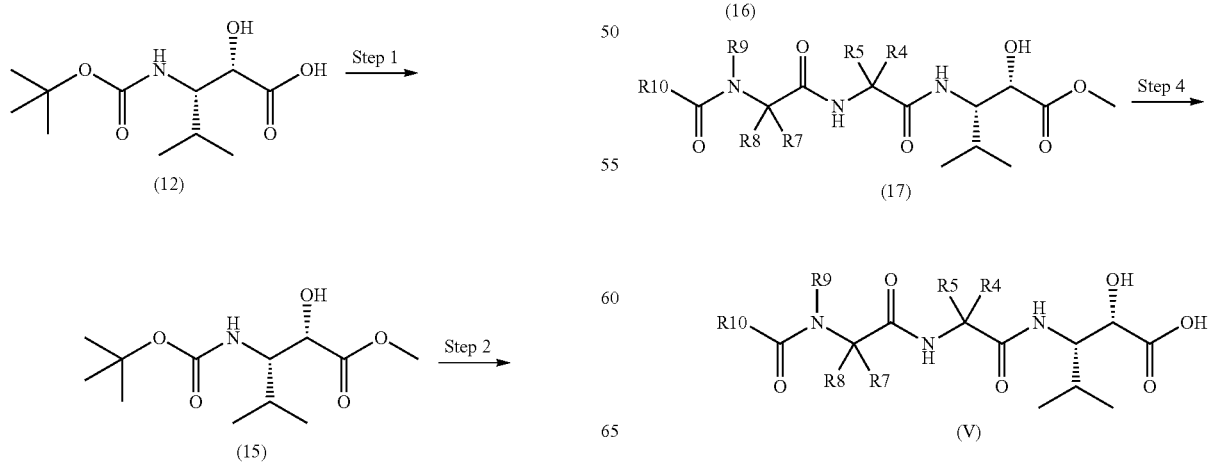 | PVA-210 | Aldehyde QC_2; Rt 5.25 min; m/z 592 (MH+); white solid | 8 mg, 9% |
| | PVA-211 | Aldehyde QC_2; Rt 5.35 min; m/z 633 (MH+); white solid | 1 mg, 2% |
| | PVA-212 | Aldehyde QC_2; Rt 7.09 min; m/z 618 (MH+); white solid | 1 mg, 2% |
| | PVA-213 | Aldehyde QC_2; Rt 4.07 min; m/z 634 (MH+); white solid | 58 mg 24% |
Synthesis of the above compounds via route 5 requires intermediate (V).
Synthesis of Intermediate (V)
Scheme 14
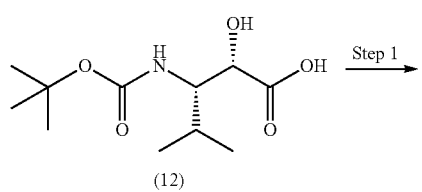
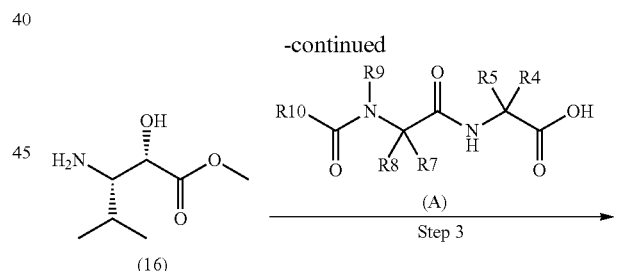

231

Typical Procedure

Step 1—Synthesis of Boc β-amino-α-hydroxyacid methyl ester (15)

To a solution of (12A) (2.0 g, 1 equiv.) in DMF (18 mL) and MeOH (2 mL) at 0° C. was added slowly dropwise TMS-diazomethane (4.9 mL, 1.2 equiv.). The reaction mixture was slowly warmed to ambient temperature and stirred for 22 h. Acetic acid (5 equiv.) was added slowly dropwise with cooling (ice-bath) to quench excess TMS-diazomethane. The reaction mixture was concentrated in vacuo and the residue was dissolved in EtOAc and washed with sat (aq.) NaHCO$_3$, H$_2$O and brine. The organic layer was subsequently dried over MgSO$_4$ and evaporated to afford the desired methyl ester (15A) (1.7 g, 83%) as a yellow solid. $^1$H NMR (400 MHz, CDCl$_3$) 4.64 (1H, d, J=9.3 Hz), 4.15 (1H, d, J=4.0 Hz), 3.66 (3H, s), 3.65-3.59 (1H, m), 1.8-1.72 (1H, m), 1.31 (9H, s), 0.81 (6H, m).

Step 2—Synthesis of β-amino-α-hydroxyacid methyl ester (16)

A solution of (15A) (1.7 g, 1 equiv.) in DCM (20 mL) was treated with a solution of HCl in dioxane (4M, 16.8 mL, 10 equiv.) at 0° C. The reaction mixture was then stirred at ambient temperature 18 h. The reaction mixture was concentrated in vacuo to afford an orange oil that was purified by column chromatography (silica gel) eluting with EtOAc then 5% MeOH/EtOAc to afford the desired product (16A) (1.2 g, 92%). 1H NMR (400 MHz, DMSO-d$_6$) 7.88 (2H, s, NH$_2$), 4.34 (1H, d, J=3.5 Hz), 3.62 (3H, s), 3.11-3.08 (1H, m), 3.44-3.42 (1H, m), 0.86 (3H, d, J=6.8 Hz), 0.82 (3H, d, J=6.8 Hz)

(16) can also be prepared using 5-10 equiv TFA in DCM.

Step 3—Synthesis of capped peptidyl α-hydroxyacid methyl esters (17)

To a solution of capped dipeptide acid (A) (1 equiv.) in THF (5 mL) was added iso-butyl chloroformate (1 equiv.) and NMM (2.5 equiv.) at −40° C. After 40 min, a solution of amine (16) (1 equiv.) in THF (2 mL) was added and stirred at −40° C. for 3 h. The reaction mixture was diluted with EtOAc (20 mL) and filtered. The filtrate was washed with 5% NaHCO$_3$ (aq.) (10 mL), brine solution (10 mL), dried (Na$_2$SO$_4$), and concentrated in vacuo. The residue was generally purified by reverse-phase preparative HPLC to afford the desired compound (17).

Step 4—Synthesis of capped peptidyl α-hydroxyacids (V)

To a solution of capped peptidyl α-hydroxyacid methyl ester (17) in THF and H$_2$O was added lithium hydroxide (2 equiv.) with cooling (ice-bath). The reaction mixture was slowly warmed to ambient temperature and stirred for 15 h. The reaction mixture was acidified with 10% aqueous acetic acid and the aqueous layer was extracted with EtOAc (3×5 volumes). The combined organic extracts were washed with H$_2$O (5 volumes) and brine (5 volumes), dried (MgSO$_4$) and concentrated in vacuo to afford the desired compound.

Route 6: Synthesis of PVA Compounds (I) Via Tri-Peptide Hydroxy Amide

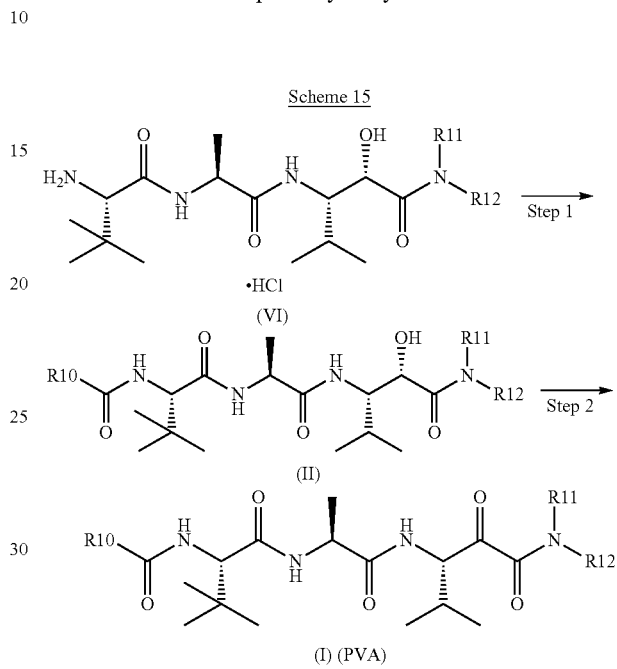

Scheme 15

Typical Procedure

Step 1—Synthesis of Capped Peptidyl α-Hydroxyamide (II)

This was carried out in an analogous fashion to Step 3/Route 2

Step 2—Synthesis of PVA Compounds (1)

See Method A.

PVA Compounds Prepared by Route 6

| Compound | Code | Analytical Data | Yield |
|---|---|---|---|
| (structure shown) | PVA-130* | Aldehyde QC_2; Rt 4.28 min; m/z 617 (MH$^+$); white solid | 14 mg, 13% |

-continued

| Compound | Code | Analytical Data | Yield |
|---|---|---|---|
| 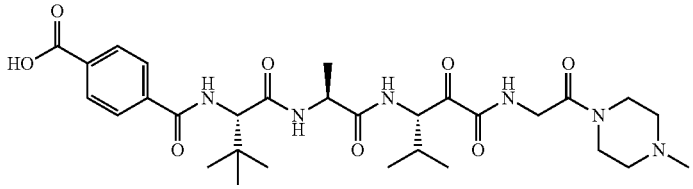 [SMILES: CC(C)[C@H](NC(=O)[C@H](C)NC(=O)[C@@H](NC(=O)c1ccc(C(=O)O)cc1)C(C)(C)C)C(=O)C(=O)NCC(=O)N1CCN(C)CC1] | PVA-131* | Aldehyde QC_2; Rt 4.23 min; m/z 617 (MH+); white solid | 7 mg, 7% |
| 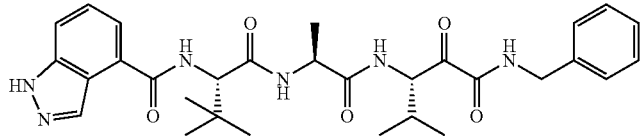 [SMILES: CC(C)[C@H](NC(=O)[C@H](C)NC(=O)[C@@H](NC(=O)c1cccc2[nH]ncc12)C(C)(C)C)C(=O)C(=O)NCc1ccccc1] | PVA-149 | Aldehyde QC_2; Rt 6.39 min; m/z 563 (MH+); white solid | 278 mg, 32% |
| 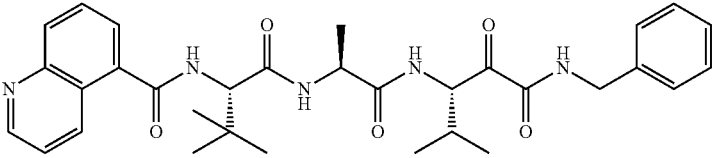 [SMILES: CC(C)[C@H](NC(=O)[C@H](C)NC(=O)[C@@H](NC(=O)c1cccc2ncccc12)C(C)(C)C)C(=O)C(=O)NCc1ccccc1] | PVA-150 | Aldehyde QC_2; Rt 5.39 min; m/z 574 (MH+); white solid | 34 mg, 27% |
| 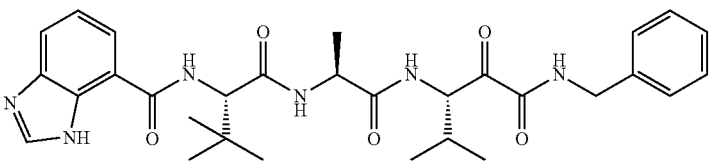 [SMILES: CC(C)[C@H](NC(=O)[C@H](C)NC(=O)[C@@H](NC(=O)c1cccc2nc[nH]c12)C(C)(C)C)C(=O)C(=O)NCc1ccccc1] | PVA-157 | Aldehyde QC_2; Rt 5.49 min; m/z 563 (MH+); white solid | 14 mg, 11% |
| 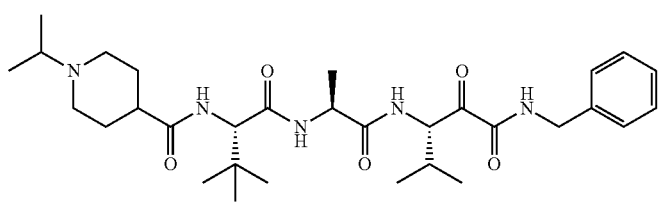 [SMILES: CC(C)[C@H](NC(=O)[C@H](C)NC(=O)[C@@H](NC(=O)C1CCN(C(C)C)CC1)C(C)(C)C)C(=O)C(=O)NCc1ccccc1] | PVA-172 | Analph9_MeOH QC_2; Rt 8.16 min; m/z 572 (MH+); white solid | 23 mg 25% |
| 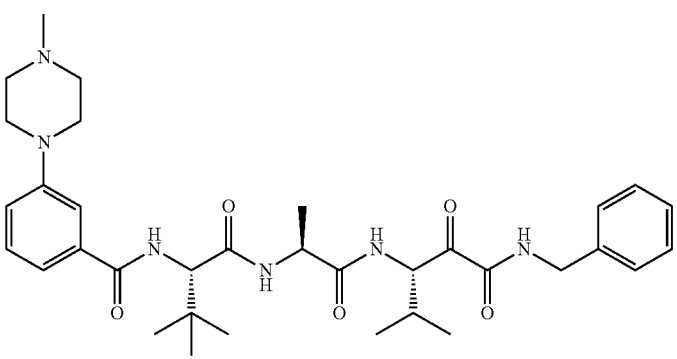 [SMILES: CC(C)[C@H](NC(=O)[C@H](C)NC(=O)[C@@H](NC(=O)c1cccc(N2CCN(C)CC2)c1)C(C)(C)C)C(=O)C(=O)NCc1ccccc1] | PVA-173 | AnalpH9_MeOH_QC; Rt 8.31 min; m/z 621 (MH+); white solid | 14 mg 13% |
| 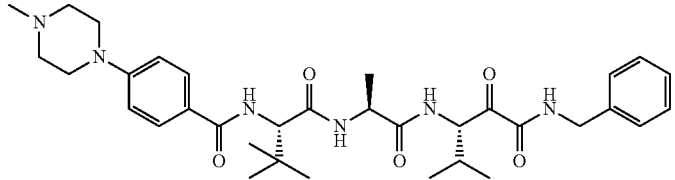 [SMILES: CC(C)[C@H](NC(=O)[C@H](C)NC(=O)[C@@H](NC(=O)c1ccc(N2CCN(C)CC2)cc1)C(C)(C)C)C(=O)C(=O)NCc1ccccc1] | PVA-176 | AnalpH2_MeOH_QC; Rt 8.31 min; m/z 621 (MH+); white solid | 17 mg, 21% |

-continued

| Compound | Code | Analytical Data | Yield |
|---|---|---|---|
| | PVA-182 | Aldehyde QC_2; Rt 7.28 min; m/z 591 (MH$^+$); white solid | 16 mg, 31% |
| | PVA-183 | Aldehyde QC_2; Rt 7.49 min; m/z 557, 559 (MH$^+$); white solid | 12 mg, 25% |
| | PVA-184 | Aldehyde QC_2; Rt 7.49 min; m/z 557, 559 (MH$^+$); white solid | 11 mg, 23% |
| | PVA-201 | AnalpH2_MeOH_QC_2; Rt 6.25 min; m/z 621 (MH$^+$); white solid | 13 mg 20% |
| | PVA-216 | AnalpH2_MeOH_QC_2; Rt 5.73 min; m/z 544 (MH$^+$); white solid | 12 mg, 1% |

($^*$)PVA-130 and PVA-131 were prepared from the mono-methyl ester, hydrolysis of the methyl ester was carried out using LiOH THF/H$_2$O prior to oxidation with Dess-Martin periodinane.

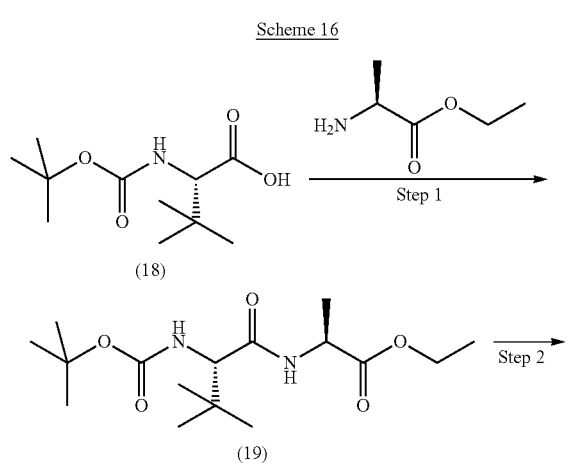

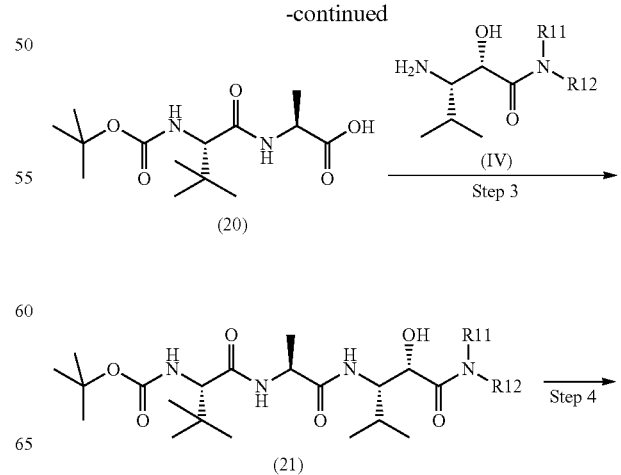

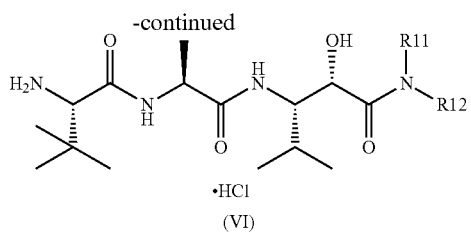

(VI)

Synthesis of the above compounds via route 6 require intermediate (VI). Compounds of formula (VI) were prepared as follows:

Step 1—Synthesis of (S)-2-((S)-2-tert-Butoxycarbonylamino-3,3-dimethyl-butylamino)-propionic acid ethyl ester (19)

To a solution of (S)-2-(tert-butoxycarbonylamino)-3,3-dimethylbutanoic acid (18) (10 g, 43.3 mmol) in THF (100 mL) at −40° C. was added isobutyl chloroformate (5.9 mL, 45.5 mmol) followed by NMM (10.45 mL, 95.23 mmol) and stirred at −40° C. for 1 h. A solution of H-Ala-OMe (7.3 g, 47.6 mmol) in DMF (5 mL) was added to the above reaction mixture and stirred at −40° C. After 2.5 h, EtOAc (500 mL) was added to the reaction mixture, stirred for 10 min and filtered to remove the salts. The filtrate was washed with 10% citric acid (3×100 mL), 5% NaHCO$_3$ solution (3×100 mL), brine solution (100 mL), dried (Na$_2$SO$_4$) and concentrated. The obtained residue was stirred with pet. ether (100 mL) for 30 min, the resulting solid was isolated by filtration to obtain the desired compound (6 g, 43%) as a white solid. R$_f$: 0.3 (20% EtOAc/pet. ether); $^1$H NMR (400 MHz, DMSO-d$_6$): 8.3 (1H, d, J=6 Hz), 6.36 (1H, d, J=9.6 Hz), 4.22 (1H, m), 4.1-4.03 (2H, m), 3.89 (1H, d, J=9.6 Hz), 1.38 (9H, s), 1.27 (3H, d, J=7.2 Hz), 1.16 (3H, t, J=6.8 Hz), 0.91 (9H, s); m/z 331 (MH)$^+$.

Step 2—Synthesis of (S)-2-((S)-2-tert-Butoxycarbonylamino-3,3-dimethyl-butyrylamino)-propionic acid (20)

To a solution of (S)-2-(tert-butoxycarbonylamino)-3,3-dimethylbutanoic acid (18) (6.5 g, 19.7 mmol) in THF (30 mL) was added NaOH (1.7 g, 43.8 mmol) in H$_2$O (60 mL) and the reaction mixture stirred at ambient temperature for 16 h. THF was subsequently removed in vacuo and the aqueous phase washed with EtOAc (50 mL). The aqueous phase was then adjusted to pH ~2 by addition of 1M HCl and extracted with EtOAc (3×50 mL). The organics were combined dried over MgSO$_4$ and evaporated to give the desired compound (20) as a white solid (5.7 g, 95%); AnalpH2_MeOH; Rt 2.61 min; m/z 303 (MH$^+$); white solid Step 3—Synthesis of Boc-Peptidyl α-Hydroxyamides (21)

To a solution of (20) (1.1 g, 1 equiv.) in THF (20 mL) was added iso-butyl chloroformate (496 μL, 1 equiv.), NMM (2.5 equiv.) at −40° C. After 40 min, a solution of compound (IV) (1 equiv.) in THF (20 mL) was added and stirred at −40° C. for 3 h. The reaction mixture was diluted with EtOAc (100 mL) and filtered. The filtrate was washed with (aq.) 5% NaHCO$_3$ solution (100 mL), brine solution (100 mL), dried (Na$_2$SO$_4$), and concentrated in vacuo. The residue was typically purified by reverse-phase preparative HPLC to afford the desired compound (21).

Step 4—Synthesis of Peptidyl α-Hydroxyamides (VI)

A solution of the Boc-peptidyl α-hydroxyamide (21) (1 equiv.) in DCM (10 volumes) was treated with TFA (6 equiv.) at 0° C. and allowed to stir at ambient temperature. After 3 h, the reaction mixture was concentrated and the residue was washed with Et$_2$O (2×10 volumes) and dried under vacuum to obtain the desired compound (VI) which was used in the next step without further purification.

In some instances, the deprotection was carried out with a solution of 4M HCl in dioxane after dissolving the Boc compound (21) in DCM.

Method B: Synthesis of PVA Compounds (I) Via Ozonolysis Chemistry

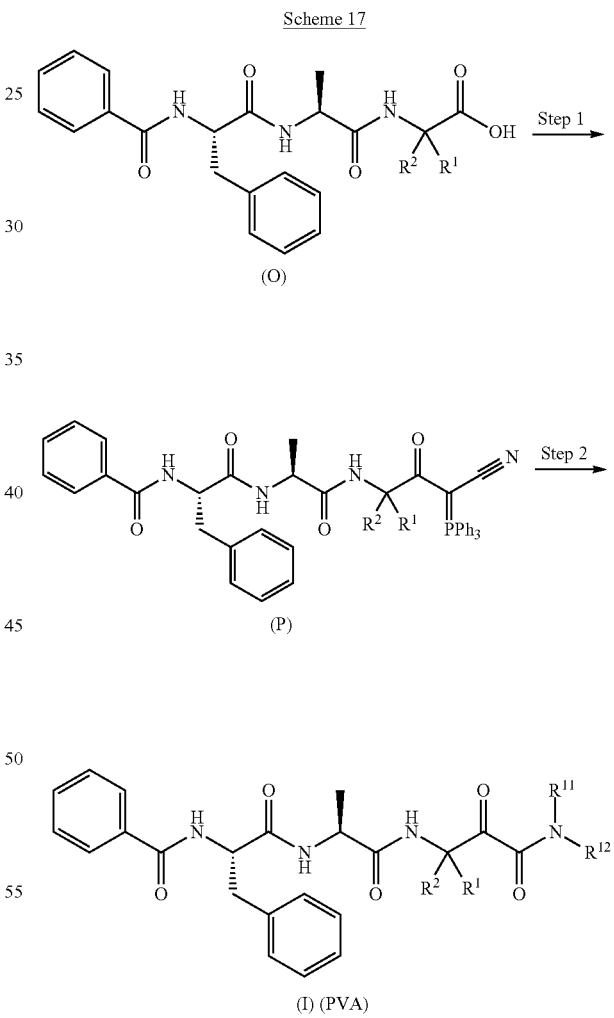

Typical Procedure

Synthesis of Tripeptide Intermediates:

The following tripeptides (O) were prepared using the same methodology as described in Route 1 for the synthesis of dipeptide intermediates (A).

| Compound | Code | Analytical Data | Yield |
|---|---|---|---|
| (structure) | O1 | AnalpH2_MeOH; Rt = 3.15 min; m/z 454 (MH⁺); white solid | 1.05 g, 36% |
| (structure) | O2 | AnalpH2_MeOH; Rt = 4.06 min; m/z 440 (MH⁺); white solid | 1.54 g, 27% |
| (structure) | O3 | AnalpH2_MeOH; Rt = 3.55 min; m/z 398 (MH⁺); white solid | 0.73 g, 14% |

Step 1—Synthesis of Cyanophosphoranyl Intermediate (P)

To a solution of tripeptide intermediate (O) (1 equiv.) in DCM (1 g/30 mL) was added EDC.HCl (2 equiv.), (triphenylphosphoranylidene)acetonitrile (2 equiv.) and DMAP (0.1 equiv.). The resulting mixture was stirred for 16 h at 22° C. after which time the solvent was removed and the resulting crude material purified by reverse phase preparative HPLC to afford the desired compound (P).

The following compounds of formula (P) were prepared using this method.

| Compound | Code | Analytical Data | Yield |
|---|---|---|---|
| (structure) | P1 | AnalpH2_MeOH; Rt = 4.03 mins; m/z 737 (MH⁺); brown solid | 210 mg, 25% |
| (structure) | P2 | AnalpH2_MeOH; Rt = 4.59 mins; m/z 723 (MH⁺); pale orange brown solid | 320 mg, 20% |

| Compound | Code | Analytical Data | Yield |
|---|---|---|---|
| (structure) | P3 | AnalpH2_MeOH; Rt = 4.37 mins; m/z 681 (MH+); pale brown solid | 250 mg, 27% |

Step 2—Synthesis of PVA Compounds (1)

Through a solution of intermediate (P) (1 equiv.) in DCM (100 volumes) at −78° C. was bubbled gaseous ozone for 5-10 min. Nitrogen was bubbled through the mixture for 5 min followed by the addition of a solution of the amine ($R^{11}R^{12}NH$) (1 equiv.) in DCM (20 volumes) after which time the reaction was stirred for 30 min at −78° C. before solvent removal. The residue was purified by reverse-phase preparative HPLC followed by lyophilisation to afford the desired compound (I).

PVA Compounds Prepared by Method B

| Compound | Code | Analytical Data | Yield |
|---|---|---|---|
| (structure) | PVA-006 | AnalpH2_QC; Rt = 6.82 min; m/z 535 (MH+); white solid | 1 mg, 4% |
| (structure) | PVA-007 | AldehydeQC_1A; Rt = 5.50 min; m/z 564 (MH+); white solid | 4 mg, 10% |
| (structure) | PVA-014 | AnalpH2_A1B1_QC; Rt = 7.45 min; m/z 541 (MH+); white solid | 3 mg, 7% |
| (structure) | PVA-018 | Aldehyde_QC (Gemini)_1; Rt = 4.18 min; m/z 536 (MH+); white solid | 9 mg, 22% |

| Compound | Code | Analytical Data | Yield |
|---|---|---|---|
| 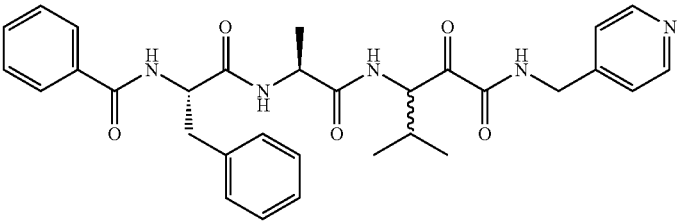 [SMILES: CC(C)C(NC(=O)[C@H](C)NC(=O)[C@H](Cc1ccccc1)NC(=O)c1ccccc1)C(=O)C(=O)NCc1ccncc1] | PVA-022 | Aldehyde_QC (Gemini)_1; Rt = 5.43 min; m/z 558 (MH$^+$); white solid | 3 mg, 8% |
| 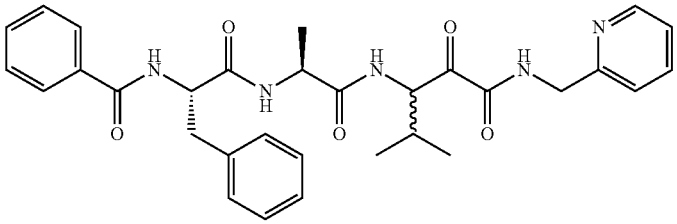 [SMILES: CC(C)C(NC(=O)[C@H](C)NC(=O)[C@H](Cc1ccccc1)NC(=O)c1ccccc1)C(=O)C(=O)NCc1ccccn1] | PVA-023 | AldehydeQC_1; Rt = 6.24 min; m/z 558 (MH$^+$); white solid | 3 mg, 9% |
| 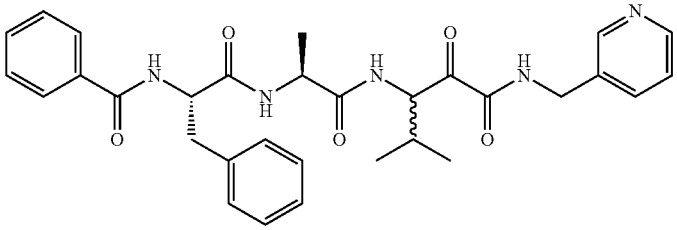 [SMILES: CC(C)C(NC(=O)[C@H](C)NC(=O)[C@H](Cc1ccccc1)NC(=O)c1ccccc1)C(=O)C(=O)NCc1cccnc1] | PVA-024 | AldehydeQC_1; Rt = 5.97 min; m/z 558 (MH$^+$); Cream solid | 1 mg 3% |
| 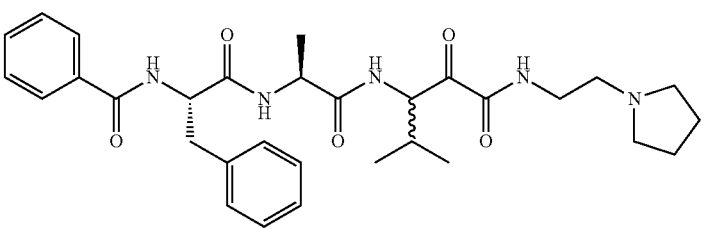 | PVA-025 | AldehydeQC_1; Rt = 5.09 min; m/z 664 (MH$^+$); Cream solid | 4 mg, 12% |

PVA Compounds Synthesized by Alternative Routes

The following PVA compounds were synthesized by alternative routes. Nonetheless, the methods described above may also be equally applicable to synthesis of these compounds.

| Compound | Code | Analytical Data | Yield |
|---|---|---|---|
| 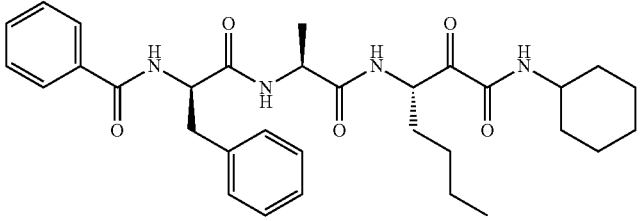 [SMILES: CCCC[C@H](NC(=O)[C@H](C)NC(=O)[C@@H](Cc1ccccc1)NC(=O)c1ccccc1)C(=O)C(=O)NC1CCCCC1] | PVA-017 | Aldehyde_QC (Gemini)_1; Rt = 7.22 min; m/z 563 (MH$^+$); white solid | 5 mg |

| Compound | Code | Analytical Data | Yield |
|---|---|---|---|
| (structure) | PVA-040 | Aldehyde_QC_1 Rt = 7.28 min; m/z 572 (MH+); white solid | 1 mg |
| (structure) | PVA-102 | AnalpH2_MeOH_QC; Rt = 7.65min; m/z 515 (MH+); beige solid | 25 mg |

PVA-017 was prepared by synthesizing Bz-D-Phe-Ala-OH (A2) on Wang resin (Route 1) and coupling it to the appropriate α-hydroxy-β-amino cyclohexylamide building block that was in turn made by Passerini chemistry on a Cbz protected norleucine aldehyde precursor. This precursor was deprotected (hydrogenolysis), coupled (iso-butyl chloroformate conditions) and oxidized (Dess-Martin periodinane) to give the desired pyruvamide.

PVA-040 was prepared from the corresponding dithiolane protected pyruvic acid and 4-picolylamine (HOAT, EDC) followed by hydrolysis of the dithiolane group with 1 M HCl (aq.) using ethylacetate as a co-solvent. The dithiolane protected pyruvic acid was prepared from the corresponding ethyl ester by hydrolysis (1M NaOH, MeOH) which was in-turn prepared from the corresponding ethyl pyruvate (24) (ethane-1,2-dithiol, BF$_3$.Et$_2$O). The ethyl pyruvate (24) was prepared in two steps from BzPheAlaNleOH (O1). Firstly, a Dakin West reaction was carried out with ethyloxalylchloride (22) to generate the ethyloxalyl enolate (23). This was subsequently hydrolysed with sodium ethoxide in ethanol to give the desired ethyl pyruvate (24).

Scheme 18

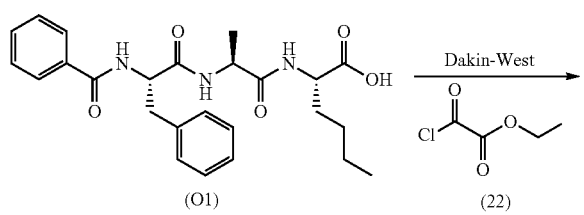

(O1) + (22) →(Dakin-West)

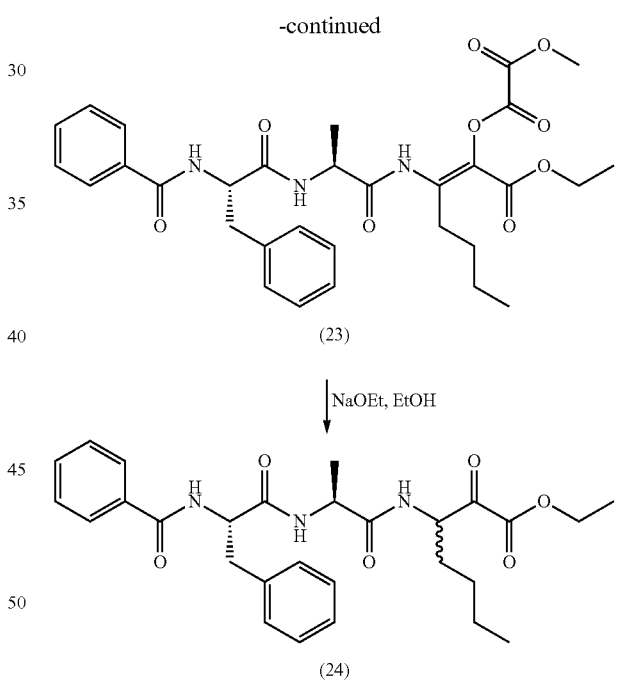

PVA-102 was prepared from the coupling of dimethylacetal (25) with BzPheAlaOH (A1) using the standard iso-butylchloroformate conditions. Hydrolysis of the acetal (26) using a mixture of TFA:acetone:water gave the desired final compound PVA-102. The dimethyl acetal (25) was prepared in 10 steps from Cbz-protected glycine (27). This was first converted to the corresponding Boc-protected hydroxyl-acid (28) using procedures analogous to those outlined for the synthesis of 12A and 12B (Scheme 10). 28 was then converted to the desired acetal (25) in 5 steps. First coupling with benzyl amine was performed under standard acid-amine coupling conditions to give the corresponding benzyl amide. The Boc protecting group was then switched to F-moc in two steps (Boc deprotection followed by Fmoc-protection using standard conditions). The alcohol was then oxidised using Dess-Martin periodinane and then converted to the acetal using methylorthofomate and p-toluenesulphonic acid in methanol. Finally the F-moc protecting group was removed using piperidine in DCM to give compound 25.

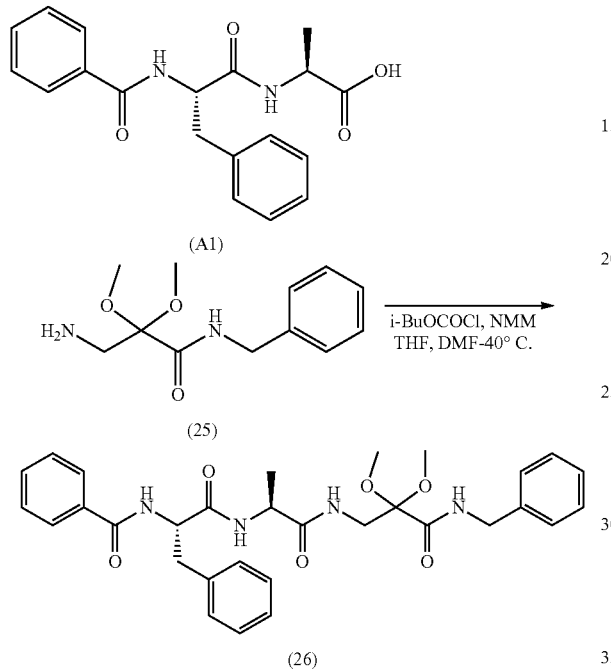

Additional Synthesis Details

Described below are the syntheses of materials and reagents that may not be readily or commercially available and synthetic sequences outside the scope of those outlined above.

Synthesis of Ether Linked Benzoic Acid Intermediates—General Procedure

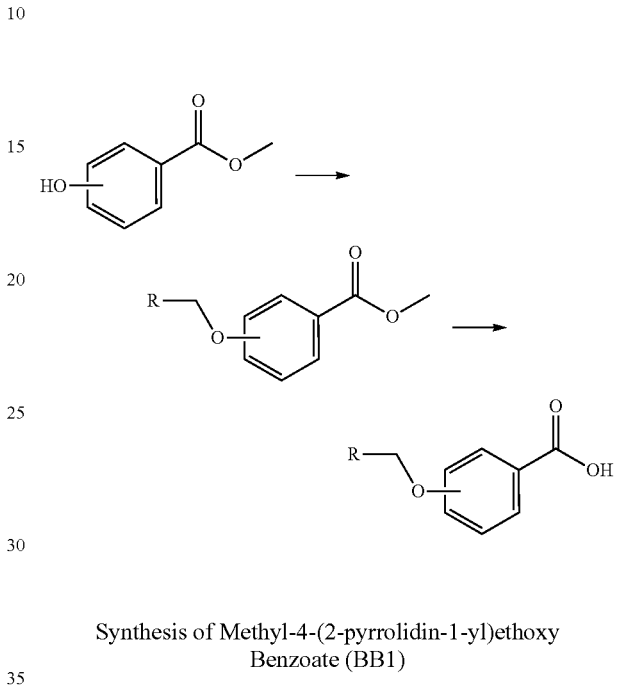

Synthesis of Methyl-4-(2-pyrrolidin-1-yl)ethoxy Benzoate (BB1)

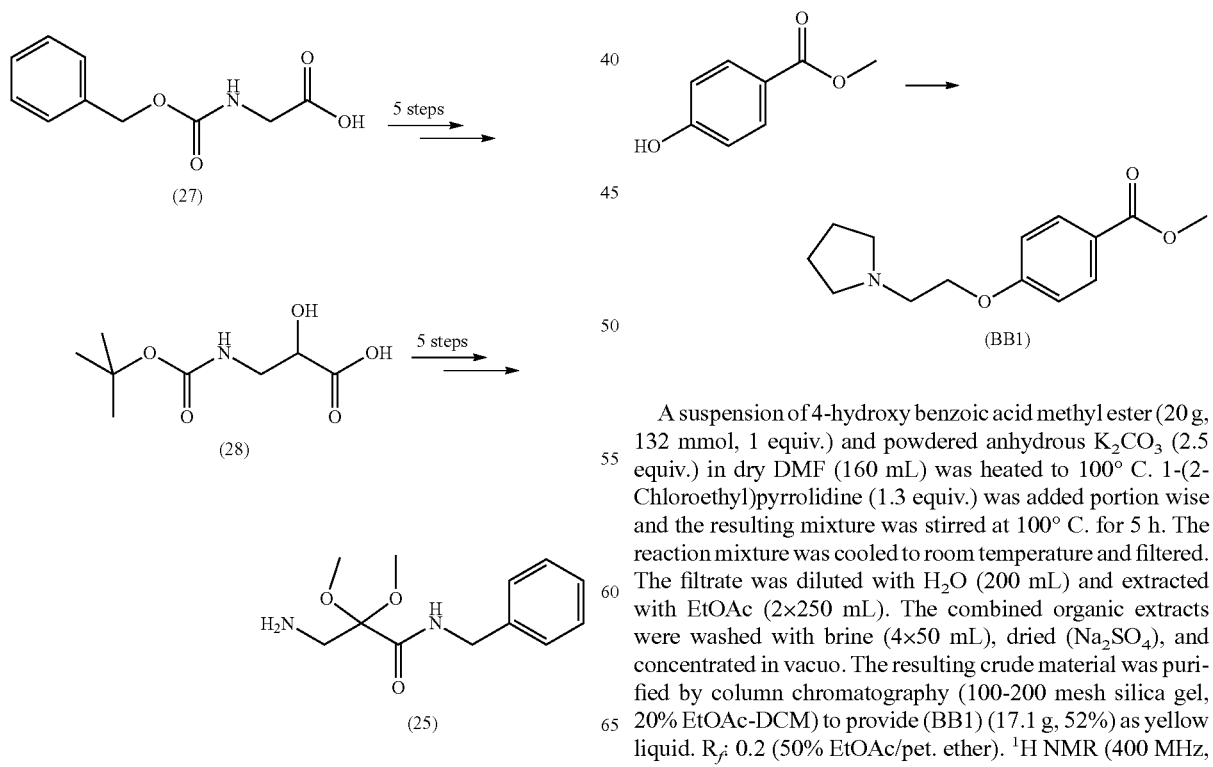

A suspension of 4-hydroxy benzoic acid methyl ester (20 g, 132 mmol, 1 equiv.) and powdered anhydrous $K_2CO_3$ (2.5 equiv.) in dry DMF (160 mL) was heated to 100° C. 1-(2-Chloroethyl)pyrrolidine (1.3 equiv.) was added portion wise and the resulting mixture was stirred at 100° C. for 5 h. The reaction mixture was cooled to room temperature and filtered. The filtrate was diluted with $H_2O$ (200 mL) and extracted with EtOAc (2×250 mL). The combined organic extracts were washed with brine (4×50 mL), dried ($Na_2SO_4$), and concentrated in vacuo. The resulting crude material was purified by column chromatography (100-200 mesh silica gel, 20% EtOAc-DCM) to provide (BB1) (17.1 g, 52%) as yellow liquid. $R_f$: 0.2 (50% EtOAc/pet. ether). $^1$H NMR (400 MHz, $CDCl_3$): δ 7.98 (2H, d, J=9.4 Hz), 6.93 (2H, d, J=9.4 Hz), 4.16

(2H, t, J=6 Hz), 3.88 (3H, s), 2.92 (2H, t, J=6 Hz), 2.65-2.61 (4H, m), 1.85-1.78 (4H, m); m/z 250 (MH)⁺.

Synthesis of Methyl-4-(2-pyrrolidin-1-yl)ethoxy Benzoic Acid Hydrochloride (BB2)

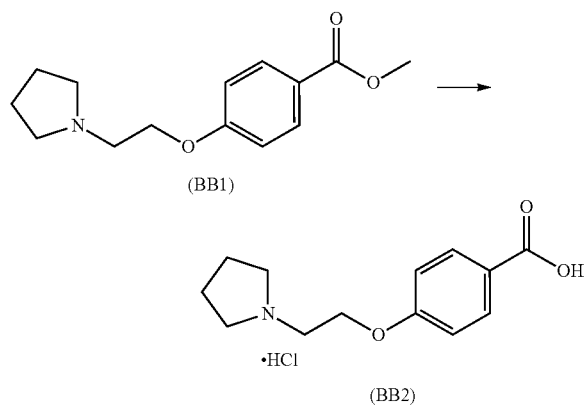

To a solution of compound (BB1) (16.9 g, 68 mmol) in MeOH (150 mL) was added 5 N aq. NaOH (40 mL) at room temperature. The reaction mixture was stirred for 5 h and concentrated in vacuo. The residue obtained was dissolved in H₂O (25 mL), cooled to 0° C. (ice-bath) and acidified with 6 N aq. HCl (pH ~6). The resulting precipitate was collected by filtration and washed with cold MeOH (25 mL) and dried to provide (BB2) (8.45 g, 53%) as an off white solid. R$_f$: 0.2 (84:15:1 MeOH/CHCl₃/AcOH). ¹H NMR (400 MHz, DMSO-d₆): δ 7.92 (2H, d, J=8.4 Hz), 7.1 (2H, d, J=8.4 Hz), 4.43-4.42 (2H, m), 3.6-3.55 (2H, m), 3.2-3.1 (4H, br s), 2.0-1.9 (4H, m); m/z 236 (MH)⁺.

Synthesis of Methyl-3-(2-pyrrolidin-1-yl)ethoxy Benzoate (BB3)

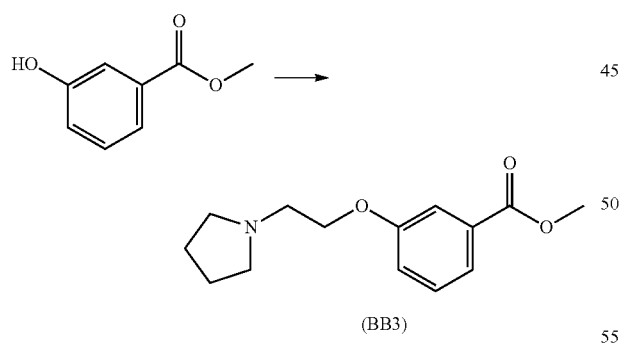

A suspension of 3-hydroxy benzoic acid methyl ester (20 g, 131.57 mmol) and powdered anhydrous K₂CO₃ (45.3 g, 328.26 mmol) in dry DMF (160 mL) was heated to 100° C. 1-(2-Chloroethyl)pyrrolidine (29.1 g, 171 mmol) was added in six portions to the reaction mixture which was stirred for 5 h. The reaction mixture was cooled to room temperature and filtered. The filtrate was dissolved in H₂O (200 mL), extracted with EtOAc (2×250 mL), washed with brine solution (4×50 mL), dried (Na₂SO₄), and concentrated in vacuo. The resulting crude compound was purified by column chromatography (100-200 mesh, silica gel, 20% EtOAc-DCM) to provide compound (BB3) (11.8 g, 36%) as yellow liquid. R$_f$: 0.2 (50% EtOAc/pet. ether). ¹H NMR (400 MHz, CDCl₃): δ 7.63 (1H, d, J=8 Hz), 7.58 (1H, s), 7.32 (1H, t, J=4 Hz), 7.13 (1H, dd, J=2.4, 8 Hz), 4.15 (2H, d, J=6 Hz), 3.91 (3H, s), 2.92 (2H, t, J=6 Hz), 2.63-2.60 (4H, m), 1.85-1.77 (4H, m); m/z 250 (MH⁺).

Synthesis of 4-(2-pyrrolidin-1-yl)ethoxy Benzoic Acid Hydrochloride (BB4)

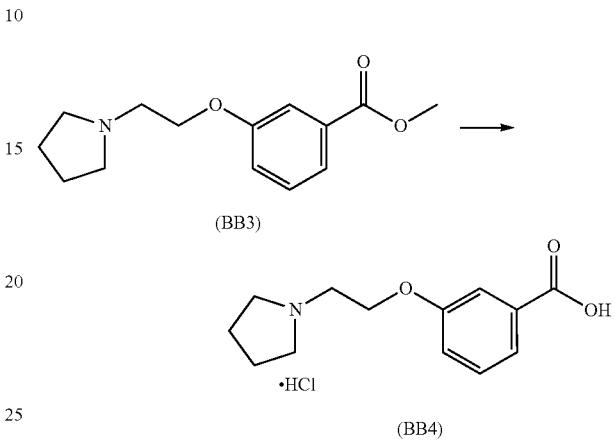

To a solution of (BB3) (11.7 g, 46.98 mmol) in MeOH (150 mL) was added 5 N aq. NaOH (40 mL) solution at room temperature, stirred for 5 h and concentrated in vacuo. The residue was dissolved in H₂O (10 mL), cooled in an ice bath, acidified with 6 N aq. HCl (pH ~6), extracted with 10% MeOH—CHCl₃ (3×50 mL), the combined organics were concentrated and the residue was treated with ethereal-HCl (100 mL) to obtain a precipitated solid which was filtered and dried to provide (BB4) (5.5 g, 49%) as a white solid. R$_f$: 0.2 (15% MeOH/CHCl₃). ¹H NMR (400 MHz, DMSO-d₆): δ 13.01 (1H, br s), 7.58 (1H, d, J=7.6 Hz), 7.51 (1H, s), 7.46 (1H, t, J=8.4 Hz), 7.13 (1H, d, J=2.4, 8 Hz), 4.45-4.35 (2H, m), 3.65-3.50 (4H, m), 3.15-3.05 (2H, m), 2.05-1.85 (4H, m).

Synthesis of 1-Methyl-1H-imidazole-2-carbaldehyde (BB5)

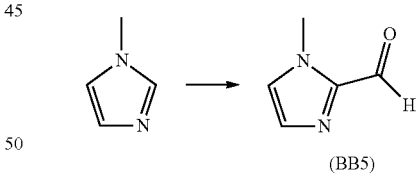

To a solution of 1-methyl imidazole (57 g, 0.7 mmol) in THF (250 mL) was added LDA (2 M solution in THF, 348 mL) at −60° C. and the stirred for 3 h. The reaction mixture was cooled −78° C., DMF (75 mL) was added rapidly, and the reaction mixture was slowly allowed to room temperature and stirred at ambient temperature overnight. The reaction mixture was cooled to 0° C., a solution of NaH₂PO₄ (100 g in 350 mL H₂O) was added and the resulting mixture was stirred for 30 min. The mixture was filtered to remove insoluble material and the filtrate was extracted with DCM (4×400 mL). The combined organic extracts were concentrated in vacuo and the crude residue was purified by column chromatography (silica gel, 100-200 mesh, 30% EtOAc/pet. ether) to provide (BB5) (41 g, 53%) as a yellow solid. R$_f$: 0.3 (15% MeOH/CHCl₃). ¹H NMR (400 MHz, CDCl₃): δ 9.82 (1H, s), 7.28 (1H, app d), 7.13 (1H, app d), 4.04 (3H, s); m/z 111 (MH)⁺.

Synthesis of (1-Methyl-1H-imidazol-2-yl)methanol (BB6)

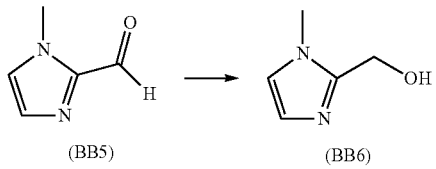

To a solution of compound (BB5) (40.5 g, 368 mmol) in MeOH (300 mL) at 0° C. was added NaBH₄ (20.89 g, 551 mmol) portion wise. The reaction mixture was slowly warmed to room temperature and stirred for 5 h. The reaction mixture was cooled to 0° C., H₂O (150 mL) was added and the mixture was stirred for 30 min at room temperature then concentrated in vacuo. The crude residue was dissolved in H₂O (150 mL) and extracted with CHCl₃ (4×200 mL). The combined organic layers were dried over Na₂SO₄ and concentrated. The residue was stirred with Et₂O (150 mL) and filtered to afford (BB6) (36 g, 87%) as a white solid. $R_f$: 0.4 (15% MeOH/CHCl₃). ¹H NMR (400 MHz, CDCl₃): δ 6.89 (1H, app d), 6.83 (1H, app d), 4.66 (2H, s), 3.72 (3H, s); m/z 113 (MH)⁺.

Synthesis of 2-(Chloromethyl)-1-methyl-1H-imidazole Hydrochloride (BB7)

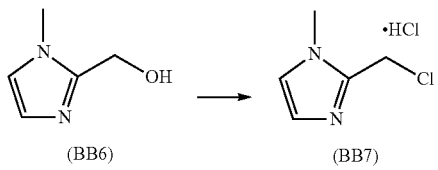

To a solution of (BB6) (35.5 g, 316.96 mmol) in DCM (1500 mL) was added SOCl₂ (330 mL, 4436 mmol) at 0° C. The reaction was warmed to ambient temperature and stirred for 5 h. The reaction mixture was concentrated, the residue was washed with DCM (2×500 mL), followed by Et₂O (2×200 mL) to obtain (BB7) (50 g, 95%) as an off-white solid. $R_f$: 0.4 (EtOAc). ¹H NMR (400 MHz, DMSO-d₆): δ 7.76 (1H, app d), 7.70 (1H, app d), 5.17 (2H, s), 3.87 (3H, s); ink 131 (MH)⁺.

Synthesis of Methyl-4-((1-methyl-1H-imidazol-2-yl)methoxy)benzoate (BB8)

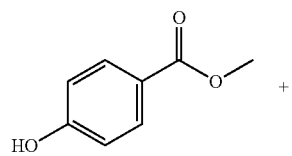

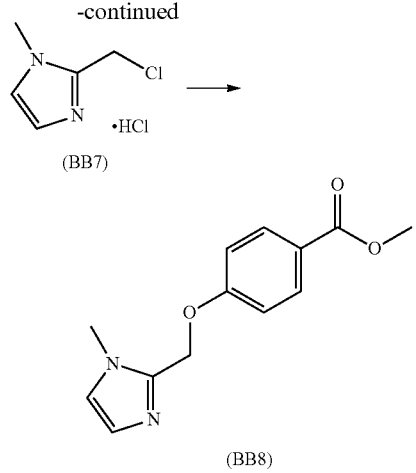

A suspension of 4-hydroxy benzoic acid methyl ester (18 g, 118.42 mmol) and powdered anhydrous K₂CO₃ (40.85 g, 296 mmol) in dry DMF (150 mL) was heated to 100° C. To the stirred reaction mixture was added (BB7) (25.5 g, 153.6 mmol) in six portions. The reaction mixture was stirred for 6 h and then cooled to room temperature and filtered. The filtrate was dissolved in H₂O (200 mL), extracted with EtOAc (2×250 mL), the combined organics were washed with brine solution (3×100 mL), dried over Na₂SO₄, concentrated in vacuo. The resulting crude compound was purified by column chromatography (100-200 mesh silica gel, eluted with 2% MeOH—CHCl₃) to provide (BB8) (17.1 g, 52%) as an off-white solid. $R_f$: 0.2 (50% EtOAc/pet. ether). ¹H NMR (400 MHz, CDCl₃): δ 8.0 (2H, d, J=8.8 Hz), 7.33 (2H, d, J=8.8 Hz), 7.02 (1H, app d), 6.91 (1H, app d), 5.22 (2H, s), 3.88 (3H, s), 3.73 (3H, s); m/z 247 (MH)⁺.

Synthesis of 4-(1-Methyl-1H-imidazol-2-yl)methoxybenzoic Acid Hydrochloride (BB9)

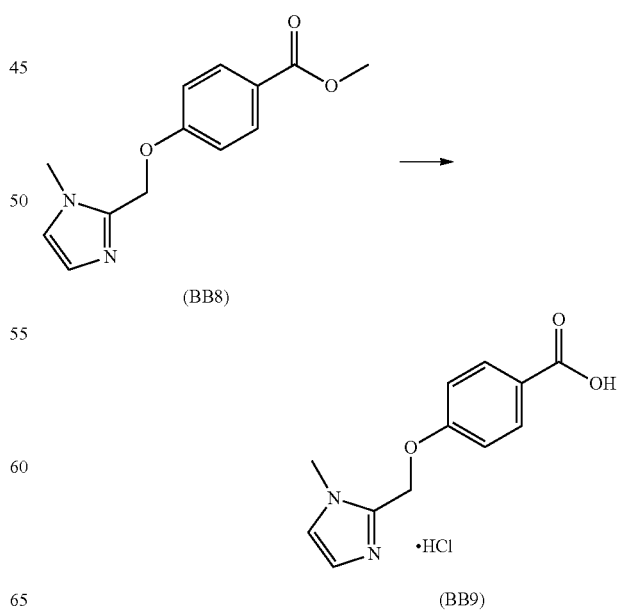

To a solution of (BB8) (24.1 g, 97.96 mmol) in MeOH (180 mL) was added aq. 5 N NaOH (70 mL) solution at room temperature. The reaction mixture was stirred at room temperature for 8 h and concentrated in vacuo. The residue was dissolved in H$_2$O (100 mL) and washed with Et$_2$O (2×100 mL), the aqueous layer was cooled in an ice bath and acidified with 6 N aq. HCl (pH ~6). The precipitated solid was collected by filtration and washed with pet ether (200 mL) and dried to provide (BB9) (20.7 g, 76%) as a white solid. R$_f$: 0.6 (5% MeOH/CHCl$_3$). $^1$H NMR (400 MHz, DMSO-d$_6$): δ 7.92 (2H, d, J=8.8 Hz), 7.42 (1H, s), 7.21-7.19 (3H, m), 5.36 (2H, s), 3.76 (3H, s); m/z 233 (MH)$^+$.

Synthesis of Methyl-3-(1-methyl-1H-imidazol-2-yl) methoxy Benzoate (BB10)

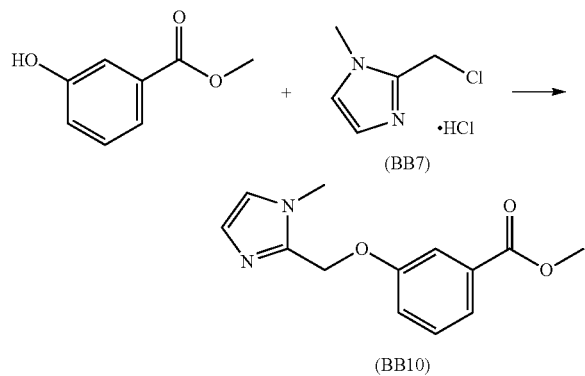

A suspension of 3-hydroxy benzoic acid methyl ester (18 g, 118.42 mmol) and powdered anhydrous K$_2$CO$_3$ (40.85 g, 296 mmol) in dry DMF (150 mL) was heated to 100° C. To the reaction mixture was added (BB7) (25.5 g, 153.6 mmol) in six portions. The reaction mixture was stirred for 6 h and then was cooled to room temperature and filtered. The filtrate was dissolved in H$_2$O (200 mL), extracted with EtOAc (2×250 mL), and the combined organics were washed with brine (3×100 mL), dried (Na$_2$SO$_4$) and concentrated in vacuo. The resulting crude compound was purified by column chromatography (100-200 mesh silica gel, 2% MeOH—CHCl$_3$) to provide (BB10) (15.3 g, 52%) as an off-white solid. R$_f$: 0.2 (50% EtOAc/pet. ether). $^1$H NMR (400 MHz, CDCl$_3$): δ 7.67-7.55 (2H, m), 7.36 (1H, t, J=7.6 Hz), 7.25 (1H, app d), 7.02 (1H, app d), 6.91 (1H, app d), 5.19 (2H, s), 3.92 (3H, s), 3.74 (3H, s); m/z 247 (MH$^+$).

Synthesis of Methyl-3-(1-methyl-1H-imidazol-2-yl) methoxy Benzoic Acid Hydrochloride (BB11)

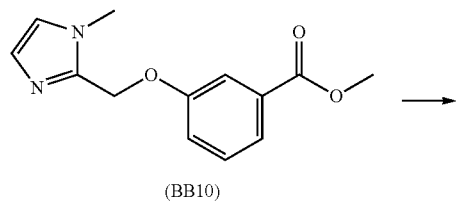

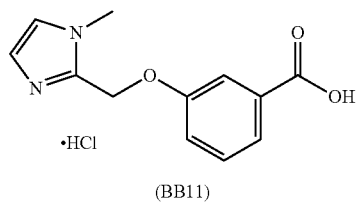

To a solution of (BB10) (15.1 g, 61.38 mmol) in MeOH (150 mL) was added 5 N aq. NaOH (40 mL) solution at room temperature. The reaction mixture was stirred at room temperature for 5 h and concentrated in vacuo. The residue was dissolved in H$_2$O (150 mL) and washed with Et$_2$O (2×100 mL), the aqueous layer was cooled in an ice bath and acidified with 6 N aq. HCl (pH ~6). The precipitated solid was collected by filtration, washed with chilled H$_2$O (50 mL) and pet. ether (200 mL) and dried to provide (BB11) (7.8 g, 46%) as an off-white solid. R$_f$: 0.6 (15% MeOH/CHCl$_3$). $^1$H NMR (400 MHz, DMSO-d$_6$): δ 7.65-7.56 (2H, m), 7.43 (1H, t, J=8 Hz), 7.35-7.30 (1H, m), 7.26-7.20 (m, 1H), 6.92-6.90 (m, 1H), 5.21 (2H, s), 3.7 (3H, s); m/z 233 (MH$^+$).

Synthesis of Pyrimidine-4-carboxylic Acid (BB12)

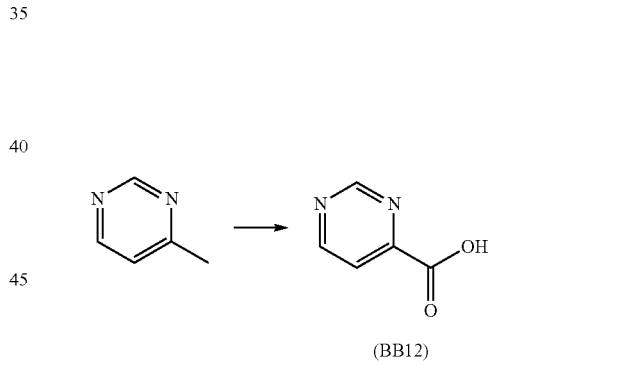

To a solution of 4-methylpyrimidine (4 g, 46.5 mmol) in pyridine (20 mL) was added SeO$_2$ (8.7 g, 79.06 mmol) at room temperature. The reaction mixture was then heated to 60° C. for 2 h, and then stirred at room temperature for 16 h. The reaction mixture was diluted with DCM (50 mL) and filtered to remove selenium waste. The filtrate was concentrated to give a residue that was stirred with H$_2$O (20 mL), the precipitated solid was filtered and washed with acetone (2×20 mL) and dried to provide (BB12) (3.1 g, 58%) as a brown solid. R$_f$: 0.2 (40% MeOH/CHCl$_3$). $^1$H NMR (400 MHz, DMSO-d$_6$): δ 13.8 (1H, br s), 9.37 (1H, s), 9.07 (1H, d, J=5.2 Hz), 8.01 (1H, d, J=4 Hz); m/z 123 (M−H)$^-$.

Synthesis of (S)-2-(tert-butoxycarbonylamino)-3-methyl-3-phenylbutanoic acid (BB17)

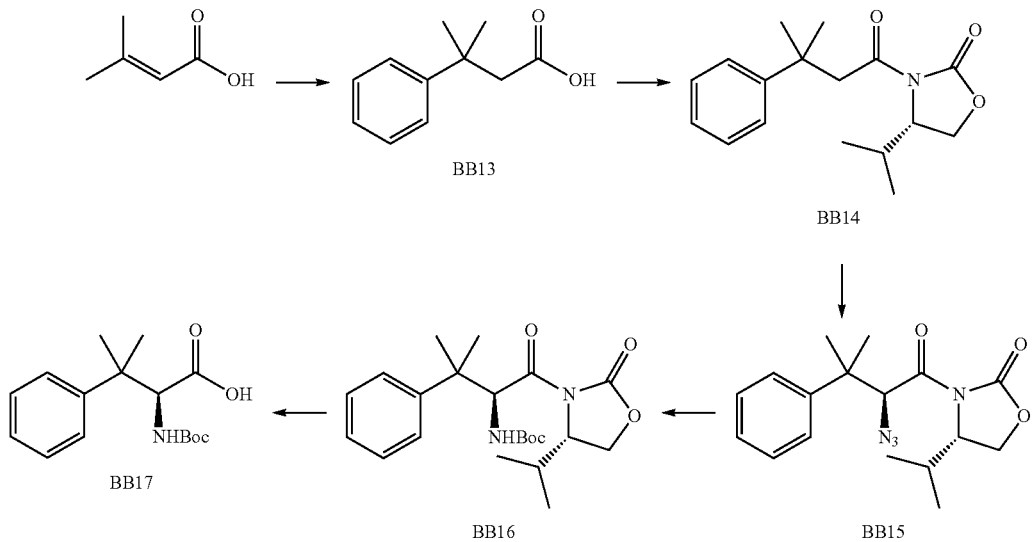

BB17 was synthesised in accordance with the procedures outlined in patent application US 2009/0264487 A1.

Synthesis of (BB19):

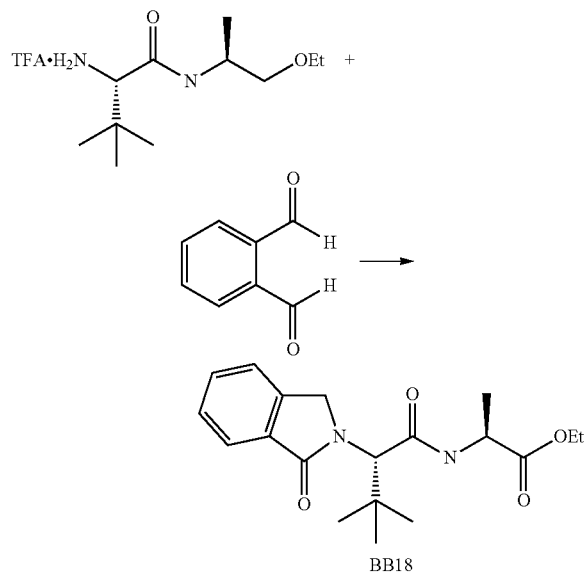

Synthesis of (BB18)

Dipeptide $NH_2$-Tle-Ala-OEt (1.5 g, 1 equiv.) was suspended in MeCN (30 mL). To the stirred suspension was added phthaldialdehyde (584 mg, 1 equiv.) and acetic acid (25 mL, 0.1 equiv.). The reaction mixture was stirred at ambient temperature for 3.5 h. The reaction was concentrated in vacuo and the crude residue was dissolved in EtOAc (50 mL). The organic phase was washed with (aq) HCl (2M, 3×20 mL), sat. aq. $NaHCO_3$ (2×20 mL) and brine (20 mL), dried ($MgSO_4$). The resulting crude material was purified by column chromatography (silica gel, 0-40% EtOAc/iso-hexane) to afford the desired compound (BB18) (1.18 g, 78%) as a cream solid. LC-MS purity 95%; m/z 347 $[MH]^+$.

Synthesis of (BB19)

To a stirred solution of (BB18) (1.18 g, 1 equiv.) in THF/$H_2O$ (1:1; 20 mL) was added $LiOH.H_2O$ (173 mg, 1.2 equiv.) and the reaction mixture was stirred at ambient temperature for 5.5 h. The THF was removed in vacuo and the aqueous phase was washed with EtOAc (5 mL) and acidified to pH 4-5 (2M HCl, ~1-2 mL). The aqueous phase was extracted with EtOAc (3×20 mL), dried ($Na_2SO_4$) and concentrated in vacuo to afford the desired compound (BB19) (669 mg, 62%) as a cream foam. LC-MS purity 98.8%; m/z 319 $[MH]^+$.

Synthesis of (BB20)

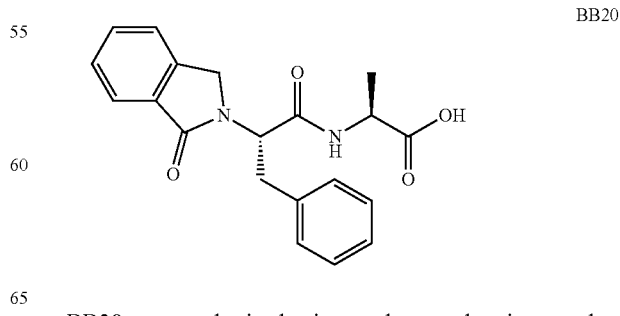

BB20 was synthesised using analagous chemistry to that described above for BB19.

Intermediate Hydrolysis Step in the Synthesis of PVA-081:

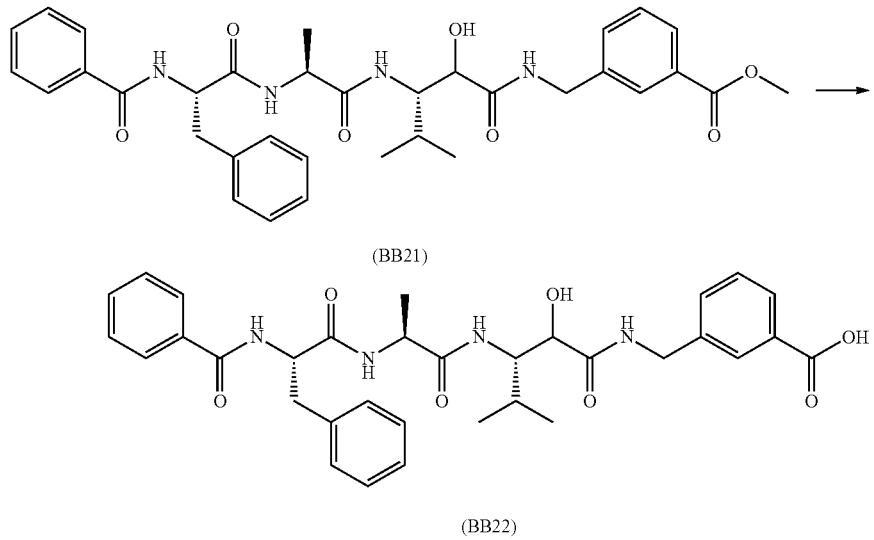

LiOH (20 mg) was added to a stirred solution of ester (BB21) (130 mg) in THF/H$_2$O (3:1, 8 mL). The reaction mixture was heated to reflux overnight and then allowed to cool to room temperature. The reaction mixture was concentrated under reduced pressure to approximately 1 mL. The pH was adjusted to 2-3 by addition of HCl (1.0 M aqueous). The resulting precipitate was filtered and washed with H$_2$O (10 mL) and diethyl ether (5 mL) and then dried in a vacuum oven at 50° C. to yield (BB22) (90 mg, 71%) as a white solid. LC-MS, R$_t$=2.81 min (AnalpH2_MeOH), m/z 603 (MH$^+$).

Isocyanide Synthesis—General Procedure:

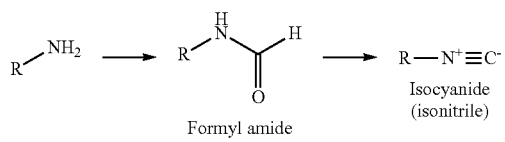

Synthesis of Formyl Amides:
A typical procedure involves:
To a solution of the amine (1 g, 1 equiv.) at 0° C. was added ethyl formate (1.2 equiv.) after which the reaction was stirred at 0° C. for 2 h. DCM (5 mL) was added and the reaction stirred for 30 min at room temperature after which time the crude reaction was triturated with iso-hexane to afford the desired compound.

Synthesis of Isocyanides:
To a solution of formyl amide (100 mg, 0.58 mmol, 1 equiv.) in DCM (5 mL) was added PS-tosyl chloride (3 equiv.) and pyridine (1.5 mL) after which time the reaction was stirred at room temperature for 20 min before removal of the PS-tosyl chloride by filtration. The organic layer was washed with (aq.) 2 M KHSO$_4$ (3×30 ml), dried over MgSO$_4$, filtered and the solvent removed in vacuo to afford the desired isocyanide which was used 'as is' without further purification.

Biological Methods—Enzyme Assays

Many of the compounds contain a centre which is sufficiently basic, and were purified in such a way, that it is likely that they were obtained as the corresponding trifluoroacetic acid (TFA) salt. Consequently, in the biological studies described herein, it is believed that the following compounds were studied in the form of the corresponding TFA salt: PVA-007, PVA-018, PVA-020, PVA-022, PVA-023, PVA-024, PVA-025, PVA-035, PVA-036, PVA-038, PVA-039, PVA-040, PVA-043, PVA-047, PVA-048, PVA-049, PVA-055, PVA-059, PVA-060, PVA-061, PVA-062, PVA-063, PVA-064, PVA-065, PVA-069, PVA-070, PVA-071, PVA-072, PVA-073, PVA-074, PVA-083, PVA-086, PVA-089, PVA-092, PVA-093, PVA-099, PVA-105, PVA-119, PVA-120, PVA-124, PVA-125, PVA-127, PVA-128, PVA-130, PVA-131, PVA-136, PVA-137, PVA-138, PVA-140, PVA-145, PVA-146, PVA-147, PVA-150, PVA-159, PVA-160, PVA-172, PVA-173, PVA-174, PVA-175, PVA-176, PVA-185, PVA-186, PVA-187, PVA-188, PVA-195, PVA-210, PVA-211, PVA-216.

Many of the compounds contain a centre which is sufficiently basic, and were purified in such a way, that it is likely that they were obtained as the corresponding formic acid salt. Consequently, in the biological studies described herein, it is believed that the following compounds were studied in the form of the corresponding formic acid salt: PVA-098.

Several of the compounds contain a quaternary ammonium group, and were purified in such a way that they were obtained with either a trifluoroacetate counter-ion or a formate counter-ion. Consequently, in the biological studies described herein, it is believed that the following compounds were studied in the form of the corresponding salt with trifluoroacetate counter-ion: PVA-153, PVA-154. Similarly, in the biological studies described herein, it is believed that the following compounds were studied in the form of the corresponding salt with formate counter-ion: PVA-096.

Assay for Der p 1
Der p 1 Purification:
House dust mites of the species *Dermatophagoides* pteronyssinus were cultured as described (see Zhang et al., 2007). Der p 1 was purified chromatographically and its identity confirmed by SDS-PAGE and MALDI-TOF mass spectrometry (see Zhang et al., 2007). Its concentration in solution was determined in a quartz cuvette by absorbance at 280 nm using an extinction coefficient of 47,705 M$^{-1}$ cm$^{-1}$.

Der p 1 Enzyme Activity Assay:

The fluorogenic substrate used for measuring Der p 1 proteolytic activity was 2-aminobenzoylvalylalanylnorleucylseryl-(3-nitro)tyrosinyl aspartamide. This compound is internally quenched by fluorescence resonance energy transfer (FRET), but upon cleavage its emission at 420 nm increases when the substrate is excited at 330 nm (see Zhang et al., 2007).

Test compounds were dissolved in dry DMSO and maintained at 4° C. as stock solutions until being diluted for use in screening assays. Final concentration of DMSO in all enzymatic assays was 0.5% v/v.

Reaction mixtures were assembled in a 96-well plate format (Perkin Elmer Optiplate 96F, Perkin Elmer LAS, Seer Green, Buckinghamshire, UK) using a Perkin Elmer Multi-PROBE II Plus HTS EX robot with Gripper attachment. Plates were pre-formatted with serial dilutions (10 µL/well) of test compound or appropriate control in reaction buffer (composition: potassium phosphate buffer pH 8.25 containing 1 mM EDTA), to which a further 60 µL of reaction buffer was added. Dithiothreitol (DTT, 10 µL/well, 1 mM final concentration) was then added together with 10 µL of Der p 1 dissolved at 2.5 µg/mL in reaction buffer supplemented with 1 mM DTT. Reaction mixtures were then incubated at room temperature for 20 minutes before initiating the reaction by the addition of 10 µL of substrate (12.5 µM final concentration). The plate was immediately transferred to a fluorescence plate reader (Perkin Elmer Fusion Alpha-FP or Perkin Elmer Envision) equipped with a temperature-controlled carrier set at 30° C. and the reaction followed by excitation/emission at 330/420 nm.

Enzyme Assay Data Analysis

Inhibitory activity was analysed from progress curves of reactions in the presence of a range of inhibitor concentrations. Initial reaction velocities were calculated by computational non-linear regression and the degree of inhibition produced by compounds determined, from which the concentration required to inhibit the reaction by 50% ($IC_{50}$) was calculated according to the scheme below:

Initial velocity in each well was converted to fractional activity by Equation 1:

Fractional activity=(Initial rate at inhibitor concentration[$X$]/Initial rate at inhibitor concentration zero)*100   Equation 1:

Then, $IC_{50}$ was determined by fitting the data of fractional activity and inhibitor concentration to a 4-parameter logistic curve, using Equation 2:

$V=V_{min}+[V_{max}-V_{min}]/[1+(X/IC_{50})\text{Hillslope}]$   Equation 2:

where:
V is the fractional activity of the enzyme in the presence of inhibitor at concentration [X];
[X] is the inhibitor concentration;
$V_{min}$ is the minimum of Y observed at high inhibitor concentration;
$V_{max}$ is the maximum of Y observed at zero inhibitor concentration; and
Hillslope is the slope of the dose-response (inhibition) curve.

Biological Data—Der p 1 Enzyme Assay

The following compounds were studied using the Der p 1 assay described above: PVA-001 to PVA-216.

All of the compounds were found to have a Der p 1 $IC_{50}$ of less than 10 µM.

The following compounds were found to have a Der p 1 $IC_{50}$ of less than 2 µM:

PVA-001, PVA-002, PVA-003, PVA-004, PVA-005, PVA-006, PVA-007, PVA-009, PVA-010, PVA-011, PVA-012, PVA-015, PVA-016, PVA-017, PVA-018, PVA-019, PVA-020, PVA-021, PVA-022, PVA-023, PVA-024, PVA-025, PVA-026, PVA-027, PVA-028, PVA-029, PVA-030, PVA-031, PVA-032, PVA-033, PVA-034, PVA-035, PVA-036, PVA-037, PVA-038, PVA-039, PVA-040, PVA-041, PVA-042, PVA-043, PVA-044, PVA-045, PVA-046, PVA-047, PVA-048, PVA-049, PVA-050, PVA-051, PVA-052, PVA-053, PVA-054, PVA-055, PVA-056, PVA-057, PVA-058, PVA-059, PVA-060, PVA-061, PVA-062, PVA-063, PVA-064, PVA-065, PVA-066, PVA-067, PVA-068, PVA-069, PVA-070, PVA-071, PVA-072, PVA-073, PVA-074, PVA-075, PVA-076, PVA-077, PVA-078, PVA-079, PVA-080, PVA-081, PVA-082, PVA-083, PVA-084, PVA-085, PVA-086, PVA-088, PVA-089, PVA-090, PVA-091, PVA-092, PVA-093, PVA-094, PVA-095, PVA-096, PVA-097, PVA-098, PVA-099, PVA-100, PVA-101, PVA-102, PVA-103, PVA-104, PVA-105, PVA-106, PVA-107, PVA-108, PVA-109, PVA-110, PVA-111, PVA-112, PVA-113, PVA-114, PVA-115, PVA-116, PVA-117, PVA-118, PVA-119, PVA-120, PVA-121, PVA-122, PVA-123, PVA-124, PVA-125, PVA-126, PVA-127, PVA-128, PVA-129, PVA-130, PVA-131, PVA-132, PVA-133, PVA-134, PVA-135, PVA-136, PVA-137, PVA-138, PVA-140, PVA-141, PVA-142, PVA-143, PVA-144, PVA-145, PVA-146, PVA-147, PVA-148, PVA-149, PVA-150, PVA-151, PVA-152, PVA-153, PVA-154, PVA-155, PVA-156, PVA-157, PVA-158, PVA-159, PVA-160, PVA-161, PVA-162, PVA-163, PVA-164, PVA-165, PVA-166, PVA-167, PVA-168, PVA-169, PVA-170, PVA-171, PVA-172, PVA-173, PVA-174, PVA-175, PVA-176, PVA-177, PVA-178, PVA-179, PVA-180, PVA-181, PVA-182, PVA-183, PVA-184, PVA-185, PVA-186, PVA-187, PVA-188, PVA-189, PVA-190, PVA-191, PVA-192, PVA-193, PVA-194, PVA-195, PVA-196, PVA-197, PVA-198, PVA-199, PVA-200, PVA-201, PVA-202, PVA-203, PVA-204, PVA-205, PVA-206, PVA-207, PVA-208, PVA-209, PVA-210, PVA-211, PVA-212, PVA-213, PVA-214, PVA-215, PVA-216.

The following compounds were found to have a Der p 1 $IC_{50}$ of less than 200 nM:

PVA-001, PVA-002, PVA-003, PVA-004, PVA-005, PVA-009, PVA-010, PVA-011, PVA-015, PVA-017, PVA-019, PVA-020, PVA-022, PVA-023, PVA-024, PVA-026, PVA-027, PVA-028, PVA-030, PVA-031, PVA-032, PVA-033, PVA-035, PVA-036, PVA-037, PVA-038, PVA-039, PVA-041, PVA-042, PVA-044, PVA-045, PVA-046, PVA-047, PVA-048, PVA-049, PVA-050, PVA-051, PVA-052, PVA-053, PVA-054, PVA-055, PVA-056, PVA-057, PVA-058, PVA-059, PVA-060, PVA-061, PVA-062, PVA-063, PVA-064, PVA-065, PVA-066, PVA-067, PVA-068, PVA-071, PVA-072, PVA-073, PVA-074, PVA-075, PVA-076, PVA-077, PVA-078, PVA-079, PVA-080, PVA-081, PVA-082, PVA-083, PVA-084, PVA-085, PVA-086, PVA-088, PVA-089, PVA-091, PVA-092, PVA-093, PVA-094, PVA-095, PVA-096, PVA-097, PVA-098, PVA-099, PVA-100, PVA-101, PVA-102, PVA-103, PVA-104, PVA-105, PVA-106, PVA-107, PVA-108, PVA-109, PVA-110, PVA-111, PVA-112, PVA-113, PVA-114, PVA-115, PVA-116, PVA-117, PVA-118, PVA-119, PVA-120, PVA-121, PVA-122, PVA-123, PVA-124, PVA-125, PVA-126, PVA-127, PVA-128, PVA-129, PVA-130, PVA-131, PVA-132, PVA-133, PVA-134, PVA-135, PVA-136, PVA-137, PVA-138, PVA-141, PVA-142, PVA-143, PVA-144, PVA-145, PVA-146, PVA-147, PVA-148, PVA-149, PVA-150, PVA-151, PVA-152, PVA-153, PVA-154, PVA-155, PVA-156, PVA-157, PVA-158, PVA-159, PVA-160, PVA-161, PVA-162, PVA-163, PVA-164, PVA-165, PVA-166, PVA-167, PVA-168, PVA-169, PVA-170, PVA-171, PVA-172, PVA-173, PVA-174,

PVA-175, PVA-176, PVA-177, PVA-178, PVA-179, PVA-180, PVA-181, PVA-182, PVA-183, PVA-184, PVA-185, PVA-186, PVA-187, PVA-188, PVA-189, PVA-190, PVA-191, PVA-192, PVA-193, PVA-194, PVA-195, PVA-196, PVA-197, PVA-198, PVA-199, PVA-200, PVA-201, PVA-202, PVA-203, PVA-204, PVA-205, PVA-206, PVA-207, 196, PVA-197, PVA-199, PVA-202, PVA-204, PVA-205, PVA-206, PVA-207, PVA-208, PVA-209, PVA-210, PVA-211, PVA-212, PVA-213, PVA-214, PVA-215, PVA-216.

Data for four PVA compounds are shown in the following table.

TABLE 1

Der p 1 IC$_{50}$ Data for PVA Compounds

| Code | Compound | Der p 1 IC$_{50}$ (nM) |
|---|---|---|
| PVA-026 | | 14 |
| PVA-037 | | 7.85 |
| PVA-038 | | 13.3 |
| PVA-039 | | 6.3 |

PVA-208, PVA-209, PVA-210, PVA-211, PVA-212, PVA-213, PVA-214, PVA-215, PVA-216.

The following compounds were found to have a Der p 1 IC$_{50}$ of less than 20 nM:

PVA-001, PVA-003, PVA-005, PVA-009, PVA-026, PVA-035, PVA-037, PVA-038, PVA-039, PVA-042, PVA-047, PVA-055, PVA-066, PVA-067, PVA-068, PVA-071, PVA-072, PVA-073, PVA-074, PVA-078, PVA-079, PVA-080, PVA-092, PVA-093, PVA-094, PVA-096, PVA-097, PVA-099, PVA-104, PVA-105, PVA-108, PVA-111, PVA-112, PVA-116, PVA-118, PVA-128, PVA-129, PVA-130, PVA-132, PVA-134, PVA-135, PVA-136, PVA-137, PVA-143, PVA-144, PVA-146, PVA-147, PVA-149, PVA-150, PVA-151, PVA-153, PVA-154, PVA-155, PVA-156, PVA-157, PVA-158, PVA-161, PVA-162, PVA-164, PVA-169, PVA-177, PVA-178, PVA-182, PVA-183, PVA-185, PVA-186, PVA-187, PVA-188, PVA-192, PVA-194, PVA-195, PVA-

Biological Methods—Allergen Challenge Studies In Vivo
Animal Identification and Randomisation:

The studies were performed in male Brown Norway rats (approximate weight 350 g at time of allergen challenge) obtained from Harlan UK Ltd. Each animal was allocated a unique identification number after sensitisation, identified by a waterproof tail mark, and randomly assigned to a treatment group. All studies were conducted in accordance with the Animals (Scientific Procedures) Act 1986, with UK Home Office Guidance on the implementation of the Act and with all applicable Codes of Practice for the care and housing of laboratory animals.

Housing and Environment:

Animals were initially housed within an air-conditioned colony room within the animal house until being transferred to a procedure room. Animals were caged in groups of up to 5. During the study, the rooms and cages were cleaned at regular intervals to maintain hygiene. The rooms were illuminated by fluorescent lights set to give a 12 hour light-dark cycle (on 07.00, off 19.00), as recommended in the Home Office Animals (Scientific Procedures) Act 1986. Air temperature (target temperature 21° C.±2° C.) and relative humidity (which was not controlled) was measured during acclimatisation and the in-life phase. A diet of RM-1 (Special Diets Services, Witham, UK) and mains tap water was offered ad libitum.

Sensitization Procedure to House Dust Mite (HDM) Allergen:

A mixture of HDM allergens was harvested from a laboratory culture of Dermatophagoides pteronyssinus. Allergen dose was standardized according to the Der p 1 content of the mixture as determined by an ELISA measurement referenced against the IUIS standard for Der p 1. The allergen sensitization dose for each animal on each day contained 10 µg Der p 1. Freeze-dried stocks of HDM allergen mixture stored at −20° C. were reconstituted in their original volumes of 0.22 µm filter-sterilised de-ionised water containing 5 mM L-cysteine and 0.05% v/v Tween 20 and diluted to working concentration using sterile Dulbecco's phosphate buffered saline containing 5 mM L-cysteine and 0.05% v/v Tween 20. Animals were sensitized to a mixture of all HDM allergens on Days 0, 7, and 14 by intraperitoneal injection (0.5 mL) of the mixture formulated as described above.

Physiological Recordings:

On Day 21 of the sensitization and challenge protocol, rats were anaesthetised with pentobarbitone (100 mg/kg, i.p.) and ventilated via a tracheal cannula (approximately 7 mL/kg, 1 Hz) with a mixture of air and oxygen (50:50). The anaesthetised, ventilated animals were paralysed with norcuron (4 mg/kg, i.m.). Ventilation was monitored by a flow transducer (Fleisch, type 0000) in-line with the respiratory pump. Coincident pressure changes within the thorax were monitored directly via an intrathoracic cannula, so that the pressure difference between the trachea and thorax could be measured and displayed. From these measurements of flow and differential pressure, both airways resistance (RL) and dynamic compliance (Cdyn) were calculated for each respiratory cycle on a digital electronic respiratory analyser (PMS, Mumed Ltd, UK). Blood pressure and heart rate were recorded from the carotid artery by means of a transducer.

Drug Delivery and Allergen Challenge:

Drugs were dissolved in DMSO as 10 mM stock solutions and then diluted in sterile saline (Baxter Healthcare, Berkshire, UK) for use in treatment. Drug solutions (100 µL of a 40 µM solution) were administered by the intra-tracheal (i.t.) route using a Penn Century IA-1C sapphire orifice aerosoliser fitted to an FMJ-250 high pressure syringe (Penn Century, Philadelphia, Pa., USA). For these studies, the tip of the IA-1C aerosoliser was inserted inside the tracheal cannula and the volume of drug delivered regulated by means of volumetric stops on the syringe plunger. This combination of aerosoliser and syringe generates a plume of liquid with droplets 16-22 µm in mass median aerodynamic diameter.

Allergen challenge was with a mixture of HDM allergens containing a 10 µg dose of Der p 1. Freeze-dried stocks of HDM allergen mixture stored at −20° C. were reconstituted in their original volumes of 0.22 µm filter-sterilised deionised water containing 5 mM L-cysteine and 0.05% v/v Tween 20 and diluted to working concentration using sterile Dulbecco's phosphate buffered saline containing 5 mM L-cysteine and 0.05% v/v Tween 20. Allergen challenge (100 µL) was performed by the intratracheal (i.t.) route using a Penn Century aerosoliser as described above.

Study Design:

The study design comprised groups of 12 animals which had been actively sensitized to HDM allergens as described above. On day 21 of the study, the groups received two separate challenges with HDM allergens by the intratracheal (i.t.) route. In all cases, the effect of challenge 1 had fully resolved before the second challenge was made. At an interval of 2 hours before the second allergen challenge, animals received a dose of test compounds.

Data Analysis:

To evaluate the effect of allergen challenge and its modification by test compounds, lung function parameters were measured prior to allergen delivery (baseline) and at the peak response. The numerical difference in the lung function parameter (e.g., change in airway resistance) was recorded as the magnitude of the allergen challenge. This process was repeated after the animals had been dosed with test compound. Statistical analysis of the responses before and after administration of the test compound was used to determine if the compound exerted a significant effect. It was found by experiment to be equally valid to conduct these statistical comparisons either by comparing the change in the lung function parameter per se before and after treatment with test compound, or by expressing the magnitude of the second allergen challenge as a percentage of the first challenge and performing the statistical evaluation using the transformed data.

Biological Data—Allergen Challenge Studies In Vivo

Validation of Study Design

FIG. 1 is a bar graph of the magnitude of response following Challenge 1 (left) and Challenge 2 (right), expressed as a percentage of the magnitude of the response following Challenge 1.

FIG. 1 illustrates the results obtained when a group of rats sensitized to HDM allergens were subjected to two successive challenges with the same allergen mixture by the intratracheal (i.t.) route on Day 21 after sensitization was commenced. The average median response for challenge 1 was determined and defined as 100%. In each rat, the magnitude of the second response was then determined and expressed as the percentage of the response to challenge 1. For the purposes of illustration of the second challenge response, the data are shown as the median and interquartile range determined in 12 animals.

These data indicate that the magnitude of the second challenge is similar to that seen in the first challenge, enabling the modulating effect of a drug administered between the two treatments to be determined.

Effects of Compounds on Acute Allergic Bronchoconstriction:

Two compounds (PVA-026 and PVA-038) were studied using in vivo allergen challenge methods described above. (PVA-038 was used in the form of the corresponding trifluoroacetic acid (TFA) salt.)

| Code | Structure |
|---|---|
| PVA-026 | 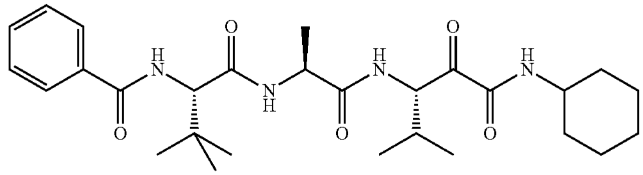 [SMILES: CC(C)[C@H](NC(=O)[C@H](C)NC(=O)[C@@H](NC(=O)c1ccccc1)C(C)(C)C)C(=O)C(=O)NC1CCCCC1] |
| PVA-038 | 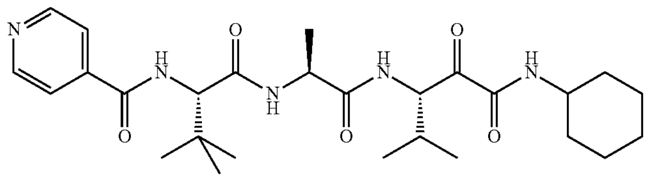 |

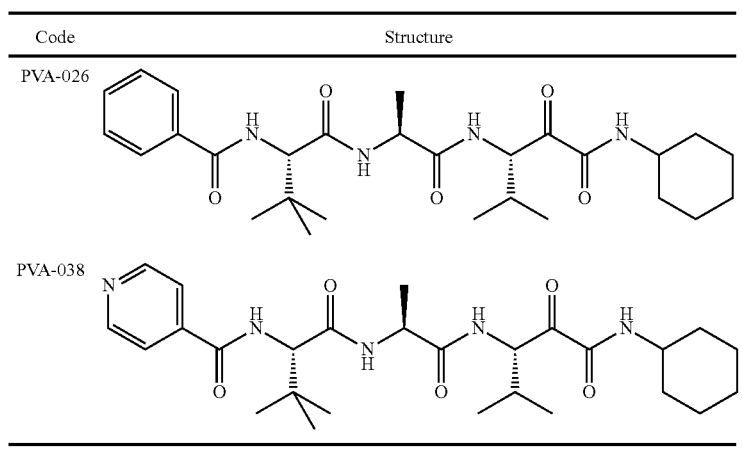

Figure 2:
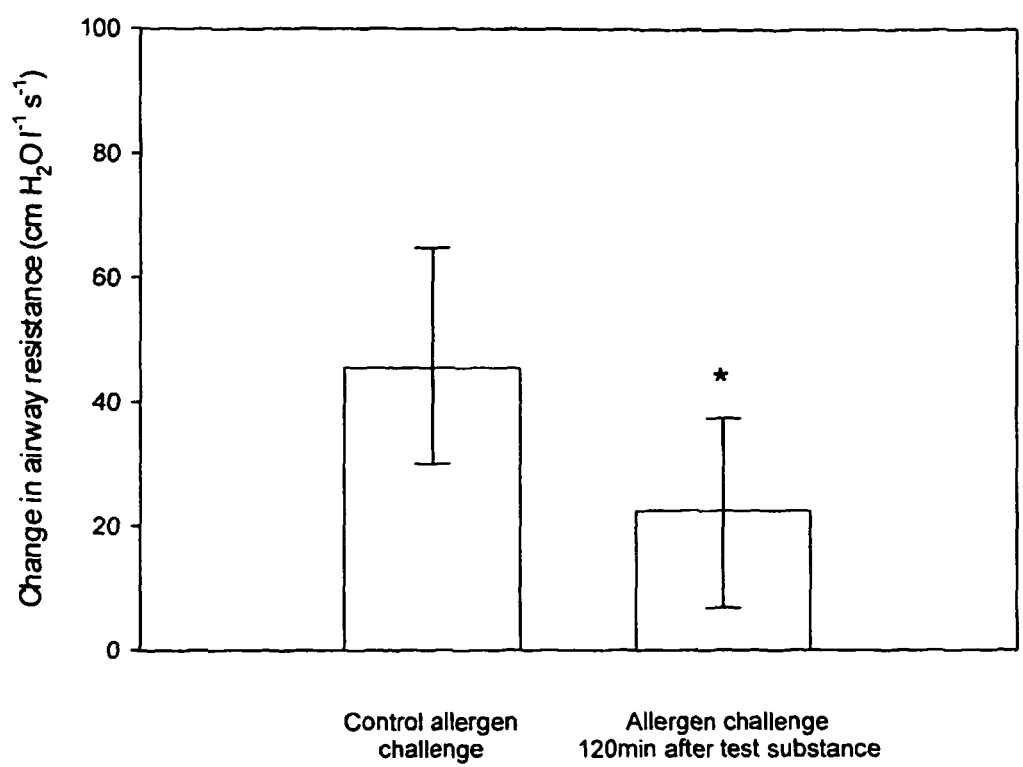
FIG. 2 is a bar graph of change in airway resistance (cm $H_2O$ $L^{-1}$ $s^{-1}$) following control allergen challenge (left) and allergen challenge 120 minutes after treatment with test compound PVA-026. (Medians reported. Error bar is for 25th/75th percentiles. For (*): $P<0.05$, Mann-Whitney Rank Sum Test, with respect to control allergen challenge.)

FIG. 2 is a bar graph of change in airway resistance (cm $H_2O$ $L^{-1}$ $s^{-1}$) following control allergen challenge (left) and allergen challenge 120 minutes after treatment with test compound PVA-026. (Medians reported. Errors are for 25th/75th percentiles. For (*): P<0.05, Mann-Whitney Rank Sum Test, with respect to control allergen challenge.)

The data in FIG. 2 illustrate the change in airway resistance in a control allergen challenge and that seen in a successive challenge made 2 hours after the animals were dosed intratracheally (i.t.) with test compound PVA-026. Data are presented as median responses with error bars indicating the interquartile range. The magnitude of the second allergen challenge was significantly reduced compared to the first challenge (P<0.05, Mann-Whitney Rank Sum Test). It is known to those of skill in the art that inhibition of acute bronchoconstriction following allergen provocation in experimental models such as this is indicative of a clinically beneficial effect in asthma.

Figure 3:
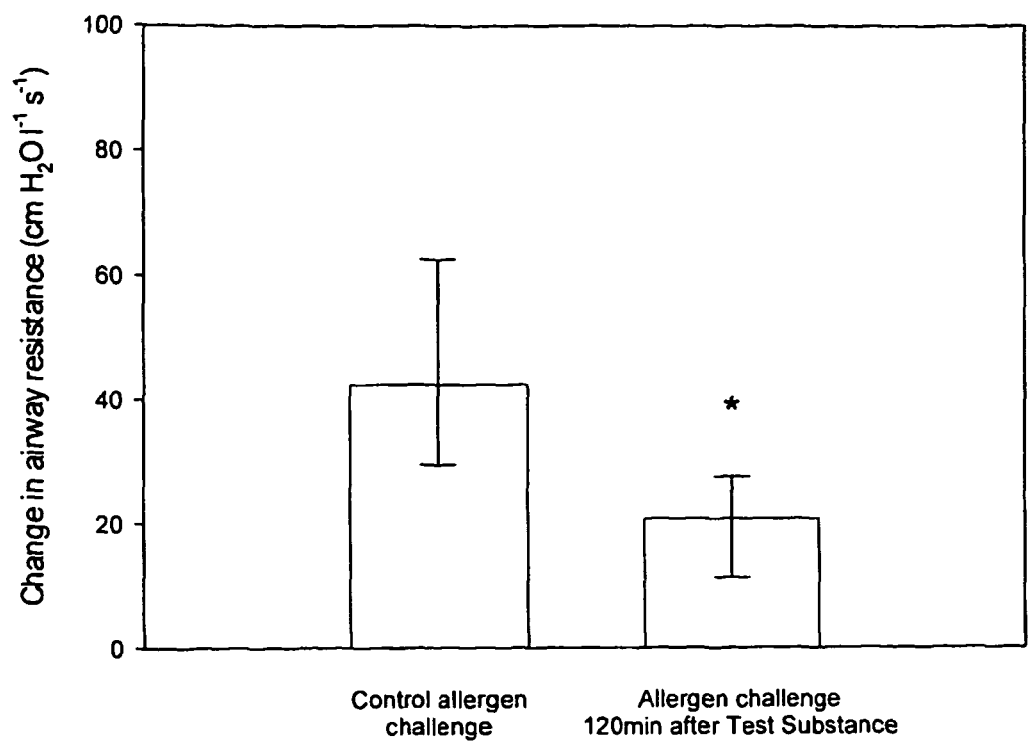
FIG. 3 is a bar graph of change in airway resistance (cm $H_2O$ $L^{-1}$ $s^{-1}$) following control allergen challenge (left) and allergen challenge 120 minutes after treatment with test compound PVA-038 (as the TFA salt). (Medians reported. Error bar is for 25th/75th percentiles. For (*): $P<0.05$, Mann-Whitney Rank Sum Test, with respect to control allergen challenge.)

FIG. 3 is a bar graph of change in airway resistance (cm $H_2O$ $L^{-1}$ $s^{-1}$) following control allergen challenge (left) and allergen challenge 120 minutes after treatment with test compound PVA-038 (as the TFA salt). (Medians reported. Errors are for 25th/75th percentiles. For (*): P<0.05, Mann-Whitney Rank Sum Test, with respect to control allergen challenge.)

The data in FIG. 3 illustrate the change in airway resistance in a control allergen challenge and that seen in a successive challenge made 2 hours after the animals were dosed intratracheally (i.t.) with test compound PVA-038 (as the TFA salt). Data are presented as median responses with error bars depicting the interquartile range. The magnitude of the second allergen challenge was significantly reduced compared to the first challenge (P<0.05, Mann-Whitney Rank Sum Test). It is known to those of skill in the art that inhibition of acute bronchoconstriction following allergen provocation in experimental models such as this is indicative of a clinically beneficial effect in asthma.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Arasappan et al., 2009, "Toward second generation hepatitis C virus NS3 serine protease inhibitors: Discovery of novel P4 modified analogues with improved potency and pharmacokinetic profile", *J. Med. Chem.*, pp. 2806-2897.

Arruda et al., 1991, "Exposure and sensitization to dust mite allergens among asthmatic children in Sao Paulo, Brazil", *Clin. Exp. Allergy*, Vol. 21, pp. 433-439.

Asokananthan et al., 2002, "House dust mite allergens induce proinflammatory cytokines from respiratory epithelial cells: the cysteine protease allergen, Der p 1, activates protease-activated receptor (PAR)-2 and inactivates PAR-1", *J. Immunol.*, Vol. 169, pp. 4572-4578.

Barrett et al., 2005, "P2-P3 conformationally constrained ketoamide-based inhibitors of cathepsin K", *Biorg. Med. Chem. Lett.*, Vol. 15, pp. 3540-3546.

Bodini et al., 2004, "Exhaled breath condensate eicosanoids and sputum eosinophils in asthmatic children: a pilot study", *Pediatr. Allergy Immunol.*, Vol. 15, pp. 26-31.

Bosch et al., 2009, "Dry powder aerosols of nanoparticulate drugs", U.S. Pat. No. 7,521,068, granted 21 Apr. 2009.

Broide et al., 1992, "Cytokines in symptomatic asthma airways", *J. Allergy Clin. Immunol.*, Vol. 89, pp. 958-967.

Charpin et al., 1991, "Altitude and allergy to house-dust mites. A paradigm of the influence of environmental exposure on allergic sensitization", *Am. Rev. Respir. Dis.*, Vol. 143, pp. 983-986.

Comoy et al., 1998, "The house dust mite allergen, *Dermatophagoides pteronyssinus*, promotes type 2 responses by modulating the balance between IL-4 and IFN-gamma", *J. Immunol.*, Vol. 160, pp. 2456-2462.

Deb et al., 2007, "Major house dust mite allergens *Dermatophagoides pteronyssinus* 1 and *Dermatophagoides farinae* 1 degrade and inactivate lung surfactant proteins A and D", *J. Biol. Chem.*, Vol. 282, pp. 36808-36819.

Dowse et al., 1985, "The association between *Dermatophagoides* mites and the increasing prevalence of asthma in village communities within the Papua New Guinea highlands", *J. Allergy Clin. Immunol.*, Vol. 75, pp. 75-83.

Eden et al., 2003, "Asthma features in severe alpha1-antitrypsin deficiency: experience of the National Heart, Lung, and Blood Institute Registry", *Chest*, Vol. 123, pp. 765-771.

Fahy et al., 1995, "Comparison of samples collected by sputum induction and bronchoscopy from asthmatic and healthy subjects", *Am. J. Respir. Crit. Care Med.*, Vol. 152, pp. 53-58.

Gelber et al., 1993, "Sensitization and exposure to indoor allergens as risk factors for asthma among patients presenting to hospital", *Am. Rev. Respir. Dis.*, Vol. 147, pp. 573-578.

Ghaemmaghami et al., 2002, "The proteolytic activity of the major dust mite allergen Der p 1 conditions dendritic cells to produce less interleukin-12: allergen-induced Th2 bias determined at the dendritic cell level", *Clin. Exp. Allergy*, Vol. 32, pp. 1468-1475.

Gough et al., 2001. "The proteolytic activity of the major dust mite allergen Der p 1 enhances the IgE antibody response to a bystander antigen", *Clin. Exp. Allergy*, Vol. 31, pp. 1594 1598.

Gourgoulianis et al., 2001, "The influence of altitude in bronchial asthma", *Arch. Med. Res.*, Vol. 32, pp. 429-431.

Grootendorst et al., 2001, "Benefits of high altitude allergen avoidance in atopic adolescents with moderate to severe asthma, over and above treatment with high dose inhaled steroids", *Clin. Exp. Allergy*, Vol. 31, pp. 400-408.

Hellings et al., 2001, "Eosinophilic rhinitis accompanies the development of lower airway inflammation and hyper-reactivity in sensitized mice exposed to aerosolized allergen", *Clin. Exp. Allergy*, Vol. 31, pp. 782-790.

Holt et al., 1990, "A contiguous network of dendritic antigen-presenting cells within the respiratory epithelium", *Int. Arch. Allergy Appl. Immunol.*, Vol. 91, pp. 155-159.

Holt, 2002, "The role of airway dendritic cell populations in regulation of T-cell responses to inhaled antigens: atopic asthma as a paradigm", *J. Aerosol Med.*, Vol. 15, pp. 161-168.

Huh et al., 2003, "Bidirectional interactions between antigen-bearing respiratory tract dendritic cells (DCs) and T cells precede the late phase reaction in experimental asthma: DC activation occurs in the airway mucosa but not in the lung parenchyma", *J. Exp. Med.*, Vol. 198, pp. 19-30.

Hyde et al., 1979, "Protease inhibitor variants in children and young adults with chronic asthma", *Ann. Allergy*, Vol. 43, pp. 8-13.

Jaakkola et al., 2006, "Are atopy and specific IgE to mites and molds important for adult asthma?", *J. Allergy Clin. Immunol.*, Vol. 117, pp. 642-648.

Marcaccini et al., "2. Post Condensation Modifications of the Passerini and Ugi Reactions", in *Multicomponent Reactions,* 1st Edition (Ed., Jieping et al., Wiley-VCH, 2005), Chapter 2, pp. 33-75, and especially pp. 41-47.

Kalsheker et al., 1996, "The house dust mite allergen Der p1 catalytically inactivates alpha 1-antitrypsin by specific reactive centre loop cleavage: a mechanism that promotes airway inflammation and asthma", *Biochem. Biophys. Res. Commun.*, Vol. 221, pp. 59-61.

King et al., 1998, "Dust mite proteolytic allergens induce cytokine release from cultured airway epithelium", *J. Immunol.*, Vol. 161, pp. 3645-3651.

Lambrecht et al., 2002, "Myeloid dendritic cells make it to the top", *Clin. Exp. Allergy*, Vol. 32, pp. 805-810.

Lambrecht et al., 2003a, "Taking our breath away: dendritic cells in the pathogenesis of asthma", *Nat. Rev. Immunol.*, Vol. 3, pp. 994-1003.

Lambrecht et al., 2003b, "The other cells in asthma: dendritic cell and epithelial cell crosstalk", *Current Opinion in Pulmonary Medicine*, Vol. 9, pp. 34-41.

McCusker et al., 2002, "Site-specific sensitization in a murine model of allergic rhinitis: role of the upper airway in lower airways disease", *J. Allergy Clin. Immunol.*, Vol. 110, pp. 891-898.

McMillan et al., 2004, "Prolonged allergen challenge in mice leads to persistent airway remodelling", *Clin. Exp. Allergy*, Vol. 34, pp. 497-507.

Miyamoto et al., 1968, "Allergenic identity between the common floor mite (*Dermatophagoides farinae* Hughes, 1961) and house dust as a causative antigen in bronchial asthma", *J. Allergy*, Vol. 42, pp. 14-28.

Muraguchi et al., 1988, "The essential role of B cell stimulatory factor 2 (BSF-2/IL-6) for the terminal differentiation of B cells", *J. Exp. Med*, Vol. 167, pp. 332-344.

Peat et al., 1991, "Sensitivity to common allergens: relation to respiratory symptoms and bronchial hyper-responsiveness in children from three different climatic areas of Australia", *Clin. Exp. Allergy*, Vol. 21, pp. 573-581.

Peat et al., 1996, "House dust mite allergens. A major risk factor for childhood asthma in Australia", *Am. J. Respir. Crit. Care Med.*, Vol. 153, pp. 141-146.

Peroni et al., 1994, "Effective allergen avoidance at high altitude reduces allergen-induced bronchial hyperresponsiveness", *Am. J. Respir. Crit. Care Med.*, Vol. 149, pp. 1442-1446.

Piacentini et al., 1998, "Mite-antigen avoidance can reduce bronchial epithelial shedding in allergic asthmatic children", *Clin. Exp. Allergy*, Vol. 28, pp. 561-567.

Piacentini et al., 1999, "Allergen avoidance at high altitude and urinary eosinophil protein X", *J. Allergy Clin. Immunol*, Vol. 104, pp. 243-244.

Platts-Mills et al., 1987, "Seasonal variation in dust mite and grass-pollen allergens in dust from the houses of patients with asthma", *J. Allergy Clin. Immunol.*, Vol. 79, pp. 781-791.

Platts-Mills et al., 1997, "Indoor allergens and asthma: report of the Third International Workshop", *J. Allergy Clin. Immunol.*, Vol. 100, pp. S2-24.

Platts-Mills et al., 2000, "The role of intervention in established allergy: avoidance of indoor allergens in the treatment of chronic allergic disease", *J. Allergy Clin. Immunol.*, Vol. 106, pp. 787-804.

Pollart et al., 1989, "Epidemiology of acute asthma: IgE antibodies to common inhalant allergens as a risk factor for emergency room visits", *J. Allergy Clin. Immunol.*, Vol 83, PP. 875-882.

Rudolph et al., 1978, "The significance of nasal protease inhibitor concentrations in house dust allergy", *Allergy*, Vol. 33, pp. 310-315.

Schultze-Werninghaus, 2006, "Should asthma management include sojourns at high altitude?", *Chem. Immunol. Allergy*, Vol. 91, pp. 16-29.

Seymour et al., 1998, "Aerosol-induced immunoglobulin (Ig)-E unresponsiveness to ovalbumin does not require CD8+ or T cell receptor (TCR)-gamma/detta+ T cells or interferon (IFN)-gamma in a murine model of allergen sensitization", *J. Exp. Med.*, Vol. 187, pp. 721-731.

Sigsgaard et al., 2000, "S and Z alpha1-antitrypsin alleles are risk factors for bronchial hyperresponsiveness in young farmers: an example of gene/environment interaction", *Eur. Respir. J*, Vol. 16, pp. 50-55.

Smith et al., 1969, "Clinical significance of skin reactions to mite extracts in children with asthma", *Br. Med. J*, Vol. 1, pp. 723-726.

Sporik et al., 1990, "Exposure to house-dust mite allergen (Der p I) and the development of asthma in childhood. A prospective study", *N. Engl. J. Med.*, Vol. 323, pp. 502-507.

Stewart et al., 2003, "Allergen structure and function", in: *Middleton's Allergy. Principles and Practice*, (Eds. Adkinson et al.; Publisher. Mosby, Philadelphia), pp. 585-609.

Stick et al., 2003, "The airway epithelium as immune modulator: the LARC ascending", *Am. J. Respir. Cell Mol. Biol*, Vol. 28, pp. 641-644.

Sture et al., 1995, "Canine atopic dermatitis: the prevalence of positive intradermal skin tests at two sites in the north and south of Great Britain", *Vet. Immunol. Immunopathol.*, Vol. 44, pp. 293-308.

van Halteren et al., 1997, "Regulation of antigen-specific IgE, IgG1, and mast cell responses to ingested allergen by mucosal tolerance induction", *J. Immunol.*, Vol. 159, pp. 3009-3015.

van Velzen et al., 1996., "Effect of allergen avoidance at high altitude on direct and indirect bronchial hyperresponsiveness and markers of inflammation in children with allergic asthma" *Thorax*, Vol. 51, pp. 582-584.

Vercelli., 1989, "Endogenous interleukin 6 plays an obligatory role in interleukin 4-dependent human IgE synthesis", *Eur. J. Immunol.*, Vol. 19, pp. 1419-1424.

Vervloet et al., 1982, "Altitude and house dust mites", *J. Allergy Clin. Immunol.*, Vol. 69, pp. 290-296.

Wan et al., 1999, "Der p 1 facilitates transepithelial allergen delivery by disruption of tight junctions", *J. Clin. Invest.*, Vol. 104, pp. 123-133.

Wan et al., 2000, "Tight junction properties of the immortalized human bronchial epithelial cell lines Calu-3 and 16HB", *Eur. Respir. J.*, Vol. 15, pp. 1058-1068.

Winton et al., 1998, "Cell lines of pulmonary and non-pulmonary origin as tools to study the effects of house dust mite proteinases on the regulation of epithelial permeability", *Clin. Exp. Allergy*, Vol. 28, pp. 1273-1285.

Zhang et al., 2007, "Interactions between mature Der p 1 and its free prodomain indicate membership of a new family of C1 peptidases," *Allergy*, Vol. 62, pp. 1302-1309.

Zhang et al., 2009, "Novel Der p 1 inhibitors attenuate HDM sensitization in mice", *Amer. J. Respir. Crit. Care Med.*, Vol. 179, p. A4249.

Zhaozhao et al., 1996, "Novel peptidyl α-keto amide inhibitors of Calpains and Other Cysteine Proteases", *J. Med. Chem.*, pp. 4089-4098.

The invention claimed is:

1. A compound selected from compounds of the following formula, and pharmaceutically acceptable salts thereof:

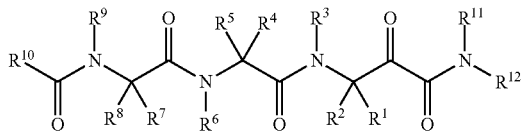

wherein:
—$R^1$ is independently —H or —$R^{1A}$;
—$R^{1A}$ is saturated aliphatic $C_{1-6}$alkyl, and is optionally substituted with one or more substituents —$R^{X1}$;
—$R^2$ is —H;
—$R^3$ is independently —H or —$R^{3A}$;
—$R^{3A}$ is saturated aliphatic $C_{1-3}$alkyl;
—$R^4$ is —$R^{4A}$;
—$R^{4A}$ is -Me;
—$R^5$ is —H;
—$R^6$ is —H or —$R^{6A}$;
—$R^{6A}$ is saturated aliphatic $C_{1-3}$alkyl;
—$R^7$ is —H, —$R^{7A}$, or —$R^{7B}$;

—$R^{7A}$ is saturated aliphatic $C_{1-6}$alkyl;
—$R^{7B}$ is independently -$L^{7B1}$-$R^{7BB}$ or —$R^{7BB}$;
-$L^{7B1}$- is saturated aliphatic $C_{1-3}$alkylene;
—$R^{7BB}$ is independently —$R^{7BB1}$, —$R^{7BB2}$, —$R^{7BB3}$, or —$R^{7BB4}$;
—$R^{7BB1}$ is independently phenyl or naphthyl, and is optionally substituted with one or more substituents —$R^{X3}$;
—$R^{7BB2}$ is $C_{5-10}$heteroaryl, and is optionally substituted with one or more substituents —$R^{X3}$;
—$R^{7BB3}$ is $C_{3-7}$cycloalkyl, and is optionally substituted with one or more substituents —$R^{X2}$, or is optionally fused to a benzene ring which is optionally substituted with one or more substituents —$R^{X3}$;
—$R^{7BB4}$ is saturated bridged $C_{5-10}$cycloalkyl, and is optionally substituted with one or more substituents —$R^{X2}$;
—$R^8$ is —H;
—$R^9$ is independently —H or —$R^{9A}$;
—$R^{9A}$ is saturated aliphatic $C_{1-4}$alkyl;
—$R^{10}$ is independently —$R^{10A}$, —$R^{10B}$, —$R^{10C}$, or —$R^{10D}$;
—$R^{10A}$ is independently phenyl or naphthyl, and is optionally substituted with one or more substituents —$R^{X3}$;
—$R^{10B}$ is $C_{5-10}$heteroaryl, and is optionally substituted with one or more substituents —$R^{X3}$;
—$R^{10C}$ is saturated $C_{3-7}$cycloalkyl, and is optionally substituted with one or more substituents —$R^{X2}$;
—$R^{10D}$ is non-aromatic $C_{3-10}$heterocyclyl, and is optionally substituted with one or more substituents —$R^{X2}$;
or —$R^9$ and —$R^{10}$, taken together with the nitrogen atom and carbon atom to which they are respectively attached, form a non-aromatic $C_{5-7}$heterocyclic lactam ring, which is optionally substituted with one or more substituents —$R^{X2}$, or which is optionally fused to a benzene ring which is optionally substituted with one or more substituents —$R^{X3}$;
—$R^{11}$ is independently —H, —$R^{11A}$, or —$R^{11B}$;
—$R^{11A}$ is independently —$R^{Z1}$, —$R^{Z2}$, —$R^{Z3}$, —$R^{Z4}$, —$R^{Z5}$, -$L^Z$-$R^{Z2}$, -$L^Z$-$R^{Z3}$, -$L^Z$-$R^{Z4}$, or -$L^Z$-$R^{Z5}$;
—$R^{Z1}$ is saturated aliphatic $C_{1-6}$alkyl, and is optionally substituted with one or more substituents —$R^{X1}$;
each —$R^{Z2}$ is saturated $C_{3-7}$cycloalkyl, and is optionally substituted with one or more substituents —$R^{X2}$;
each —$R^{Z3}$ is independently —$R^{Z3A}$ or —$R^{Z3B}$;
each —$R^{Z3A}$ is non-aromatic $C_{3-7}$heterocyclyl, and is optionally substituted with one or more substituents —$R^{X2}$;
each —$R^{Z3B}$ is saturated bridged $C_{5-10}$heterocyclyl, and is optionally substituted with one or more substituents —$R^{X2}$;
each —$R^{Z4}$ is independently phenyl or naphthyl, and is optionally substituted with one or more substituents —$R^{X3}$;
each —$R^{Z5}$ is $C_{5-10}$heteroaryl, and is optionally substituted with one or more substituents —$R^{X3}$;
each -$L^Z$- is saturated aliphatic $C_{1-4}$alkylene;
—$R^{11B}$ is —C$R^{J1}R^{J2}$—C(=O)—N$R^{J3}R^{J4}$;
—$R^{J1}$ is independently —H or saturated aliphatic $C_{1-4}$alkyl;
—$R^{J2}$ is independently —H or saturated aliphatic $C_{1-4}$alkyl;
—$R^{J3}$ is independently —H, saturated aliphatic $C_{1-4}$alkyl, phenyl, or benzyl;
—$R^{J4}$ is independently —H, saturated aliphatic $C_{1-4}$alkyl, phenyl, or benzyl;

or —NR$^{J3}$R$^{J4}$ is a C$_{3-10}$heterocyclyl group, and is optionally substituted with one or more substituents —R$^{X2}$;
—R$^{12}$ is independently —H or —R$^{12A}$;
—R$^{12A}$ is saturated aliphatic C$_{1-4}$alkyl;
wherein each —R$^{X1}$ is independently selected from:
—F, —Cl, —Br, —I, phenyl, —CF$_3$, —OH, —OR$^S$, —OCF$_3$, —NH$_2$, —NHR$^S$, —NR$^S_2$, pyrrolidino, piperidino, morpholino, piperizino, N—(C$_{1-4}$alkyl)-piperizino, —NHC(=O)R$^S$, —NR$^S$C(=O)R$^S$, —C(=O)R$^S$, —C(=O)OH, —C(=O)OR$^S$, —C(=O)NH$_2$, —C(=O)NHR$^S$, —C(=O)NR$^S_2$, —C(=O)-pyrrolidino, —C(=O)-piperidino, —C(=O)-morpholino, —C(=O)-piperizino, —C(=O)—{N—(C$_{1-4}$alkyl)-piperizino}-, —SR$^S$, —S(=O)R$^S$, and —S(=O)$_2$R$^S$;
wherein each —R$^S$ is independently saturated aliphatic C$_{1-6}$alkyl, phenyl, or —CH$_2$-phenyl;
wherein each phenyl is optionally substituted with one or more groups selected from: —F, —Cl, —Br, —I, —R$^{SS}$, —CF$_3$, —OH, —OR$^{SS}$, or —OCF$_3$, wherein each —R$^{SS}$ is saturated aliphatic C$_{1-4}$alkyl;
and wherein each —R$^{X2}$ is independently selected from:
—F, —Cl, —Br, —I, —R$^T$, phenyl, —OH, —OR$^T$, —C(=O)R$^T$, —NH$_2$, —NHR$^T$, —NR$^T_2$, pyrrolidino, piperidino, morpholino, piperizino, N—(C$_{1-4}$alkyl)-piperizino, —NHC(=O)R$^T$, and —NR$^T$C(=O)R$^T$;
wherein each —R$^T$ is independently saturated aliphatic C$_{1-6}$alkyl, phenyl, or —CH$_2$-phenyl;
wherein each phenyl is optionally substituted with one or more groups selected from: —F, —Cl, —Br, —I, —R$^{TT}$, —CF$_3$, —OH, —OR$^{TT}$, or —OCF$_3$, wherein each —R$^{TT}$ is saturated aliphatic C$_{1-4}$alkyl,
and wherein each —R$^{X3}$ is independently selected from:
—F, —Cl, —Br, —I,
—R$^V$,
—CH=CH$_2$, —C≡CH, cyclopropyl,
—CF$_3$, —CHF$_2$, —OCF$_3$, —OCHF$_2$,
—CN,
—NO$_2$,
—OH, —OR$^V$,
-L$^V$-OH, -L$^V$-OR$^V$,
—O-L$^V$-OH, —O-L$^V$-OR$^V$,
—NH$_2$, —NHR$^V$, —NR$^V_2$,
pyrrolidino, piperidino, morpholino,
piperizino, N—(C$_{1-4}$alkyl)-piperizino,
-L$^V$-NH$_2$, -L$^V$-NHR$^V$, -L$^V$-NR$^V_2$,
-L$^V$-pyrrolidino, -L$^V$-piperidino, -L$^V$-morpholino,
-L$^V$-piperizino, -L$^V$-{N—(C$_{1-4}$alkyl)-piperizino},
-L$^V$-imidazol-2-yl, -L$^V$-{N—(C$_{1-4}$alkyl)-imidazol-2-yl},
—O-L$^V$-NH$_2$, —O-L$^V$-NHR$^V$, —O-L$^V$-NR$^V_2$,
—O-L$^V$-pyrrolidino, —O-L$^V$-piperidino, —O-L$^V$-morpholino,
—O-L$^V$-piperizino, —O-L$^V$-{N—(C$_{1-4}$alkyl)-piperizino},
—O-L$^V$-imidazol-2-yl, —O-L$^V$-{N—(C$_{1-4}$alkyl)-imidazol-2-yl},
—NHC(=O)R$^V$, —NR$^V$C(=O)R$^V$,
—C(=O)R$^V$,
—C(=O)OH, —C(=O)OR$^V$,
—C(=O)NH$_2$, —C(=O)NHR$^V$, —C(=O)NR$^V_2$,
—C(=O)-pyrrolidino, —C(=O)-piperidino, —C(=O)-morpholino,
—C(=O)-piperizino, —C(=O)—{N—(C$_{1-4}$alkyl)-piperizino}-,
—NHC(=O)NH$_2$, —NHC(=O)NHR$^V$, —NHC(=O)NR$^V_2$,
—NHC(=O)-pyrrolidino, —NHC(=O)-piperidino,
—NHC(=O)-morpholino,
—NHC(=O)-piperizino, —NHC(=O)—{N—(C$_{1-4}$alkyl)-piperizino}-,
—S(=O)$_2$R$^V$,
—S(=O)$_2$NH$_2$, —S(=O)$_2$NHR$^V$, —S(=O)$_2$NR$^V_2$, and
=O;
wherein each -L$^V$- is saturated aliphatic C$_{1-4}$alkylene;
wherein each —R$^V$ is independently saturated aliphatic C$_{1-6}$alkyl, phenyl, —CH$_2$-phenyl, C$_{5-6}$heteroaryl, or —CH$_2$—C$_{5-6}$heteroaryl;
wherein each phenyl is optionally substituted with one or more groups selected from: —F, —Cl, —Br, —I, —R$^{VV}$, —CF$_3$, —OH, —OR$^{VV}$, or —OCF$_3$;
wherein each C$_{5-6}$heteroaryl is optionally substituted with one or more groups selected from: —F, —Cl, —Br, —I, —R$^{VV}$, —CF$_3$, —OH, —OR$^{VV}$, or —OCF$_3$;
wherein each —R$^{VV}$ is saturated aliphatic C$_{1-4}$alkyl;
and additionally, two adjacent groups —R$^{X3}$ may together form —OCH$_2$O—, —OCH$_2$CH$_2$O—, —CH$_2$OCH$_2$— or —OCH$_2$CH$_2$—;
and additionally, two adjacent groups —R$^{X3}$ may, together with the ring atoms to which they are attached, form a C$_{5-7}$carbocyclic ring or a C$_{5-7}$heterocyclic ring.

2. The compound according to claim 1, wherein —R$^1$ is —R$^{1A}$, and —R$^{1A}$ is -iPr.

3. The compound according to claim 1, wherein —R$^3$ is —H and —R$^6$ is —H.

4. The compound according to claim 2, wherein —R$^3$ is —H and —R$^6$ is —H.

5. The compound according to claim 1, wherein —R$^7$ is independently —R$^{7A}$ or —R$^{7B}$; —R$^{7A}$ is -tBu; —R$^{7B}$ is -L$^{7B1}$-R$^{7BB}$; -L$^{7B1}$- is —CH$_2$—; —R$^{7BB}$ is —R$^{7BB1}$; and —R$^{7BB1}$ is phenyl.

6. The compound according to claim 4, wherein —R$^7$ is independently —R$^{7A}$ or —R$^{7B}$; —R$^{7A}$ is -tBu; —R$^{7B}$ is -L$^{7B1}$-R$^{7BB}$; -L$^{7B1}$- is —CH$_2$—; —R$^{7BB}$ is —R$^{7BB1}$; and —R$^{7BB1}$ is phenyl.

7. The compound according to claim 1, wherein —R$^9$ is —H; —R$^{10}$ is —R$^{10A}$; and —R$^{10A}$ is phenyl, and is optionally substituted with one or more substituents —R$^{X3}$.

8. The compound according to claim 6, wherein —R$^9$ is —H; —R$^{10}$ is —R$^{10A}$; and —R$^{10A}$ is phenyl, and is optionally substituted with one or more substituents —R$^{X3}$.

9. The compound according to claim 1, wherein —R$^9$ is —H; —R$^{10}$ is —R$^{10B}$; and —R$^{10B}$ is pyridyl, and is optionally substituted with one or more substituents —R$^{X3}$.

10. The compound according to claim 6, wherein —R$^9$ is —H; —R$^{10}$ is —R$^{10B}$; and —R$^{10B}$ is pyridyl, and is optionally substituted with one or more substituents —R$^{X3}$.

11. The compound according to claim 1, wherein —R$^9$ is —H; —R$^{10}$ is —R$^{10B}$; and —R$^{10B}$ is independently indazolyl, benzimidazolyl, benzothiazolyl, quinolinyl, or isoquinolinyl, and is optionally substituted with one or more substituents —R$^{X3}$.

12. The compound according to claim 6, wherein —R$^9$ is —H; —R$^{10}$ is —R$^{10B}$; and —R$^{10B}$ is independently indazolyl, benzimidazolyl, benzothiazolyl, quinolinyl, or isoquinolinyl, and is optionally substituted with one or more substituents —R$^{X3}$.

13. The compound according to claim 1, wherein —R$^9$ is —H; —R$^{10}$ is —R$^{10D}$; and —R$^{10D}$ is independently:

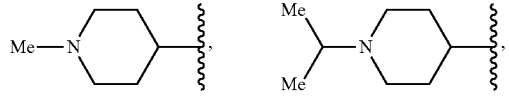

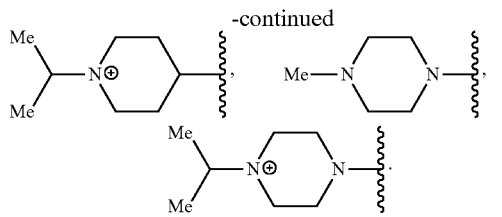

14. The compound according to claim 6, wherein —R$^9$ is —H; —R$^{10}$ is —R$^{10D}$; and —R$^{10D}$ is independently:

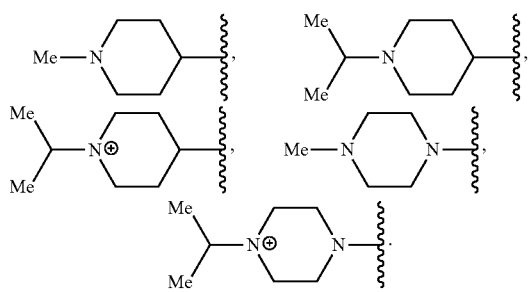

15. The compound according to claim 1, wherein the group —N(R$^9$)—C(=O)—R$^{10}$ is the following group:

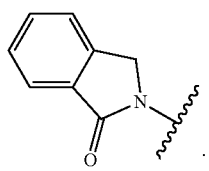 [SMILES: *N1Cc2ccccc2C1=O]

16. The compound according to claim 6, wherein the group —N(R$^9$)—C(=O)—R$^{10}$ is the following group:

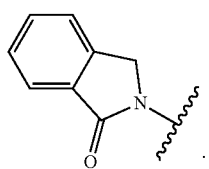 [SMILES: *N1Cc2ccccc2C1=O]

17. The compound according to claim 1, wherein:
—R$^{11}$ is —R$^{11A}$;
—R$^{11A}$ is -L$^Z$-R$^{Z4}$;
-L$^Z$- is —CH$_2$— or —CH(Me)-; and
—R$^{Z4}$ is independently selected from:

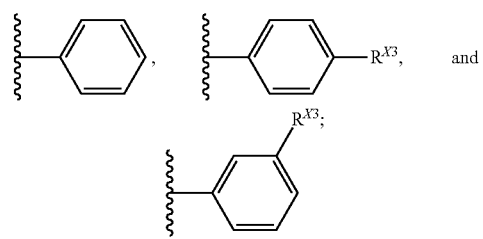

and
—R$^{12}$ is —H.

18. The compound according to claim 8, wherein:
R$^{11}$ is —R$^{11A}$;
—R$^{11A}$ is -L$^Z$-R$^{Z4}$;
-L$^Z$- is —CH$_2$— or —CH(Me)-; and
—R$^{Z4}$ is independently selected from:

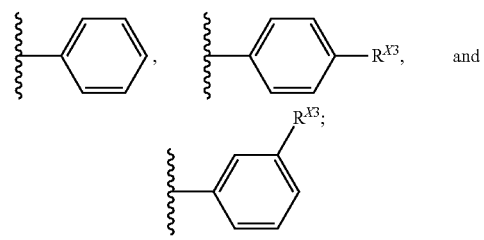

and
—R$^{12}$ is —H.

19. The compound according to claim 10, wherein:
R$^{11}$ is —R$^{11A}$;
—R$^{11A}$ is -L$^Z$-R$^{Z4}$;
-L$^Z$- is —CH$_2$— or —CH(Me)-; and
—R$^{Z4}$ is independently selected from:

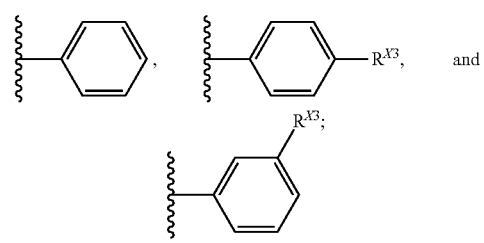

and
—R$^{12}$ is —H.

20. The compound according to claim 12, wherein:
—R$^{11}$ is —R$^{11A}$;
—R$^{11A}$ is -L$^Z$-R$^{Z4}$;
-L$^Z$- is —CH$_2$— or —CH(Me)-; and
—R$^{Z4}$ is independently selected from:

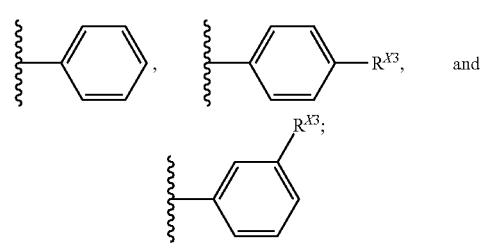

and
—R$^{12}$ is —H.

21. The compound according to claim 14, wherein:
—R$^{11}$ is —R$^{11A}$;
—R$^{11A}$ is -L$^Z$-R$^{Z4}$;
-L$^Z$- is —CH$_2$— or —CH(Me)-; and —R$^{Z4}$ is independently selected from:

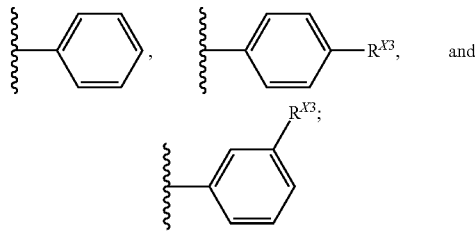

and
—R$^{12}$ is —H.

22. The compound according to claim 16, wherein:
—R$^{11}$ is —R$^{11A}$;
—R$^{11A}$ is -L$^Z$-R$^{Z4}$;
-L$^Z$- is —CH$_2$— or —CH(Me)-; and
—R$^{Z4}$ is independently selected from:

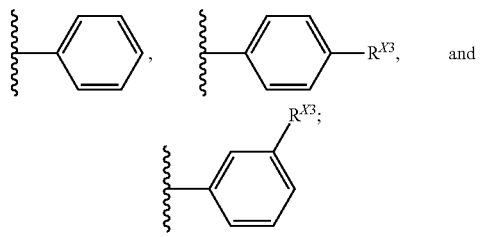

and
—R$^{12}$ is —H.

23. The compound according to claim 1, wherein:
—R$^{11}$ is —R$^{11B}$;
—R$^{J1}$ is independently —H, -Me, -Et, -nPr, or -iPr;
—R$^{J2}$ is —H;
—NR$^{J3}$R$^{J4}$ is independently selected from:

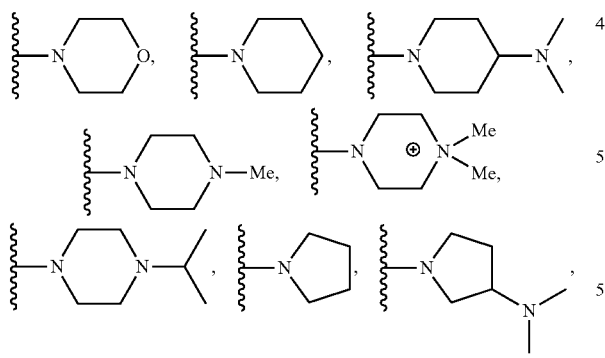

1,2,3,4-tetrahydro-isoquinolin-2-yl, and
2,3-dihydro-1H-indol-1-yl; and
—R$^{12}$ is —H.

24. The compound according to claim 8, wherein:
—R$^{11}$ is —R$^{11B}$;
—R$^{J1}$ is independently —H, -Me, -Et, -nPr, or -iPr;
—R$^{J2}$ is —H;
—NR$^{J3}$R$^{J4}$ is independently selected from:

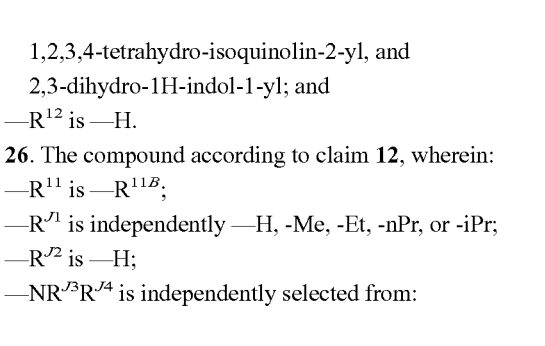

1,2,3,4-tetrahydro-isoquinolin-2-yl, and
2,3-dihydro-1H-indol-1-yl; and
—R$^{J2}$ is —H.

25. The compound according to claim 10, wherein:
—R$^{11}$ is —R$^{11B}$;
—R$^{J1}$ is independently —H, -Me, -Et, -nPr, or -iPr;
—R$^{J2}$ is —H;
—NR$^{J3}$R$^{J4}$ is independently selected from:

1,2,3,4-tetrahydro-isoquinolin-2-yl, and
2,3-dihydro-1H-indol-1-yl; and
—R$^{12}$ is —H.

26. The compound according to claim 12, wherein:
—R$^{11}$ is —R$^{11B}$;
—R$^{J1}$ is independently —H, -Me, -Et, -nPr, or -iPr;
—R$^{J2}$ is —H;
—NR$^{J3}$R$^{J4}$ is independently selected from:

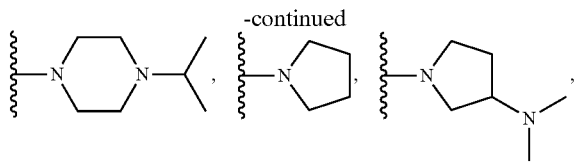

1,2,3,4-tetrahydro-isoquinolin-2-yl, and
2,3-dihydro-1H-indol-1-yl; and
—$R^{12}$ is —H.

27. The compound according to claim 14, wherein:
—$R^{11}$ is —$R^{11B}$;
—$R^{J1}$ is independently —H, -Me, -Et, -nPr, or -iPr;
—$R^{J2}$ is —H;
—$NR^{J3}R^{J4}$ is independently selected from:

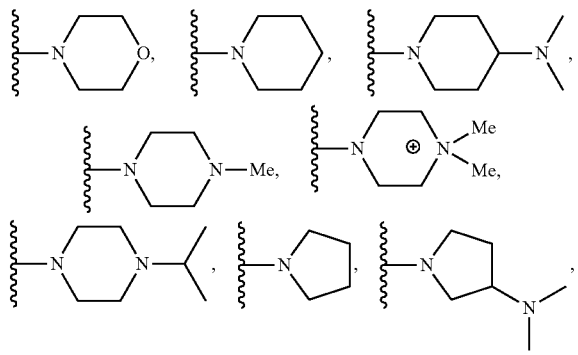

1,2,3,4-tetrahydro-isoquinolin-2-yl, and
2,3-dihydro-1H-indol-1-yl; and
—$R^{12}$ is —H.

28. A compound according to claim 16, wherein:
—$R^{11}$ is —$R^{11B}$;
—$R^{J1}$ is independently —H, -Me, -Et, -nPr, or -iPr;
—$R^{J2}$ is —H;
—$NR^{J3}R^{J4}$ is independently selected from:

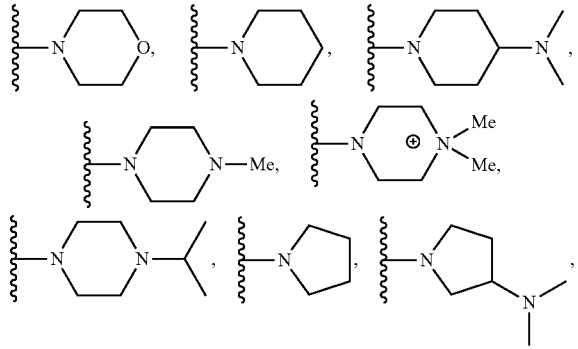

1,2,3,4-tetrahydro-isoquinolin-2-yl, and
2,3-dihydro-1H-indol-1-yl; and
—$R^{12}$ is —H.

29. The compound according to claim 1, wherein
each —$R^{X1}$, if present, is independently selected from:
—F, —Cl, —Br, —I, —OH, —$OR^S$, —$NH_2$, —$NHR^S$,
—$NR^S_2$, pyrrolidino, piperidino, morpholino, piperizino, N—($C_{1-4}$alkyl)-piperizino, —$NHC(=O)R^S$,
—$NR^SC(=O)R^S$, —$C(=O)NH_2$, —$C(=O)NHR^S$,
—$C(=O)NR^S_2$, —$C(=O)$-pyrrolidino, —$C(=O)$-piperidino, —$C(=O)$-morpholino, —$C(=O)$-piperizino,
and —$C(=O)$—{N—($C_{1-4}$alkyl)-piperizino}-;
each —$R^{X2}$, if present, is independently selected from:
—$R^T$, —OH, —$OR^T$, —$C(=O)R^T$, —$NH_2$, —$NHR^T$,
—$NR^T_2$, pyrrolidino, piperidino, morpholino, piperizino, N—($C_{1-4}$alkyl)-piperizino, —$NHC(=O)R^T$, and
—$NR^TC(=O)R^T$; and
each —$R^{X3}$, if present, is independently selected from:
—F, —Cl, —Br, —I, —$R^V$, —CN, —OH, —$OR^V$,
—$NH_2$, —$NHR^V$, —$NR^V_2$, pyrrolidino, piperidino,
morpholino, piperizino, N—($C_{1-4}$alkyl)-piperizino,
-$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —$C(=O)OH$, —$C(=O)OR^V$,
—$C(=O)NH_2$, —$C(=O)NHR^V$, —$C(=O)NR^V_2$,
—$NHC(=O)NH_2$, —$S(=O)_2NH_2$, —$S(=O)_2NHR^V$,
—$S(=O)_2NR^V_2$, and =O.

30. The compound according to claim 18, wherein
each —$R^{X1}$, if present, is independently selected from:
—F, —Cl, —Br, —I, —OH, —$OR^S$, —$NH_2$, —$NHR^S$,
—$NR^S_2$, pyrrolidino, piperidino, morpholino, piperizino, N—($C_{1-4}$alkyl)-piperizino, —$NHC(=O)R^S$,
—$NR^SC(=O)R^S$, —$C(=O)NH_2$, —$C(=O)NHR^S$,
—$C(=O)NR^S_2$, —$C(=O)$-pyrrolidino, —$C(=O)$-piperidino, —$C(=O)$-morpholino, —$C(=O)$-piperizino,
and —$C(=O)$—{N—($C_{1-4}$alkyl)-piperizino}-;
each —$R^{X2}$, if present, is independently selected from:
—$R^T$, —OH, —$OR^T$, —$C(=O)R^T$, —$NH_2$, —$NHR^T$,
—$NR^T_2$, pyrrolidino, piperidino, morpholino, piperizino, N—($C_{1-4}$alkyl)-piperizino, —$NHC(=O)R^T$, and
—$NR^TC(=O)R^T$; and
each —$R^{X3}$, if present, is independently selected from:
—F, —Cl, —Br, —I, —$R^V$, —CN, —OH, —$OR^V$,
—$NH_2$, —$NHR^V$, —$NR^V_2$, pyrrolidino, piperidino,
morpholino, piperizino, N—($C_{1-4}$alkyl)-piperizino,
-$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —$C(=O)OH$, —$C(=O)OR^V$,
—$C(=O)NH_2$, —$C(=O)NHR^V$, —$C(=O)NR^V_2$,
—$NHC(=O)NH_2$, —$S(=O)_2NH_2$, —$S(=O)_2NHR^V$,
—$S(=O)_2NR^V_2$, and =O.

31. The compound according to claim 19, wherein
each —$R^{X1}$, if present, is independently selected from:
—F, —Cl, —Br, —I, —OH, —$OR^S$, —$NH_2$, —$NHR^S$,
—$NR^S_2$, pyrrolidino, piperidino, morpholino, piperizino, N—($C_{1-4}$alkyl)-piperizino, —$NHC(=O)R^S$,
—$NR^SC(=O)R^S$, —$C(=O)NH_2$, —$C(=O)NHR^S$,
—$C(=O)NR^S_2$, —$C(=O)$-pyrrolidino, —$C(=O)$-piperidino, —$C(=O)$-morpholino, —$C(=O)$-piperizino,
and —$C(=O)$—{N—($C_{1-4}$alkyl)-piperizino}-;
each —$R^{X2}$, if present, is independently selected from:
—$R^T$, —OH, —$OR^T$, —$C(=O)R^T$, —$NH_2$, —$NHR^T$,
—$NR^T_2$, pyrrolidino, piperidino, morpholino, piperizino, N—($C_{1-4}$alkyl)-piperizino, —$NHC(=O)R^T$, and
—$NR^TC(=O)R^T$; and
each —$R^{X3}$, if present, is independently selected from:
—F, —Cl, —Br, —I, —$R^V$, —CN, —OH, —$OR^V$,
—$NH_2$, —$NHR^V$, —$NR^V_2$, pyrrolidino, piperidino,
morpholino, piperizino, N—($C_{1-4}$alkyl)-piperizino,
-$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —$C(=O)OH$, —$C(=O)OR^V$,
—$C(=O)NH_2$, —$C(=O)NHR^V$, —$C(=O)NR^V_2$,
—$NHC(=O)NH_2$, —$S(=O)_2NH_2$, —$S(=O)_2NHR^V$,
—$S(=O)_2NR^V_2$, and =O.

32. The compound according to claim 20, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

33. The compound according to claim 21, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

34. The compound according to claim 22, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

35. The compound according to claim 24, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

36. The compound according to claim 25, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

37. The compound according to claim 26, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^S$C(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;

each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^T$C(=O)$R^T$; and each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

38. The compound according to claim 27, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^SC$(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;
each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^TC$(=O)$R^T$; and
each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

39. The compound according to claim 28, wherein
each —$R^{X1}$, if present, is independently selected from:
—F, —Cl, —Br, —I, —OH, —$OR^S$, —$NH_2$, —$NHR^S$, —$NR^S_2$, pyrrolidino, piperidino, morpholino, piperizino, N—($C_{1-4}$alkyl)-piperizino, —NHC(=O)$R^S$, —$NR^SC$(=O)$R^S$, —C(=O)$NH_2$, —C(=O)$NHR^S$, —C(=O)$NR^S_2$, —C(=O)-pyrrolidino, —C(=O)-piperidino, —C(=O)-morpholino, —C(=O)-piperizino, and —C(=O)—{N—($C_{1-4}$alkyl)-piperizino}-;
each —$R^{X2}$, if present, is independently selected from:
—$R^T$, —OH, —$OR^T$, —C(=O)$R^T$, —$NH_2$, —$NHR^T$, —$NR^T_2$, pyrrolidino, piperidino, morpholino, piperizino, N—($C_{1-4}$alkyl)-piperizino, —NHC(=O)$R^T$, and —$NR^TC$(=O)$R^T$; and
each —$R^{X3}$, if present, is independently selected from:
—F, —Cl, —Br, —I, —$R^V$, —CN, —OH, —$OR^V$, —$NH_2$, —$NHR^V$, —$NR^V_2$, pyrrolidino, piperidino, morpholino, piperizino, N—($C_{1-4}$alkyl)-piperizino, -$L^V$-$NH_2$, -$L^V$-$NHR^V$, -$L^V$-$NR^V_2$, -$L^V$-pyrrolidino, -$L^V$-piperidino, -$L^V$-morpholino, -$L^V$-piperizino, -$L^V$-{N—($C_{1-4}$alkyl)-piperizino}, —C(=O)OH, —C(=O)$OR^V$, —C(=O)$NH_2$, —C(=O)$NHR^V$, —C(=O)$NR^V_2$, —NHC(=O)$NH_2$, —S(=O)$_2NH_2$, —S(=O)$_2NHR^V$, —S(=O)$_2NR^V_2$, and =O.

40. A compound selected from the following compounds and pharmaceutically acceptable salts thereof:

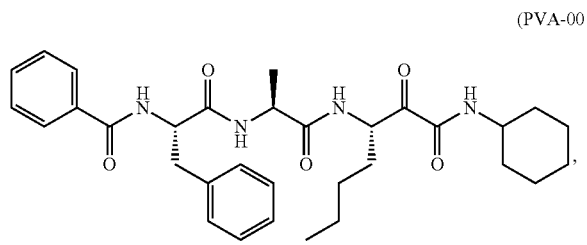

(PVA-001)

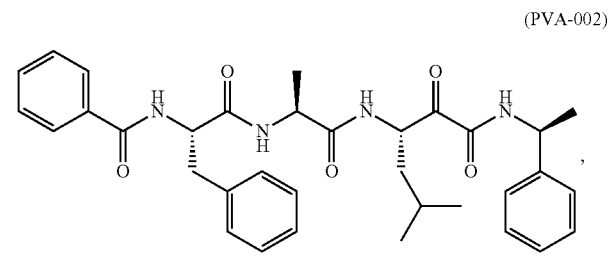

(PVA-002)

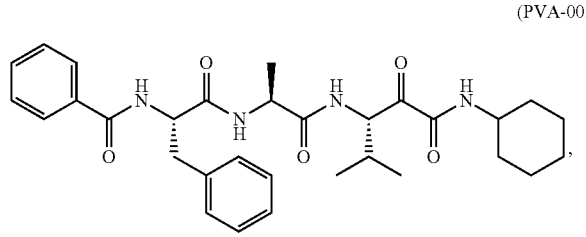

(PVA-003)

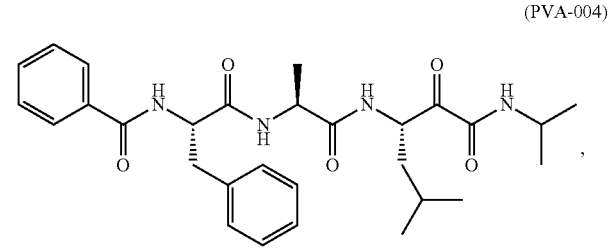

(PVA-004)

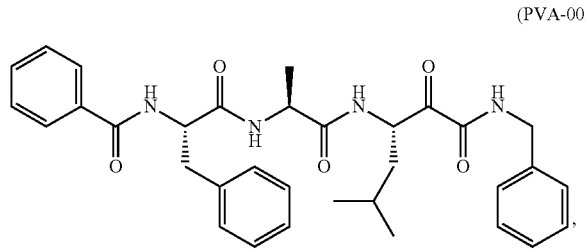

(PVA-005)

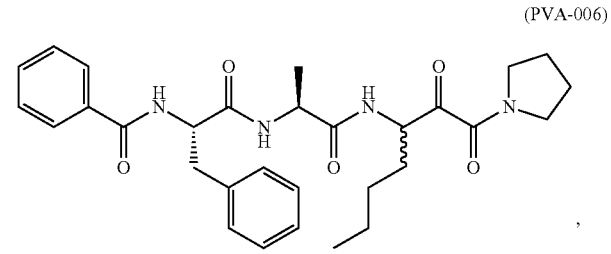

(PVA-006)

-continued
(PVA-007)
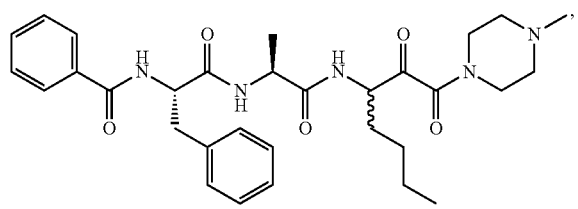
(PVA-008)
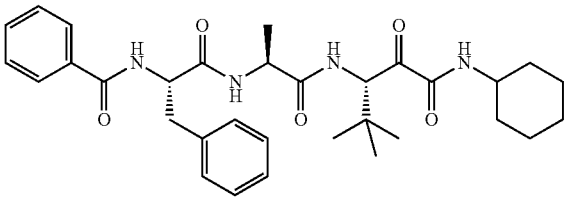
(PVA-009)
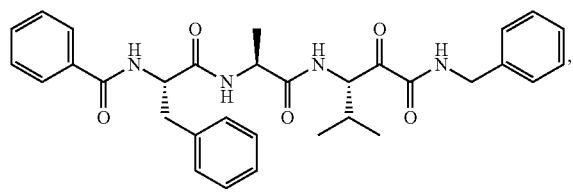
(PVA-010)
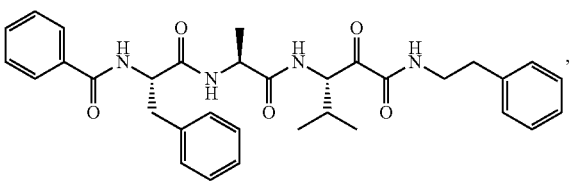
(PVA-011)
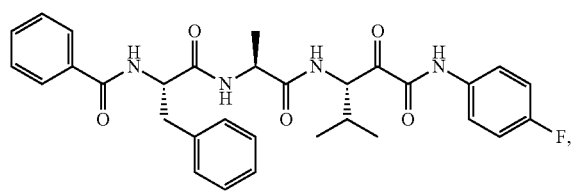
(PVA-012)
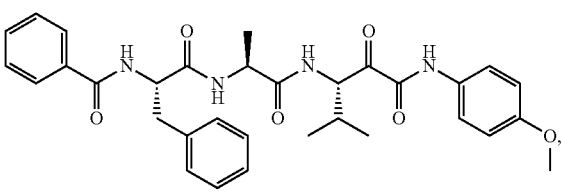
(PVA-013)
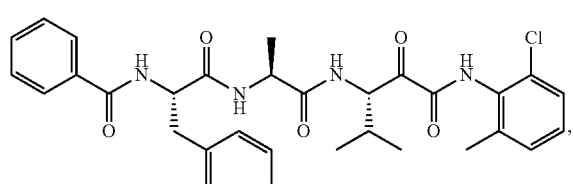
(PVA-014)
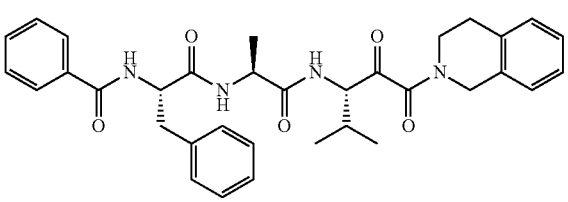
(PVA-015)
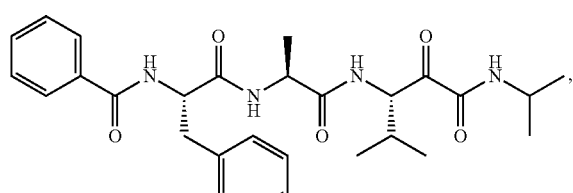
(PVA-016)
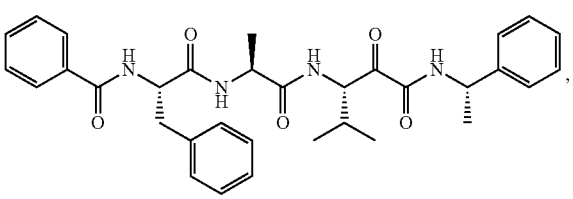
(PVA-017)
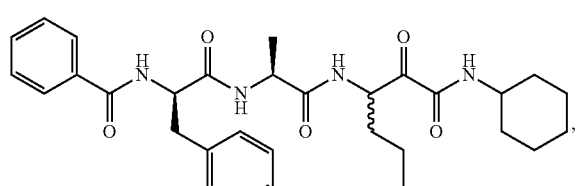
(PVA-018)
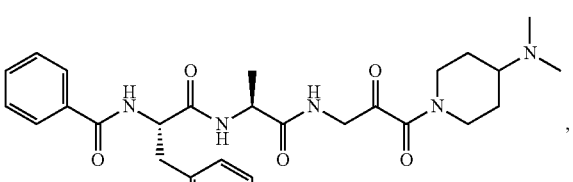
(PVA-019)
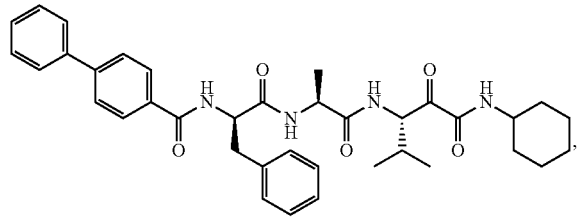
(PVA-020)
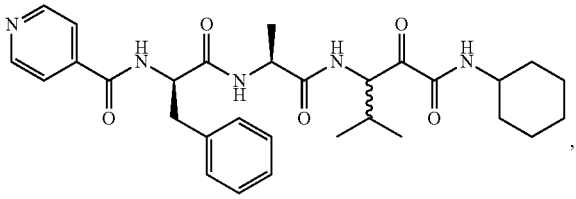

-continued
(PVA-021)
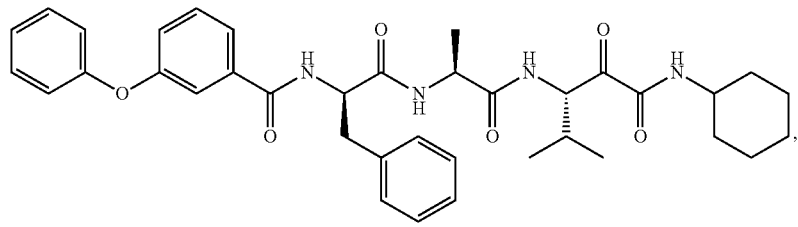
(PVA-022) (PVA-023)
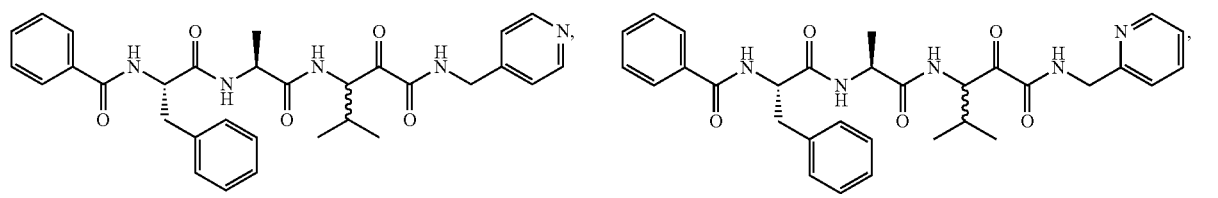
(PVA-024) (PVA-025)
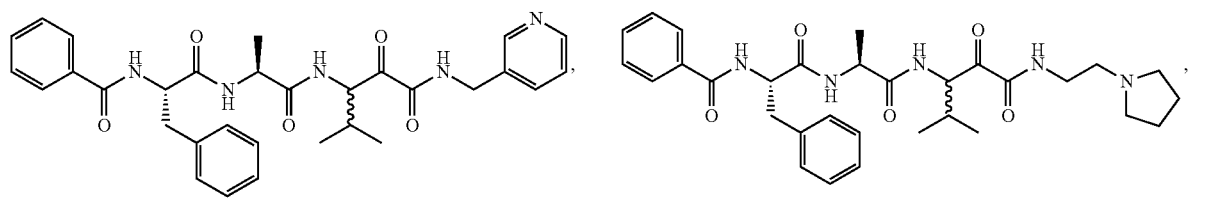
(PVA-026) (PVA-027)
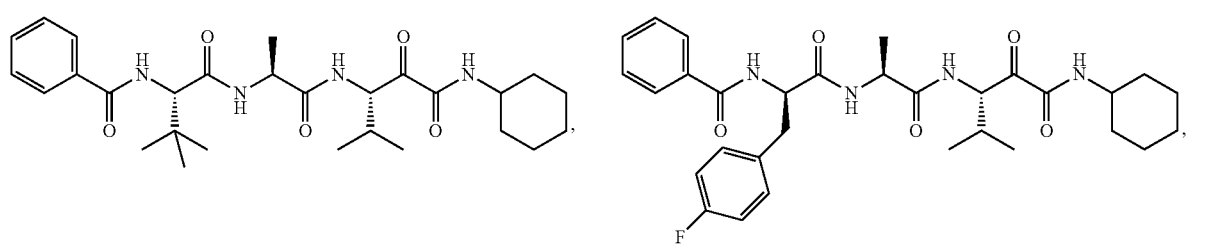
(PVA-028) (PVA-029)
(PVA-030) (PVA-031)
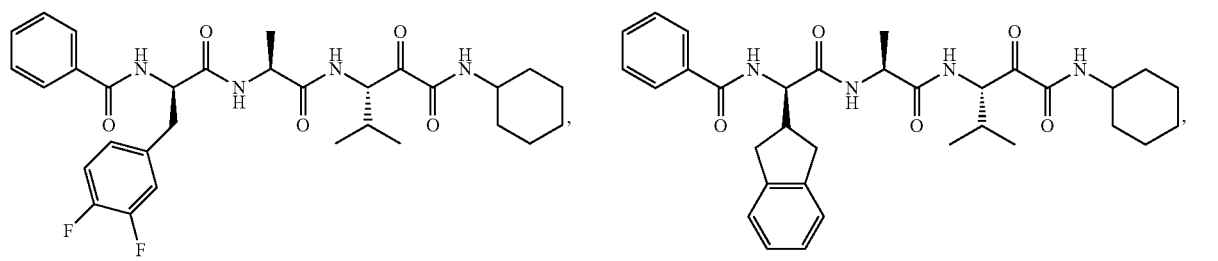

-continued
(PVA-032) 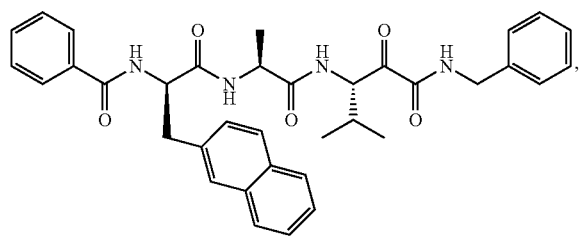
(PVA-033) 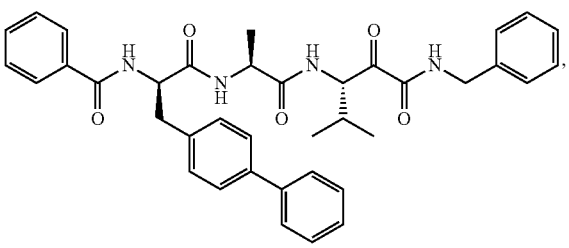
(PVA-034) 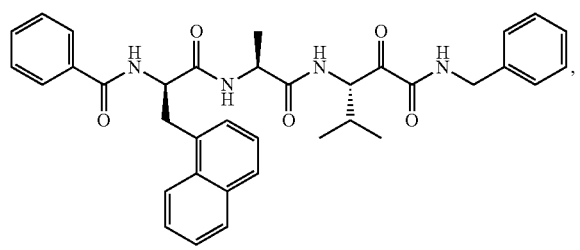
(PVA-035) 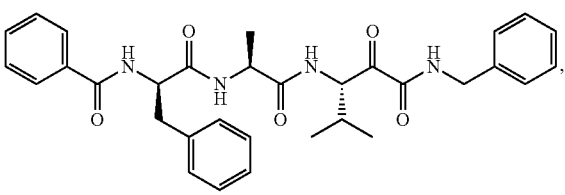
(PVA-036) 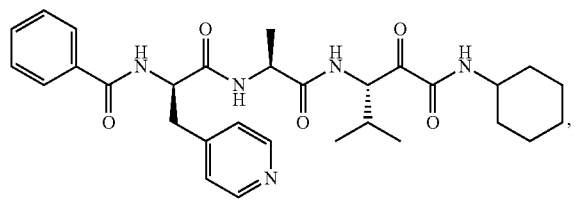
(PVA-037) 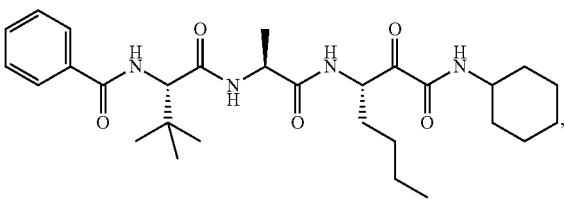
(PVA-038) 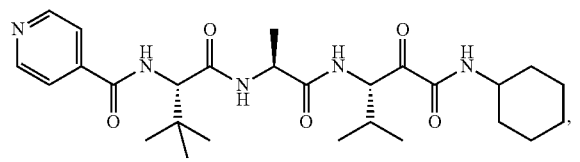
(PVA-039) 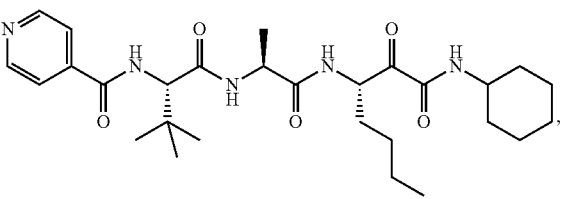
(PVA-040) 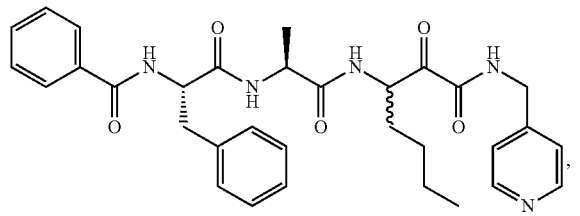
(PVA-041)
(PVA-042) 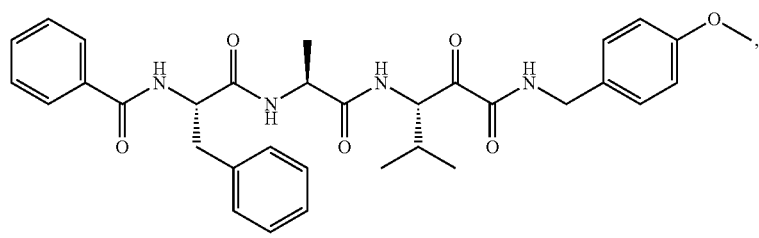

(PVA-043)
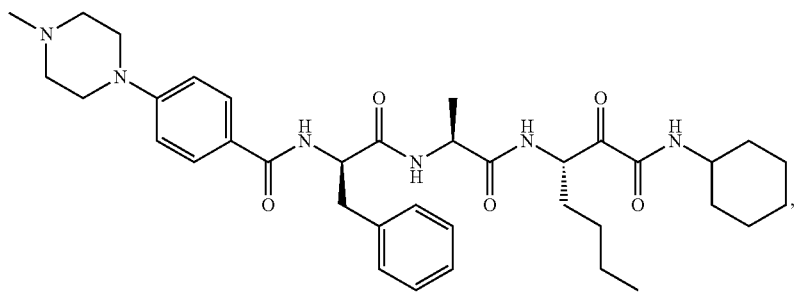
(PVA-044)
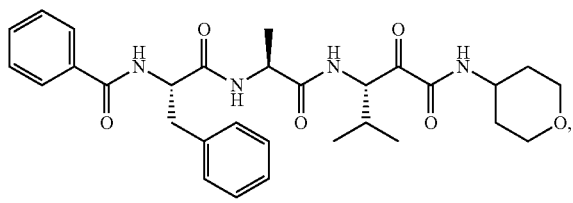
(PVA-045)
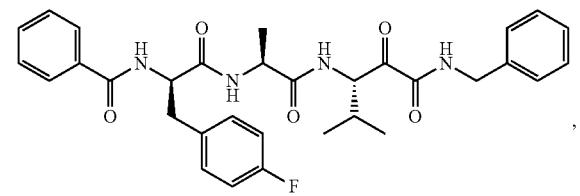
(PVA-046)
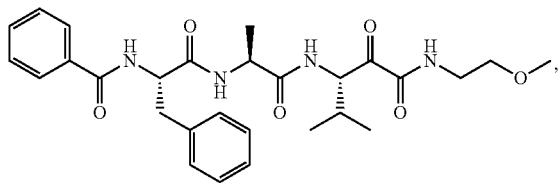
(PVA-047)
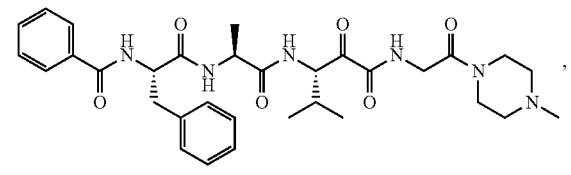
(PVA-048)
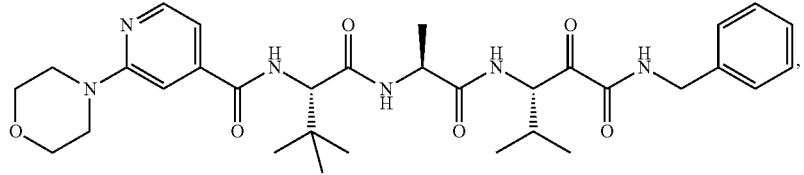
(PVA-049)
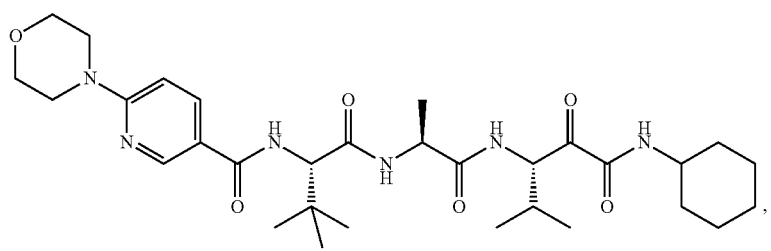
(PVA-050)
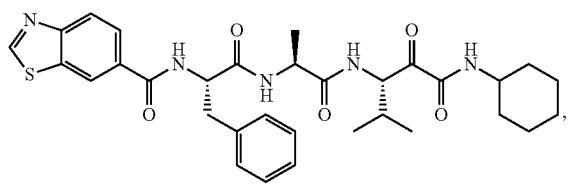
(PVA-051)
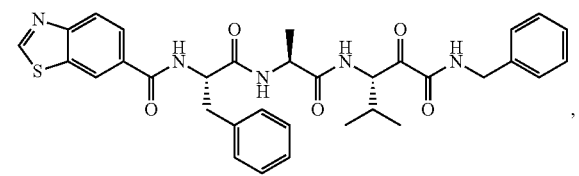
(PVA-052)
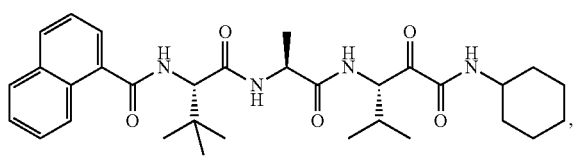
(PVA-053)
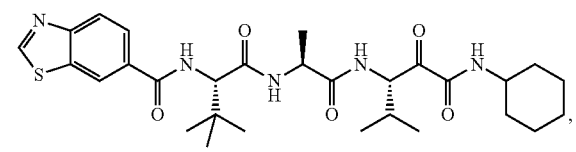

-continued
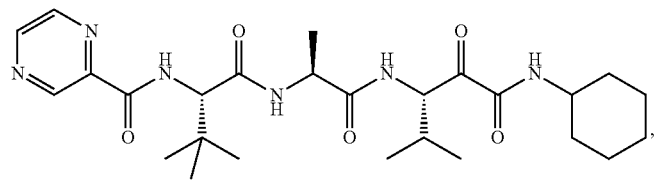
(PVA-054)
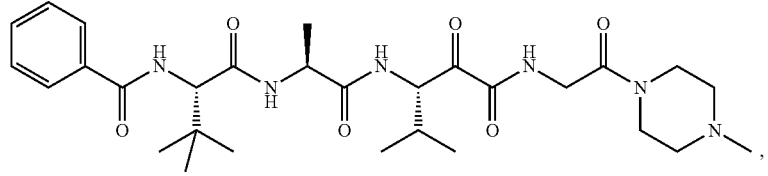
(PVA-055)
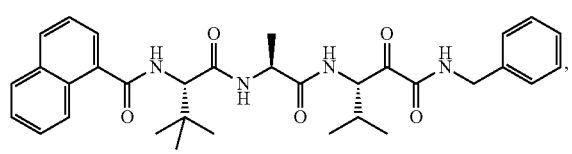
(PVA-057)
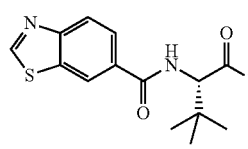
(PVA-056)
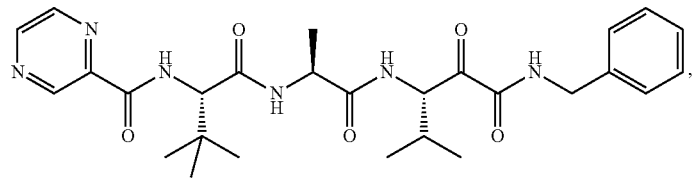
(PVA-058)
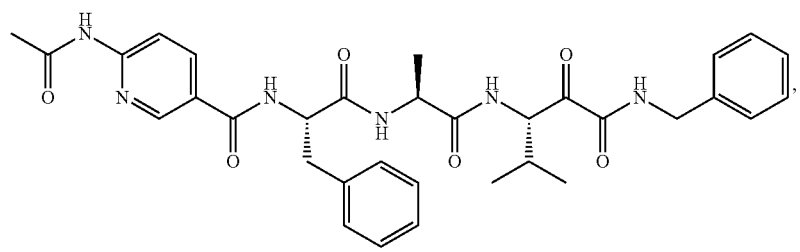
(PVA-059)
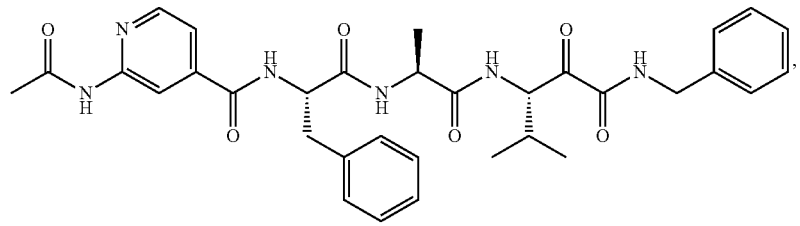
(PVA-060)
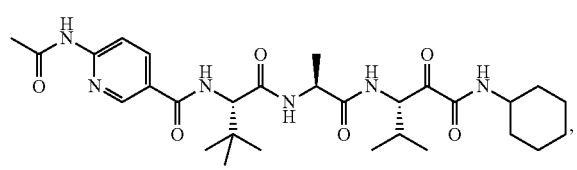
(PVA-061)
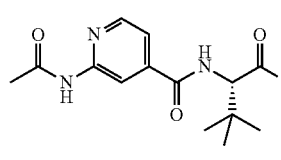
(PVA-062)
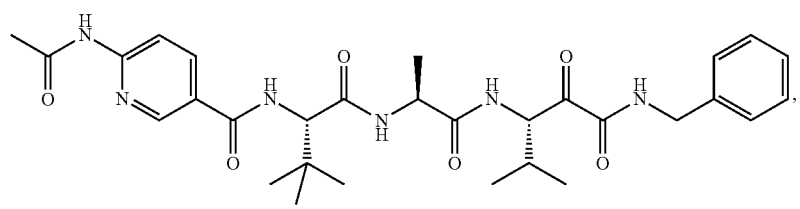
(PVA-063)

-continued
(PVA-064)
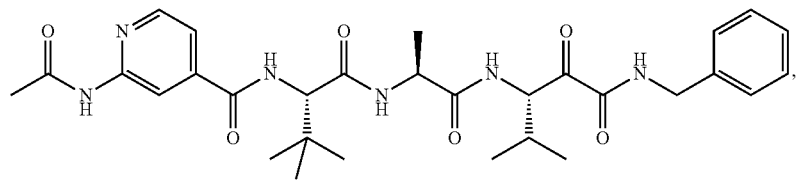
(PVA-065)
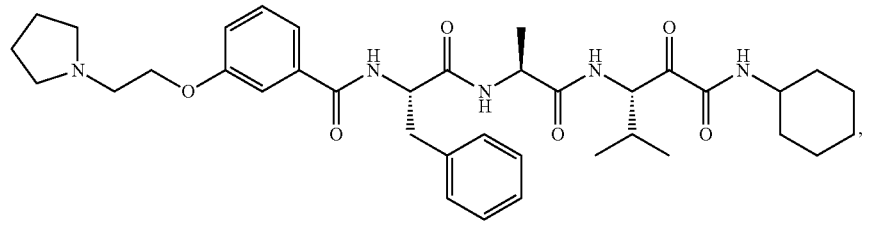
(PVA-066) (PVA-067)
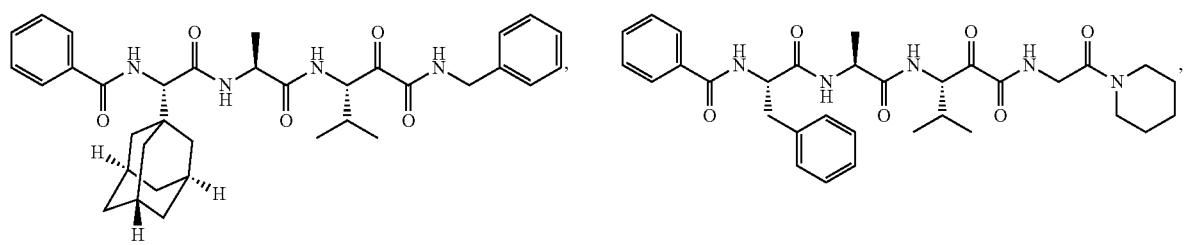
(PVA-068)
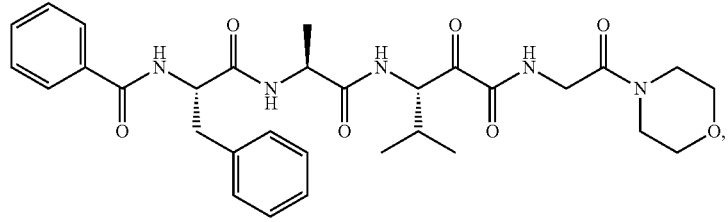
(PVA-069)
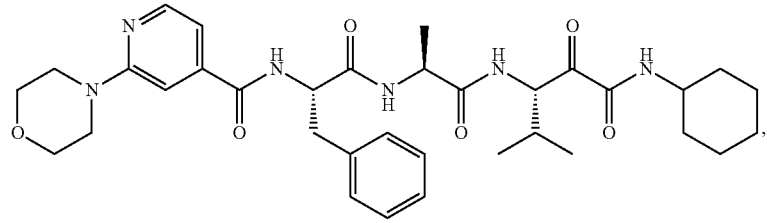
(PVA-070)
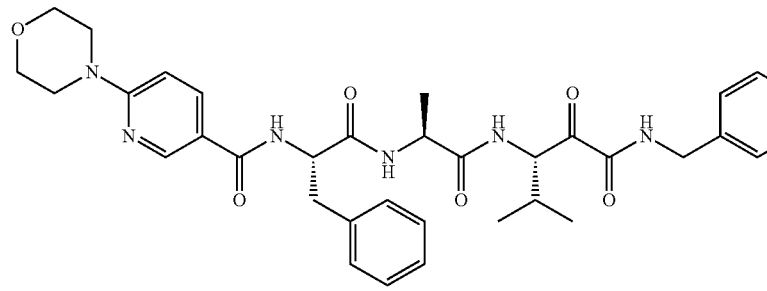
(PVA-071) (PVA-072)
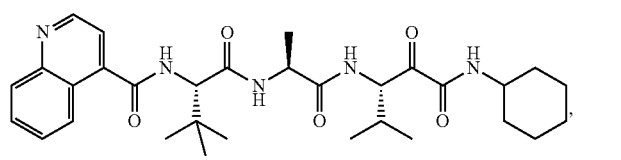 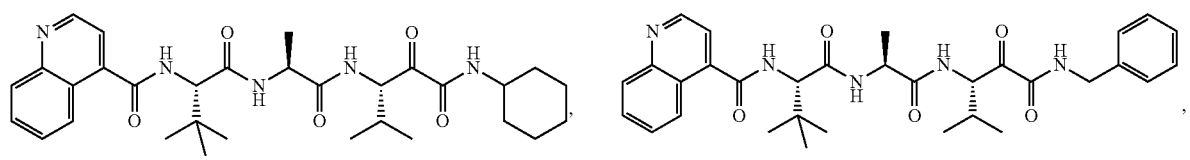

-continued
(PVA-073)
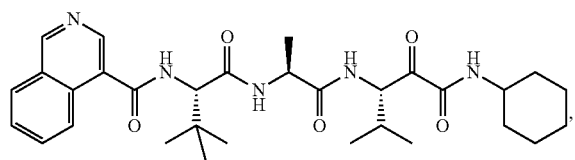
(PVA-074)
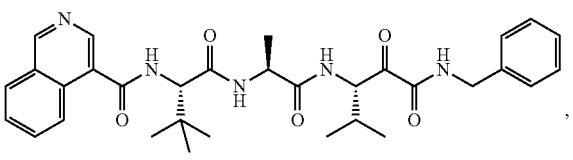
(PVA-075)
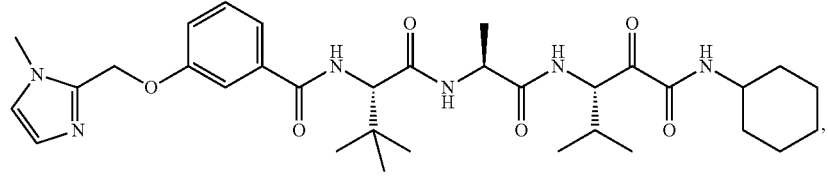
(PVA-076)
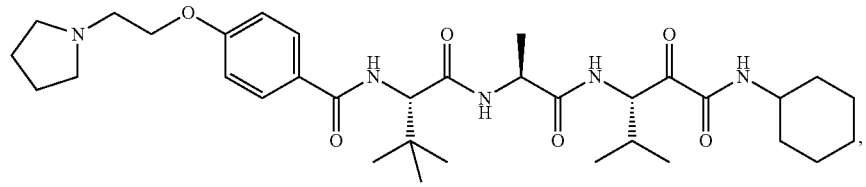
(PVA-077)
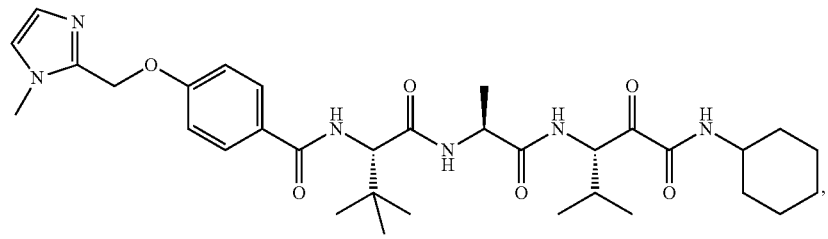
(PVA-078)
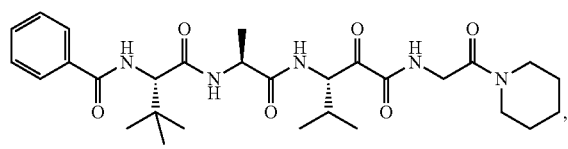
(PVA-079)
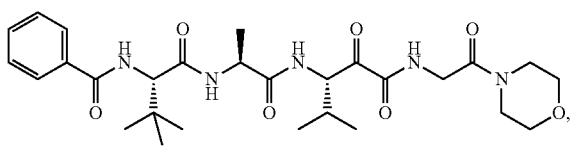
(PVA-080)
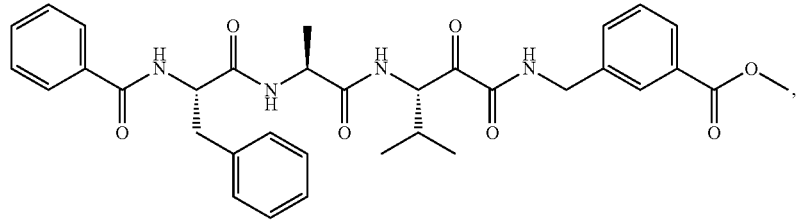
(PVA-081)
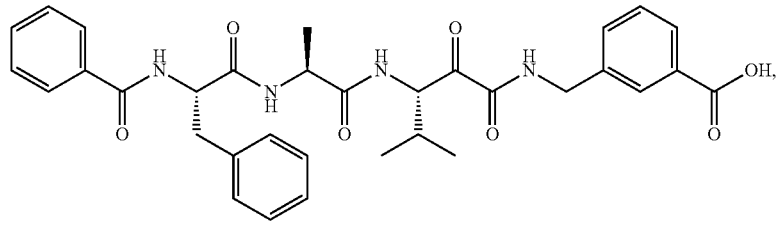

-continued
(PVA-082)
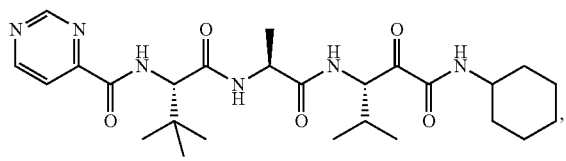
(PVA-083)
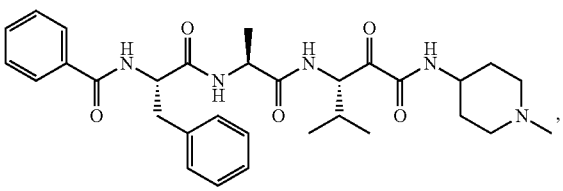
(PVA-084)
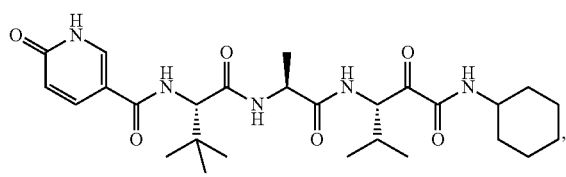
(PVA-085)
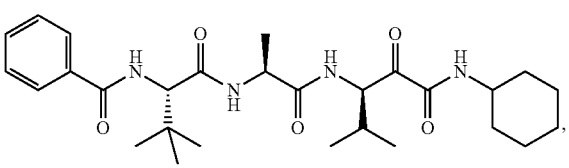
(PVA-086)
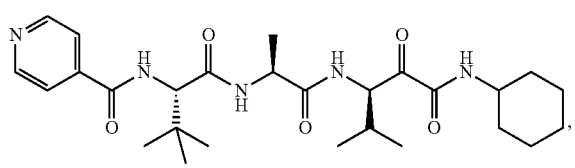
(PVA-087)
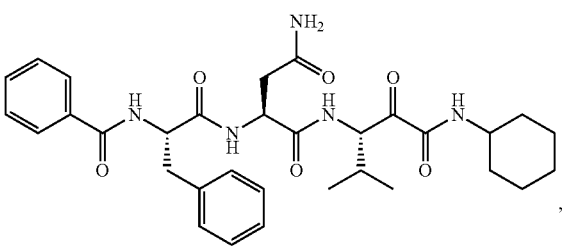
(PVA-088)
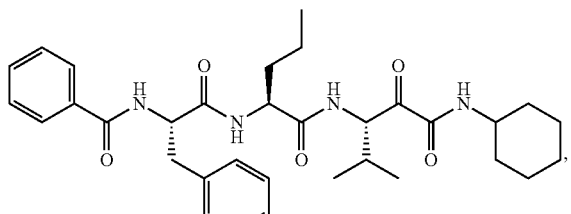
(PVA-089)
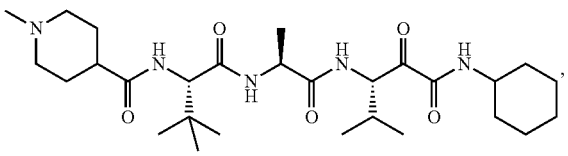
(PVA-090)
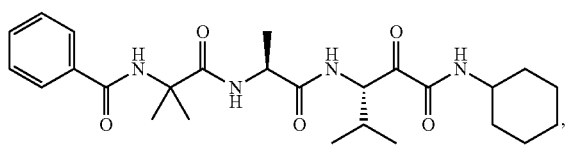
(PVA-091)
(PVA-092)
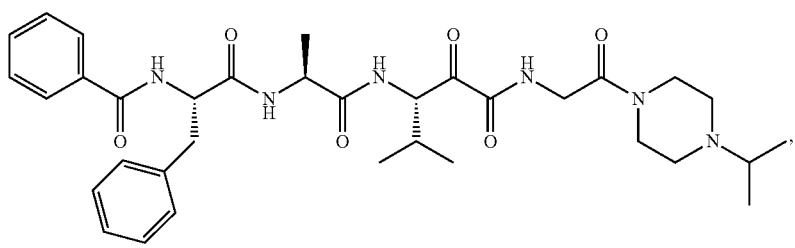
(PVA-093)

-continued
(PVA-094)
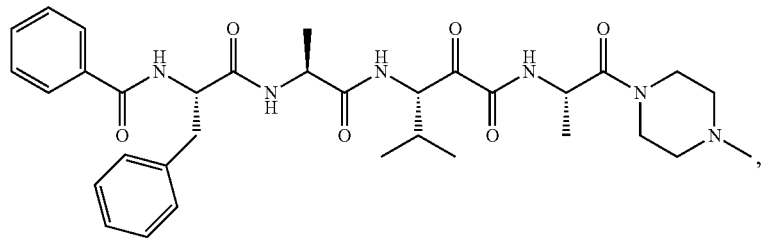
(PVA-095)
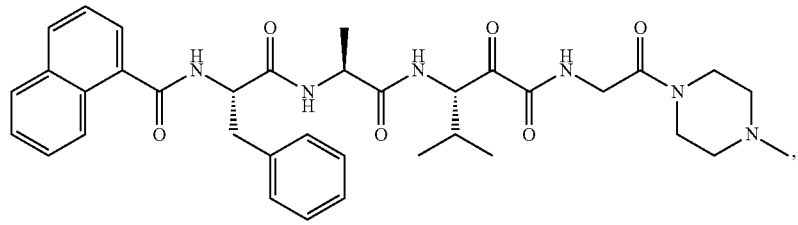
(PVA-096)
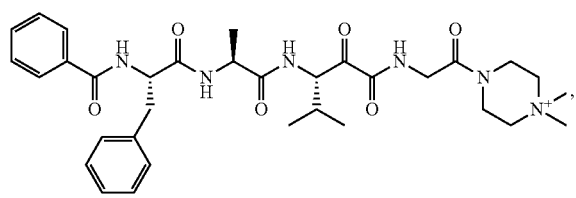
(PVA-097)
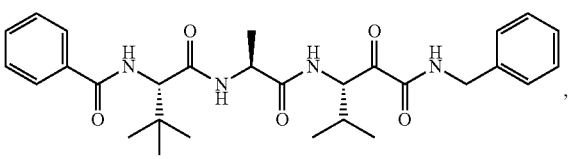
(PVA-098)
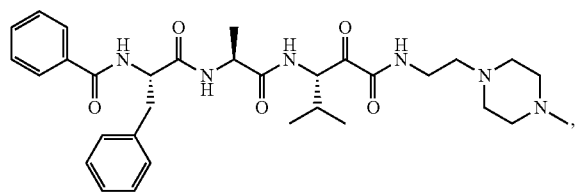
(PVA-099)
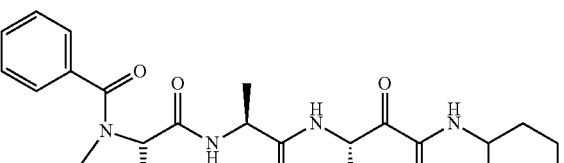
(PVA-100)
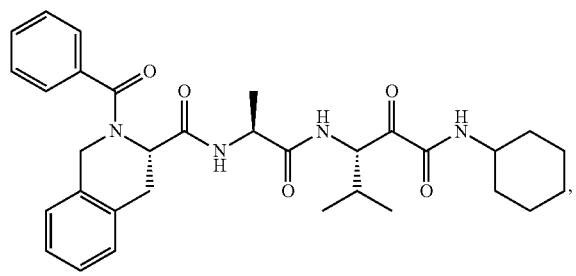
(PVA-101)
(PVA-102)
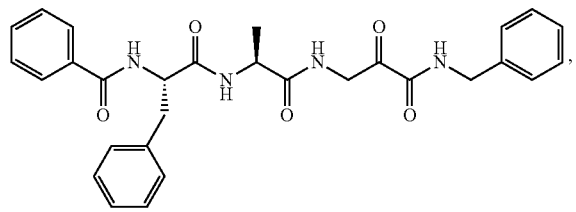
(PVA-103)
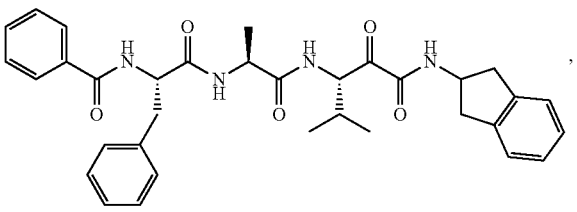

(PVA-104)
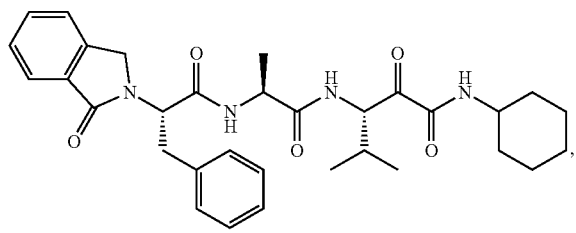
(PVA-105)
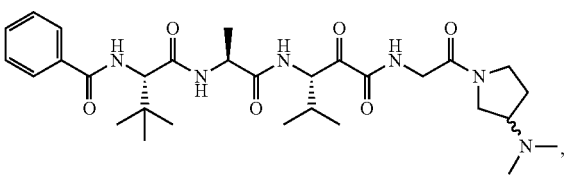
(PVA-106)
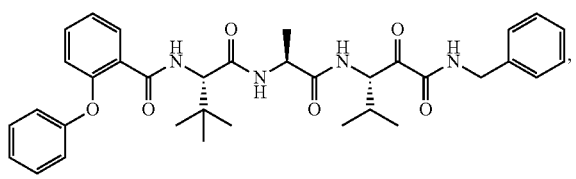
(PVA-107)
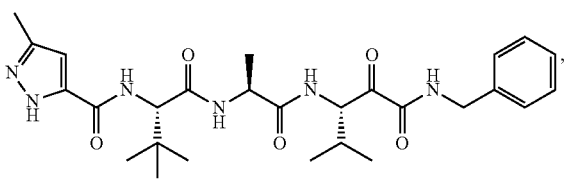
(PVA-108)
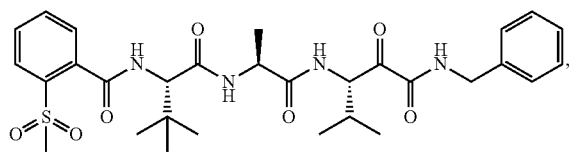
(PVA-109)
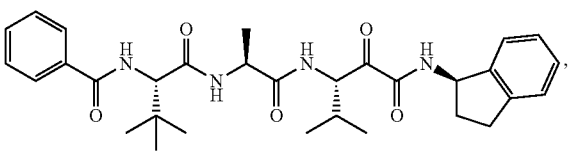
(PVA-110)
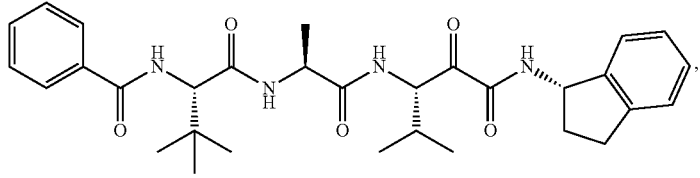
(PVA-111)
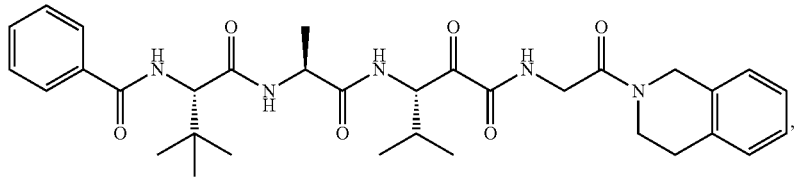
(PVA-112)
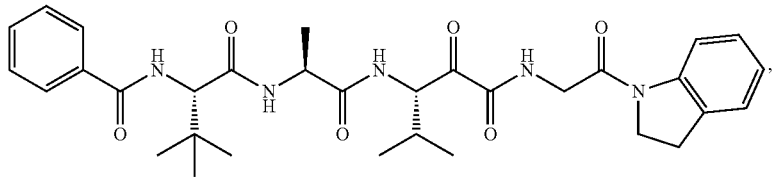
(PVA-113)
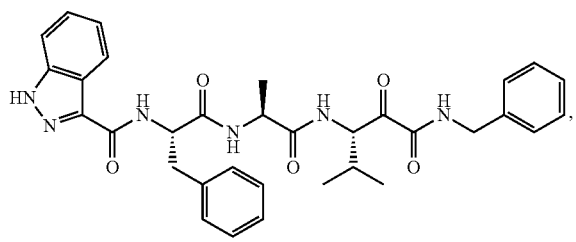
(PVA-114)
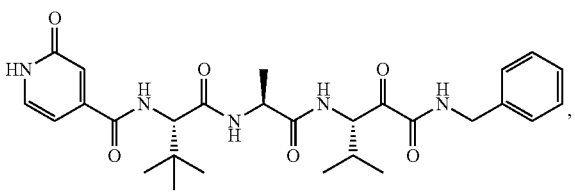

-continued
(PVA-115)
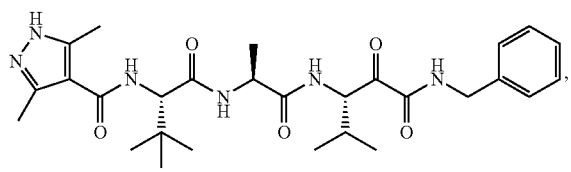
(PVA-116)
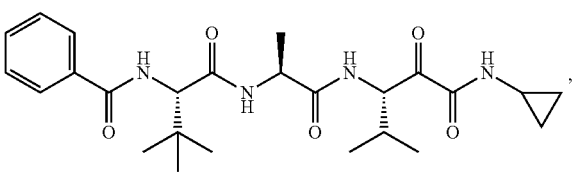
(PVA-117)
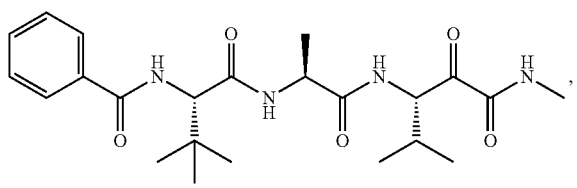
(PVA-118)
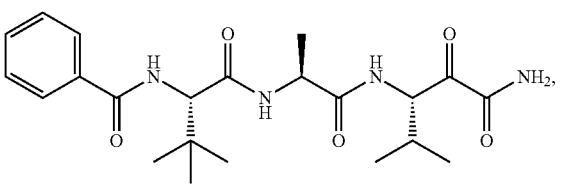
(PVA-119)
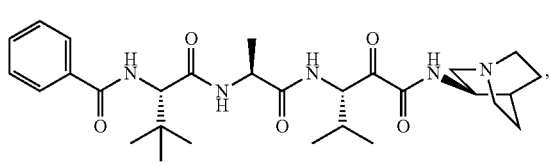
(PVA-120)
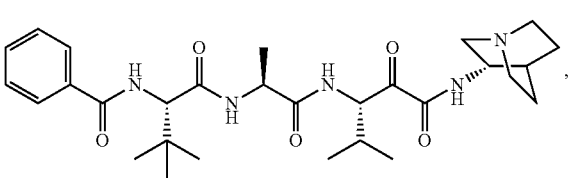
(PVA-121)
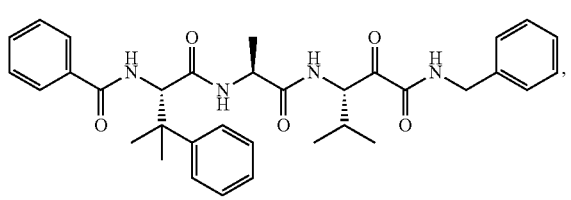
(PVA-122)
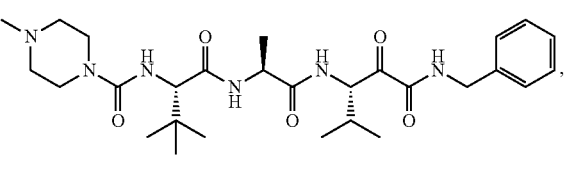
(PVA-123)
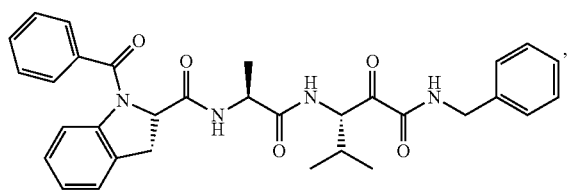
(PVA-124)
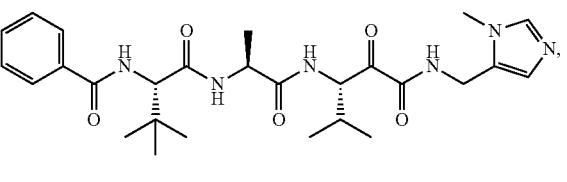
(PVA-125)
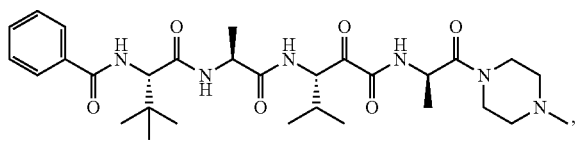
(PVA-126)
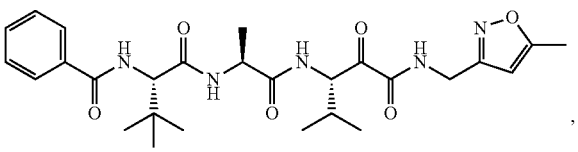
(PVA-127)
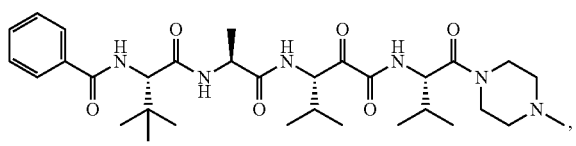
(PVA-128)
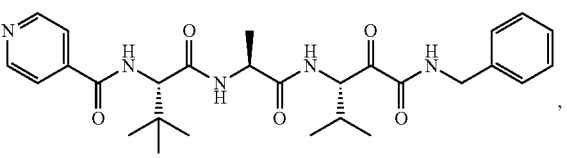
(PVA-129)
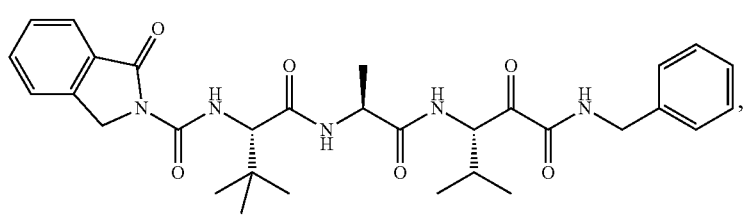

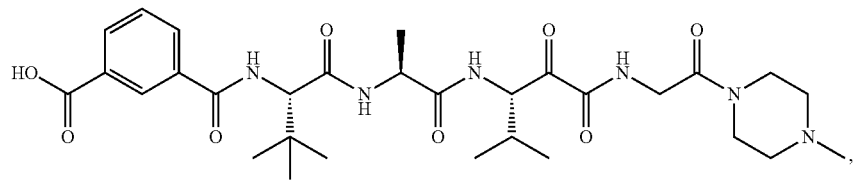
(PVA-130)
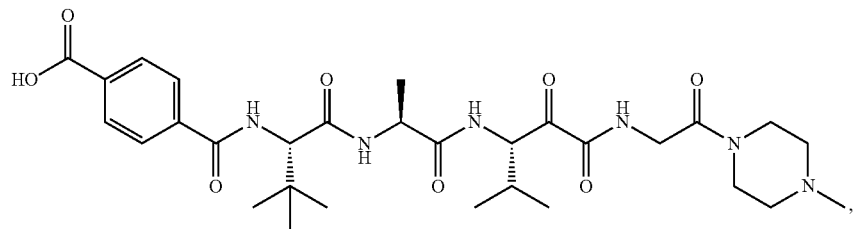
(PVA-131)
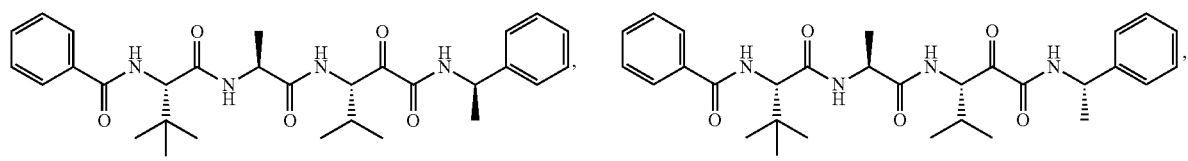
(PVA-132)       (PVA-133)
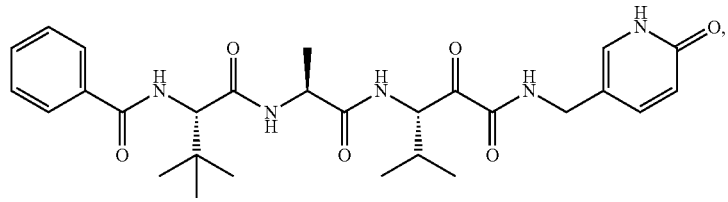
(PVA-134)
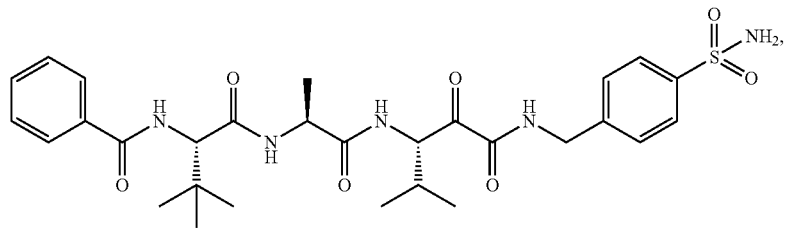
(PVA-135)
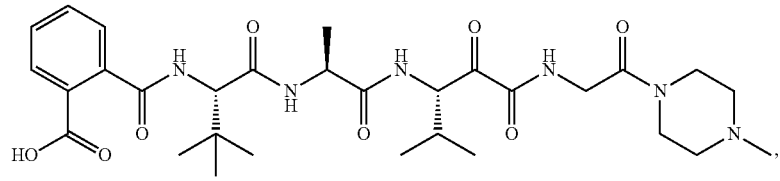
(PVA-136)
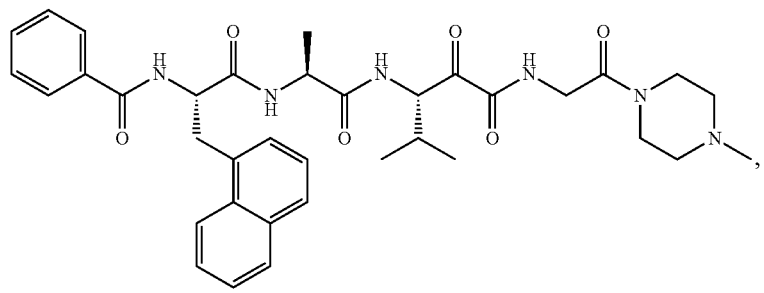
(PVA-137)

(PVA-138)
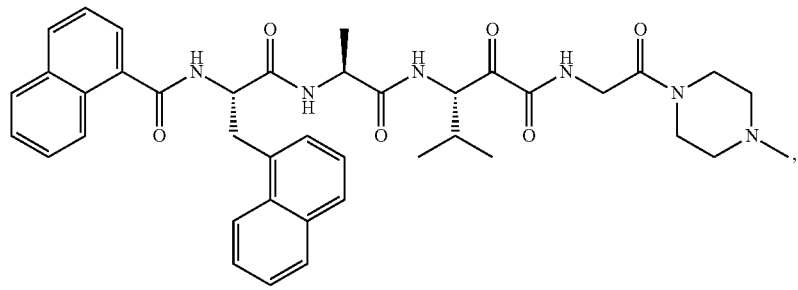
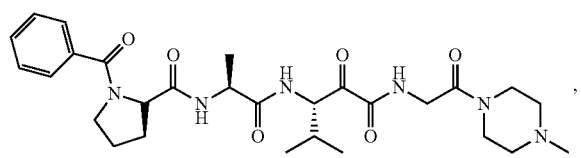
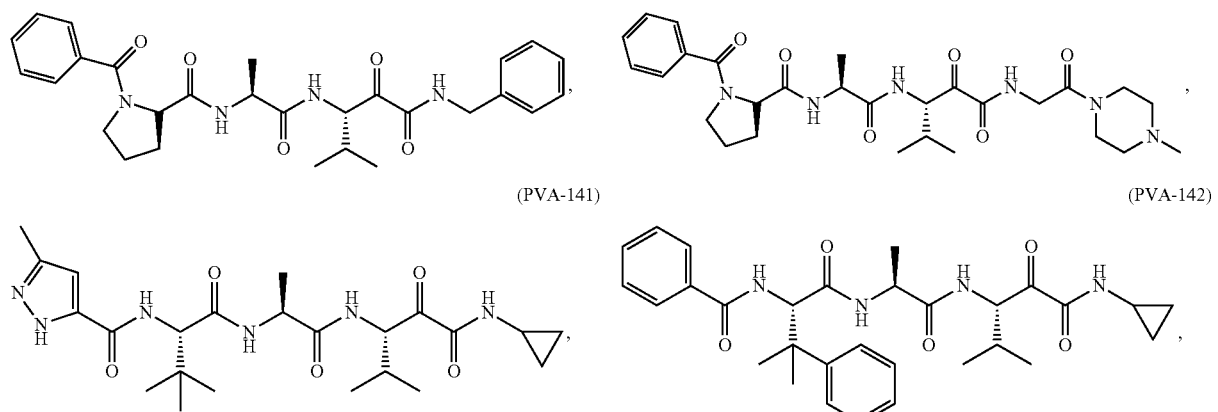
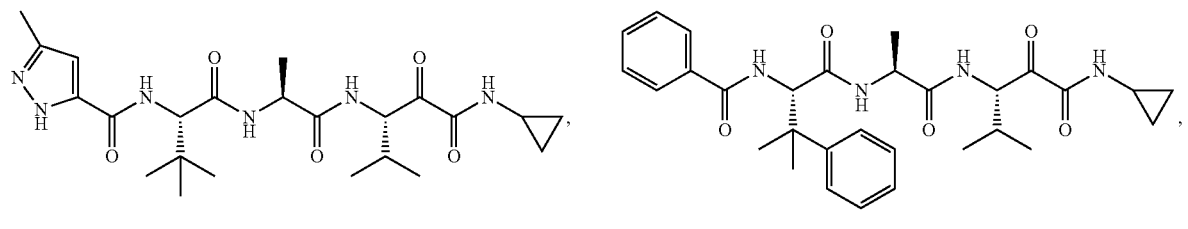
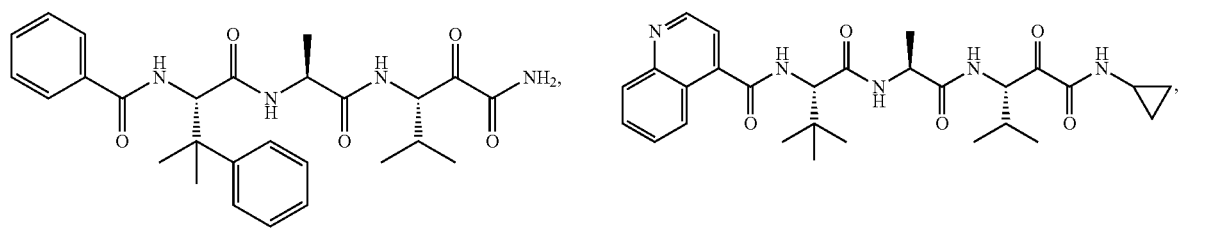
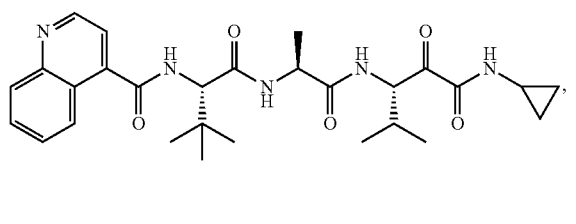
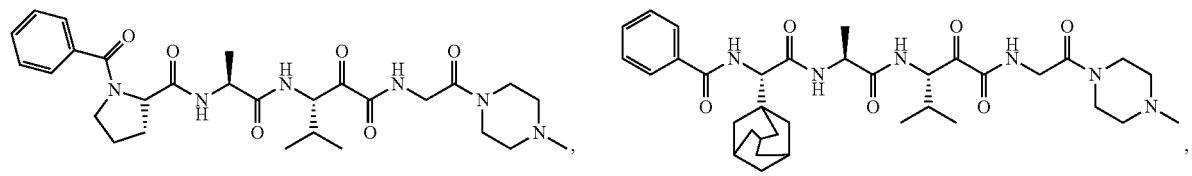
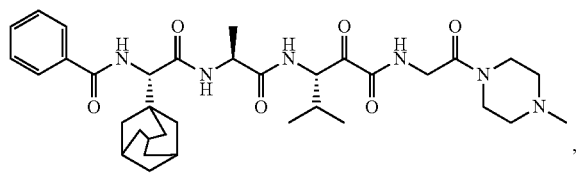
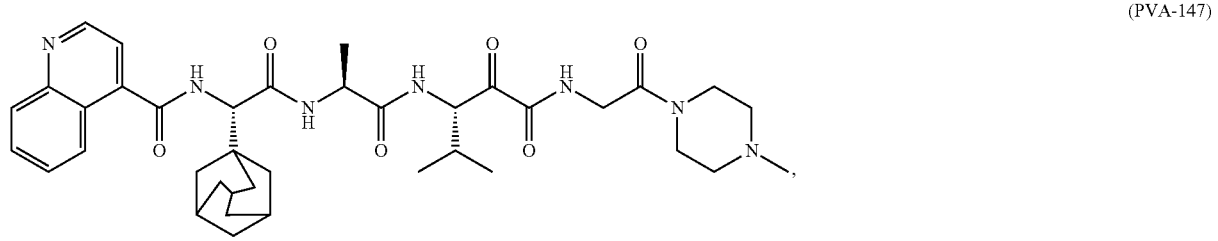

-continued
(PVA-148)
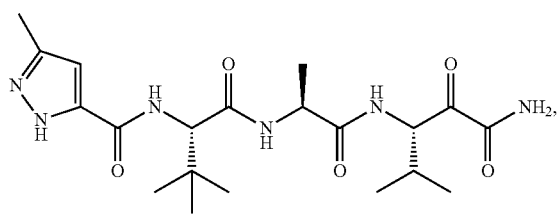
(PVA-149)
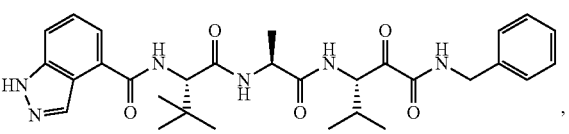
(PVA-150)
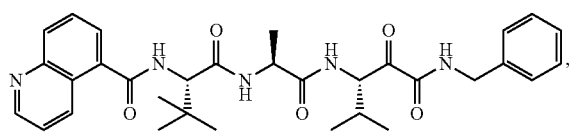
(PVA-151)
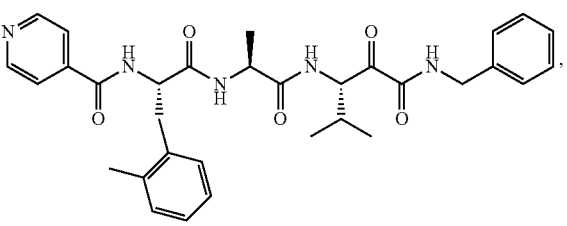
(PVA-152)
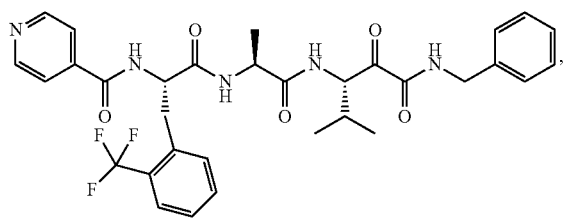
(PVA-153)
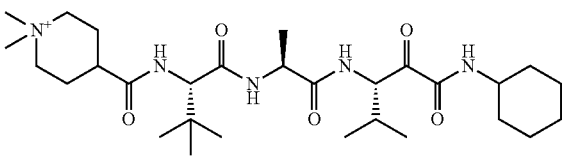
(PVA-154)
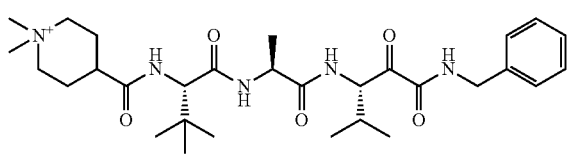
(PVA-155)
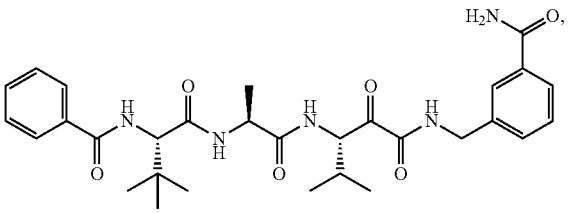
(PVA-156)
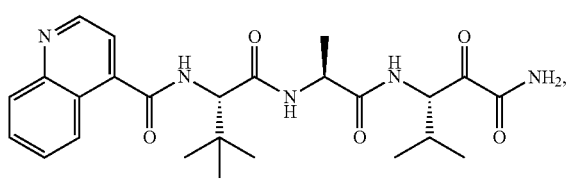
(PVA-157)
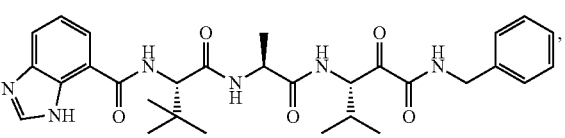
(PVA-158)
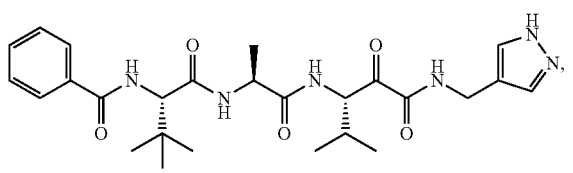
(PVA-159)
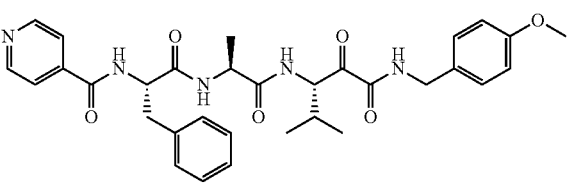
(PVA-160)
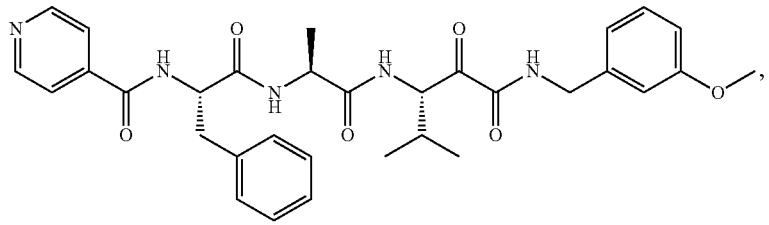

(PVA-161)
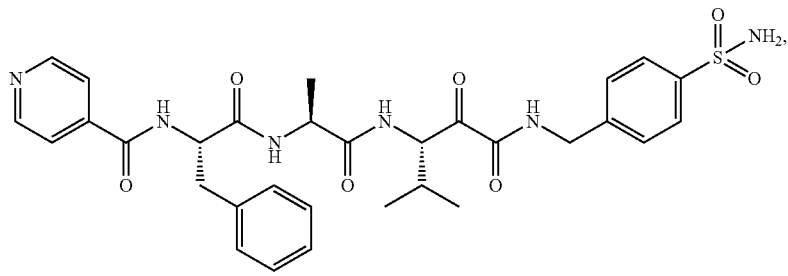
(PVA-162)
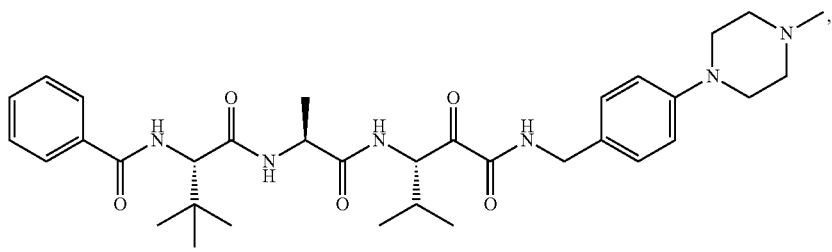
(PVA-163)
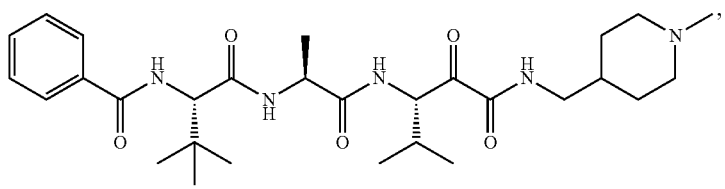
(PVA-164)
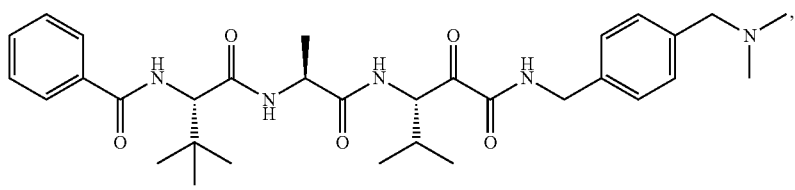
(PVA-165)
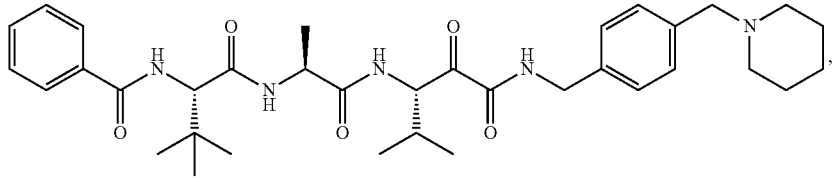
(PVA-166)
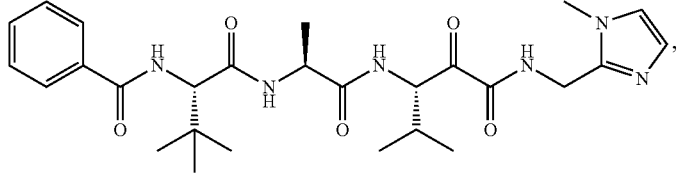
(PVA-167)
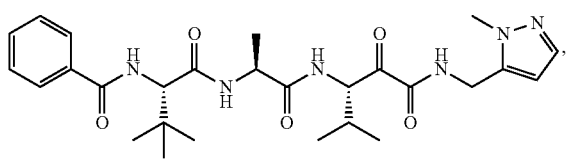
(PVA-168)
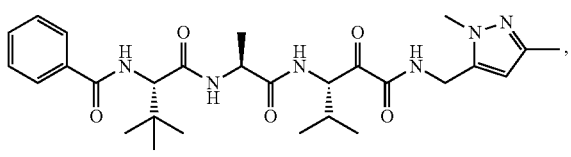

-continued
(PVA-169)
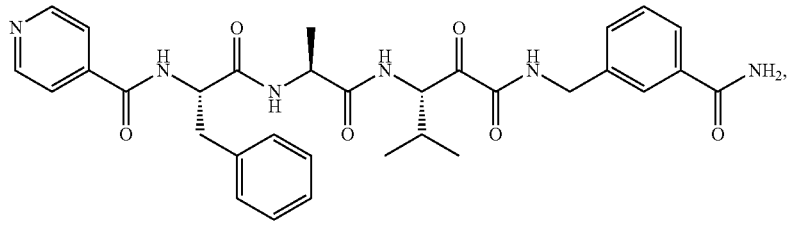
(PVA-170)
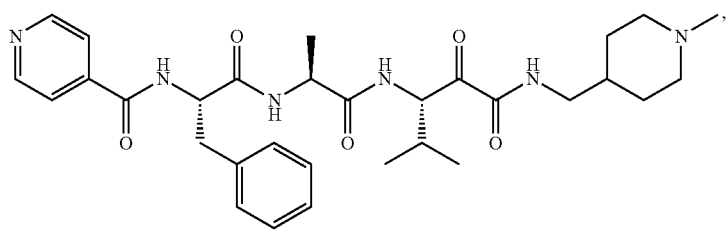
(PVA-171)
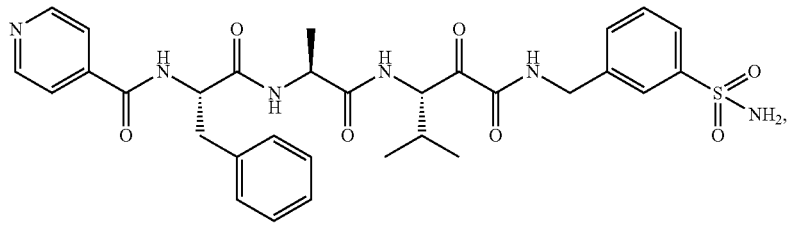
(PVA-172) (PVA-173)
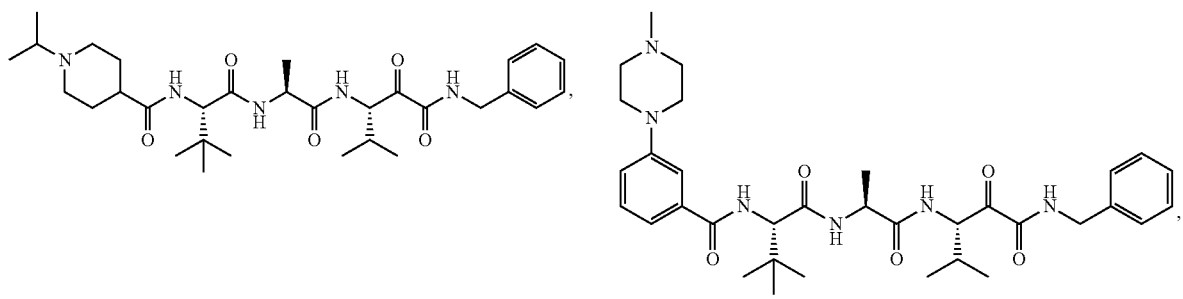
(PVA-174) (PVA-175)
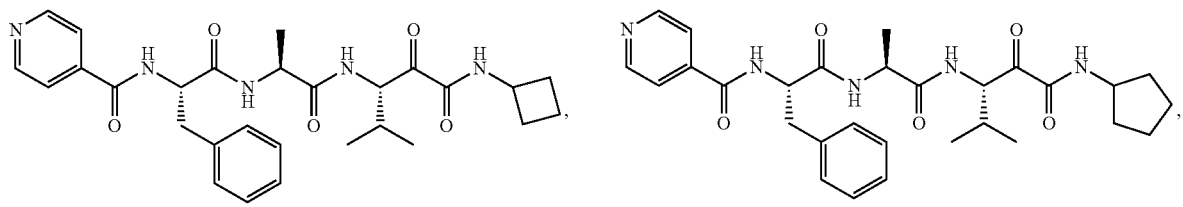
(PVA-176)
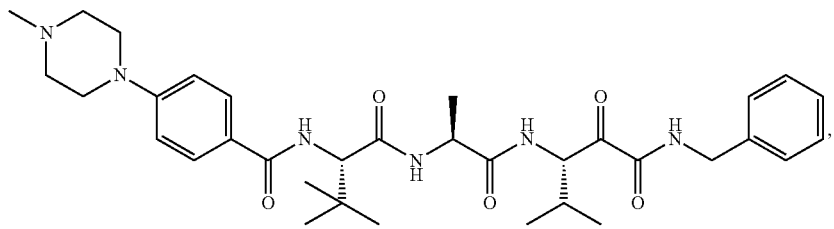

(PVA-177)
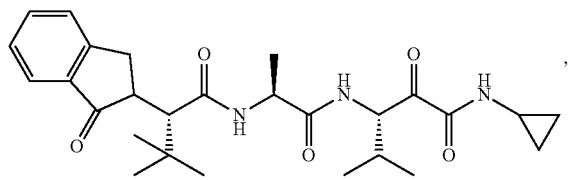
(PVA-178)
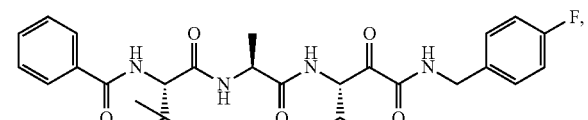
(PVA-179)
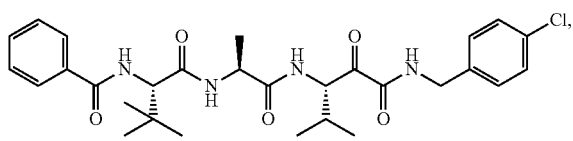
(PVA-180)
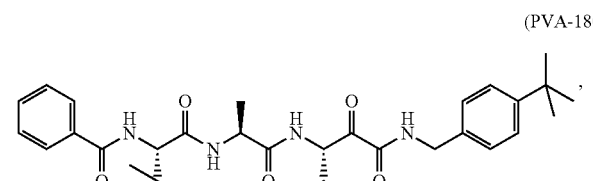
(PVA-181)
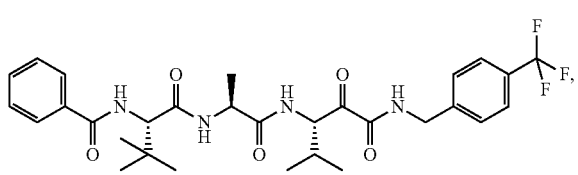
(PVA-182)
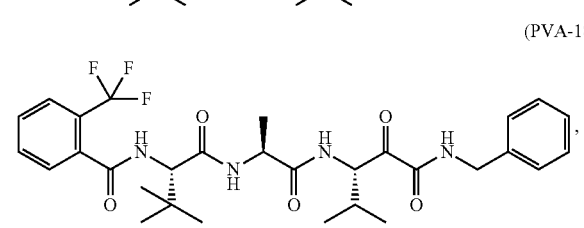
(PVA-183)
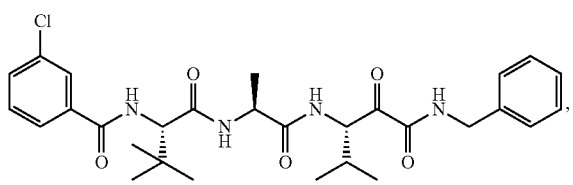
(PVA-184)
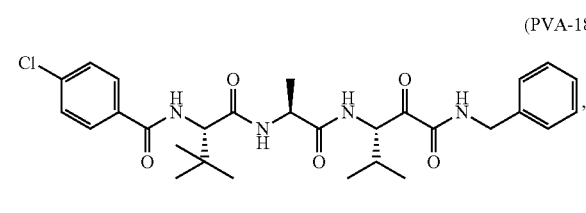
(PVA-185)
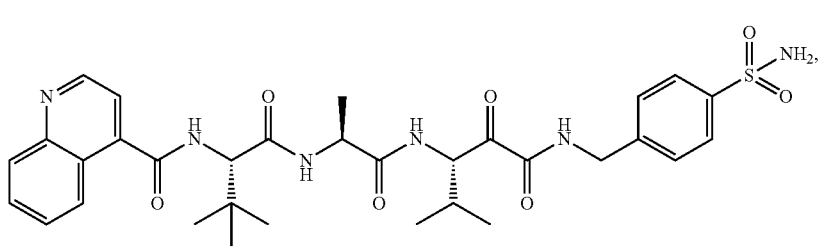
(PVA-186)
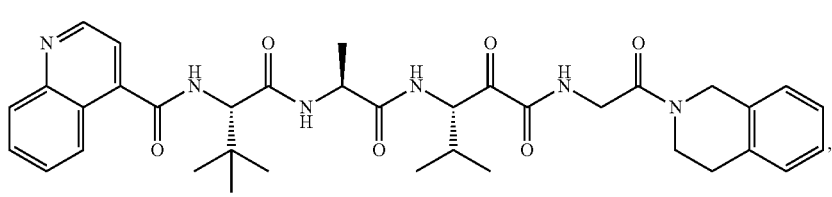
(PVA-187)
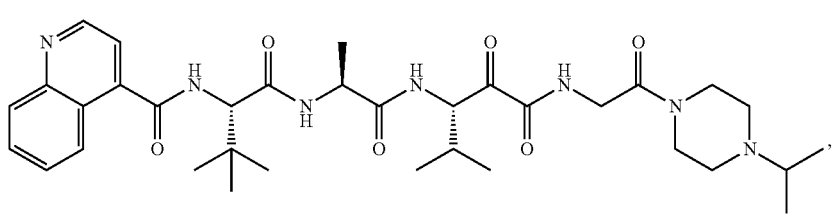

-continued
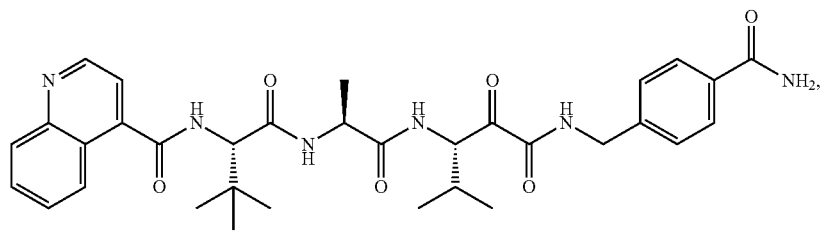
(PVA-188)
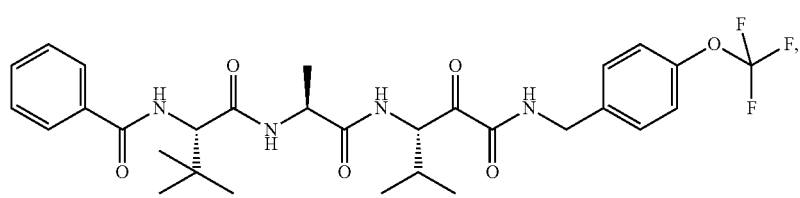
(PVA-189)
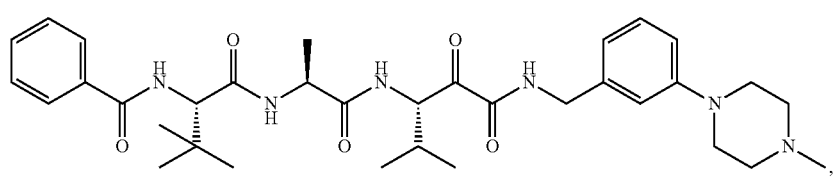
(PVA-190)
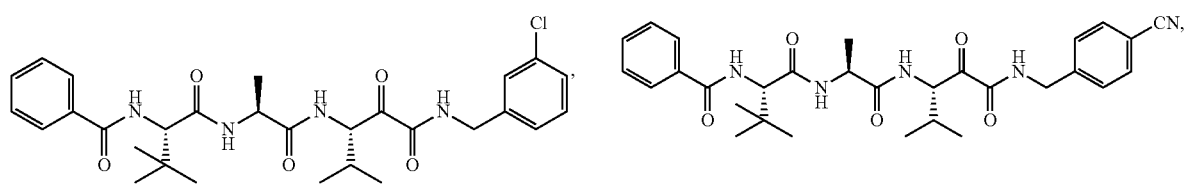
(PVA-191) (PVA-192)
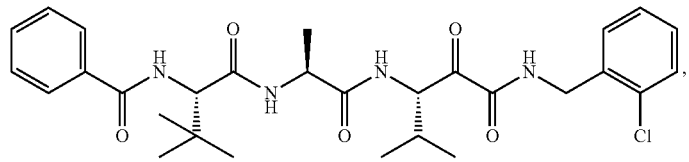
(PVA-193)
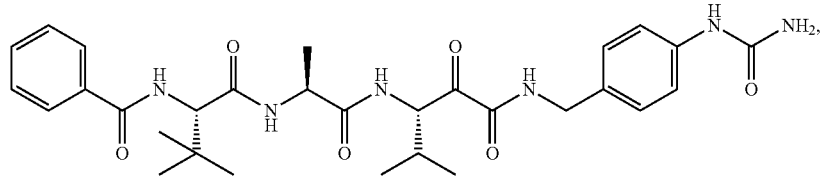
(PVA-194)
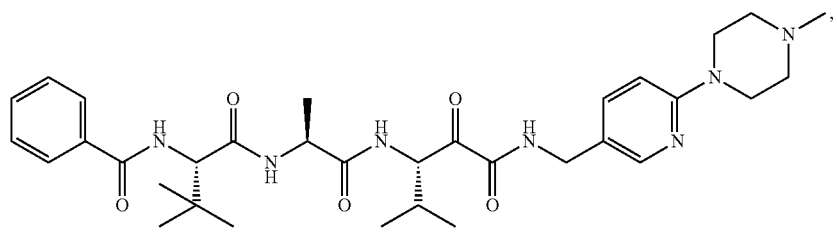
(PVA-195)
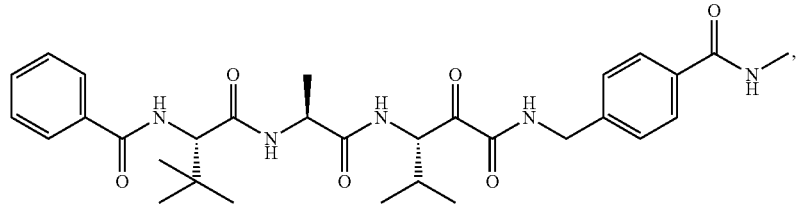
(PVA-196)

(PVA-197)
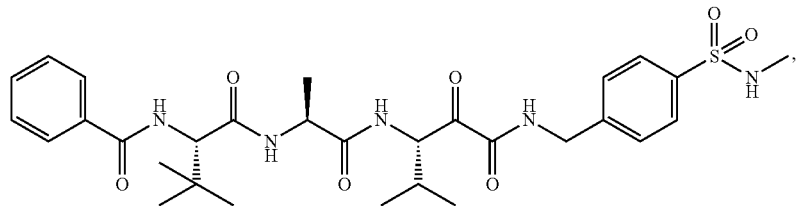
(PVA-198)
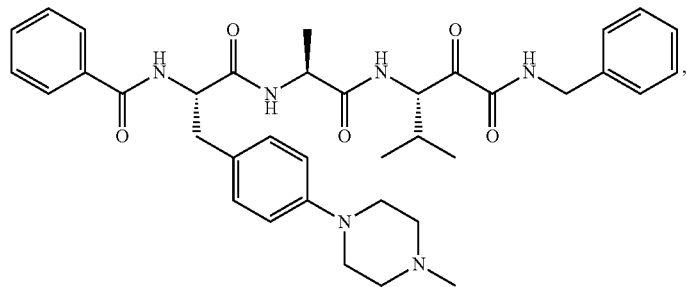
(PVA-199)
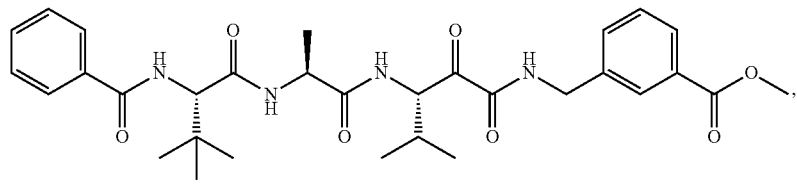
(PVA-200)
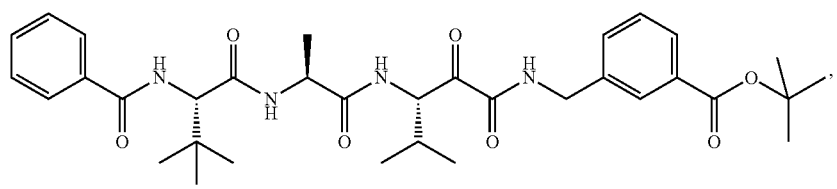
(PVA-201)
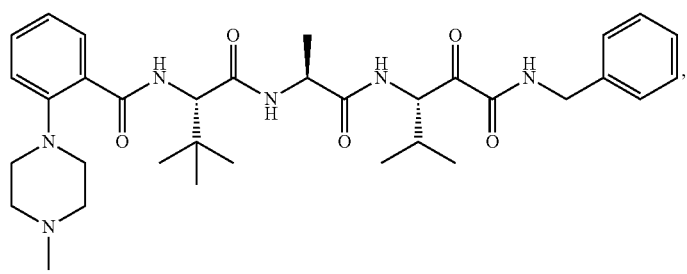
(PVA-202)
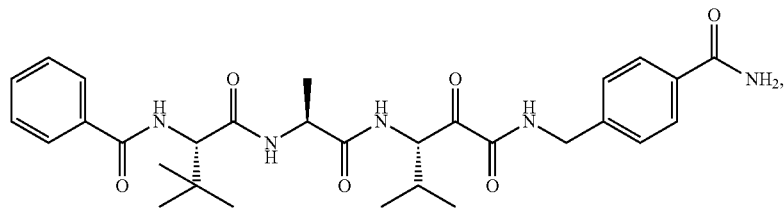
(PVA-203)
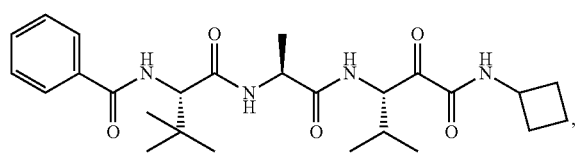
(PVA-204)
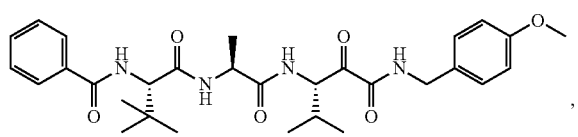

-continued
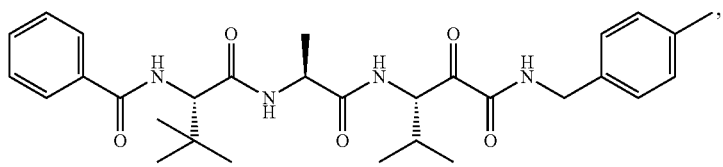
(PVA-205)
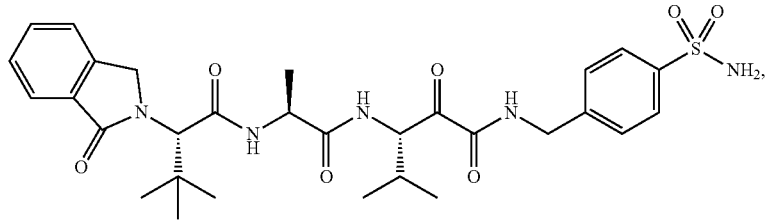
(PVA-206)
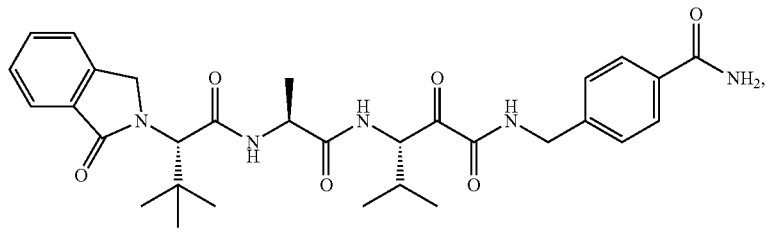
(PVA-207)
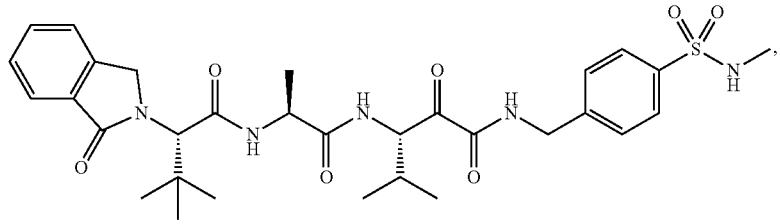
(PVA-208)
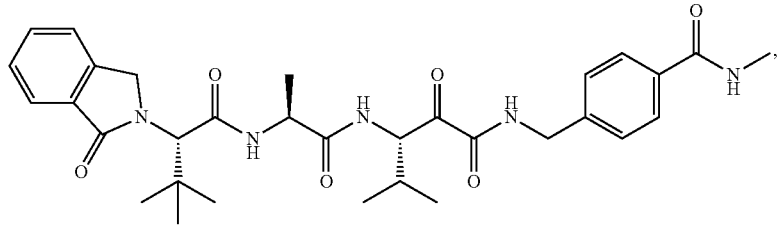
(PVA-209)
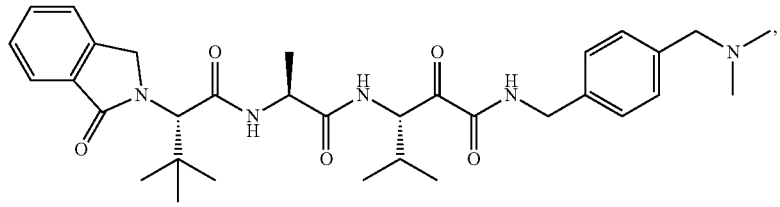
(PVA-210)
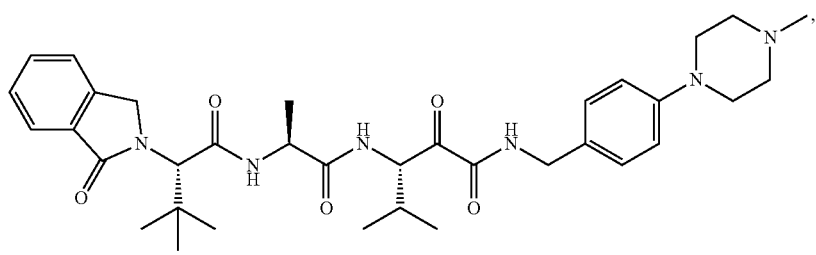
(PVA-211)

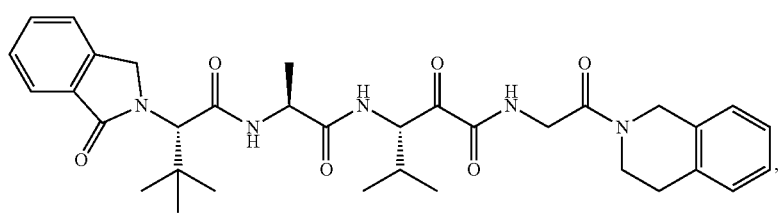
(PVA-212)

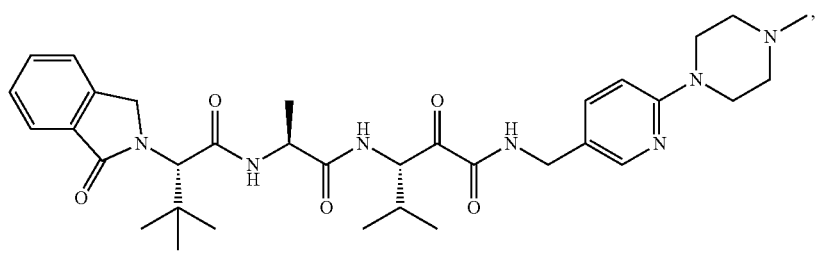
(PVA-213)

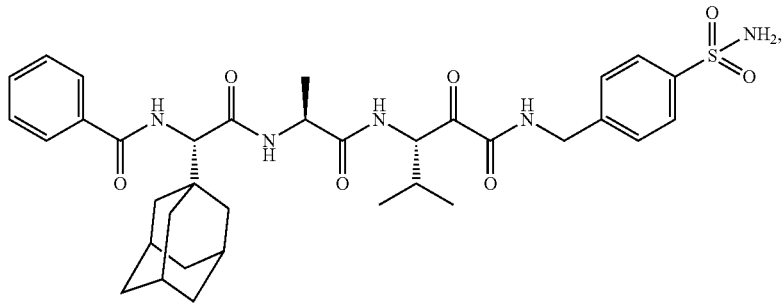
(PVA-214)

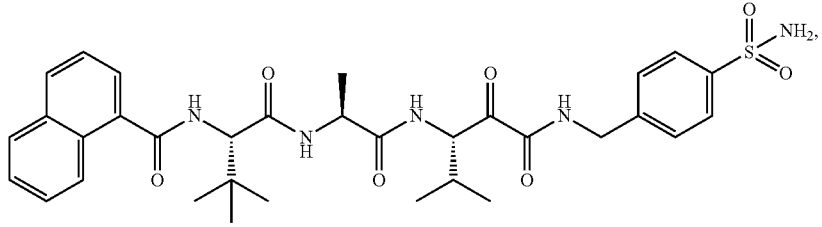
(PVA-215) and

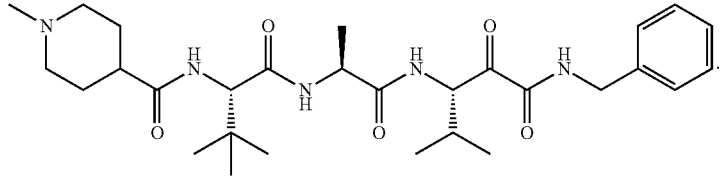
(PVA-216).

41. A composition comprising the compound according to claim 1 and a pharmaceutically acceptable carrier, diluent, or excipient.

42. A method of preparing a composition comprising admixing the compound according to claim 1 and a pharmaceutically acceptable carrier, diluent, or excipient.

43. A method of treatment, comprising administering to a subject in need of treatment a therapeutically-effective amount of the compound according to claim 1, wherein the treatment is treatment of:
asthma;
bronchial hyperreactivity associated with asthma; or bronchial hyperresponsiveness associated with asthma;
airway remodelling associated with an allergic lung disease;
asthma co-presented with a chronic obstructive lung disease;
rhinitis;
allergic conjunctivitis;
atopic dermatitis;
an allergic condition which is triggered by dust mites;
an allergic condition which is triggered by dust mite Group 1 peptidase allergen; or
canine atopy.

44. The method according to claim 43, wherein the treatment further comprises treatment with one or more additional therapeutic agents selected from agents used, or likely to be used, in the treatment of a respiratory disease.

45. A method of inhibiting a dust mite Group 1 peptidase allergen, in vitro or in vivo, comprising contacting said dust mite Group 1 peptidase allergen with an effective amount of the compound according to claim 1.

46. A method of inhibiting a dust mite Group 1 peptidase allergen in a cell, in vitro or in vivo, comprising contacting the cell with an effective amount of the compound according to claim 1.

47. An acaricide composition comprising the compound according to claim 1.

48. A method of killing mites, comprising exposing said mites to an effective amount of the compound according to claim 1.

49. A method of controlling a mite population comprising exposing mites to an effective amount of the compound according to claim 1.

50. A method of treatment, comprising administering to a subject in need of treatment a therapeutically-effective amount of the compound according to claim 1, wherein the treatment is treatment of:
 asthma.

51. A method of treatment, comprising administering to a subject in need of treatment a therapeutically-effective amount of the compound according to claim 1, wherein the treatment is treatment of:
 atopic asthma; allergic asthma; atopic bronchial IgE-mediated asthma; bronchial asthma; extrinsic asthma; allergen-induced asthma; or allergic asthma exacerbated by respiratory virus infection.

52. A method of treatment, comprising administering to a subject in need of treatment a therapeutically-effective amount of the compound according to claim 1, wherein the treatment is treatment of:
 infective asthma.

53. A method of treatment, comprising administering to a subject in need of treatment a therapeutically-effective amount of the compound according to claim 1, wherein the treatment is treatment of:
 infective asthma caused by bacterial infection; infective asthma caused by fungal infection; infective asthma caused by protozoal infection; or infective asthma caused by viral infection.

54. A method of treatment, comprising administering to a subject in need of treatment a therapeutically-effective amount of the compound according to claim 1, wherein the treatment is treatment of:
 bronchial hyperreactivity associated with asthma; or bronchial hyperresponsiveness associated with asthma.

55. A method of treatment, comprising administering to a subject in need of treatment a therapeutically-effective amount of the compound according to claim 1, wherein the treatment is treatment of:
 airway remodelling associated with an allergic lung disease.

56. A method of treatment, comprising administering to a subject in need of treatment a therapeutically-effective amount of the compound according to claim 1, wherein the treatment is treatment of:
 airway remodelling associated with asthma.

57. A method of treatment, comprising administering to a subject in need of treatment a therapeutically-effective amount of the compound according to claim 1, wherein the treatment is treatment of:
 asthma co-presented with a chronic obstructive lung disease.

58. A method of treatment, comprising administering to a subject in need of treatment a therapeutically-effective amount of the compound according to claim 1, wherein the treatment is treatment of:
 asthma co-presented with emphysema; or asthma co-presented with chronic bronchitis.

59. A method of treatment, comprising administering to a subject in need of treatment a therapeutically-effective amount of the compound according to claim 1, wherein the treatment is treatment of:
 rhinitis.

60. A method of treatment, comprising administering to a subject in need of treatment a therapeutically-effective amount of the compound according to claim 1, wherein the treatment is treatment of:
 allergic rhinitis; perennial rhinitis; persistent rhinitis; or IgE-mediated rhinitis.

61. A method of treatment, comprising administering to a subject in need of treatment a therapeutically-effective amount of the compound according to claim 1, wherein the treatment is treatment of:
 allergic conjunctivitis.

62. A method of treatment, comprising administering to a subject in need of treatment a therapeutically-effective amount of the compound according to claim 1, wherein the treatment is treatment of:
 IgE-mediated conjunctivitis.

63. A method of treatment, comprising administering to a subject in need of treatment a therapeutically-effective amount of the compound according to claim 1, wherein the treatment is treatment of:
 atopic dermatitis.

64. A method of treatment, comprising administering to a subject in need of treatment a therapeutically-effective amount of the compound according to claim 1, wherein the treatment is treatment of:
 an allergic condition which is triggered by dust mites.

65. A method of treatment, comprising administering to a subject in need of treatment a therapeutically-effective amount of the compound according to claim 1, wherein the treatment is treatment of:
 an allergic condition which is triggered by dust mite Group 1 peptidase allergen.

66. A method of treatment, comprising administering to a subject in need of treatment a therapeutically-effective amount of the compound according to claim 1, wherein the treatment is treatment of:
 canine atopy.

\* \* \* \* \*